(12) United States Patent
Hatayama et al.

(10) Patent No.: US 8,138,182 B2
(45) Date of Patent: Mar. 20, 2012

(54) DIKETOHYDRAZINE DERIVATIVE COMPOUNDS AND DRUGS CONTAINING THE COMPOUNDS AS THE ACTIVE INGREDIENT

(75) Inventors: Akira Hatayama, Osaka (JP); Hiroshi Tsuruta, Osaka (JP); Yasuo Ochi, Osaka (JP); Haruo Imawaka, Osaka (JP); Kazuyuki Ohmoto, Osaka (JP)

(73) Assignee: Ono Pharmaceutical Co., Ltd., Osaka (JP)

(*) Notice: Subject to any disclaimer, the term of this patent is extended or adjusted under 35 U.S.C. 154(b) by 170 days.

(21) Appl. No.: 12/566,416

(22) Filed: Sep. 24, 2009

(65) Prior Publication Data

US 2010/0087442 A1    Apr. 8, 2010

Related U.S. Application Data

(63) Continuation of application No. 10/512,348, filed as application No. PCT/JP03/05252 on Apr. 24, 2003, now Pat. No. 7,655,804.

(30) Foreign Application Priority Data

Apr. 25, 2002    (JP) .................. 2002-123796

(51) Int. Cl.
  *C07D 207/22*  (2006.01)
  *C07D 233/32*  (2006.01)
  *C07D 263/20*  (2006.01)
  *C07D 265/33*  (2006.01)
  *C07D 403/12*  (2006.01)
  *C07D 413/12*  (2006.01)
  *C07D 417/12*  (2006.01)

(52) U.S. Cl. ............... 514/231.5; 514/315; 514/368; 514/370; 514/422; 514/424; 514/425; 514/614; 544/164; 546/207; 546/208; 546/209; 548/134; 548/161; 548/185; 548/194; 548/216; 548/302.7; 548/311.1; 548/322.1; 548/546

(58) Field of Classification Search ................... None
See application file for complete search history.

(56) References Cited

U.S. PATENT DOCUMENTS

| 6,117,870 A |   | 9/2000 | Hosoda et al. |
| 7,632,813 B2 | * | 12/2009 | Ochi et al. ............... 514/1.1 |
| 7,655,804 B2 | * | 2/2010 | Hatayama et al. ............ 548/194 |

FOREIGN PATENT DOCUMENTS

| CN | 1274283 A | 11/2000 |
| WO | 95/07269 A1 | 3/1995 |
| WO | 99/17775 A1 | 4/1999 |
| WO | 03/013518 A1 | 2/2003 |

OTHER PUBLICATIONS

Golub et al, Science, 286, 531-537, 1999.

* cited by examiner

*Primary Examiner* — Fiona T Powers
(74) *Attorney, Agent, or Firm* — Sughrue Mion, PLLC

(57) ABSTRACT

The present invention relates to a diketohydrazine derivative of formula (I) and a pharmaceutically acceptable salt thereof (the symbols in the formula have the same meaning as described in the specification).

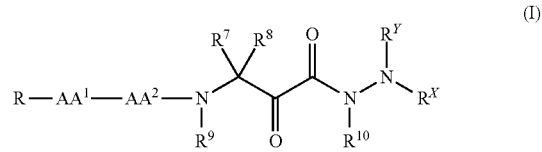

The compound of formula (I) has an inhibitory activity against cysteine protease, and it is useful for the treatment of inflammatory diseases, immune diseases, ischemic diseases, respiratory diseases, circulatory diseases, blood diseases, neuronal diseases, hepatic or biliary diseases, osseous or articular diseases, metabolic diseases, etc. And the compound has inhibitory activity against elastase and it is also useful for the treatment of COPD (chronic obstacle pulmonary diseases).

10 Claims, No Drawings

DIKETOHYDRAZINE DERIVATIVE COMPOUNDS AND DRUGS CONTAINING THE COMPOUNDS AS THE ACTIVE INGREDIENT

CROSS REFERENCE TO RELATED APPLICATIONS

This is a continuation application of U.S. application Ser. No. 10/512,348, filed Jan. 10, 2006, now U.S. Pat. No. 7,655,804, which is a National Stage of Application No. PCT/JP03/05252 filed Apr. 24, 2003, which claims priority of Japanese Patent Application No. 2002-123796, filed Apr. 25, 2002. The entire disclosures of the prior applications are hereby incorporated by reference.

TECHNICAL FIELD

The present invention relates to diketohydrazine derivatives. More specifically, the present invention relates to
1) a diketohydrazine derivative of formula (I)

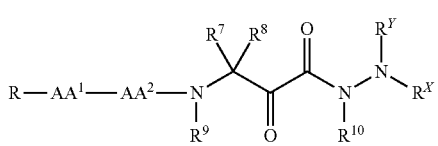

(wherein all symbols have the same meaning as described hereafter) and a pharmaceutically acceptable salt thereof,
2) a method for the preparation thereof and
3) a pharmaceutical composition comprising it as active ingredient.

BACKGROUND OF ART

Cysteine protease is a generic name of proteases which have a cysteine residue in the activity center and catalyze protein degradation thereat. In animal cells, many cysteine proteases are known; for example, cathepsin family, calpain, caspase, etc. Cysteine protease exists in various kinds of cells extensively and plays a basic and essential role in the homeostasis, such as conversion of precursor protein into its active form (processing) and degradation of proteins which have become out of use, etc. Until now, its physiological effects are being vigorously studied, and as the studies progress and characters of the enzymes are revealed, cysteine protease came to be taken as a cause of really various kinds of diseases.

It is revealed that cathepsin S (see J. Immunol., 161, 2731 (1998)), cathepsin L (see J. Exp. Med., 183, 1331 (1996)) and cathepsin F (J. Exp. Med., 191, 1177 (2000)) play a role in processing of major histocompatibility complex class-II in antigen presenting cells which play an important role in the early stage of immune responses.

In an experimental inflammatory response model induced by antigens, a specific inhibitor of cathepsin S showed an inhibitory effect (see J. Clin. Invest., 101, 2351 (1998)). It is also reported that in a leishmania-infected immune response model a cathepsin B inhibitor controlled an immune response and by means of this effect it inhibited the proliferation of protozoans (see J. Immunol., 161, 2120 (1998)). In vitro, a result is given that a calpain inhibitor and a cysteine protease inhibitor E-64 inhibited apoptosis which is induced by stimuli on T cell receptors (see J. Exp. Med., 178, 1693 (1993)). And cathepsin W, which is expressed in CD8 T cells and NK cells specifically, is known to increase its expression by stimuli of IL-2 by 7 times and so it is conceived that it is concerned with immune responses [J. Immunol., 167, 2172 (2001)]. It is also reported that in leukemia patients, gene expression of cathepsin C and cathepsin W increases and cytotoxic T cells are activated [Int. J. Oncol., 22, 33 (2003)]. Therefore, it is conceivable that cysteine protease is much concerned with the progress of immune responses.

It is speculated that caspase or a similar cysteine protease thereto occupies an important position in the mechanism of cell death including apoptosis. Therefore it is expected for a cysteine protease inhibitor to be used as an agent for the prophylaxis and/or treatment of those diseases concerning apoptosis, such as infectious diseases, deterioration or sthenia of immune function and brain function, or tumors etc. Diseases concerning apoptosis include, acquired immune deficiency syndrome (AIDS), AIDS-related complex (ARC), adult T cell leukemia, hairy cell leukemia, spondylopathy, respiratory apparatus disorder, arthritis, virus-related diseases (HIV, HTLV-1 related diseases (uveitis etc.) and hepatitis C etc.), cancer, collagenosis (systemic lupus erythematosus, rheumatoid arthritis, etc.), autoimmune diseases (inflammatory bowel diseases, Sjoegren syndrome, primary biliary cirrhosis, spontaneous thrombocytopenic purpura, autoimmune hemolytic anemia, myasthenia gravis, insulin dependent (type-I) diabetes, etc.), diseases accompanied by thrombocytopenia (osteomyelodysplasia syndrome, periodic thrombocytopenia, aplastic anemia, spontaneous thrombocytopenia, disseminated intravascular coagulation (DIC) etc.), hepatic diseases such as viral hepatitis (C, A, B, F, etc.) or hepatitis medicamentosa and cirrhosis, dementia (Alzheimer's disease, Alzheimer's senile dementia, etc.), cerebrovascular injury, nerve degeneration diseases, adult acute respiratory distress syndrome, infectious diseases, prostate hypertrophy, hysteromyoma, bronchial asthma, arteriosclerosis, all kinds of lusus naturae, nephropathy, senile cataract, chronic fatigue syndrome, myodystrophy, peripheral neuropathy, etc.

Moreover, caspase-1 is concerned with various inflammatory diseases and those diseases caused by immune disorders, by means of interleukin-1β (IL-1β) production. A lot of diseases are shown to be involved with caspase-1; for example, inflammatory bowel diseases such as ulcerative colitis, inflammatory diseases (insulin-dependent (type-I) diabetes, autoimmune thyroid diseases, infectious diseases, rejection of an organ transplant, graft versus host diseases, psoriasis, periodontitis (above, see N. Eng. J. Med., 328, 106 (1993)), pancreatitis (see J. Interferon Cytokine Res., 17, 113 (1997)), hepatitis (see J. Leuko. Biol., 58, 90 (1995)), glomerulonephritis (see Kidney Int., 47, 1303 (1995)), endocarditis (see Infect. Immun., 64, 1638 (1996)), myocarditis (see Br. Hearat J., 72, 561 (1995)), systemic lupus erythematosus (see Br. J. Rheumatol., 34, 107 (1995)), Hashimoto's diseases (see Autoimmunity, 16, 141 (1993)), etc.), autoimmune diseases, etc. Experimentally, it is reported that in liver injury model induced by lipopolysaccharide and D-galactosamine, a caspase-1 inhibitor improved the symptoms, and it is expected that a caspase inhibitor shows an effect in sepsis, ischemic reperfusion and hepatitis gravis.

It is also shown that cysteine protease is concerned with rheumatoid arthritis. IL-1β is shown to be concerned with this disease (see Arthritis Rheum., 39, 1092 (1996)), and in addition, as autoantibody toward calpastatin (endogenous calpain inhibitor) was found in the serum of the patients [Proc. Natl. Acad. Sci. USA, 92, 7267 (1995)], it is thought that increase of calpain activity leads to the cause of diseases. Also, it is also reported that cathepsin B and cathepsin C activity is increased in leukocyte of patients suffering from rheumatoid arthritis [Biol. Chem., 383, 865 (2002)]. It is reported that in experimental arthritis model the production of inflammatory cytokine is suppressed and affection of arthritis completely in cathepsin C knock-out mice, so it is expected that cathepsin C inhibition leads to treatment of rheumatoid arthritis [J. Clin. Invest., 109, 357 (2002)].

It is also known that cysteine protease causes a disease symptom by decomposing various proteins which compose the organism.

It is reported that cathepsin B plays a role in decomposing muscular protein in the chronic phase of sepsis (see J. Clin. Invest., 97, 1610 (1996)), and in decomposing muscular protein in myodystrophy model (see Biochem. J., 288, 643 (1992)). At the same time it is reported that calpain decomposes the myocyte cell proteins of myodystrophy patients (see J. Biol. Chem., 270, 10909 (1995)).

In ischemic reperfusion model, a result is given that calpain causes degeneration of brain tissues by means of degradation of protein kinase C-β (see J. Neurochem., 72, 2556 (1999)) and that a cathepsin B inhibitor inhibits nerve injury (see Eur. J. Neurosci., 10, 1723 (1998)).

In the brain ischemic model, it is known that the degradation of spectrin by calpain causes a damage and its function disorder in the neurocyte (see Brain Res., 790, 1 (1998)) and it is reported that an IL-1β receptor antagonist relieved the symptoms (see Brain Res. Bull., 29, 243 (1992)).

In myocardial ischemic model it is confirmed that cathepsin B activity increases in the lesion (see Biochem. Med. Metab. Biol., 45, 6 (1991)).

In the experiment utilizing ischemic liver injury model, it proved that necrosis and apoptosis of hepatocyte were induced by means of protein-decomposing activity of calpain (see Gastroenterology, 116, 168 (1999)).

Otherwise, it is known that calpain causes cornea turbid by means of degradation of crystalline (see Biol. Chem., 268, 137 (1993)) and that in the lesion of contracted gut mucosa model it was confirmed that the activity of cathepsin B, H and L increased (see J. Parenter. Enteral. Nutr., 19, 187 (1995)) and it is shown that cysteine protease is a cause of the diseases resulting from these protein degradation.

It has been revealed that cysteine protease is concerned with systemic disorders of organs and tissues by shock.

It is shown that IL-1β is concerned with septic shock and systemic inflammatory response syndrome (see Igakuno ayumi, 169, 850 (1994)) and besides, it is reported that in endotoxin shock model induced by lipopolysaccharide, a calpain inhibitor prevented circulatory system disorder, disorders of liver and pancreas and acidosis by means of inhibitory effect of activation of nuclear factor κB (see Br. J. Pharmacol., 121, 695 (1997)).

Since it is reported that calpain is concerned with platelet coagulation process and a calpain inhibitor prevented platelet coagulation (see Am. J. Physiol., 259, C862 (1990)), it is conceivable that a cysteine protease inhibitor is useful for the disorder of blood coagulation. From the fact that calpain activity increased in the serum of the patients of purpura (thrombocytopenia) resulting from marrow transplantation, so it is conceivable that calpain is concerned with the actual disease symptoms (see Bone Marrow Transplant., 24, 641 (1999)).

Caspase-1 inhibitor suppressed apoptosis of blood vessel endothelial cells, which is seen in the early phase of purpura (thrombocytopenia) and is thought to be important for the progression of the pathology afterwards (see Am. J. Hematol., 59, 279 (1998)), so it is expected that a cysteine protease inhibitor makes effect on purpura and hemolytic uremic syndrome.

The effect of cysteine protease and its inhibitor is being investigated in the area of cancer and metastasis of cancer. Since the proliferations of pancreas cancer cells (see Cancer Res., 59, 4551 (1999)) and acute myeloid leukemia cells (see Clin. Lab. Haematol., 21, 173 (1999)) were inhibited by a caspase-1 inhibitor or its receptor antagonist, it is expected that caspase-1 activity is essential for the process of proliferation of tumor cells, and that an inhibitor thereof is effective for these cancers. Also, from the facts that cathepsin B activity increased in colon cancer metastasis model (see Clin. Exp. Metastasis, 16, 159 (1998)), that cathepsin L activity increased in urine of bladder cancer patients (see Urology, 59, 308 (2002)), that cathepsin Z expression was recognized in tumor cells (see J. Biol. Chem., 273, 16816 (1998)), that cathepsin K protein expression recognized in human breast cancer cells proved the relationship of cathepsin K and bone metastasis (see Cancer Res., 57, 5386 (1997)), and that a calpain inhibitor suppressed migration of the cells, which implies that calpain inhibition might be able to inhibit metastasis of cancer (see J. Biochem., 272, 32719 (1997)), a cysteine protease inhibitor is expected to exhibit an inhibitory effect on the metastasis of various malignant tumors.

As to AIDS (AIDS, 10, 1349 (1996)) and AIDS-related complex (ARC) (Arch. Immunol. Ther. Exp. (Warsz), 41, 147 (1993)), it is implied that IL-1 is concerned with the progress of symptoms, and so it is conceivable that cysteine protease inhibition leads to an effective therapy of AIDS and its complication.

Some parasites have cysteine protease activity in their bodies. Cysteine protease in the phagosome of malaria protozoan is an essential enzyme for supplying nutrition of the parasites. Its inhibitor show an inhibitory effect of the proliferation of the protozoan (see Blood, 87, 4448 (1996)).

In Alzheimer-type dementia, it is said that adhesion of non-physiological protein called amyloid to brain is deeply involved with nervous function disorders. Cysteine protease has an activity of generating amyloid by decomposing its precursor protein. Clinically, it is shown that cathepsin B possesses a processing activity of amyloid proteins in the brains of Alzheimer-type dementia patients (see Biochem. Biophys. Res. Commun., 177, 377 (1991)). And expressions of cathepsin B protein (see Virchows Arch. A. Pathol. Anat. Histpathol., 423, 185 (1993)), cathepsin S protein (see Am. J. Pathol., 146, 848 (1995)) and calpain protein (see Proc. Natl. Acad. Sci. USA, 90, 2628 (1993)) and increase of caspase-1 activity (see J. Neuropathol. Exp. Neurol., 58, 582 (1999)) were confirmed in the brain lesions. And it is implied that cysteine protease is concerned with the disease symptoms, by the fact that calpain is concerned with the formation of paired helical filaments which accumulate in Alzheimer dementia patients and production of protein kinase C which stabilizes the protein (see J. Neurochem., 66, 1539 (1996)) and by the knowledge that caspase is concerned with neurocyte death by β amyloid protein adhesion (see Exp. Cell Res., 234, 507 (1997)).

As to Huntington's chorea, cathepsin H activity increased in the patient's brain (see J. Neurol. Sci., 131, 65 (1995)), and the ratio of activated form of calpain (see J. Neurosci., 48, 181 (1997)) increased. In Parkinson's disease, the increase of expression of m-calpain was recognized in the mesencephalon in the patients (see Neuroscience, 73, 979 (1996)) and IL-1β protein was expressed in brain (see Neurosci. Let., 202, 17 (1995)). Therefore, it is speculated that cysteine protease is concerned with the genesis and progress of these diseases.

Otherwise, in the central nervous system, spectrin degradation by calpain is found in the process of injury on neurocyte observed in the traumatic brain injury model (see J. Neuropathol. Exp. Neurol., 58, 365 (1999)).

In spinal cord injured model it was recognized that in glia cells calpain messenger RNA increased and its activity increased in the lesion and the possibility was shown that calpain had much to do with the degeneration of myelin and actin (see Brain Res., 816, 375 (1999)). And IL-1β was shown to be concerned with the genesis of multiple sclerosis (see Immunol. Today, 14, 260 (1993)). Therefore, it is conceivable that a cysteine protease inhibitor is hopeful as an agent for the treatment of these nerve-injured diseases.

Normally, cathepsin S and cathepsin K do not exist in human arterial walls, but it was confirmed that they expressed in arteriosclerosis lesion and they had an decomposing activity of alveolus elastica (see J. Clin. Invest, 102, 576 (1998)) and a calpain inhibitor and antisense of m-calpain inhibited the proliferation of human blood vessel smooth muscle cells and it is shown that m-calpain is concerned with the proliferation of smooth muscle (see Arterioscler. Thromb. Vssc. Biol., 18, 493 (1998)), so it is conceivable that a cysteine protease inhibitor is hopeful for the treatment of blood vessel lesion such as arteriosclerosis, restenosis after percutaneous transluminal coronary angioplasty (PTCA) etc. And it is also reported that LDL induces cathepsin H expression in human monocyte and cathepsin H is concerned with LDL transformation and it is implied that LDL is concerned with circulatory disorder (arteriosclerosis) [Arterioscler. Thromb. Vasc. Biol., 27 (2003)].

It is reported that in liver, cathepsin B is activated in the process of injuring hepatocyte by bile acid (see J. Clin. Invest., 103, 137 (1999)) and so it is expected that a cysteine protease inhibitor is useful for cholestatic cirrhosis.

It is reported that in spleen, cathepsin Y is concerned with production of bradykinin potentiating peptide (BPP) which plays some role in converting kinin into bradykinin [Immunopharmacology, 45, 207 (1999)]. Therefore, it is expected that cathepsin Y inhibitor has anti-allergy effect.

In lungs and respiratory system, it is shown that cathepsin S is an enzyme that plays a role in elastin degradation by alveolus macrophages (see J. Biol. Chem., 269, 11530 (1994)), so it is probable that cysteine protease is a cause of pulmonary emphysema. In IL-13 transgenic mice in which COPD-like pathology is recognized, increase of cathepsin B, S, L, H and H expression is recognized and it is also reported that administration of a cysteine protease inhibitor suppresses lung inflammation and lung emphysema [J. Clin. Invest., 106, 1081 (2000)]. And it is also shown that lung injury (see J. Clin. Invest., 97, 963 (1996)), lung fibrosis (see Cytokine, 5, 57 (193)) and bronchial asthma (see J. Immunol., 149, 3078 (1992)) are caused by way of production of IL-1β by caspase-1. It is also shown that blood cathepsin H concentration is increased in asthma patients, so antiasthma effect by its inhibitor is expected [Clin. Chim. Acta, 310, 113 (2001)]. It is known that cathepsin H functions in the excision of surfactant protein C which is synthesized by type-2 pneumonia cells [Am. J. Respir. Cell Mol. Biol., 26, 659 (2002)].

It is pointed out that cysteine protease is also concerned with diseases concerning bones and joints. Cathepsin K is specifically recognized in osteoclast and it has a decomposing activity against bone matrix [J. Biol. Chem., 271, 12517 (1996)], so its inhibitor is expected to show an effect in osteoporosis, arthritis, rheumatoid arthritis, osteoarthritis, hypocalcaemia, osteometastasis of cancer, where pathologic bone resorption is recognized. Also, since IL-1β is shown to be concerned with bone resorption and cartilage degradation, and a caspase-1 inhibitor and IL-1β receptor antagonist inhibit the symptoms of bone resorption and arthritis, so it is expected that it is effective for arthritis (see Cytokine, 8, 377 (1996)) and osteoporosis (see J. Clin. Invest., 93, 1959 (1994)). And it is also reported that IL-1β is concerned with osteoarthritis (see Life Sci., 41, 1187 (1987)).

Cysteine protease is involved with production of various hormones. Since increase of messenger RNA of cathepsin S was recognized by stimuli of thytropin on thyroid epitheliocyte strains (see J. Biol. Chem., 267, 26038 (1992)), it is conceivable that a cysteine protease inhibitor is effective for hyperthyroidism.

Since quantity and activity of cathepsin B protein increased in the gingival sulcus liquid of periodontitis patients [J. Clin. Periodontal., 25, 34 (1998)], it is pointed out that cysteine protease is concerned with periodontitis.

On the other hand, serine proteases include thrombin, chymase, trypsin, chymotrypsin, urokinase, plasmin, elastase, etc. Thrombin, which is produced in blood coagulation cascades, decomposed fibrinogen to form fibrin and activates the factor VIII. Thrombin is concerned with thrombophlebitis, thrombosis and asthma.

Pancreatic elastase is concerned with pancreatitis. Chymase is an important enzyme in angiotensin synthesis and it is concerned with hypertension, myocardiac infarction, and coronary heart diseases. Cathepsin G is concerned with abnormal connective tissue decomposition.

Therefore, those compounds which have an inhibitory activity against cysteine proteases, are useful as agents for the prophylaxis and/or treatment of inflammatory diseases (periodontitis, arthritis, inflammatory bowel diseases, infectious diseases, pancreatitis, hepatitis, glomerulonephritis, endocarditis, myocarditis, ulcerative colitis, etc.), immune diseases (diseases induced by immune response disorder (graft versus host diseases, rejection during transplantation, allergic diseases (asthmatic bronchitis, atopic dermatitis, allergic rhinitis, hay fever, diseases by house dust, hypersensitive pneumonia, food allergy, etc.), psoriasis, rheumatoid arthritis, etc.), autoimmune diseases (insulin dependent (type I) diabetes, systemic lupus erythematosus, Hashimoto's diseases, multiple sclerosis, etc.), acquired immune deficiency syndrome (AIDS, AIDS-related complex (ARC), etc.), ischemic diseases (brain ischemia, brain disorder by ischemic reperfusion, cardiac infarction, ischemic liver damage, etc.). respiratory diseases (adult acute respiratory distress syndrome, lung disorder, fibroid lungs, decomposition of alveolus elastica (emphysema etc.), etc.), circulatory diseases (arteriosclerosis, restenosis after PTCA (percutaneous transluminal coronary angioplasty), hyperlipidemia, etc.), blood diseases (thrombocytopenic purpura, hemolytic uremic syndrome, myelodysplastic syndrome, cyclic thrombocytopenia, aplastic anemia, spontaneous thrombocytopenia, disseminated intravascular coagulation (DIC), spontaneous thrombocytopenic purpura, autoimmune hemolytic anemia, hyperlipidemia, etc.), neuronal diseases (dementia such as Alzheimer's disease, Alzheimer-type senile dementia, cerebrovascular injury, peripheral nerve injury, neurodegenerative disease (Huntington's chorea, Parkinson's disease, multiple sclerosis, traumatic encephalopathy, traumatic spondylopathy, etc.), etc.), hepatic or biliary diseases (primary biliary cirrhosis, viral hepatitis (A, B, C, F, etc.) or hepatitis medicamentosa and cirrhosis, etc.), osseous or articular diseases (osteoporosis, rheumatoid arthritis, arthritis, osteoarthritis, hypocalcaemia, osteometastasis of cancer, bone fracture, etc.), metabolic diseases (osteoporosis, rheumatoid arthritis, arthritis, osteoarthritis, hypocalcaemia, bone metastasis of cancer, endocrinesthenia (hyperthyroidism etc.), diseases induced by apoptosis (graft versus host diseases, rejection during transplantation, acquired immunodeficiency syndrome (AIDS), AIDS-related complex (ARC), adult T cell leukemia, hairy cells leukemia, spondylopathy, disorders of respiratory apparatus, arthritis, HIV or HTLV-1 related diseases (uveitis etc.), virus related diseases (hepatitis C etc.), cancer, collagenosis (systemic lupus erythematosus, rheumatoid arthritis, etc.), Sjoegren syndrome, myasthenia gravis, autoimmune diseases (insulin dependent (type I) diabetes, etc.), infectious diseases, prostatomegaly, hysteromyoma, bronchial asthma, nephritis, senile cataract, chronic fatigue syndrome, myodystrophy, etc.), diseases induced by decomposition of proteins which compose a body (myodystrophy, cataract, periodontitis, hepatocyte injury by bile acid (cholestatic cirrhosis etc.), etc., shock (septic shock, systemic inflammatory responsive syndrome, endotoxin shock, acidosis, etc.), malignant tumor, AIDS-related complex, parasitic diseases (malaria etc.)

Further, an elastase inhibitor is useful for the treatment and/or prophylaxis of diseases resulting from hyperactivity of decomposition of elastin, collagen fiber and/or proteoglycan by elastase in mammals, particularly in humans, for example, chronic obstructive pulmonary diseases (COPD) such as decomposition of alveolus elastica (emphysema etc.), rheumatoid arthritis, atherosclerosis, adult respiratory distress syndrome (ARDS), glomerulonephritis, myocardial infarction, ulcerative colitis, parodontitis apicalis, etc.

On the other hand, what is the most important for inhibitors in inhibiting the activity of proteases is, the special reaction site which interacts with the amino acid residues the activity center of proteases. The surrounding structure of the reaction sites are represented by ---P3P2P1-P1'P2'P3'---, centering peptide binding (P1-P1') of the reaction site, and at P1 site there exist amino acid residues which fit the substance specificity of proteases which the inhibitors aim. Some reaction sites against cysteine proteases are known, for example, in the specification of WO99/54317, the followings are described;
P1 position against calpain I, II—norvaline, phenylalanine, etc.
P1 position against calpain I—arginine, lysine, tyrosine, valine, etc.
P1 position against papain—homophenylalanine, arginine, etc.
P1 position against cathepsin B—homophenylalanine, phenylalanine, tyrosine, etc.
P1 position against cathepsin S—valine, norleucine, phenylalanine, etc.
P1 position against cathepsin L—homophenylalanine, lysine, etc.
P1 position against cathepsin K—arginine, homophenylalanine, leucine, etc.
P1 position against caspase—aspartic acid, etc.

The followings are known to possess alpha amino acid-derived diketohydrazine skeletons.

EP1008592 discloses a compound of formula (A)

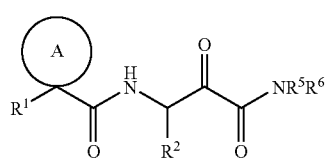

as cathepsin K inhibitor, wherein the following compound (CAS Reg. No. 274684-59-2)

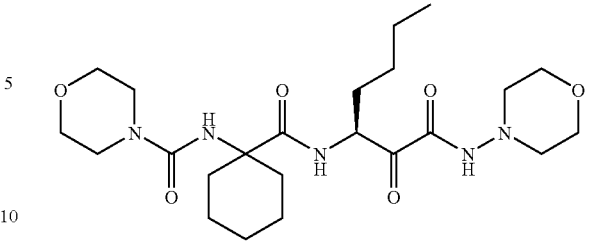

is disclosed specifically.

WO 99/17775 discloses a quinoline derivative of formula (B)

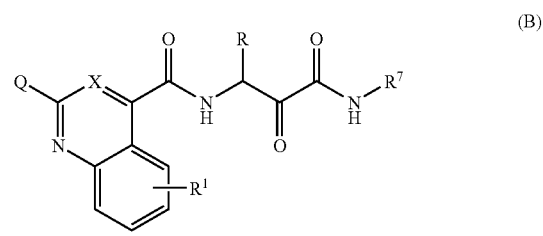

as cysteine protease and serine protease inhibitor, wherein the following compound (CAS Reg. No. 222959-79-7)

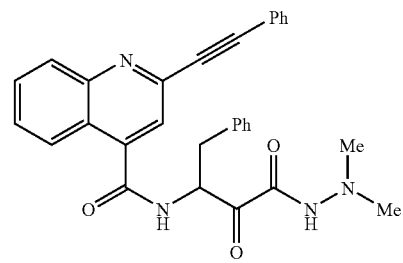

is disclosed.

U.S. Pat. No. 6,242,494 discloses a compound of formula (C)

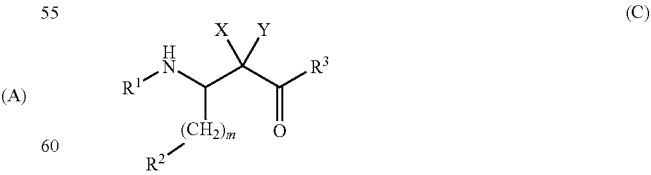

as methionine aminopeptidase-2 inhibitor.

Croatia Chemica Acta 1978, 51(1), 81-92 discloses that the following compound has anti-inflammatory activity.

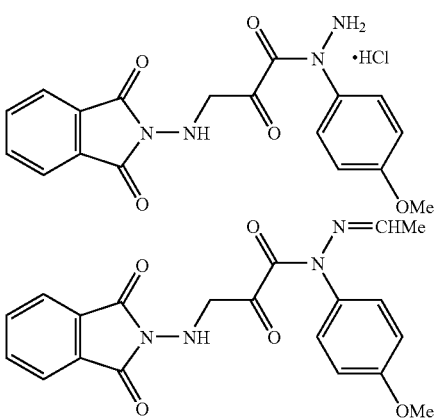

DISCLOSURE OF THE INVENTION

The present inventors have energetically investigated to find out such compounds having cysteine protease inhibitory activity, to find out that the diketohydrazine derivative of formula (I) accomplishes the purpose.

It was also confirmed that the compound of formula (I) has an inhibitory activity against serine proteases, represented by elastase.

That is, the present invention relates to
(1) a compound of formula (I)

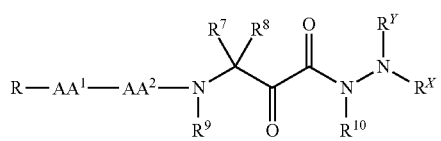

(I)

[wherein R is (1) hydrogen, (2) CycA, (3) C1-8 alkyl optionally substituted with 1 to 5 groups selected from halogen, CycA, nitro, trifluoromethyl and cyano,

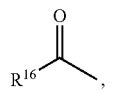 (4)

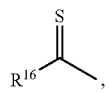 (5)

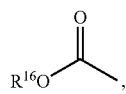 (6)

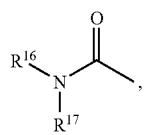 (7)

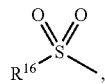 (8)

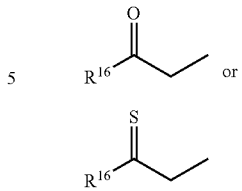 or (9)

(10)

(wherein CycA is a C3-15 mono-, bi- or tri-cyclic carboring or a 3-15 membered mono-, bi- or tri-cyclic heteroring comprising 1-4 of nitrogen, 1-2 of oxygen and/or 1-2 of sulfur;
$R^{16}$ is (1) C1-8 alkyl, (2) C2-8 alkenyl, (3) C2-8 alkynyl, (4) CycA or (5) C1-8 alkyl, C2-8 alkenyl or C2-8 alkynyl substituted with substituted with 1 to 5 groups selected from halogen, nitro, trifluoromethyl, cyano, CycA, —$NR^{18}R^{19}$, —$OR^{18}$, —$SR^{18}$, —NHC(O)-CycA and —NHC(O)—(C1-8 alkyl);
$R^{17}$, $R^{18}$ and $R^{19}$ are each independently, hydrogen, C1-4 alkyl, CycA, C1-4 alkyl substituted with CycA),
$AA^1$ is (1) a bond, or

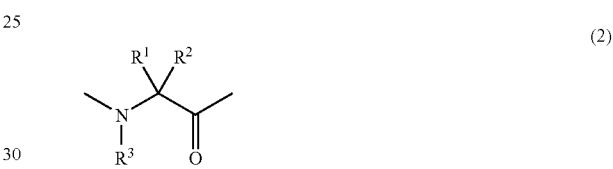

(2)

(wherein $R^1$ and $R^2$ are each independently, (i) hydrogen, (ii) C1-8 alkyl, (iii) CycA or (iv) C1-8 alkyl substituted with substituted with 1 to 5 groups selected from the following (a) to (j):
(a) —$NR^{21}R^{22}$, (b) —$OR^{23}$, (c) —$SR^{23}$, (d) —$COR^{24}$, (e) —$NR^{25}C(O)NR^{21}R^{22}$, (f) guanidino, (g) amidino, (h) CycA, (j) —$NR^{25}SO_2R^{21}$; or
$R^1$ and $R^2$ are taken together to form C2-8 alkylene (wherein one carbon of the alkylene chain may be replaced by oxygen, sulfur or —$NR^{20}$— and the alkylene may be substituted with —$NR^{21}R^{22}$, —$OR^{23}$ or oxo),
(wherein $R^{20}$ is hydrogen, C1-4 alkyl, —C(O)O—(C1-4 alkyl), CycA or C1-4 alkyl substituted with CycA; $R^{21}$, $R^{22}$, $R^{23}$ and $R^{25}$ are each independently, hydrogen, C1-4 alkyl, CycA or C1-4 alkyl substituted with CycA; $R^{24}$ is C1-4 alkyl, CycA, —$NR^{21}R^{22}$, —$OR^{23}$, —$SR^{23}$ or C1-4 alkyl substituted with CycA),
$R^3$ is hydrogen, C1-8 alkyl, CycA or C1-8 alkyl substituted with CycA or
$R^3$ may be taken together with $R^1$ to form C2-6 alkylene (wherein one carbon of the alkylene chain may be replaced by oxygen, sulfur or —$NR^{20}$— and the alkylene may be substituted with —$NR^{21}R^{22}$, —$OR^{23}$, —$SR^{23}$ or oxo)) or
R and $AA^1$ may be taken together to form

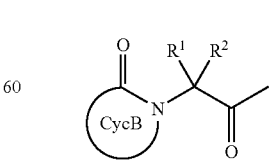

(wherein CycB is a 5-12 membered mono- or bi-cyclic heteroring and the other symbols have the same meaning as hereinbefore), AA² is (1) a bond,

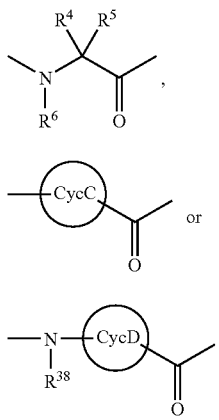

(wherein R⁴ and R⁵ are each independently, (i) hydrogen, (ii) C1-8 alkyl, (iii) CycA or (iv) C1-8 alkyl substituted with 1 to 5 groups selected from the following (a) to (h):
(a) —NR³¹R³², (b) —OR³³, (c) —SR³³, (d) —COR³⁴, (e) —NR³⁵C(O)NR³¹R³², (f) guanidino, (g) amidino, (h) CycA, (j) —NR³⁵SO₂R³¹; or
R⁴ and R⁵ may be taken together to form C2-8 alkylene (wherein one carbon of the alkylene chain may be replaced by oxygen, sulfur or —NR³⁰— and the alkylene may be substituted with —NR³¹R³², —OR³³, —SR³³ or oxo),
(wherein R³⁰ is hydrogen, C1-4 alkyl, —C(O)O—(C1-4 alkyl), CycA or C1-4 alkyl substituted with CycA; R³¹, R³², R³³ and R³⁵ are each independently, hydrogen, C1-4 alkyl, CycA or C1-4 alkyl substituted with CycA; R³⁴ is C1-4 alkyl, CycA, —NR³¹R³², —OR³³, —SR³³ or C1-4 alkyl substituted with CycA),
R⁶ is hydrogen, C1-8 alkyl, CycA or C1-8 alkyl substituted with CycA or
R⁶ may be taken together with R⁴ or R to form C2-6 alkylene (wherein one carbon of the alkylene chain may be replaced by oxygen, sulfur or —NR³⁰— and the alkylene may be substituted with NR³¹R³², OR³³, SR³³ or oxo),
R³⁸ is hydrogen, C1-4 alkyl, CycA or C1-4 alkyl substituted with CycA or when AA¹ is a bond, R³⁸ may be taken together with R to form C2-6 alkylene (wherein one carbon of the alkylene chain may be replaced by oxygen, sulfur or —NR³⁷— (wherein R³⁷ is hydrogen or C1-4 alkyl)),
CycC is a 3-17 membered mono- or bi-cyclic heteroring,
CycD is a C3-14 mono- or bi-cyclic carboring or a 3-14 membered mono- or bi-cyclic heteroring) or
AA² may be taken together with AA¹ to form

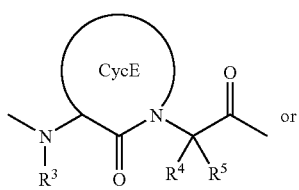

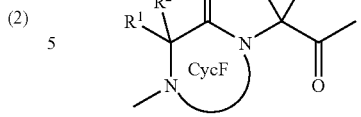

(wherein CycE is a 4-18 membered mono- or bi-cyclic heteroring, CycF is a 5-8 membered monocyclic heterocyclic, and the other symbols have the same meaning as hereinbefore),
R⁷ and R⁸ are each independently (1) hydrogen, (2) C1-8 alkyl, (3) CycA or (4) C1-8 alkyl substituted with 1 to 5 groups selected from the following (i)~(x);
(i) —NR⁴¹R⁴², (ii) —OR⁴³, (iii) —SR⁴³, (iv) —COR⁴⁴, (v) —NR⁴⁵C(O)NR⁴¹R⁴², (vi) guanidino, (vii) amidino, (viii) CycA, (ix) —NR⁴⁵SO₂R⁴¹, (x) —P(O)(OR⁴⁶)(OR⁴⁷), or R⁷ and R⁸ may be taken together to form C2-8 alkylene (wherein one carbon of the alkylene chain may be replaced by oxygen, sulfur or —NR⁴⁰— and the alkylene may be substituted with —NR⁴¹R⁴², —OR⁴³, —SR⁴³ or oxo),
R⁴⁰ is hydrogen, C1-4 alkyl, —C(O)O—(C1-4 alkyl), CycA or C1-4 alkyl substituted with CycA,
R⁴¹, R⁴², R⁴³ and R⁴⁵ are each independently hydrogen, C1-4 alkyl, CycA or C1-4 alkyl substituted with CycA, R⁴⁴ is C1-4 alkyl, CycA, —NR⁴¹R⁴², —OR⁴³, —SR⁴³ or C1-4 alkyl substituted with CycA,
R⁴⁶ and R⁴⁷ are each independently, hydrogen or C1-8 alkyl,
R⁹ is hydrogen, C1-8 alkyl, CycA or C1-8 alkyl substituted with CycA or
R⁹ may be taken together with R⁷ or R to form C2-6 alkylene (wherein one carbon of the alkylene chain may be replaced by oxygen, sulfur or —NR⁴⁰— and the alkylene may be substituted with —NR⁴¹R⁴², —OR⁴³, —SR⁴³ or oxo), (wherein all symbols have the same meaning as hereinbefore),

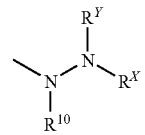

is a group selected from the following (1), (2) or (3);

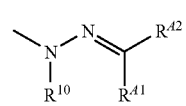

[wherein R^{A1} and R^{A2} are each independently, (i) hydrogen, (ii) C1-8 alkyl, (iii) C2-8 alkenyl, (iv) —NR^{Z1}R^{Z2}, (v) —OR^{Z3}, (vi) —SR^{Z3}, (vii) —COR^{Z4}, (viii) CycP or (ix) C1-8 alkyl or C2-8 alkenyl substituted with 1 to 5 groups selected from CycP, —NR^{Z1}R^{Z2}, —OR^{Z3}, —SR^{Z3}, —COR^{Z4}, —SO₂R^{Z4}, —COOR^{Z3}, —CONR^{Z1}R^{Z2}, —SO₂NR^{Z1}R^{Z2} and —P(O)(OR^{Z5})(OR^{Z6})
(wherein R^{Z1} and R^{Z2} are each independently, hydrogen, C1-8 alkyl, C2-8 alkenyl, CycP, C2-8 acyl, or C1-8 alkyl substituted with CycP, C2-8 acyl, C1-8 alkoxy, C1-8 alkylthio, C1-8 monoalkylamino or di(C1-8 alkyl)amino;
R^{Z3} is hydrogen, C1-8 alkyl, C2-8 alkenyl, CycP or C1-8 alkyl substituted with 1 to 5 groups selected from CycP, C1-8 alkoxy, C1-8 alkylthio, amino, C1-8 monoalkylamino, di(C1-8 alkyl)amino and C2-8 acyl;

$R^{Z4}$ is C1-8 alkyl, CycP or C1-8 alkyl substituted with 1 to 5 groups selected from CycP, C1-8 alkoxy, C1-8 alkylthio, mono(C1-8 alkyl)amino, di(C1-8 alkyl)amino or C2-8 acyl;

$R^{Z5}$ and $R^{Z6}$ are each independently, hydrogen or C1-8 alkyl,

CycP is a C4-10 carboring or 5-10 membered heteroring comprising 1-4 of nitrogen, 1-2 of oxygen and/or 1-2 of sulfur and $R^{10}$ has the same meaning as hereinbefore) or $R^{41}$ and $R^{42}$ may be taken together with the adjacent carbon to represent CycH

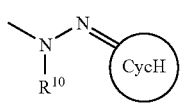

(wherein CycH is a C4-10 mono- or bi-cyclic carboring or 4-10 membered mono- or bi-cyclic heteroring and $R^{10}$ has the same meaning as hereinbefore) or $R^{41}$ and $R^{10}$ may be taken together with the adjacent carbon and nitrogen to represent

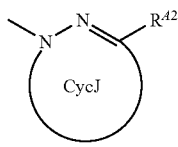

(wherein CycJ is a 5-10 membered mono- or bi-cyclic heteroring and $R^{42}$ has the same meaning as hereinbefore).],

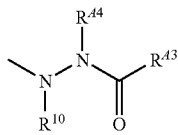
(2)

[wherein $R^{43}$ is (i) C1-8 alkyl, (ii) C2-8 alkenyl, (iii) —$NR^{Z1}R^{Z2}$, (ix) —$OR^{Z3}$, (v) —$SR^{Z3}$, (vi) —$COR^{Z4}$, (vii) CycP or C1-8 alkyl or C2-8 alkenyl substituted with 1 to 5 groups selected from —$NR^{Z1}R^{Z2}$, —$OR^{Z3}$, —$SR^{Z3}$, —$COR^{Z4}$, —$SO_2R^{Z4}$, CycP and —$P(O)(OR^{Z5})(OR^{Z6})$ (wherein all symbols have the same meaning as hereinbefore), $R^{44}$ is (i) hydrogen, (ii) C1-8 alkyl, (iii) C2-8 alkenyl, (iv) —$COR^{Z4}$, (v) CycP or (vi) C1-8 alkyl or C2-8 alkenyl substituted with 1 to 5 groups selected from CycP, $NR^{Z1}R^{Z2}$, —$OR^{Z3}$, —$SR^{Z3}$, —$COR^{Z4}$, —$SO_2R^{Z4}$, —$COOR^{Z3}$, —$CONR^{Z1}R^{Z2}$, —$SO_2NR^{Z1}R^{Z2}$ and —$P(O)(OR^{Z5})(OR^{Z6})$ (wherein all symbols have the same meaning as hereinbefore), $R^{10}$ has the same meaning as hereinbefore, or $R^{43}$ and $R^{44}$ may be taken together with the adjacent carbon and nitrogen to represent

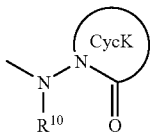

(wherein CycK is a 5-10 membered mono- or bi-cyclic heteroring and $R^{10}$ has the same meaning as hereinbefore), $R^{43}$ and $R^{10}$ may be taken together with the adjacent carbon and nitrogens to represent

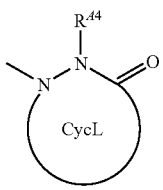

(wherein CycL is a 5-10 membered mono- or bi-cyclic heteroring and $R^{44}$ has the same meaning as hereinbefore)],

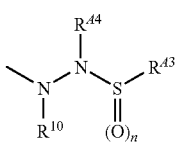
(3)

[wherein n is an integer of 1 or 2, and the other symbols have the same meaning as hereinbefore, and $R^{43}$ and $R^{44}$ may be taken together with the adjacent nitrogen and sulfur to represent

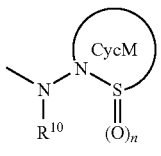

(wherein CycM is a 5-10 membered mono- or bi-cyclic heteroring and the other symbols have the same meaning as hereinbefore) or $R^{43}$ and $R^{10}$ may be taken together with the nitrogens and sulfur to represent

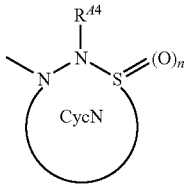

(wherein CycN is a 5-10 membered mono- or bi-cyclic heteroring and the other symbols have the same meaning as hereinbefore)], CycA's, CycB, CycC, CycD, CycE, CycF, CycH, CycJ, CycK, CycL, CycM, CycN and CycP may be each independently substituted with 1-5 of $R^{27}$, $R^{27}$ is (1) C1-8 alkyl, (2) halogen, (3) —$NR^{11}R^{12}$, (4) —$OR^{13}$, (5) —$SR^{13}$, (6) CycG, (7) nitro, (8) cyano, (9) oxo, (10) —$COR^{14}$, (11) —$SO_2R^{14}$, (12) —$P(O)(OR^{15})(OR^{16})$, (13) guanidino, (14) amidino or (15) C1-8 alkyl substituted with 1 to 5 groups selected from the following (i)-(xii):

(i) halogen, (ii) —$NR^{11}R^{12}$, (iii) —$OR^{13}$, (iv) —$SR^{13}$, (v) CycG, (vi) nitro, (vii) cyano, (viii) —$COR^{14}$, (ix) —$SO_2R^{14}$, (x) —$P(O)(OR^{15})(OR^{16})$, (xi) guanidino, (xii) amidino (wherein $R^{11}$ and $R^{12}$ are each independently, hydrogen, C1-4 alkyl, C1-4 alkoxy, —C(O)O—(C1-4 alkyl), CycG or C1-4 alkyl substituted with CycG, $R^{13}$ is hydrogen, C1-4 alkyl, trifluoromethyl, CycG or C1-4 alkyl substituted with CycG, CycG's are each independently, a C4-10 mono- or bi-cyclic carboring or a 5-10 membered mono- or bi-cyclic heteroring comprising 1-4 of nitrogen, 1-2 of oxygen and/or 1-2 of sulfur, $R^{14}$ is C1-8 alkyl, CycG, —$NR^{11}R^{12}$, —$OR^{13}$, —$SR^{13}$ or C1-8 alkyl substituted with CycG, —$NR^{11}R^{12}$, —$OR^{13}$ or —$SR^{13}$, $R^{15}$'s are each independently, hydrogen or C1-8 alkyl), when a saturated carbon atom exists in CycH, CycJ, CycK, CycL, CycM or CycN, the saturated carbon atom may form a Spiro bond with CycQ (wherein CycQ is a C3-10 saturated or partially unsaturated mono-cyclic carboring or a 5-8 membered saturated or partially unsaturated monocyclic heteroring comprising 1 of —$NR^Q$— (wherein $R^Q$ is C1-8 alkyl, C2-8 acyl, —$SO_2$—(C1-8 alkyl), benzoyl, benzenesulfonyl, or toluenesulfonyl), 1 of oxygen and/or 1 of sulfur which may be oxidized)] or a pharmaceutically acceptable salt thereof.

(2) a pharmaceutical composition comprising it as active ingredient, and (3) a method for the preparation thereof.

More specifically, the present invention relates to a compound of formula (I-i)

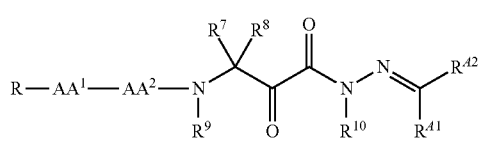

(I-i)

(wherein all symbols have the same meaning as described hereinbefore) or a pharmaceutically acceptable salt thereof, a compound of formula (I-ii)

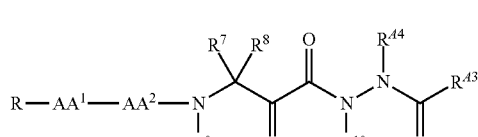

(I-ii)

(wherein all symbols have the same meaning as described hereinbefore) or a pharmaceutically acceptable salt thereof, a compound of formula (I-iii)

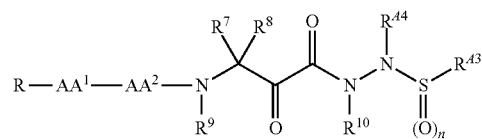

(I-iii)

(wherein all symbols have the same meaning as described hereinbefore) or a pharmaceutically acceptable salt thereof.

In the compound of formula (I), CycB is a 5-12 membered heteroring comprising 1 of nitrogen and 1 of oxo and optionally further comprising 1-2 of nitrogen, 1 of oxygen and/or 1 of sulfur.

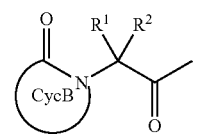

which R and $AA^1$ are taken together to form is specifically,

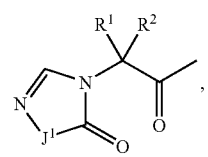

(i)

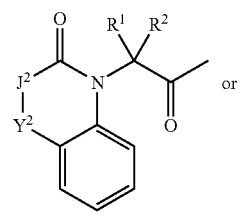

(ii)

or

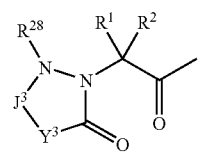

(iii)

(wherein $J^1$ is oxygen, sulfur, —$NR^{29}$— (wherein $R^{29}$ is hydrogen, C1-4alkyl, CycA, or C1-4 alkyl substituted with CycA), C1-3 alkylene, or C2-3 alkenylene, $J^2$ is a bond or C1-2 alkylene, $Y^2$ is —N=CH—, —CH=N—, or C1-2 alkylene, $J^3$ is carbonyl or C1-3 alkylene, $Y^3$ is C1-3 alkylene, oxygen, or —$NR^{29}$— (wherein $R^{29}$ has the same meaning as described hereinbefore), $R^{28}$ is hydrogen, C1-4 alkyl, CycA, or C1-4 alkyl substituted with CycA, or $R^{28}$ and $R^1$ may be taken together to form C2-4 alkylene, the other symbols have the same meaning as described hereinbefore, each ring may be substituted with 1-5 of $R^{27}$).

CycC is a 3-17 membered heteroring comprising 1-2 of nitrogen, 1 of oxygen and/or 1 of sulfur.

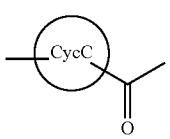

is specifically

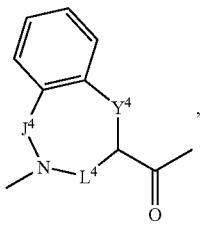
(iii-1)

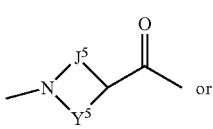
(iii-2) or

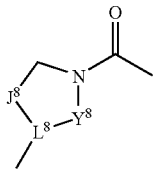
(iii-3)

(wherein $J^4$, $Y^4$, $L^4$ are each independently, a bond or C1-3 alkylene (wherein $J^4$, $Y^4$ and $L^4$ are not a bond at the same time), $J^5$ is C1-6 alkylene, $Y^5$ is bond, C1-3 alkylene, or —$NR^{67}$— (wherein $R^{67}$ is hydrogen, C1-4 alkyl, phenyl, or C1-4 alkyl substituted with phenyl), $J^8$ is C1-5 alkylene (wherein one carbon may be replaced by oxygen), $Y^8$ is a bond or C1-4 alkylene, $L^8$ is —N— or —CH— and the other symbols have the same meaning as described hereinbefore).

CycD is a C3-14 mono- or bi-cyclic carboring, or 3-14 membered heteroring comprising 1-2 of nitrogen, 1 of oxygen and/or 1 of sulfur.

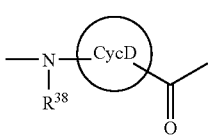

is specfically

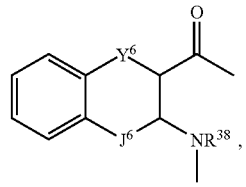
(iv-1)

(iv-2)

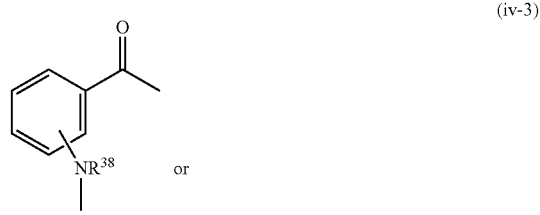
(iv-3) or

(iv-4)

(wherein $J^6$ and $Y^6$ are each independently, a bond or C1-3 alkylene (with proviso that $J^6$ and $Y^6$ are not a bond at the same time), $J^7$ is C1-6 alkylene (wherein one carbon may be replaced by oxygen, sulfur, or —$NR^{67}$— (wherein $R^{67}$ has the same meaning as described hereinbefore), $J^9$ is C1-3 alkylene, oxygen, sulfur, or —$NR^{67}$— (wherein $R^{67}$ has the same meaning as described hereinbefore) and, the other symbols have the same meaning as described hereinbefore).

CycE is a 4-18 membered heteroring comprising 1 of nitrogen and 1 of oxo and optionally further comprising 1 of nitrogen, 1 of oxygen and/or 1 of —$S(O)_p$— (wherein p is 0 or an integer of 1-2).

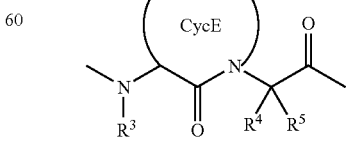

is specifically,

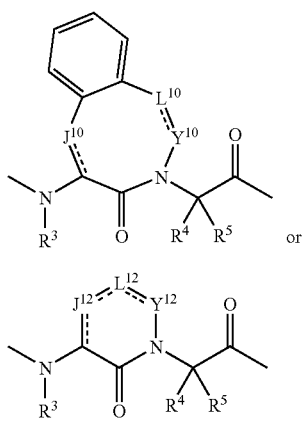

(wherein ════ is a bond or a double bond,
$J^{10}$ and $Y^{10}$ are each independently, a bond or C1-3 alkylene, $L^{10}$ is a bond, C1-3 alkylene, —NR$^{57}$— (wherein R$^{57}$ is hydrogen, C1-4 alkyl, phenyl, or C1-4 alkyl substituted with phenyl), —N═, oxygen, or —S(O)$_p$— (wherein p is 0 or an integer of 1-2),
$J^{12}$ and $Y^{12}$ are each independently, a bond or C1-3 alkylene, $L^{12}$ is C1-3 alkylene, —NR$^{57}$— (wherein R$^{57}$ has the same meaning as described hereinbefore), —N═, ═N—, oxygen, or —S(O)$_p$— (wherein p has the same meaning as described hereinbefore),
the other symbols have the same meaning as described hereinbefore).

CycF is a 5-8 membered mono-cyclic heteroring comprising 2 of nitrogen and 1 of oxo and optionally further comprising 1-2 of nitrogen, 1-2 of oxygen and/or 1 of sulfur.

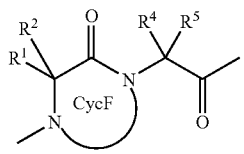

is specifically,

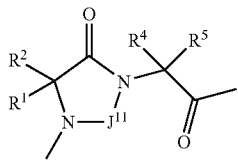

(wherein $J^{11}$ is carbonyl or C2-4 alkylene, and the other symbols have the same meaning as described hereinbefore).

The C4-10 mono- or bi-cyclic carboring which CycH represents is a C4-10 mono- or bi-cyclic carboaryl or partially or completely saturated one thereof, and the 4-10 membered heteroring which CycH represents is a 4-10 membered mono- or bi-cyclic heteroaryl comprising 1-3 of atom selected from nitrogen, oxygen and sulfur or partially or completely saturated one thereof.

The 5-10 membered mono- or bi-cyclic heteroring which CycJ represents is a 5-10 membered mono- or bi-cyclic heteroring comprising 2 of nitrogen and 1 of double bond and optionally further comprising 1-3 of atom selected from nitrogen, oxygen and sulfur.

The 5-10 membered mono- or bi-cyclic heteroring which CycK represents is a 5-10 membered mono- or bi-cyclic heteroaryl comprising 1 of nitrogen and 1 of carbonyl and optionally further comprising 1-3 of atom selected from nitrogen, oxygen or sulfur, or partially or completely saturated one thereof.

The 5-10 membered mono- or bi-cyclic heteroring which CycL represents is a 5-10 membered mono- or bi-cyclic heteroaryl comprising 2 of nitrogen and 1 of carbonyl and optionally further comprising 1-3 of atom selected from nitrogen, oxygen and sulfur or a partially or completely saturated one thereof.

The 5-10 membered mono- or bi-cyclic heteroring which CycM represents is a 5-10 membered mono- or bi-cyclic heteroaryl comprising 1 of nitrogen and 1 of oxidized sulfur, and optionally further comprising 1-3 of atom selected from nitrogen, oxygen and sulfur or partially or completely saturated one thereof.

The 5-10 membered mono- or bi-cyclic heteroring which CycN represents is a 5-10 membered mono- or bi-cyclic heteroaryl comprising 2 of nitrogen and 1 of optionally oxidized sulfur and optionally further comprising 1-3 of atom selected from nitrogen, oxygen and sulfur or partially or completely saturated one thereof.

In the present specification,

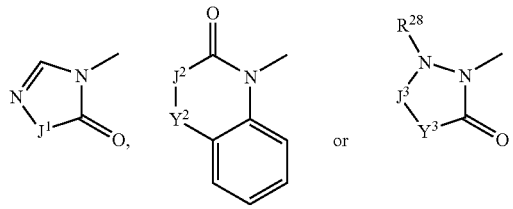

which CycB represents is specifically, 2-oxo-1,3,4-triazoline, 5-oxo-1,2,4-oxadiazoline, 5-oxo-1,2,4-thiadiazoline, 4-oxoimidazoline, 3,4-dihydro-4-oxopyrimidine, 3,4,5,6-tetrahydro-4-oxopyrimidine, 2-oxoindoline, 2-oxo-tetrahydroquinoline, 1,2-dihydro-2-oxoquinazoline, 1,2-dihydro-2-oxoquinoxaline, 3-oxopyrazolidine, perhydro-3-oxopyridazine, 2-oxo-1,3,4-oxadiazolidine, perhydro-2-oxo-1,3,4-oxadiazine, etc.

In the present specification, the 3-17 membered mono- or bicyclic heteroring, i.e.

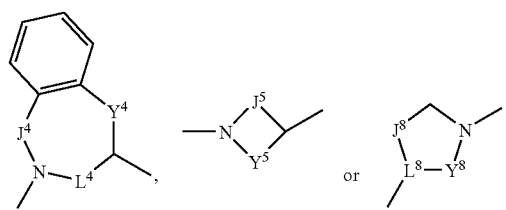

which CycC represents is specifically, pyrrolidine, imidazolidine, pyrazolidine, piperidine, piperazine, perhydropyrimidine, perhydropyridazine, thiazolidine, indoline, isoindoline, tetrahydroquinoline, tetrahydroisoquinoline, etc.

In the present specification,

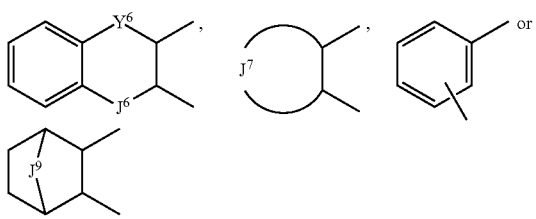

which CycD represents is specifically, cyclopentane, cyclohexane, cycloheptane, benzene, indan, tetrahydronaphthalene, oxolane, oxane, thiolane, thiane, pyrrolidine, piperidine, bicyclo[2.2.1]heptane, bicyclo[2.2.2]octane, 7-azabicyclo[2.2.1]heptane, 7-oxobicyclo[2.2.1]heptane, 7-thiabicyclo[2.2.1]heptane, etc.

In the present specification,

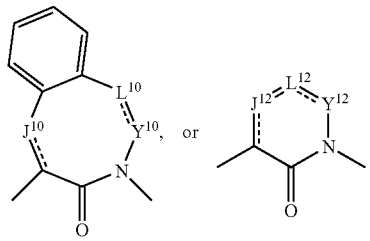

which CycE represents is specifically, 2-oxopyrrolidine, 2-oxopiperidine, 2-oxoperhydroazepine, 2-oxopiperazine, 3-oxomorpholine, 1,1,-dioxo-3-iso thiazolidine, 1,1-dioxo-3-isothiazine, 4-oxodiazepine, 2-oxoindoline, 2-oxo-tetra hydroquinoline, 1,1-dioxo-3-benzisothiazolidine, 1,1-dioxo-3-benzisothiazine, etc.

In the present specification,

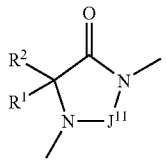

which CycF represents is 2,4-dioxoimidazolidine, 2-oxopiperazine, 2-oxoperhydrodiazepine, etc. substituted with $R^1$ and $R^2$.

CycH is a C4-10 mono- or bi-cyclic carboring or 4-10 membered mono- or bi-cyclic heteroring comprising 1-3 of nitrogen, 1-2 of oxygen and/or 1-2 of optionally oxidized sulfur.

The C4-10 mono- or bi-cyclic carboring which CycH represents is specifically, cyclobutane, cyclopentane, cyclohexane, cycloheptane, cyclooctane, cyclononane, cyclodecane, cyclopentene, cyclohexene, cycloheptene, cyclooctene, cyclononene, cyclodecene, bicyclo[4.4.0]decane, bicyclo[4.3.0]nonane, bicyclo[3.3.1]nonane, bicyclo[3.3.0]octane, bicyclo[2.2.2]octane, bicyclo[3.2.1]octane, indan, dihydronaphthalene, tetrahydronaphthalene, etc.

The 4-10 membered mono- or bi-cyclic heteroring comprising 1-3 of nitrogen, 1-2 of oxygen and/or 1-2 of optionally oxidized sulfur which CycH represents is specifically

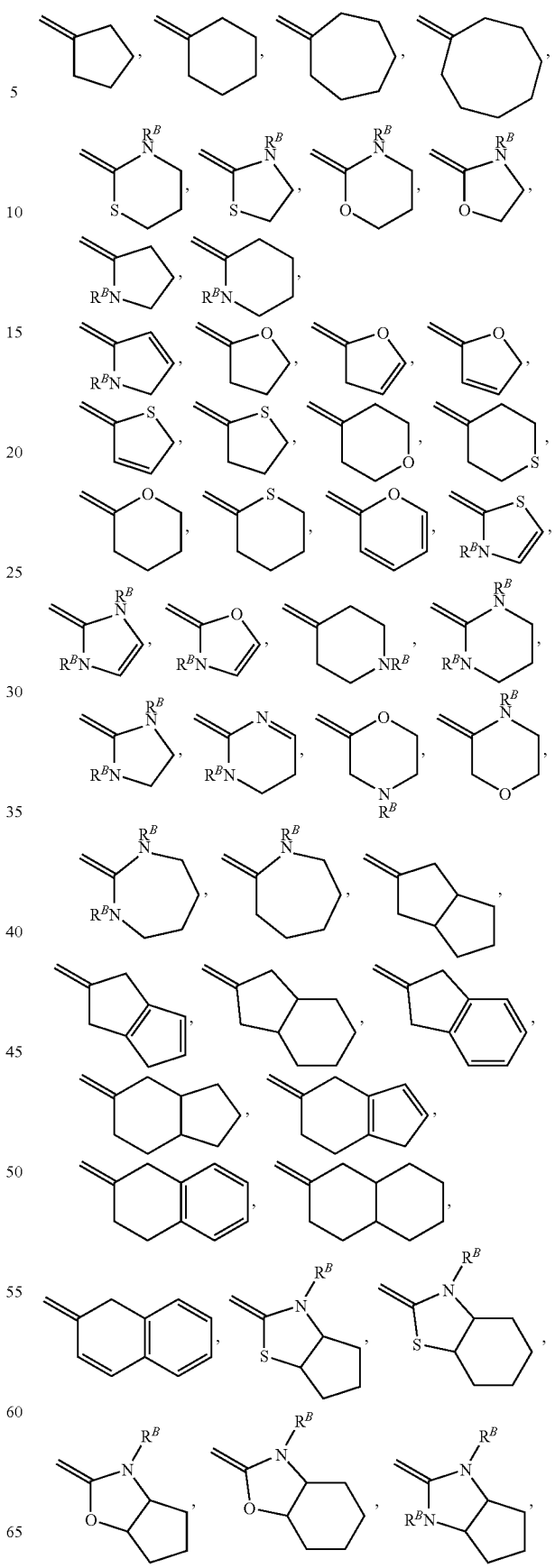

-continued

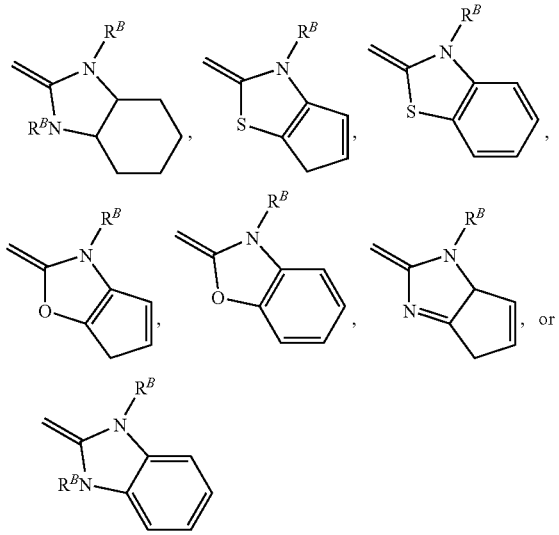

(wherein $R^B$ is C1-8 alkyl, C2-8 alkenyl, C2-8 acyl, —SO$_2$(C1-8 alkyl), —(C1-8 alkyl)-O—(C1-8 alkyl), or C1-8 alkyl substituted with CycG, C2-8 acyl, carboxy, —C(O)O(C1-8 alkyl), cyano, amino, mono(C1-8 alkyl)amino, di(C1-8 alkyl)amino or hydroxy).

The 5-8 membered mono-cyclic heteroring comprising 2 of nitrogen and optionally further comprising 1 of nitrogen, 1 of oxygen and/or 1 of optionally oxidized sulfur which CycJ represents is specifically,

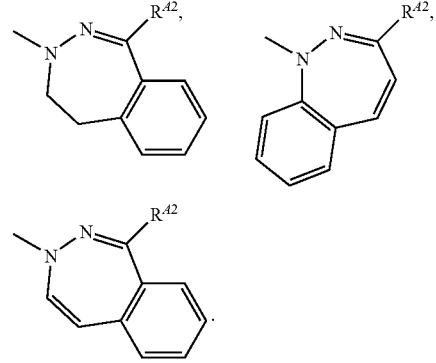

The 5-10 membered mono- or bi-cyclic heteroring comprising 1 of nitrogen and 1 of oxo and optionally further comprising 1-3 of atom selected from nitrogen, oxygen or sulfur which CycK represents is specifically,

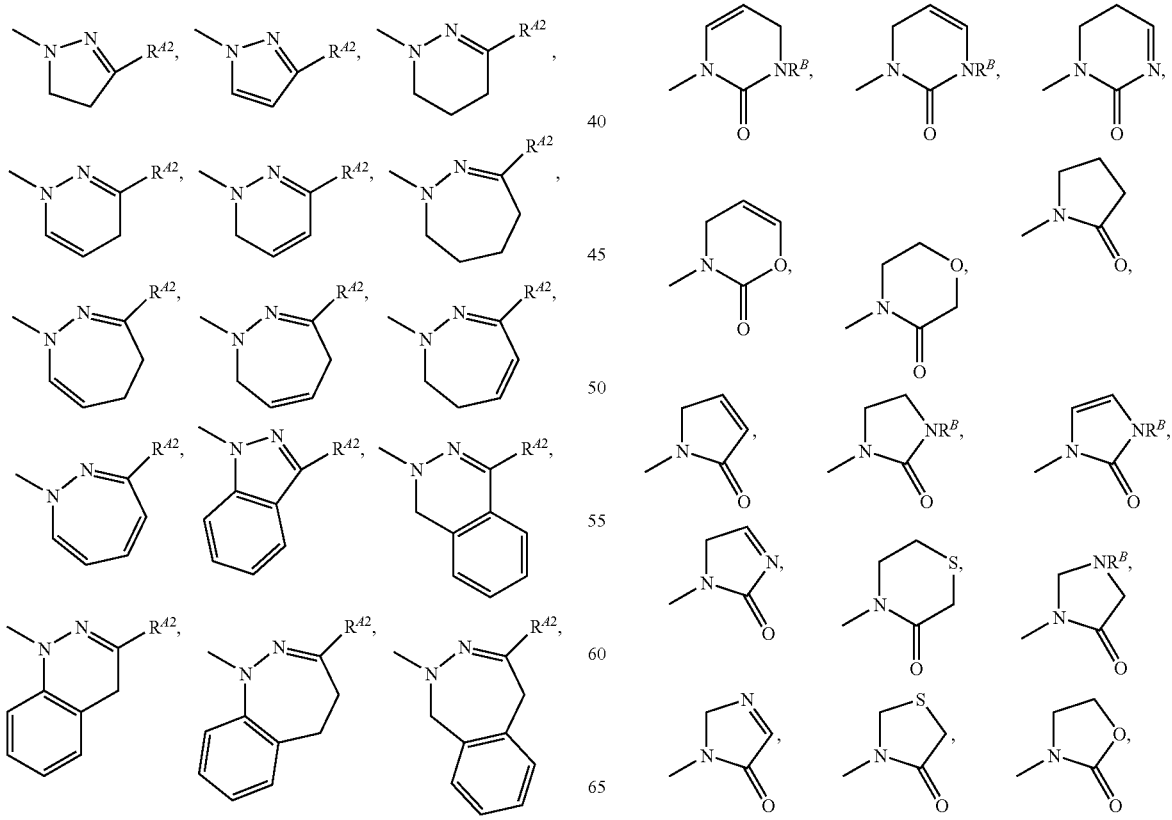

-continued
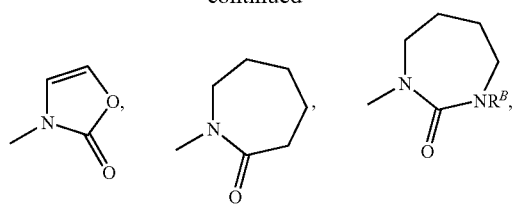
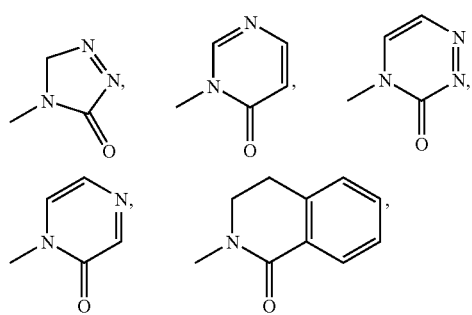
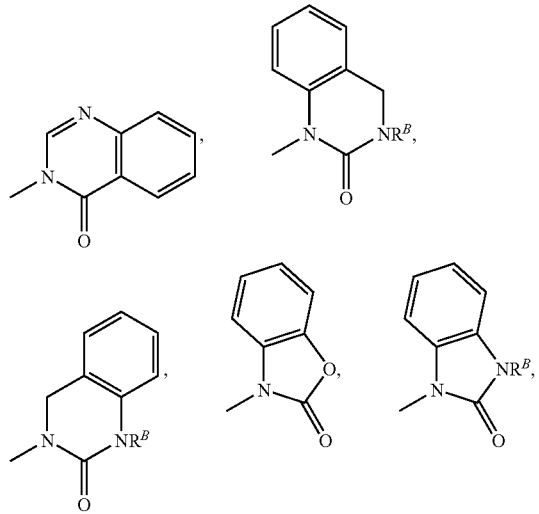
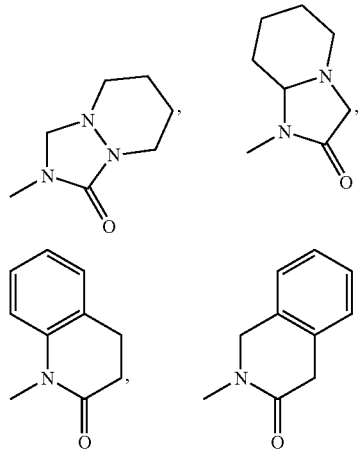
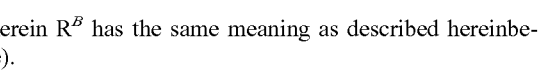
(wherein $R^B$ has the same meaning as described hereinbefore).
The 5-10 membered mono- or bi-cyclic heteroring comprising 2 of nitrogen and 1 of oxo and optionally further comprising 1-3 of atom selected from nitrogen, oxygen or sulfur which CycL represents is specifically
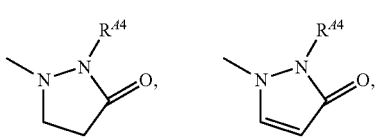
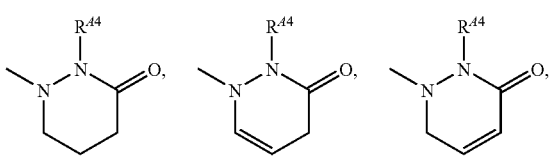
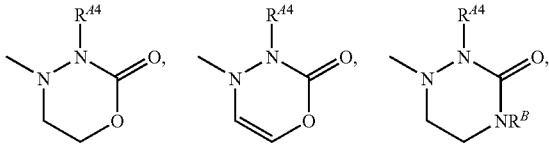
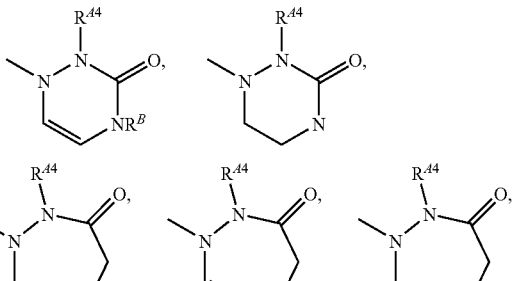
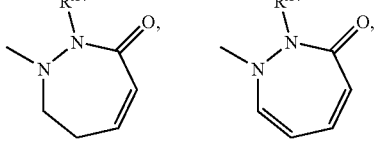
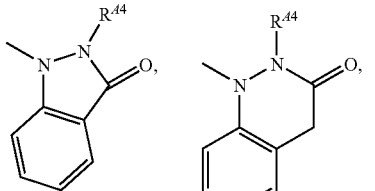
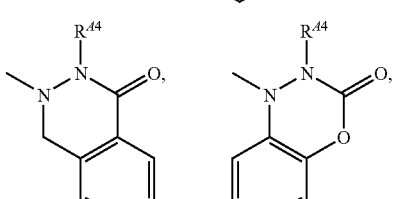
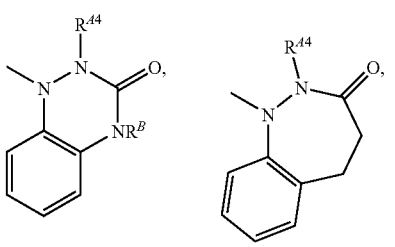

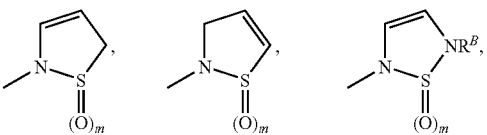
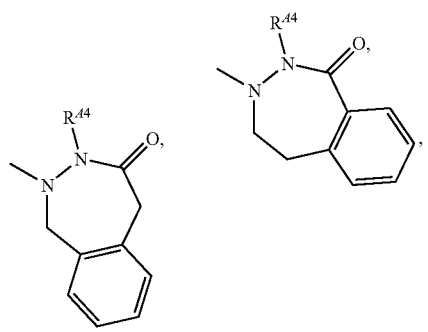
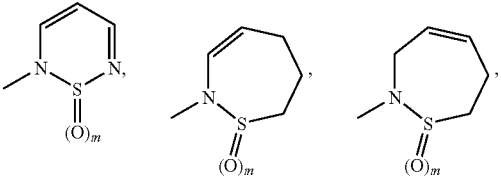
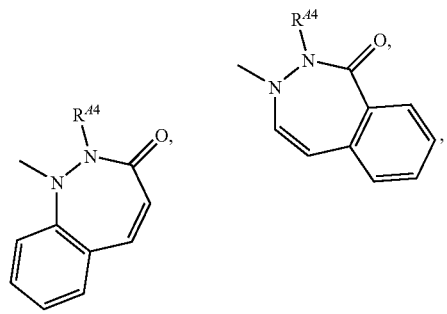
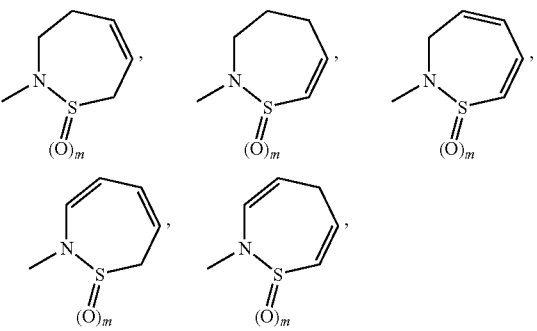
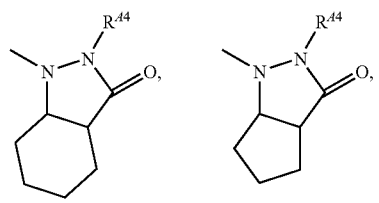
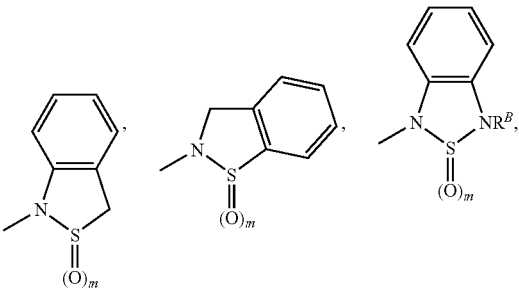
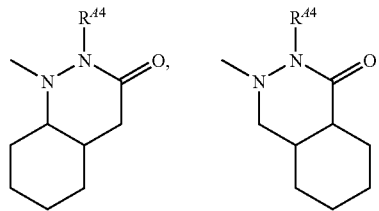
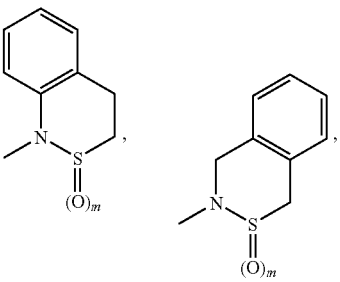
(wherein all symbols have the same meaning as described hereinbefore).
The 5-10 membered mono- or bi-cyclic heteroring comprising 1 of nitrogen and 1 of oxidized sulfur and optionally further comprising 1-3 of atom selected from nitrogen, oxygen or sulfur which CycM represents is specifically,
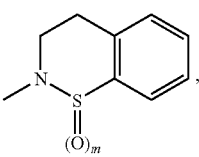
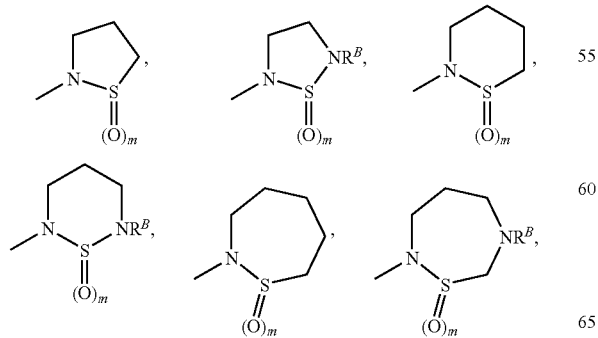
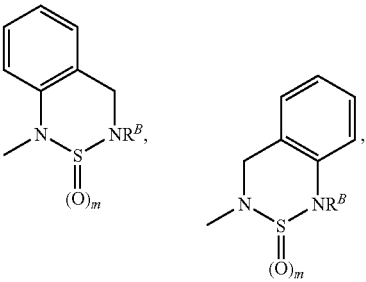

-continued

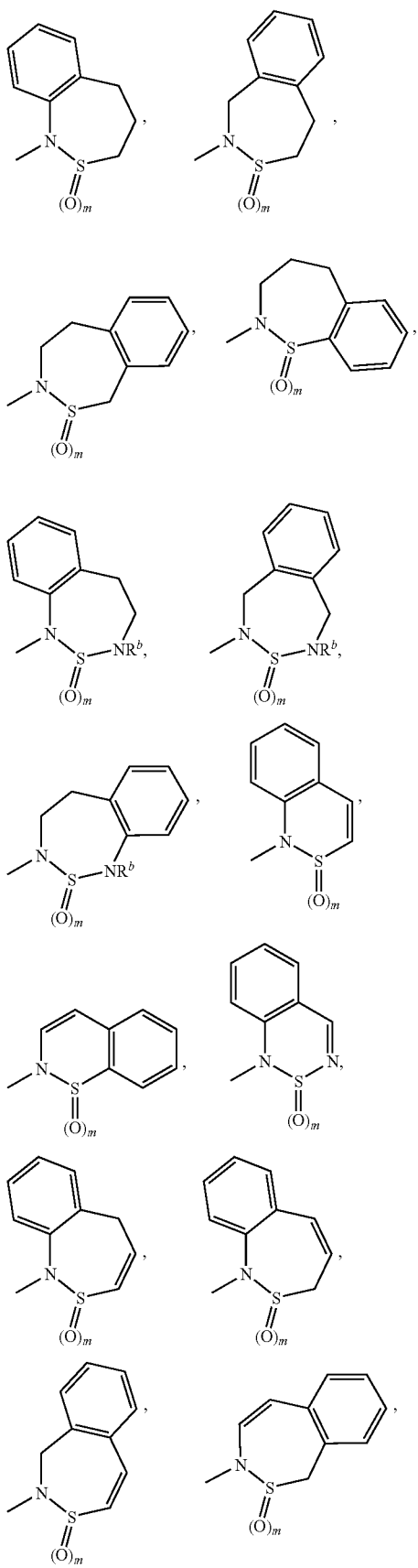

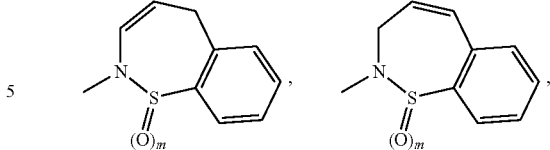

(wherein all symbols have the same meaning as described hereinbefore).

The 5-10 membered mono- or bi-cyclic heteroring having 2 of nitrogen and 1 of oxidized sulfur and optionally further comprising 1-3 of atom selected from nitrogen, oxygen or sulfur which CycN represents is specifically,

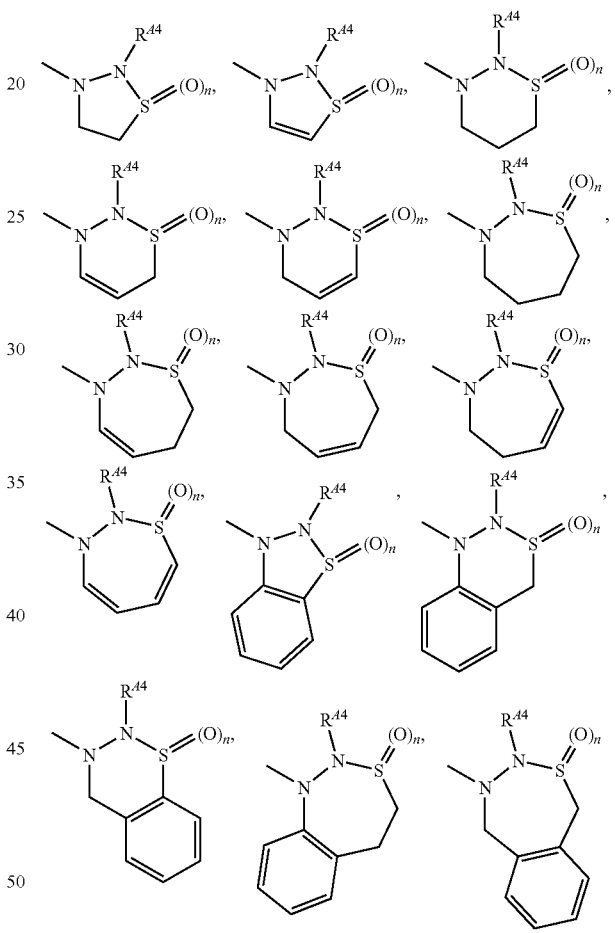

(wherein all symbols have the same meaning as described hereinbefore), etc.

CycQ includes, for example, cyclopropyl, cyclobutyl, cyclohexyl, cycloheptyl, pyrrolidine, piperidine, perhydroazepine, perhydroazocine, tetrahydrofuran, tetrahydropyran, tetrahydrothiophene, tetrahydrothiin, tetrahydrothiin-S-dioxide, etc.

In the present specification, C1-4 alkyl is methyl, ethyl, propyl, butyl and isomers thereof.

In the present specification, C1-8 alkyl is methyl, ethyl, propyl, butyl, pentyl, hexyl, heptyl, octyl and isomers thereof.

In the present specification, C1-4 alkoxy is methoxy, ethoxy, propoxy, butoxy and isomers thereof.

In the present specification, C1-8 alkoxy is methoxy, ethoxy, propoxy, butoxy, pentyloxy, hexyloxy, heptyloxy, octyloxy and isomers thereof.

In the present specification, C2-8 alkenyl is ethyl, propyl, butyl, pentyl, hexyl, heptyl, octyl having 1-3 of double bond and isomers thereof, for example, vinyl, propenyl, butenyl, hexenyl, hexadienyl, octadienyl, etc.

In the present specification, C2-8 alkynyl includes ethyl, propyl, butyl, pentyl, hexyl, heptyl, octyl having 1-3 of triple bond and isomers thereof. For example, ethynyl, propynyl, butynyl, pentynyl, hexynyl, heptynyl, octynyl, etc.

In the present specification, C1-4 alkyl substituted with phenyl is phenylmethyl, phenylethyl, phenylpropyl, phenylbutyl and isomers thereof.

In the present specification, C1-2 alkylene is methylene, ethylene and isomers thereof.

In the present specification, C1-3 alkylene is, methylene, ethylene, trimethylene and isomers thereof.

In the present specification, C1-4 alkylene is, methylene, ethylene, trimethylene, tetramethylene and isomers thereof.

In the present specification, C1-5 alkylene is, methylene, ethylene, trimethylene, tetramethylene, pentamethylene and isomers thereof.

In the present specification, C1-6 alkylene is, methylene, ethylene, trimethylene, tetramethylene, pentamethylene, hexamethylene and isomers thereof.

In the present specification, C2-4 alkylene is, ethylene, trimethylene, tetramethylene and isomers thereof.

In the present specification, C2-6 alkylene is, ethylene, trimethylene, tetramethylene, pentamethylene, hexamethylene and isomers thereof.

In the present specification, C2-8 alkylene is ethylene, trimethylene, tetramethylene, pentamethylene, hexamethylene, heptamethylene, octamethylene and isomers thereof.

In the present specification, C1-8 monoalkylamino is amino group having one C1-8 alkyl as a substituent, for example, methylamino, ethylamino, propylamino, butylamino, pentylamino, hexylamino, heptylamino, octylamino and isomers thereof.

In the present specification, di(C1-8 alkyl)amino is amino group to which two C1-8 alkyls (they are the same or different) are attached, for example, dimethylamino, diethylamino, dipropylamino, dibutylamino, dipentylamino, dihexylamino, diheptylamino, dioctylamino, ethyl methylamino, methylpropylamino, ethylpropylamino, hexylmethylamino, etc and isomers thereof.

In the present invention, C2-6 alkylene wherein one carbon may be replaced by oxygen, sulfur or —$NR^{20}$—, —$NR^{40}$— or —$NR^{60}$— is, ethylene, trimethylene, tetramethylene, pentamethylene, hexamethylene and one carbon of these isomers are replaced by oxygen, sulfur, —$NR^{20}$—, —$NR^{40}$— or —$NR^{60}$—, for example, —$CH_2$—O—$CH_2$—, —$CH_2$—$CH_2$—O—$CH_2$—, —$CH_2$—$CH_2$—S—$CH_2$—, —$CH_2$—$CH_2$—NH—$CH_2$—, —$CH_2$—$CH_2$—O—$CH_2CH_2$—, —$CH_2$—$CH_2$—S—$CH_2$—$CH_2$—, —$CH_2$—$CH_2$—NH—$CH_2$—$CH_2$—, —$CH_2$—$CH_2$—N(CH_3)—$CH_2$—$CH_2$—, etc.

In the present invention, C2-8 alkylene wherein one carbon may be replaced by oxygen, sulfur, —$NR^{20}$—, —$NR^{40}$— or —$NR^{60}$— is, ethylene, trimethylene, tetramethylene, pentamethylene, hexamethylene, heptamethylene, octamethylene and isomers thereof and one carbon thereof is replaced by oxygen, sulfur, —$NR^{20}$—, —$NR^{40}$— or —$NR^{60}$—, for example, —$CH_2$—O—$CH_2$—, —$CH_2$—$CH_2$—O—$CH_2$—, —$CH_2$—$CH_2$—S—$CH_2$—, —$CH_2$—$CH_2$—NH—$CH_2$—, —$CH_2$—$CH_2$—O—$CH_2$—$CH_2$—, —$CH_2$—$CH_2$—S—$CH_2$—$CH_2$—, —$CH_2$—$CH_2$—NH—$CH_2$—$CH_2$—, —$CH_2$—$CH_2$—N(CH_3)—$CH_2$—$CH_2$—, etc.

In the present specification, C2-3 alkenylene is vinylene, allylene and isomers thereof.

In the present specification, halogen is chlorine, fluorine, bromine and iodine.

C3-15 mono-, bi- or tri-cyclic carboring which CycA represents includes C3-15 mono-, bi- or tri-cyclic carboaryl and partially or completely saturated one thereof, for example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantan ring, etc.

3-15 membered heteroring comprising 1-4 of nitrogen, 1-2 of oxygen and/or 1 of sulfur which CycA represents includes 3-15 membered heteroaryl comprising 1-4 of nitrogen, 1-2 of oxygen and/or 1 of sulfur and partially or completely saturated one thereof.

Above 3-15 membered heteroaryl comprising 1-4 of nitrogen, 1-2 of oxygen and/or 1 of sulfur includes, for example, pyrrole, imidazole, triazole, tetrazole, pyrazole, pyridine, pyrazine, pyrimidine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzoxadiazole, benzothiazole, benzoimidazole, carbazole, acridine ring, etc.

Partially or completely saturated 5-15 membered heteroaryl comprising 1-4 of nitrogen, 1-2 of oxygen and/or 1 of sulfur includes, for example, aziridine, oxyrane, azetidine, oxetane, thiirane, thietane, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydropyran, tetrahydrofuran, dihydropyran, tetrahydropyran, dihydrothiophene, tetrahydrothiophene, dihydrothiain (dihydrothiopyran), tetrahydrothiain (tetrahydrothiopyran), oxazoline (dihydroxazole), oxazolidine (tetrahydroxazole), dihydroisoxazole, tetrahydroisoxazole, oxadiazoline (dihydrooxadiazole), oxadiazolidine (tetrahydrooxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydro quinazoline, perhydroquinazoline, dihydrocinnoline, tetrahydrocinnoline, perhydro cinnoline, dihydrobenzoxazole, perhydrobenzoxazole, dihydrobenzothiazole, perhydrobenzothiazole, dihydrobenzimidazole, perhydrobenzoimidazole, benzoxazepine, benzoxadiazepine, benzothiazepine, benzothiadiazepine, benzoazepine, benzodiazepine, indoloxoazepine, indolotetrahydroxazepine, indoloxadiazepine, indolotetrahydroxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolan, dioxane, dioxazine ring, etc.

C4-10 carboring which CycG and CycP represent includes, mono- or bi-cyclic C4-10 carboring, i.e. mono- or bi-cyclic C5-10 carboaryl or partially or completely saturated one thereof, for example, cyclobutane, cyclopentane, cyclohexane, cycloheptane, cyclopentene, cyclohexene, cyclopentadiene, cyclohexadiene, benzene, pentalene, indene, naphthalene, azulene, perhydropentalene, perhydroindene, perhydronaphthalene, perhydroazulene, adamantly ring, etc.

5-10 membered heteroring comprising 1-4 of nitrogen, 1-2 of oxygen and/or 1 of sulfur which CycG and CycP represent includes, mono- or bi-cyclic 5-10 membered heteroring comprising 1-4 of nitrogen, 1 of oxygen and 1 of sulfur, i.e. 5-10 membered mono- or bi-cyclic heteroaryl comprising 1-4 of nitrogen, 1 of oxygen and/or 1 of sulfur and partially or completely saturated one thereof.

Above 5-10 membered heteroaryl comprising 1-4 of nitrogen, 1-2 of oxygen and/or 1 of sulfur includes, pyrrole, imidazole, triazole, tetrazole, pyrazole, pyridine, pyrazine, pyrimidine, pyridazine, azepine, diazepine, furan, pyran, oxepin, thiophene, thiain (thiopyran), thiepin, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzoimidazole ring, etc.

Above partially or completely saturated 5-10 membered mono- or bi-cyclic heteroaryl comprising 1-4 of nitrogen, 102 of oxygen and/or 1 of sulfur includes, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzoimidazole, perhydrobenzoimidazole, etc.

The C3-8 carboring which CycQ represents is cyclopropyl, cyclobutane, cyclopentane, cyclohexane, cycloheptane, cyclooctane, cyclopentene, cyclohexene, cycloheptene, cyclooctene, cyclohexadiene, cycloheptadiene, cyclooctadiene, etc.

The 5-8 membered heteroring which CycQ represents includes, pyrrolidine, piperidine, perhydroazepine, perhydroazocine, tetrahydrofuran, tetrahydropyran, oxepin, oxocan, thiolan, tetrahydrothiophene, thian, thiepan, thiocan, dihydropyrrole, dihydropyridine, dihydroazepine, dihydroazocine, dihydrofuran, dihydropyran, dihydrothiophene, etc.

In the present invention, as may be easily understood by those skilled in the art, the symbol:

indicates that the substituent attached thereto is in front of the sheet (β-position) unless specified, ⁓ indicates that the substituent attached thereto is behind the sheet (α-position) unless specified, and ⁓ indicates that the substituent attached thereto is in β-position or α-position or a mixture thereof.

In the formula (I), R is all preferable, and more preferably, (i) hydrogen, (ii) C1-8 alkyl, (iii) CycA, (iv) C1-8 alkyl substituted with CycA or nitro,

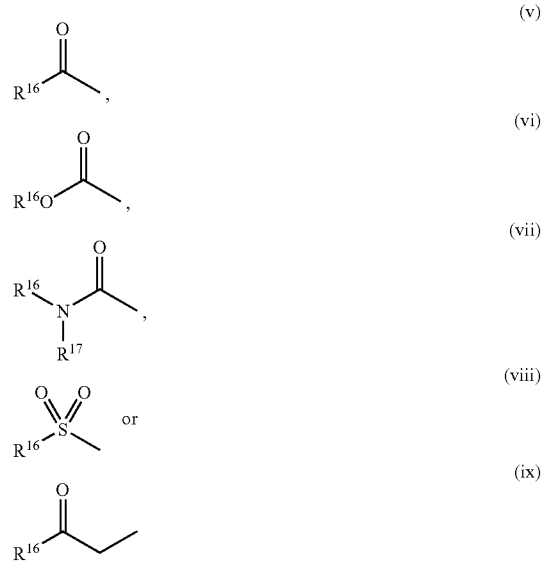

further preferably hydrogen, C1-8 alkyl, CycA, C1-8 alkyl substituted with CycA, nitro,

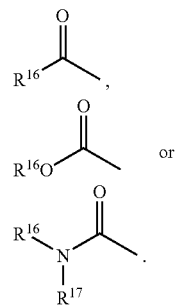

$R^{16}$ is all preferable, and more preferably

[I] (1) C1-8 alkyl, (2) C2-8 alkenyl, (3) C2-8 alkynyl, (4) CycA, (5) C1-8 alkyl substituted with 1-5 of group selected from halogen, CycA, —NHC(O)-CycA or —NHC(O)—(C1-8alkoxy), (6) C2-8 alkenyl substituted with CycA, or (7) C2-8 alkynyl substituted with CycA,
wherein CycA may be substituted with 1-5 of $R^{27a}$,
$R^{27a}$ is (1) C1-8 alkyl, (2) halogen, (3) —$NR^{11}R^{12}$, (4) —$OR^{13}$, (5) phenyl, (6) nitro, (7) cyano, (8) tetrazole, (9) —$SR^{13}$, (10) —$COR^{14}$, (11) oxo, or (12) C1-8 alkyl substituted with 1-5 of group selected from the following (a)-(k):
(a) halogen, (b) —$NR^{11}R^{12}$, (c) —$OR^{13}$, (d) phenyl, (e) nitro, (f) trifluoromethyl, (g) cyano, (h) tetrazole, (j) —$SR^{13}$, (k) —$COR^{14}$, or

[II] (a) C1-8 alkyl, C2-8 alkenyl or C2-8 alkynyl substituted with a group selected from halogen, trifluoromethyl, nitro, cyano or —$NR^{18}R^{19}$ or
(b) (1) CycA having 1-5 of substituent $R^{27}$, or
(2) C1-8 alkyl, C2-8 alkenyl or C2-8 alkynyl substituted with CycA having 1-5 of substituent $R^{27}$
(with proviso that, at least one $R^{27}$ in (1) or (2) is a group selected from (i) C5-10 mono- or bi-cyclic carboring, (ii) 5-10 membered mono- or bi-cyclic heteroring, (iii) —$SO_2R^{15}$, (iv) trifluoromethoxy, and (v) C1-8 alkyl substituted with 1-5 of group selected from (a) halogen, (b) —$NR^{11}R^{12}$, (c) —$OR^{13}$, (d) C5-10 mono- or bi-cyclic carboring, (e) nitro, (f) trifluoromethyl, (g) cyano, (h) 5-10 membered mono- or bi-cyclic heteroring, (j) —$SR^{13}$, (k) —$COR^{14}$, (l) —$SO_2R^{14}$ or (m) trifluoromethoxy (with proviso that at least one group is C5-10 mono- or bi-cyclic carboring, 5-10 membered heteroring, —$SO_2R^{14}$ or trifluoromethoxy)).

Further preferably $R^{16}$ is
[I] (1) C1-8 alkyl, (2) C2-8 alkenyl, (3) C2-8 alkynyl, (4) CycA, (5) C1-8 alkyl substituted with a group selected from CycA or —NHC(O)-CycA, (6) C2-8 alkenyl substituted with CycA, or (7) C2-8 alkynyl substituted with CycA, wherein CycA is a C5-10 mono- or bi-cyclic carboaryl or partially or completely saturated one thereof, or a 5-10 membered heteroaryl comprising 1-2 of nitrogen, 1-2 of oxygen and/or 1 of sulfur or partially or completely saturated one thereof which may be substituted with 1-5 of $R^{27a}$, or
[II] (a) C1-8 alkyl, C2-8 alkenyl or C2-8 alkynyl substituted with halogen, trifluoromethyl, nitro, cyano or —$NR^{18}R^{19}$, or
(b) (1) CycA having 1-5 of substituent $R^{27}$, or
(2) C1-8 alkyl, C2-8 alkenyl or C2-8 alkynyl having 1-5 of substituent $R^{27}$
(with proviso that, at least one group in (1) or (2) is,
(i) a C5-10 mono- or bi-cyclic carboring, (ii) a 5-10 membered mono- or bi-cyclic heteroring, (iii) —$SO_2R^{14}$, (iv) trifluoromethoxy, and (v) C1-8 alkyl substituted with 1-5 of group selected from (a) halogen, (b) —$NR^{11}R^{12}$, (c) —$OR^{13}$, (d) a C5-10 mono- or bi-cyclic carboring, (e) nitro, (f) trifluoromethyl, (g) cyano, (h) a 5-10 membered mono- or bi-cyclic heteroring, (j) —$SR^{13}$, (k) —$COR^{14}$, (l) —$SO_2R^{14}$ and (m) trifluoromethoxy (with proviso that at least one group is selected from a C5-10 mono- or bi-heteroring, a 5-10 membered mono- or bi-cyclic heteroring, —$SO_2R^{14}$ or trifluoromethoxy)), wherein CycA is a mono- or bi-cyclic C5-10 carboaryl or partially or completely saturated one thereof, or a 5-10 membered heteroaryl comprising 1-4 of atom selected from nitrogen, oxygen and/or sulfur, or partially or completely saturated one thereof.

Particularly preferably, $R^{16}$ is
[I] (1) C1-4 alkyl, (2) C2-4 alkenyl, (3) C2-4 alkynyl, (4) CycA, or (5) C1-4 alkyl, C2-4 alkenyl or C2-4 alkynyl substituted with CycA, wherein CycA is preferably cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, tetrahydroquinoxaline which may be substituted with 1-5 of $R^{27a}$, or
[II] (a) C1-8 alkyl, C2-8 alkenyl or C2-8 alkynyl substituted with a group selected from halogen, trifluoromethyl, nitro, cyano and —$NR^{18}R^{19}$ or
(b) (1) CycA having 1-5 of substituent $R^{27}$, or
(2) C1-8 alkyl, C2-8 alkenyl or C2-8 alkynyl substituted with CycA having 1-5 of substituent $R^{27}$
(with proviso that, at least one of $R^{27}$ in (1) or (2) is
(i) a C5-10 mono- or bi-cyclic carboring, (ii) a 5-10 membered heteroring, (iii) —$SO_2R^{14}$, (iv) trifluoromethoxy, and (v) C1-8 alkyl substituted with 1-5 of group selected from (a) halogen, (b) —$NR^{11}R^{12}$, (c) —$OR^{13}$, (d) a C5-10 mono- or bi-cyclic carboring, (e) nitro, (f) trifluoromethyl, (g) cyano, (h) a 5-10 membered mono- or bi-cyclic heteroring, (j) —$SR^{13}$, (k) —$COR^{14}$, (l) —$SO_2R^{14}$ and (m) trifluoromethoxy (with proviso that at least one is selected from a C5-10 mono- or bi-cyclic carboring, a 5-10 membered mono- or bi-cyclic heteroring, —$SO_2R^{14}$ or trifluoromethoxy)),
CycA is preferably cyclopentane, cyclohexane, cycloheptane, cyclooctane, cyclopentene, cyclohexene, cycloheptene, cyclooctene, benzene, naphthalene, indan, indene, dihydronaphthalene, tetrahydronaphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, tetrahydroquinoxaline.

In the formula (I), $AA^1$ is preferably a bond, or

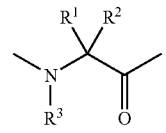

or $AA^1$ is also preferably taken together with R to represent

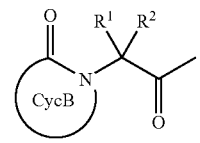

and more preferably a bond or

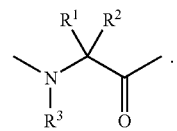

$R^1$ is all preferable and more preferably hydrogen, C1-8 alkyl, phenyl, or C1-8 alkyl substituted with $NH_2$, C1-4 alkoxy, SH, $SCH_3$, phenyl, hydroxyphenyl, COOH, $CONH_2$, guanidino, amidino, imidazole or indole.

$R^1$ is particularly preferably hydrogen, C1-8 alkyl, phenyl, or C1-8 alkyl substituted with C1-4 alkoxy or phenyl. In this case, $R^2$ is all preferable and particularly preferably hydrogen.

Or, $R^1$ and $R^2$ are also preferably taken together to form C3-6 alkylene.

$R^3$ is all preferable, particularly preferably hydrogen or C1-4 alkyl.

Or, $R^3$ and $R^1$ are also preferably taken together to form C2-4 alkylene.

In the formula (I), $AA^2$ is all preferable and more preferably a bond,

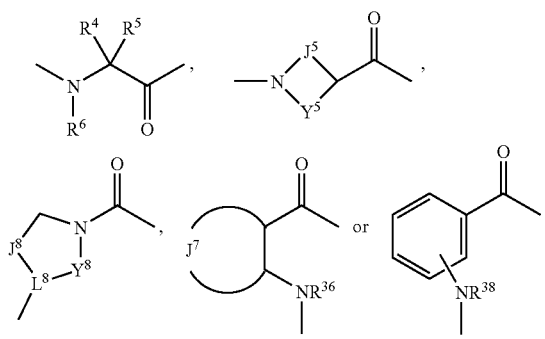

and more preferably a bond,

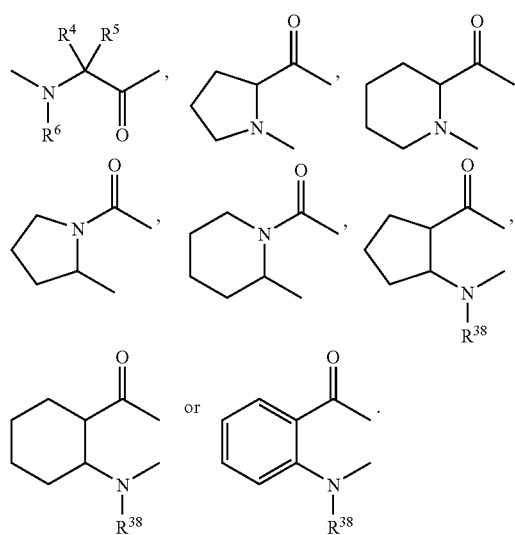

$R^4$ is all preferable and more preferably, hydrogen, C1-8 alkyl, phenyl, or C1-8 alkyl substituted with $NH_2$, C1-4 alkoxy, SH, $SCH_3$, phenyl, hydroxyphenyl, carboxy, carbamoyl, guanidino, amidino, imidazole or indole.

$R^4$ is particularly preferably hydrogen, C1-8 alkyl, phenyl, or C1-8 alkyl substituted with C1-4 alkoxy or phenyl. In this case, $R^5$ is all preferable and particularly preferably hydrogen.

Or, $R^4$ and $R^5$ are also preferably to form C3-6 alkylene.

$R^6$ is all preferable and particularly preferably hydrogen or C1-4 alkyl.

Or, $R^6$ and $R^4$ are also preferably taken together to form C2-4 alkylene.

$R^{38}$ is all preferable and more preferably,

[I] hydrogen, C1-4 alkyl, phenyl or C1-4 alkyl substituted with phenyl, or

[II] when $AA^1$ is a bond, $R^{38}$ is taken together with R to form C2-6 alkylene (wherein one carbon may be replaced with oxygen, sulfur or —$NR^{37}$— (wherein $R^{37}$ is hydrogen or C1-4 alkyl)).

$R^{38}$ is particularly preferably [I] hydrogen or C1-4 alkyl, or [II] when $AA^1$ is a bond, taken together with R to form tetramethylene, pentamethylene, —$CH_2$—$CH_2$—O—$CH_2$—$CH_2$—, —$CH_2$—$CH_2$—NH—$CH_2$—$CH_2$— or —$CH_2$—$CH_2$—N($CH_3$)—$CH_2$—$CH_2$—.

In the formula (I), the group which $AA^1$ and $AA^2$ are taken together to form is all preferable and more preferably

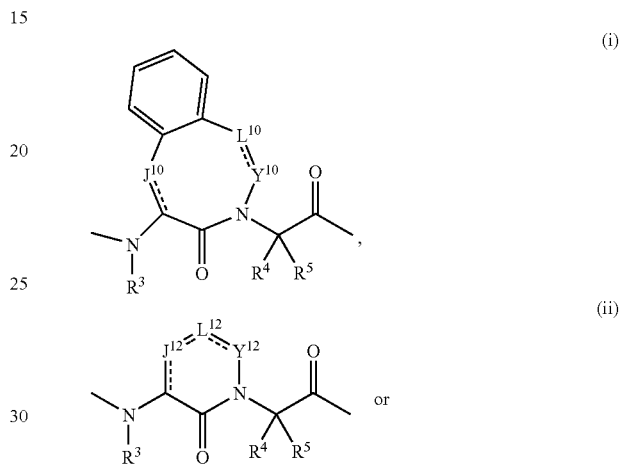

and particularly preferably

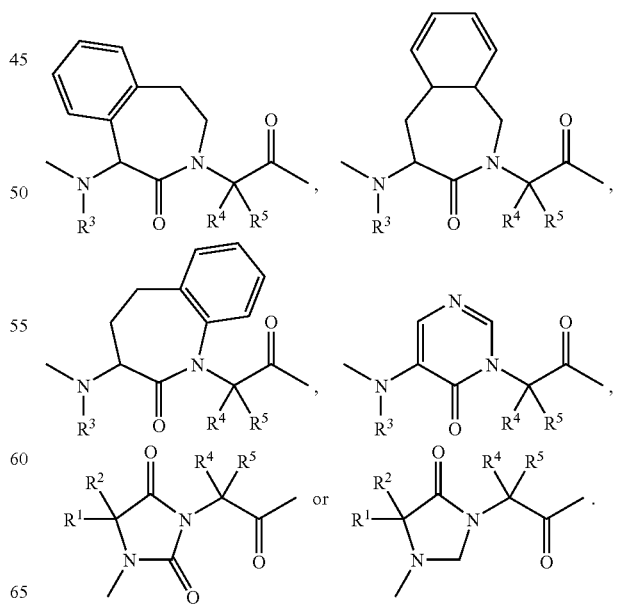

R⁷ is all preferable and more preferably hydrogen, C1-8 alkyl, optionally substituted phenyl, pyridyl, tetrahydropyranyl, piperidin-4-yl or cycloheptyl, or C1-8 alkyl substituted with amino, C1-4 alkoxy, mercapto, methylthio, phenyl, hydroxyphenyl, COOH, CONH₂, guanidino, amidino, imidazole, or indole.

R⁷ is particularly preferably, hydrogen, C1-8 alkyl; optionally substituted phenyl, tetrahydropyranyl, piperidin-4-yl, cycloheptyl, cyclohexyl, cyclopentyl; C1-8 alkyl substituted with C1-4 alkoxy or phenyl. In this case, R⁸ is all preferable and more preferably hydrogen.

Or, R⁷ and R⁸ are also preferably taken together to form C3-6 alkylene.

R⁷ is also preferably taken together with R⁸ to form C3-6 alkylene which R⁷ and R⁸ together form is also preferable.

R⁹ is all preferable and particularly preferably hydrogen or C1-4 alkyl.

Or, R⁹ and R⁷ are also preferably taken together to form C2-4 alkylene.

As

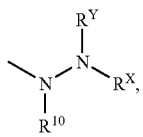

each of

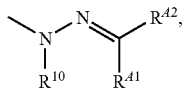
(i)

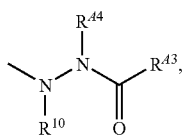
(ii)

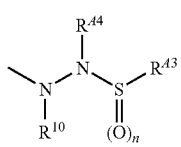
(iii)

is preferable.
In

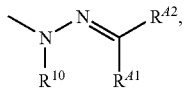
(i)

each of $R^{A1}$ and $R^{A2}$ are preferable and particularly C1-4 alkyl optionally substituted with —OR$^{Z1}$, —SR$^{Z1}$, —CO$^{Z2}$, —NR$^{Z3}$R$^{Z4}$, phenyl or heteroring comprising 1 to 2 atoms selected from nitrogen, oxygen and sulfur; —OR$^{Z1}$, —SR$^{Z1}$, —CO$^{Z2}$, —NR$^{Z3}$R$^{Z4}$, phenyl, and R$^{A1}$ and R$^{A2}$ are also preferably taken together to form CycH. CycH is preferably a C4-10 carboring or a 5-10 membered heteroring comprising 1 to 2 atoms selected from nitrogen, sulfur or oxygen.

The ring which CycH forms is preferably

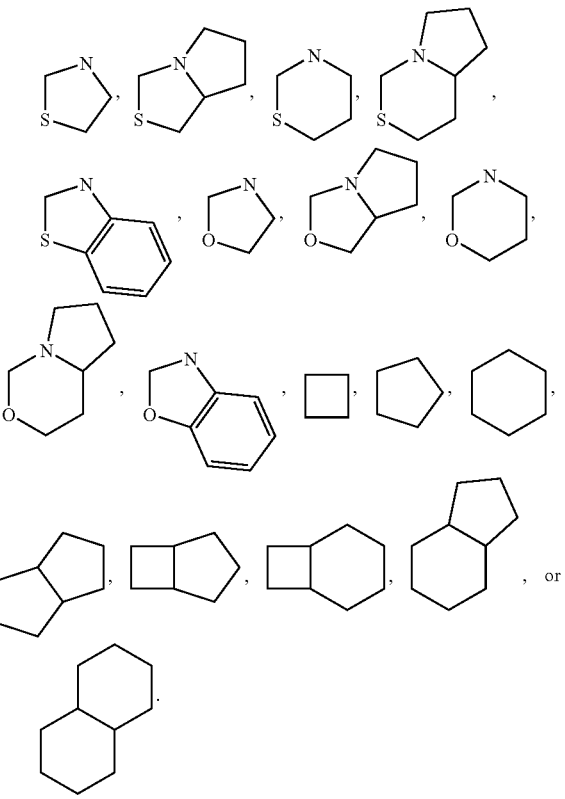

In

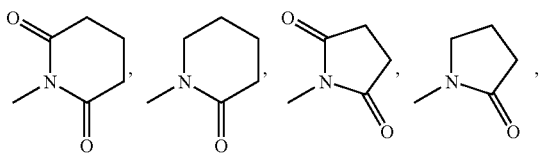
(ii)

$R^{A3}$ is all preferable, particularly $R^{A3}$ is C1-4 alkyl optionally substituted with —OR$^{Z1}$, —SR$^{Z1}$, —CO$^{Z2}$, —NR$^{Z3}$R$^{Z4}$, phenyl or 5-8 membered heteroring comprising 1 to 2 atoms selected from nitrogen, oxygen and sulfur; and 5-8 membered heteroring comprising 1 to 2 atoms selected from nitrogen, oxygen and sulfur.

$R^{A4}$ is all preferable, particularly, hydrogen, —COR$^{Z4}$, phenyl, heteroring comprising 1 to 2 atoms selected from nitrogen, oxygen and sulfur, —OR$^{Z1}$, —SR$^{Z1}$, —CO$^{Z2}$, —NR$^{Z3}$R$^{Z4}$, phenyl or C1-4 alkyl substituted with heteroring comprising 1 to 2 atoms selected from nitrogen, oxygen and sulfur.

And R$^{A3}$ and R$^{A4}$ are also preferably taken together to form CycK.

CycK is preferably

-continued

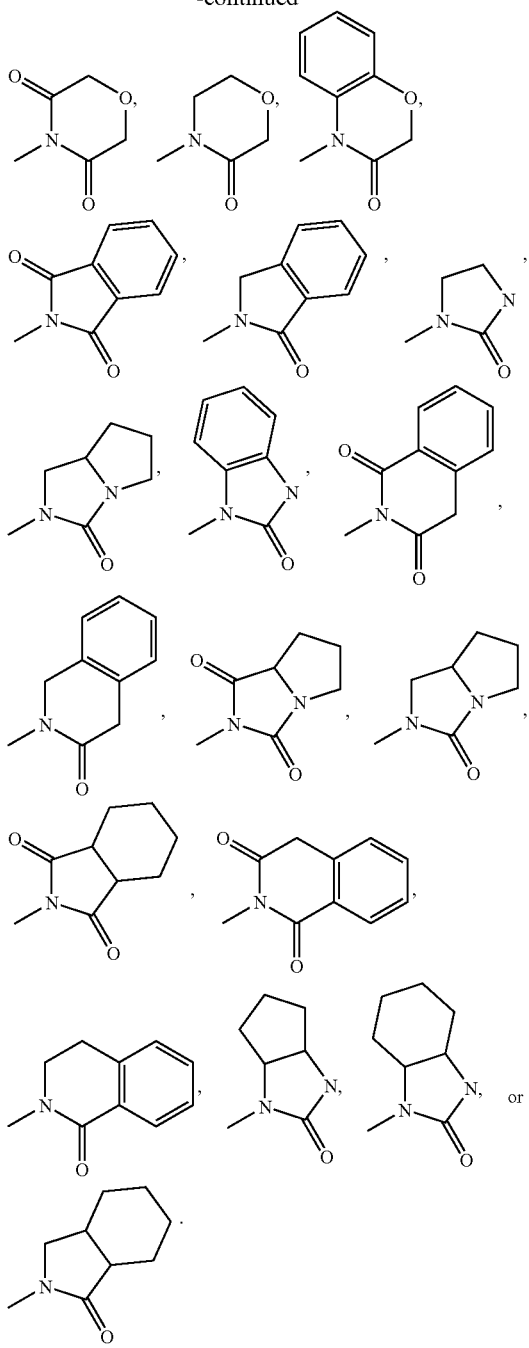

And in

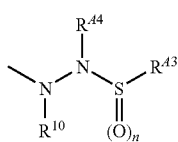
(iii)

$R^{A3}$ is all preferable, and particularly preferably $R^{A3}$ is —$OR^{Z1}$, —$SR^{Z1}$, —$CO^{Z2}$, —$NR^{Z3}R^{Z4}$, phenyl or C1-4 alkyl optionally substituted with 1 to 2 atoms selected from nitrogen, oxygen and sulfur, or phenyl, 5-8 membered heteroring comprising 1 to 2 atoms selected from nitrogen, oxygen and sulfur.

$R^{A4}$ is all preferable, particularly hydrogen, —$COR^{Z4}$, phenyl, heteroring comprising 1 to 2 atoms selected from nitrogen, oxygen and sulfur, C1-4 alkyl substituted with —$OR^{Z1}$, —$SR^{Z1}$, —$CO^{Z2}$, —$NR^{Z3}R^{Z4}$, phenyl or heteroring comprising 1 to 2 atoms selected from nitrogen, oxygen and sulfur.

Or, $R^{A3}$ and $R^{A4}$ are also preferably taken together to form CycM.

$R^{10}$ is all preferable and more preferably hydrogen or C1-4 alkyl.

In the present invention, preferable compounds are, in addition to the compounds shown in examples, as follows; the compound of formula (Ia-1)

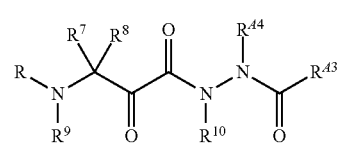
(Ia-1)

(wherein all symbols have the same meaning as described hereinbefore), the compound of formula (Ib-1)

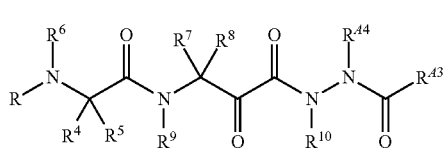
(Ib-1)

(wherein all symbols have the same meaning as described hereinbefore), the compound of formula (Ic-1)

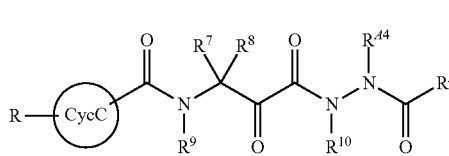
(Ic-1)

(wherein all symbols have the same meaning as described hereinbefore), the compound of formula (Id-1)

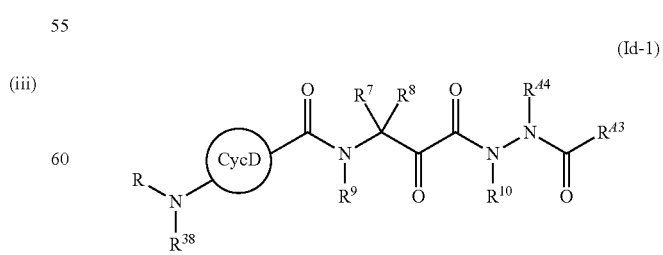
(Id-1)

(wherein all symbols have the same meaning as described hereinbefore), the compound of formula (Ie-1)

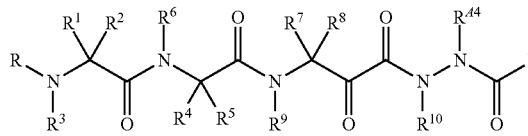

(wherein all symbols have the same meaning as described hereinbefore), the compound of formula (If-1)

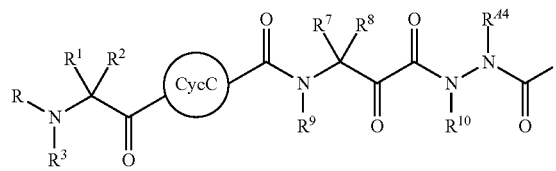

(wherein all symbols have the same meaning as described hereinbefore), the compound of formula (Ig-1)

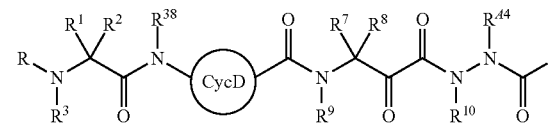

(wherein all symbols have the same meaning as described hereinbefore), the compound of formula (Ih-1)

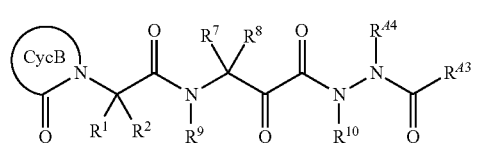

(wherein all symbols have the same meaning as described hereinbefore), the compound of formula (Ij-1)

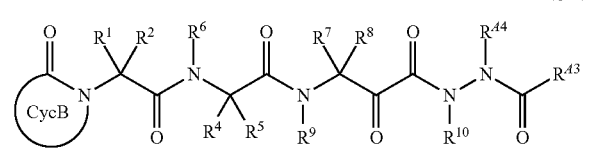

(wherein all symbols have the same meaning as described hereinbefore), the compound of formula (Ik-1)

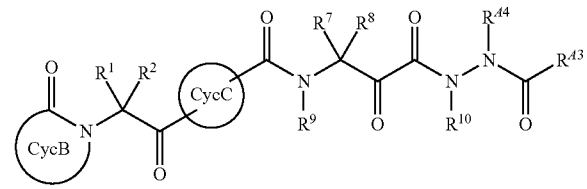

(wherein all symbols have the same meaning as described hereinbefore), the compound of formula (Im-1)

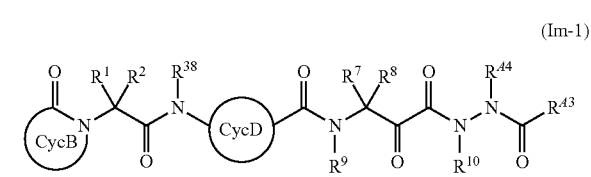

(wherein all symbols have the same meaning as described hereinbefore). the compound of formula (In-1)

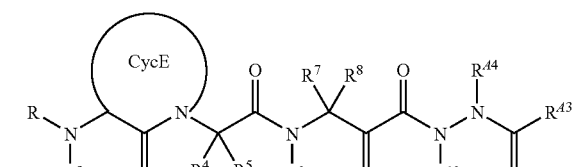

(wherein all symbols have the same meaning as described hereinbefore), the compound of formula (Ip-1)

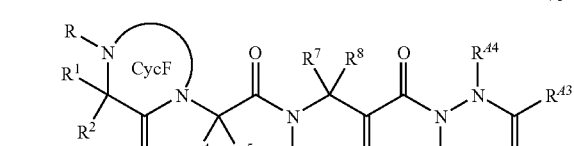

(wherein all symbols have the same meaning as described hereinbefore), the compound of formula (Ia-2)

(Ia-2)

(wherein all symbols have the same meaning as described hereinbefore), the compound of formula (Ib-2)

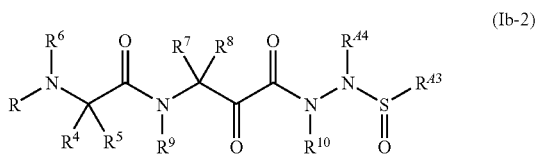

(Ib-2)

(wherein all symbols have the same meaning as described hereinbefore), the compound of formula (Ic-2)

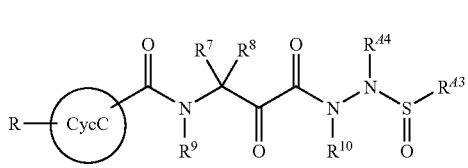

(Ic-2)

(wherein all symbols have the same meaning as described hereinbefore), the compound of formula (Id-2)

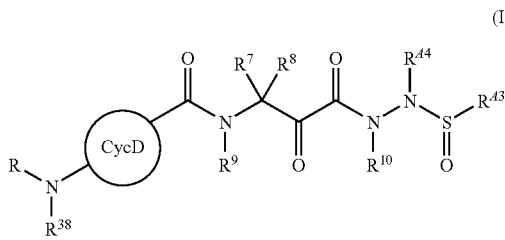

(Id-2)

(wherein all symbols have the same meaning as described hereinbefore), the compound of formula (Ie-2)

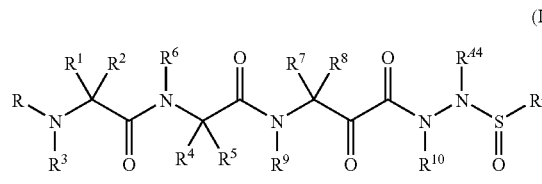

(Ie-2)

(wherein all symbols have the same meaning as described hereinbefore), the compound of formula (If-2)

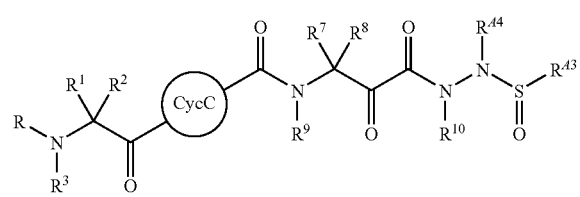

(If-2)

(wherein all symbols have the same meaning as described hereinbefore), the compound of formula (Ig-2)

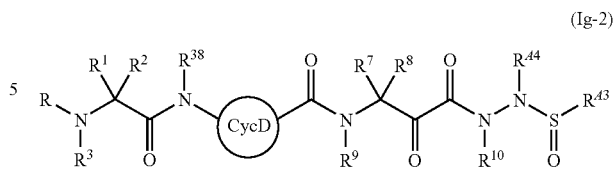

(Ig-2)

(wherein all symbols have the same meaning as described hereinbefore), the compound of formula (Ih2)

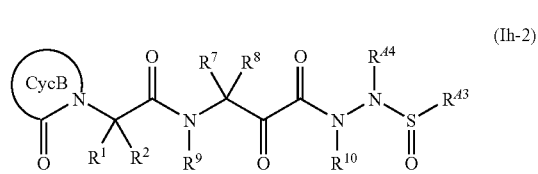

(Ih-2)

(wherein all symbols have the same meaning as described hereinbefore), the compound of formula (Ij-2)

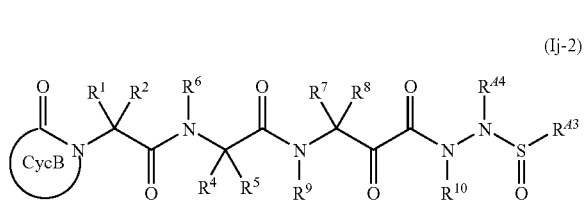

(Ij-2)

(wherein all symbols have the same meaning as described hereinbefore), the compound of formula (Ik-2)

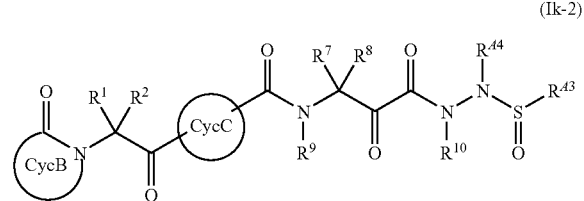

(Ik-2)

(wherein all symbols have the same meaning as described hereinbefore), the compound of formula (Im-2)

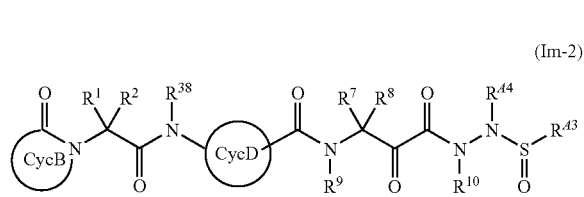

(Im-2)

(wherein all symbols have the same meaning as described hereinbefore), the compound of formula (In-2)

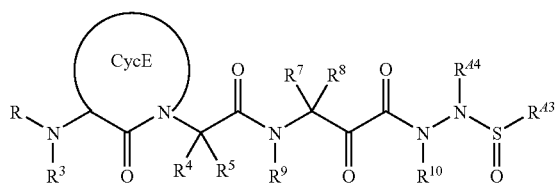

(In-2)

(wherein all symbols have the same meaning as described hereinbefore), the compound of formula (Ip-2)

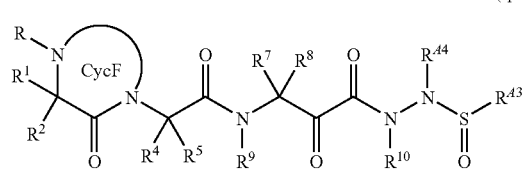

(Ip-2)

(wherein all symbols have the same meaning as described hereinbefore), the compound of formula (Ia-3)

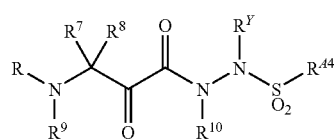

(Ia-3)

(wherein all symbols have the same meaning as described hereinbefore), the compound of formula (Ib-3)

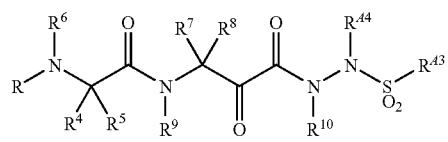

(Ib-3)

(wherein all symbols have the same meaning as described hereinbefore), the compound of formula (Ic-3)

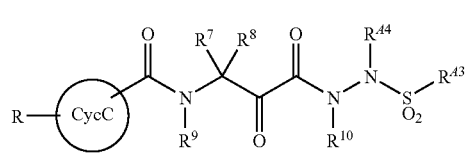

(Ic-3)

(wherein all symbols have the same meaning as described hereinbefore), the compound of formula (Id-3)

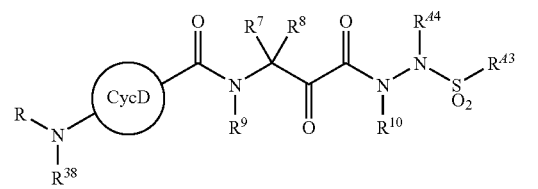

(Id-3)

(wherein all symbols have the same meaning as described hereinbefore), the compound of formula (Ie-3)

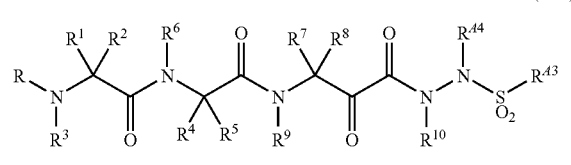

(Ie-3)

(wherein all symbols have the same meaning as described hereinbefore), the compound of formula (If-3)

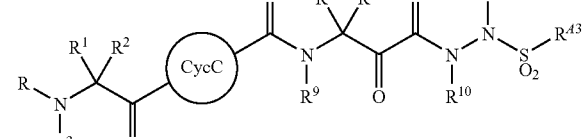

(If-3)

(wherein all symbols have the same meaning as described hereinbefore), the compound of formula (Ig-3)

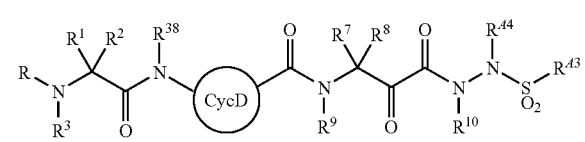

(Ig-3)

(wherein all symbols have the same meaning as described hereinbefore), the compound of formula (Ih-3)

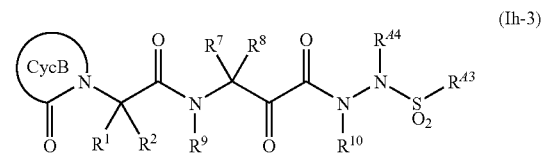

(Ih-3)

(wherein all symbols have the same meaning as described hereinbefore), the compound of formula (Ij-3)

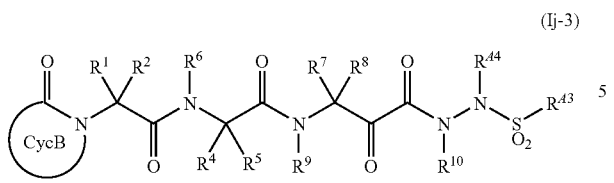

(Ij-3)

(wherein all symbols have the same meaning as described hereinbefore), the compound of formula (Ik-3)

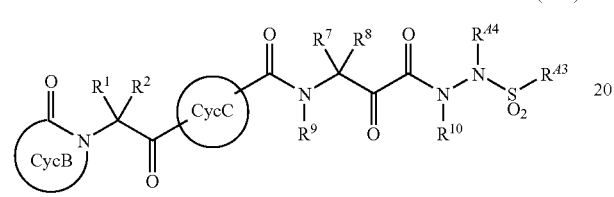

(Ik-3)

(wherein all symbols have the same meaning as described hereinbefore), the compound of formula (Im-3)

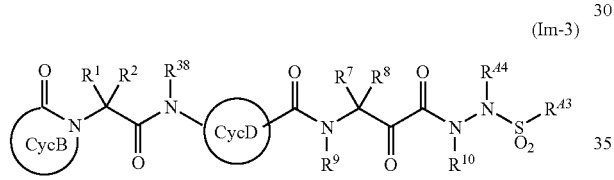

(Im-3)

(wherein all symbols have the same meaning as described hereinbefore), the compound of formula (In-3)

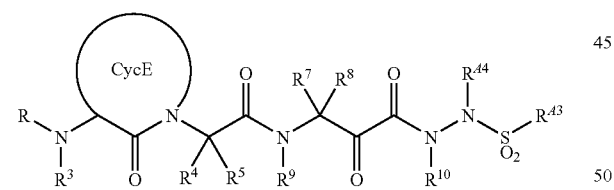

(In-3)

(wherein all symbols have the same meaning as described hereinbefore), the compound of formula (Ip-3)

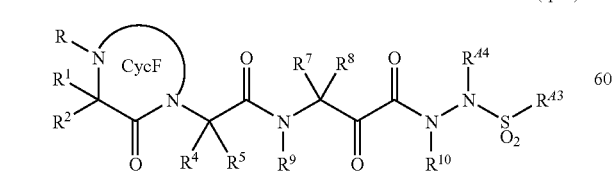

(Ip-3)

(wherein all symbols have the same meaning as described hereinbefore), the compound of formula (Ia-4)

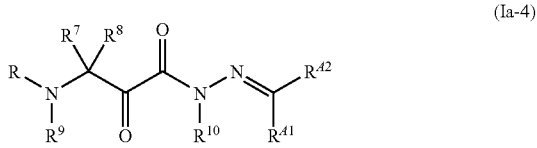

(Ia-4)

(wherein all symbols have the same meaning as described hereinbefore), the compound of formula (Ib-4)

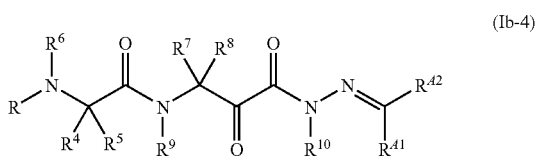

(Ib-4)

(wherein all symbols have the same meaning as described hereinbefore), the compound of formula (Ic-4)

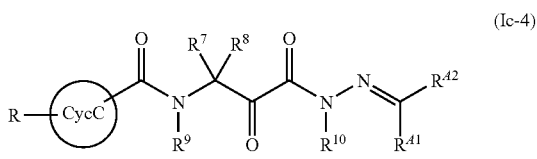

(Ic-4)

(wherein all symbols have the same meaning as described hereinbefore), the compound of formula (Id-4)

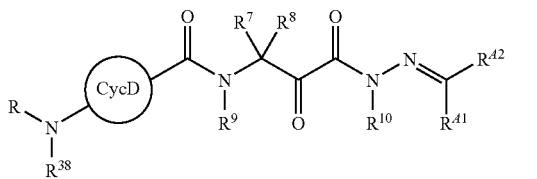

(Id-4)

(wherein all symbols have the same meaning as described hereinbefore), the compound of formula (Ie-4)

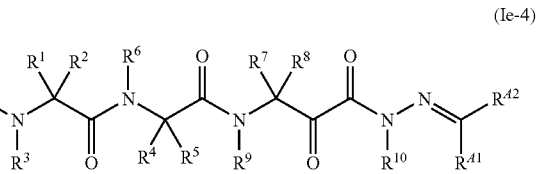

(Ie-4)

(wherein all symbols have the same meaning as described hereinbefore), the compound of formula (If-4)

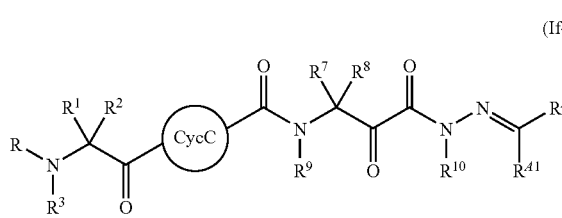
(If-4)

(wherein all symbols have the same meaning as described hereinbefore), the compound of formula (Ig-4)

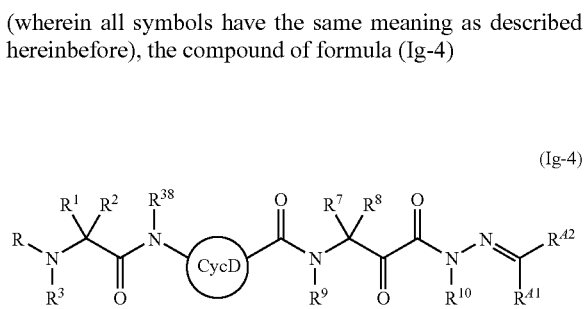
(Ig-4)

(wherein all symbols have the same meaning as described hereinbefore), the compound of formula (Ih-4)

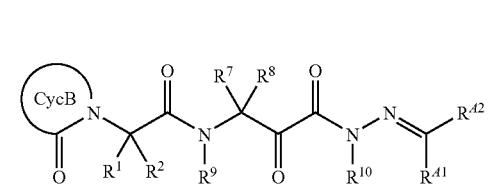
(Ih-4)

(wherein all symbols have the same meaning as described hereinbefore), the compound of formula (Ij-4)

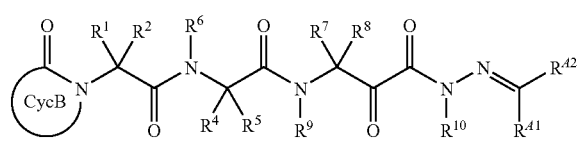
(Ij-4)

(wherein all symbols have the same meaning as described hereinbefore), the compound of formula (Ik-4)

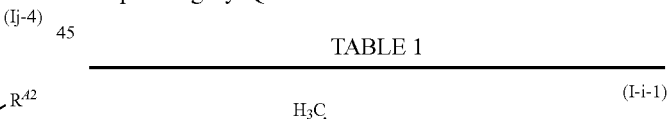
(Ik-4)

(wherein all symbols have the same meaning as described hereinbefore), the compound of formula (Im-4)

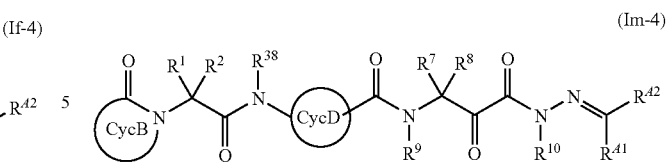
(Im-4)

(wherein all symbols have the same meaning as described hereinbefore), the compound of formula (In-4)

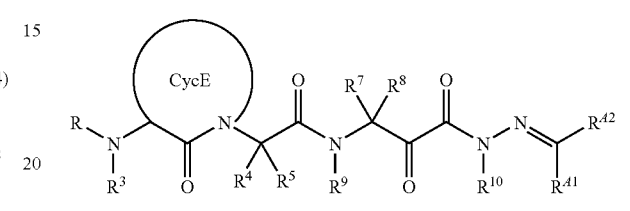
(In-4)

(wherein all symbols have the same meaning as described hereinbefore), the compound of formula (Ip-4)

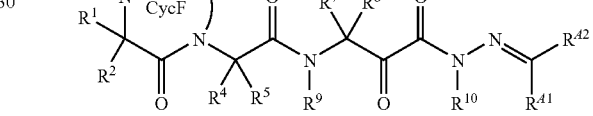
(Ip-4)

(wherein all symbols have the same meaning as described hereinbefore) and a pharmaceutically acceptable salts.

Specifically, the compounds of the examples described hereafter and the compounds in the following tables 1 to 16 and pharmaceutically acceptable salts thereof are preferable. In the tables, Ph is phenyl, tBu is t-butyl. $(R^q)_t$ represents $R^{27}$, or more than one $R^q$ are taken together to form a fused ring or a Spiro ring CycQ.

TABLE 1

(I-i-1)

| No. | $R^B$ |
|---|---|
| 1 | —CH₃ (ethyl) |
| 2 | propyl |
| 3 | isobutyl |

TABLE 1-continued
(I-i-1)
| No. | $R^B$ |
|---|---|
| 4 | 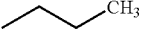 |
| 5 | 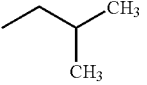 |
| 6 | 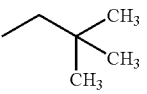 |
| 7 | 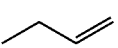 |
| 8 | 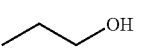 |
| 9 | 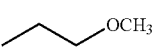 |
| 10 | 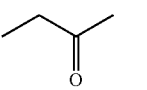 |
| 11 | 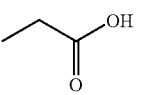 |
| 12 | 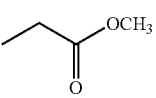 |
| 13 |  |
| 14 | 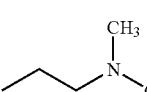 |
| 15 |  |
| 16 | 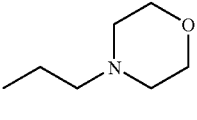 |
| 17 | Ph |
| 18 |  |
| 19 | 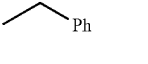 |
TABLE 2
(I-i-2)
| No. | 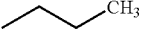 |
|---|---|
| 1 | |
| 2 | |
| 3 | |
| 4 | |
| 5 | |
| 6 | |
| 7 | |
| 8 | |
| 9 | |
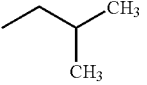

TABLE 2-continued (I-i-2)

[Structure: cyclohexanecarbonyl-NH-CH(CH2CH(CH3)2)-C(O)-C(O)-NH-N=C(thiazolidine with N-CH3, (Rq)r)]

No. | =⟨thiazolidine N-CH3, (Rq)r⟩
--- | ---
10 | [N-methyl thiazolidine spiro cyclohexane, =CH2]
11 | [N-methyl thiazolidine spiro tetrahydropyran, =CH2]
12 | [N-methyl thiazolidine spiro N-methylpiperidine, =CH2]
13 | [N-methyl-4-oxo-thiazolidine, =CH2]
14 | [N-methyl-4-oxo-5,5-dimethyl-thiazolidine, =CH2]
15 | [N-methyl-thiazole, =CH2]
16 | [N-methyl-benzothiazoline, =CH2]

TABLE 3

(I-i-3)

[Structure: cyclohexanecarbonyl-NH-CH(CH2CH(CH3)2)-C(O)-C(O)-NH-N=C(R41)(R42)]

=C(R41)(R42)

No. | 
--- | ---
1 | =CH-CH3
2 | =CH-cyclohexyl
3 | =CH-(4-oxocyclohexyl)
4 | =CH-(tetrahydropyran-4-yl)
5 | =CH-(N-methylpiperidin-4-yl)
6 | =CH-(tetrahydrothiopyran-4-yl)
7 | =CH-Ph
8 | =C(CH3)2
9 | =cyclohexylidene
10 | =(4-oxocyclohexylidene)
11 | =(tetrahydropyran-4-ylidene)
12 | =(N-methylpiperidin-4-ylidene)

TABLE 3-continued
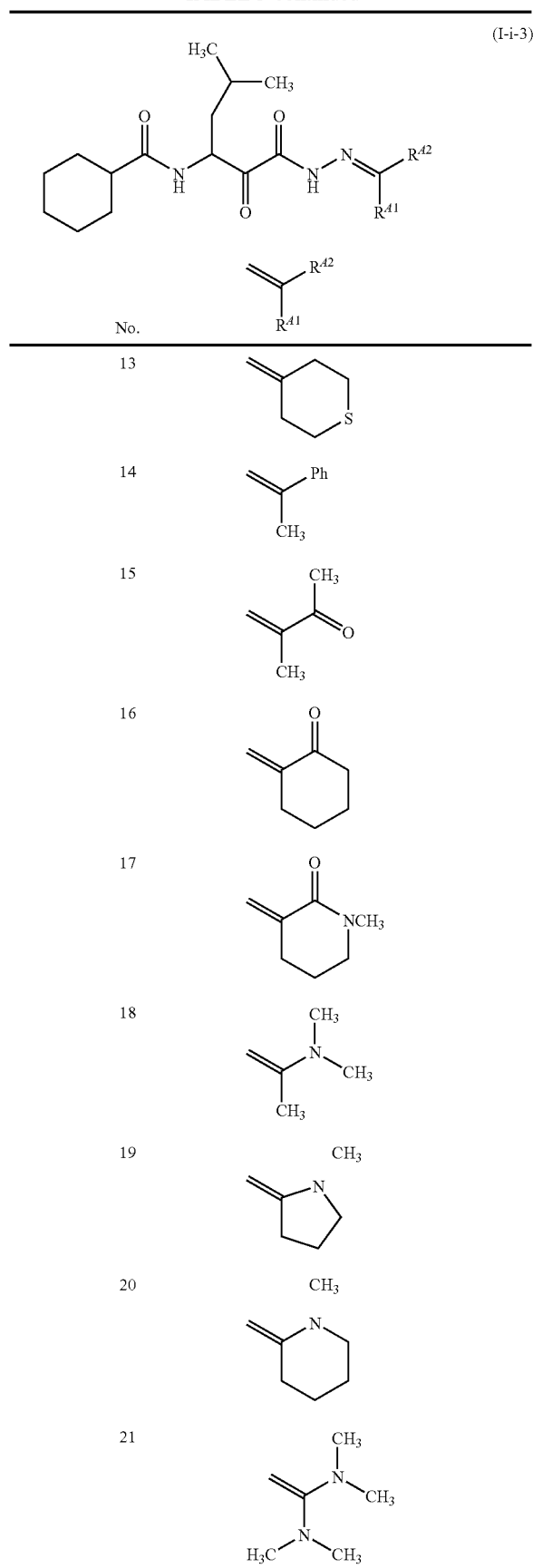
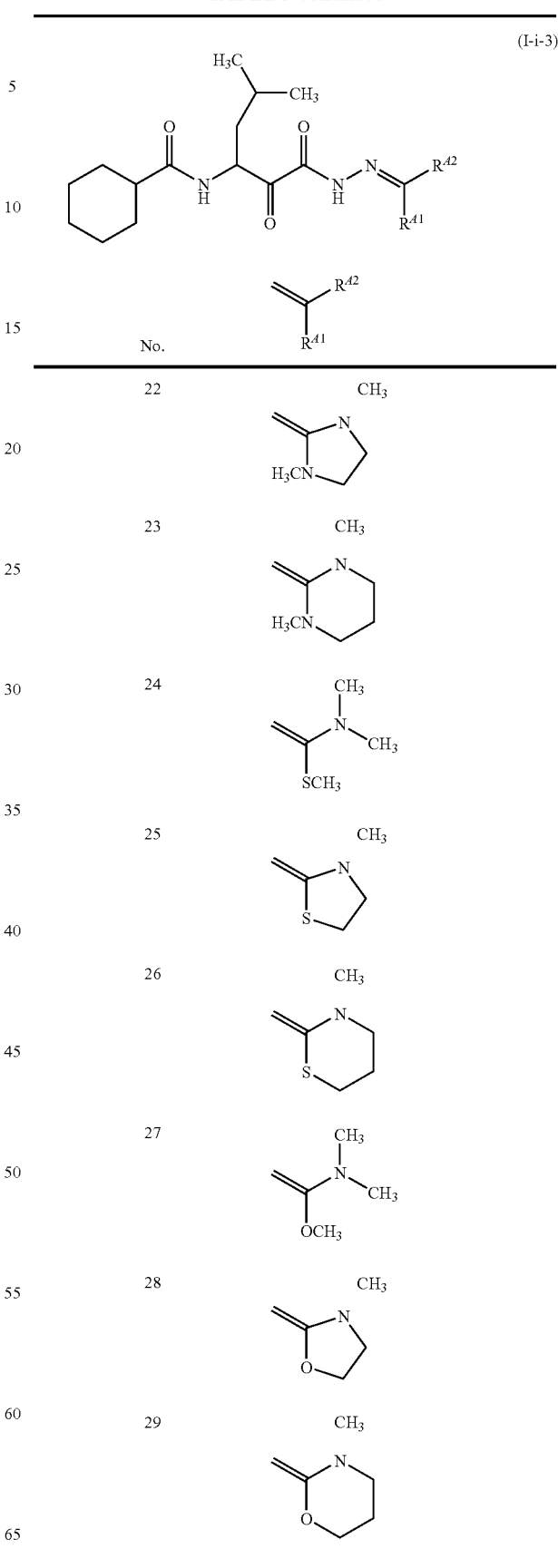

TABLE 3-continued
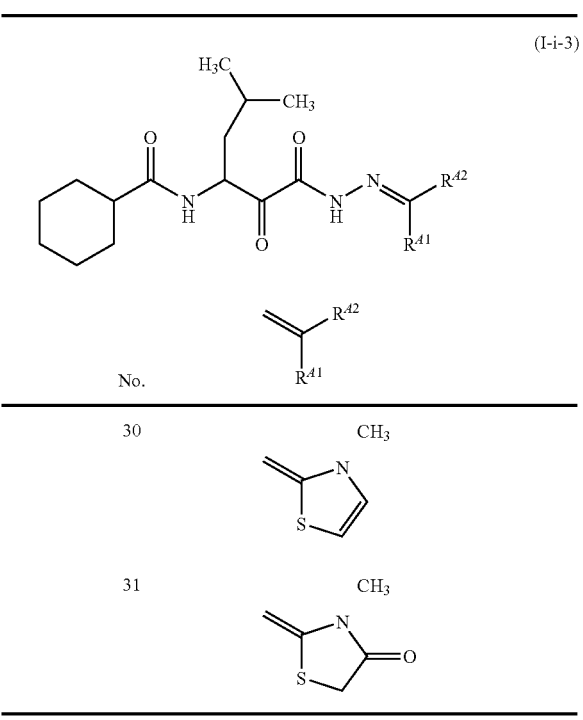
TABLE 4
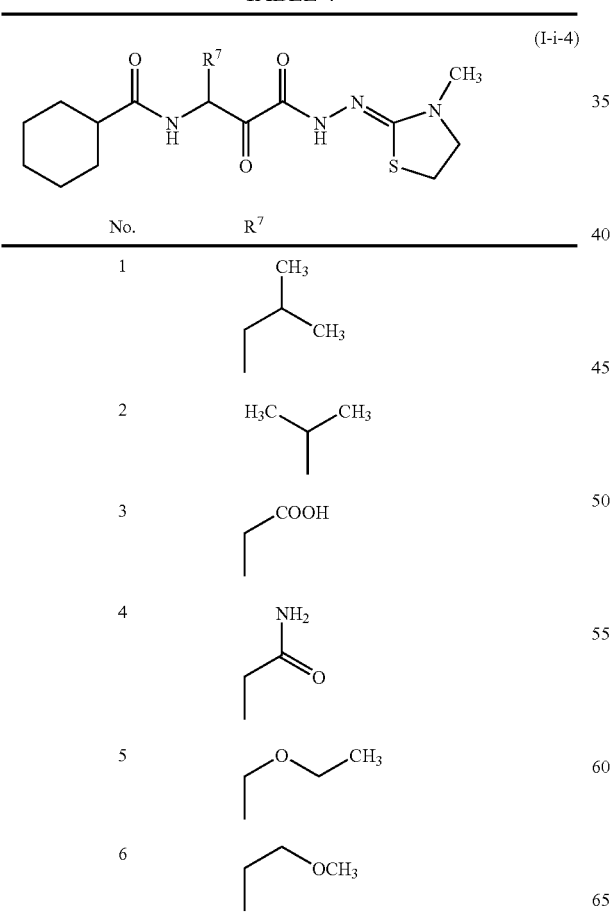
TABLE 4-continued
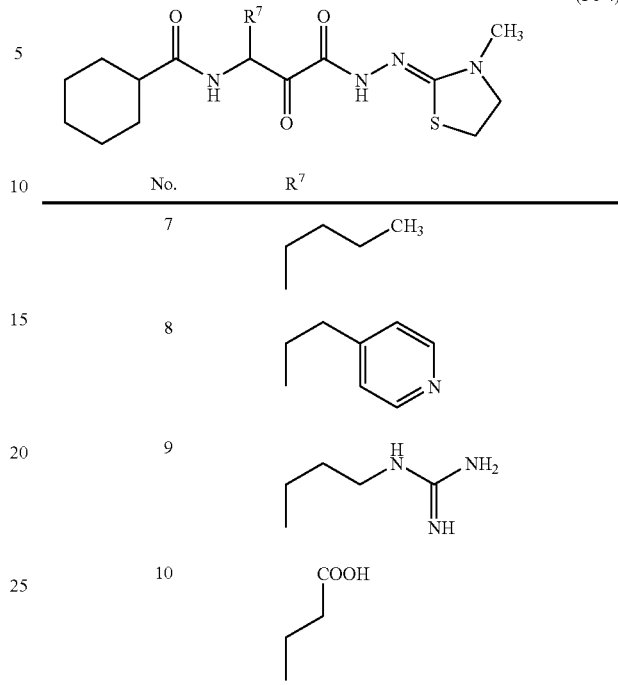
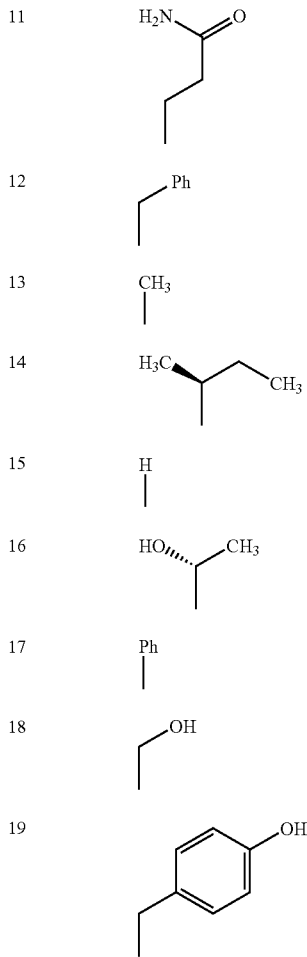

TABLE 4-continued (I-i-4)

Structure: cyclohexyl-C(=O)-NH-CH(R⁷)-C(=O)-C(=O)-NH-N=C(thiazolidine with N-CH₃)

| No. | R⁷ |
|---|---|
| 20 | -(CH₂)₄-NH₂ |
| 21 | -CH₂-CH₂-(4-imidazolyl, NH) |
| 22 | -CH₂-CH₂-CH₃ |
| 23 | -CH₂-CH₂-CH₂-CH₃ |
| 24 | -(CH₂)₄-CH₃ |
| 25 | -(CH₂)₅-CH₃ |
| 26 | -CH₂-CH₂-tBu |
| 27 | -CH₂-CH₂-CH(CH₃)₂ |
| 28 | -CH₂-CH₂-CH₂-tBu |
| 29 | -CH₂-CH₂-CH₂-CH(CH₃)₂ |
| 30 | -(CH₂)₃-CH₂-tBu |
| 31 | -CH₂-CH₂-OCH₃ |
| 32 | -CH₂-CH₂-SCH₃ |
| 33 | -CH₂-CH₂-N(CH₃)₂ |
| 34 | -CH₂-C(CH₃)₂-OCH₃ |
| 35 | -CH₂-CH₂-CH₂-OCH₃ |
| 36 | -CH₂-CH₂-CH₂-N(CH₃)₂ |
| 37 | -CH₂-CH₂-C(CH₃)₂-OCH₃ |
| 38 | -CH₂-CH₂-CH₂-OCH₃ |
| 39 | -CH₂-CH₂-CH₂-SCH₃ |
| 40 | -CH₂-CH₂-CH₂-N(CH₃)₂ |
| 41 | -(CH₂)₃-C(CH₃)₂-OCH₃ |
| 42 | -CH₂-CH(CH₂CH₃)-CH₃ |
| 43 | -CH₂-CH₂-CH(CH₃)-CH₂-CH₃ |
| 44 | -CH₂-cyclopropyl |
| 45 | -CH₂-cyclobutyl |
| 46 | -CH₂-cyclopentyl |
| 47 | -CH₂-cyclohexyl |
| 48 | -CH₂-(4-oxocyclohexyl) |
| 49 | -CH₂-(tetrahydropyran-4-yl) |

TABLE 4-continued (I-i-4)

| No. | R⁷ |
|-----|-----|
| 50 | (4-thianyl) |
| 51 | (4-piperidinyl, NH) |
| 52 | (1-methyl-4-piperidinyl) |
| 53 | (cycloheptyl) |
| 54 | (1-acetyl-4-piperidinyl) |
| 55 | (1-pivaloyl-4-piperidinyl) |
| 56 | (1-benzoyl-4-piperidinyl) |
| 57 | (1-methanesulfonyl-4-piperidinyl) |
| 58 | (1-phenylsulfonyl-4-piperidinyl) |
| 59 | (1-phenyl-4-piperidinyl) |

TABLE 4-continued (I-i-4)

| No. | R⁷ |
|-----|-----|
| 60 | ((4-methylpiperidin-1-yl)bis(phosphonic acid) methyl) |
| 61 | CH₂CH₂SH |
| 62 | CH₂CH₂CH₂Ph |
| 63 | (6-methyl-2-naphthyl) |
| 64 | (4-phenylphenyl, biphenyl) |
| 65 | (3-ethyl-1H-indol-?-yl) |
| 66 | CH₂CH₂CH₂SCH₃ |

TABLE 5

(I-i-5)

| No. | R |
|-----|---|
| 1 | 1-(NHC(O)Ph) |
| 2 | 1-(NHC(O)-2-naphthyl) |

TABLE 5-continued
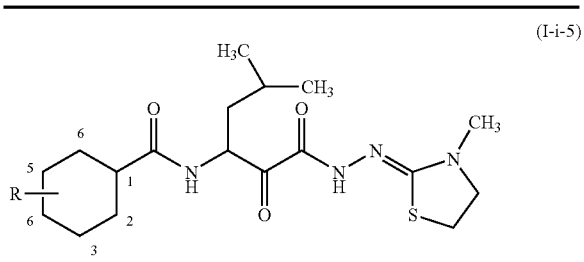

TABLE 6

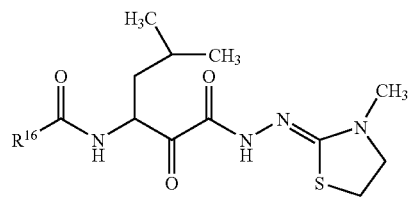

(I-i-6)

| No. | R[116] |
|---|---|
| 1 | cyclohexyl-CH2- |
| 2 | cyclopentyl-CH2- |
| 3 | cycloheptyl-CH2- |
| 4 | cyclooctyl-CH2- |
| 5 | cycloheptyl-CH2- |
| 6 | cyclooctyl-CH2- |
| 7 | cyclobutyl- |
| 8 | cyclopropyl-CH2- |
| 9 | 2-naphthyl-CH2- |
| 10 | 1-naphthyl-CH2- |
| 11 | benzothiophen-6-yl-CH2- |

TABLE 6-continued

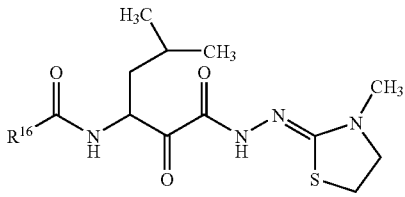

(I-i-6)

| No. | R[116] |
|---|---|
| 12 | benzofuran-6-yl-CH2- |
| 13 | quinolin-7-yl-CH2- |
| 14 | isoquinolin-7-yl-CH2- |
| 15 | Ph-CH2- |
| 16 | tBu-O-CH2- |
| 17 | Ph-CH2-O-CH2- |
| 18 | H3C-O-CH2- |
| 19 | cyclopentyl-O-CH2- |
| 20 | tBu-O-CH2-CH2-O-CH2- |
| 21 | 2-methyl-3-ethyl-4-oxo-3,4-dihydropyrimidin-(substituted)methyl |
| 22 | 2-phenyl-3-ethyl-4-oxo-3,4-dihydropyrimidin-(substituted)methyl |
| 23 | 2-(cyclohexylmethyl)-3-ethyl-4-oxo-3,4-dihydropyrimidin-(substituted)methyl |

TABLE 6-continued
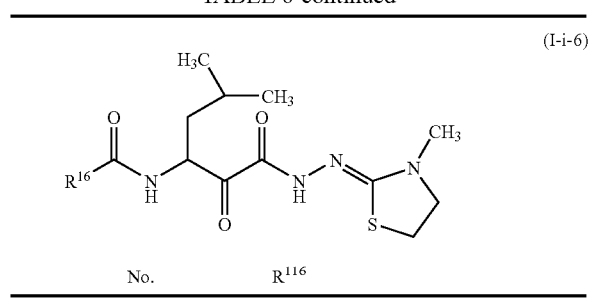
(I-i-6)
| No. | R[116] |
|---|---|
| 24 | ethyl-adamantyl |
| 25 | methyl-adamantyl |
| 26 | 2-butyl-thiophene |
| 27 | 1-propyl-piperidine |
| 28 | 2-methyl-benzothiophene |
| 29 | 2-methyl-benzofuran |
| 30 | CCl₃CH₂CH₂OCH₃ |
| 31 | cyclopentyl-propyl |
| 32 | (CH₃)₂C-CH=CH-CH₃ |
| 33 | (CH₃)₂C(CH₂)₂CH₃ |
| 34 | CH(CH₃)CH₂OCH₃ with methyl |
| 35 | C(CH₃)₂CH₂OCH₃ |
TABLE 7
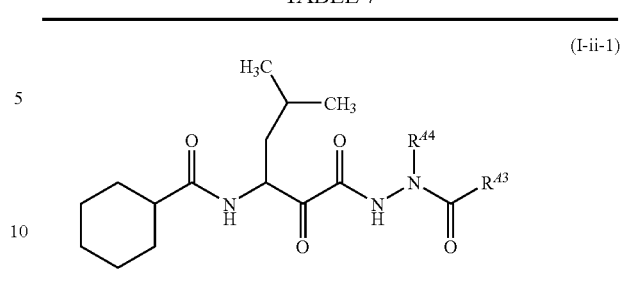
(I-ii-1)
| No. | |
|---|---|
| 1 | N(CH₃)C(O)CH₃ |
| 2 | N(cyclohexyl)C(O)CH₃ |
| 3 | N(tBu)C(O)CH₃ |
| 4 | N(Ph)C(O)CH₃ |
| 5 | N(2-pyridyl)C(O)CH₃ |
| 6 | N(CH₃)C(O)tBu |
| 7 | N(CH₃)C(O)cyclohexyl |

TABLE 7-continued (I-ii-1)

| No. | $R^{44}$, $R^{43}$ group |
|-----|---|
| 8 | N(CH₃)–C(O)–OCH₃ |
| 9 | N(cyclohexyl)–C(O)–OCH₃ |
| 10 | N(tBu)–C(O)–OCH₃ |
| 11 | N(Ph)–C(O)–OCH₃ |
| 12 | N(2-pyridyl)–C(O)–OCH₃ |
| 13 | N(CH₃)–C(O)–cyclohexyl |
| 14 | N(CH₃)–C(O)–OtBu |
| 15 | N(cyclohexyl)–C(O)–OtBu |
| 16 | N(tBu)–C(O)–OtBu |
| 17 | N(Ph)–C(O)–OtBu |
| 18 | N(2-pyridyl)–C(O)–OtBu |
| 19 | N(CH₃)–C(O)–N(CH₃)₂ |
| 20 | N(cyclohexyl)–C(O)–N(CH₃)₂ |
| 21 | N(tBu)–C(O)–N(CH₃)₂ |

TABLE 7-continued
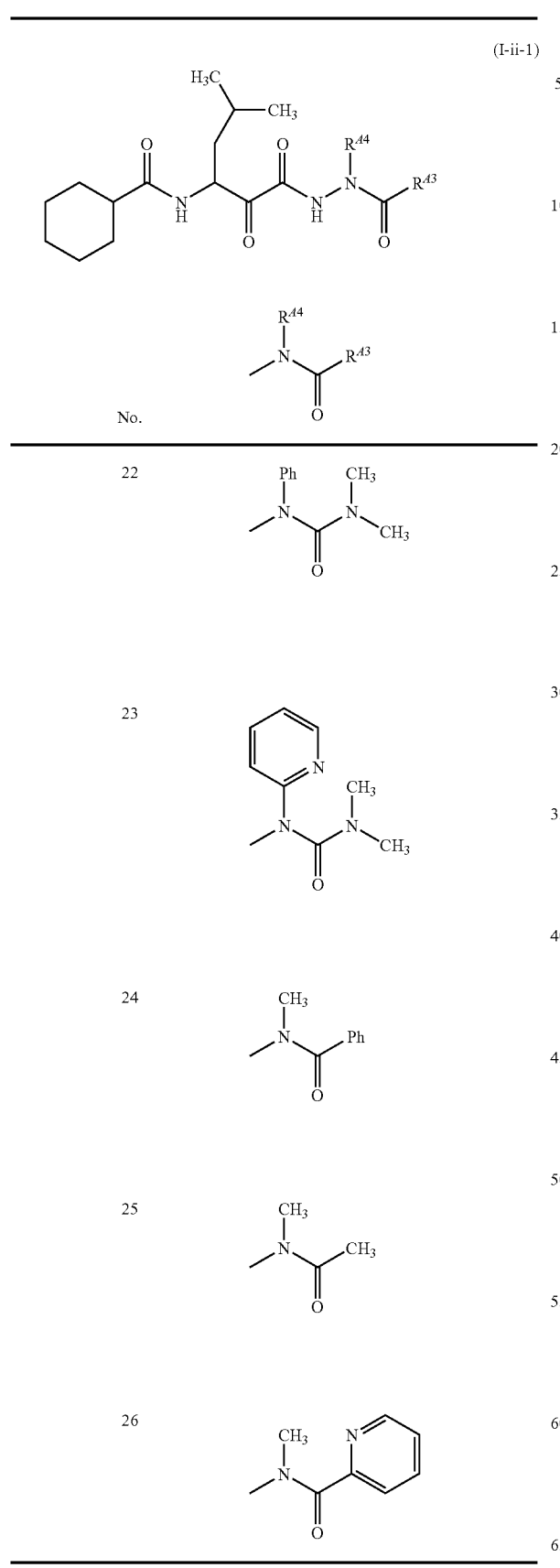
TABLE 8
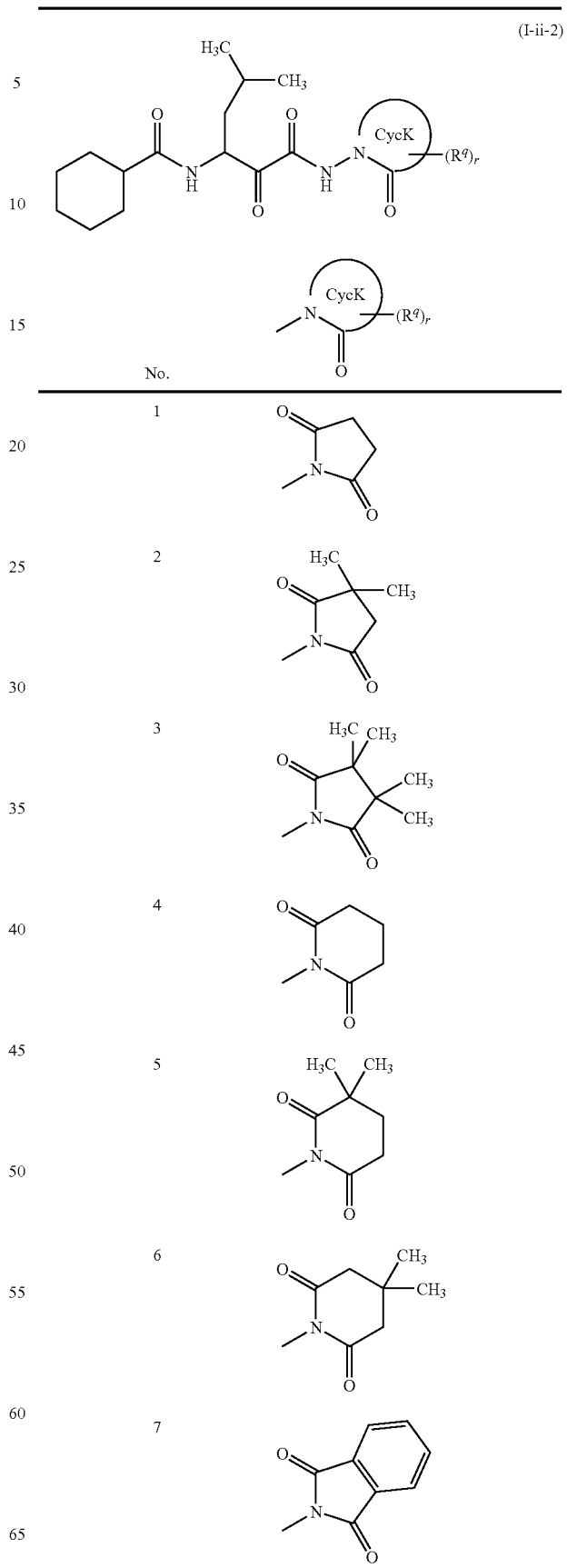

TABLE 8-continued
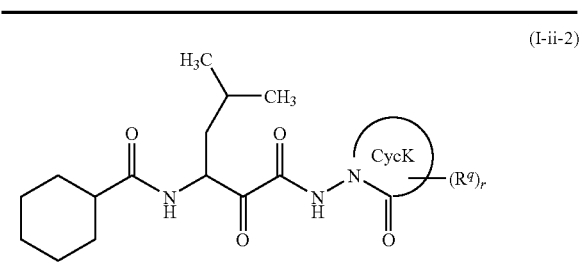
(I-ii-2)
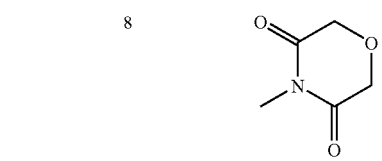
| No. | |
|---|---|
| 8 | 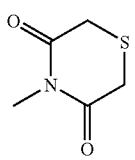 |
| 9 | 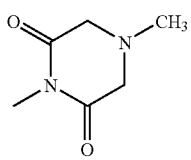 |
| 10 | 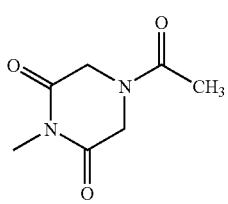 |
| 11 | 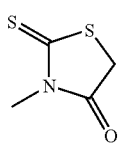 |
| 12 | 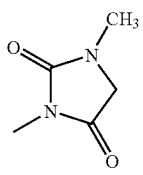 |
| 13 | 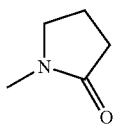 |
| 14 | |
TABLE 8-continued
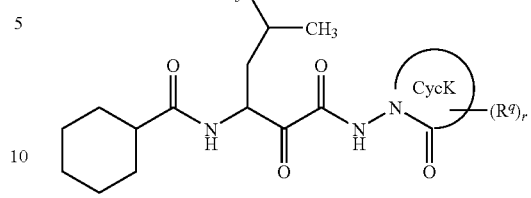
(I-ii-2)
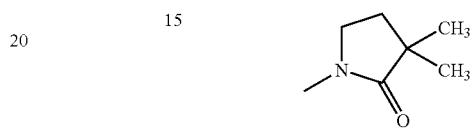
| No. | |
|---|---|
| 15 | 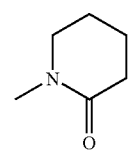 |
| 16 | 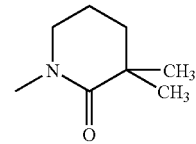 |
| 17 | |
| 18 | 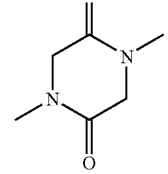 |
| 19 | 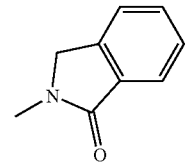 |
| 20 | 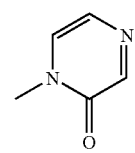 |
| 21 | 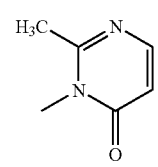 |

TABLE 8-continued
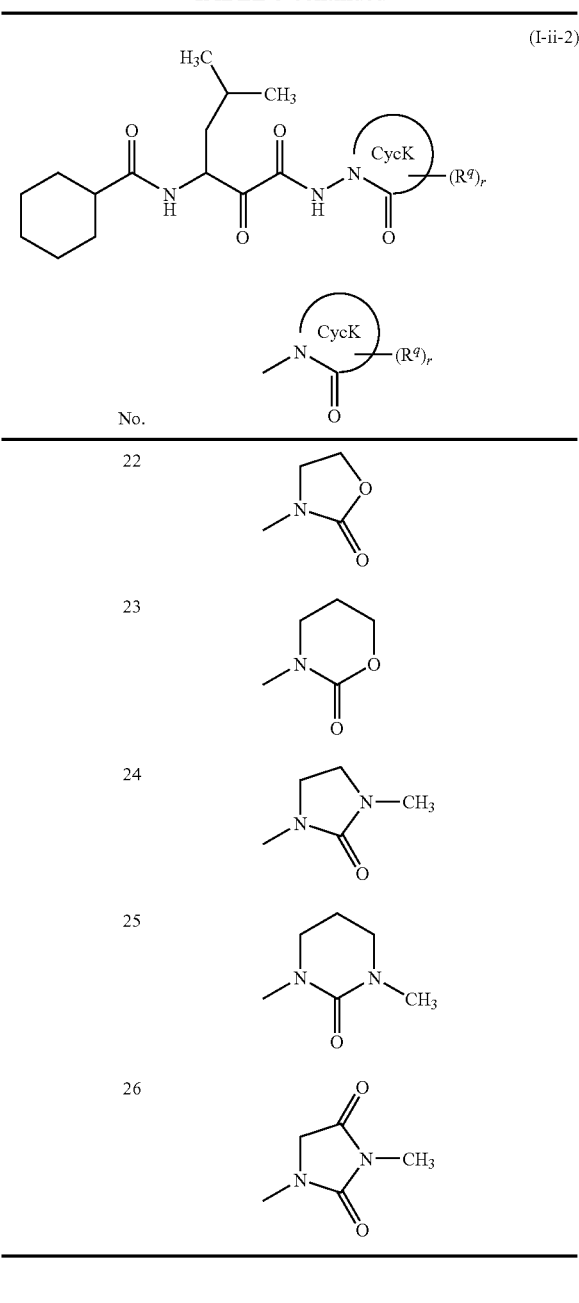
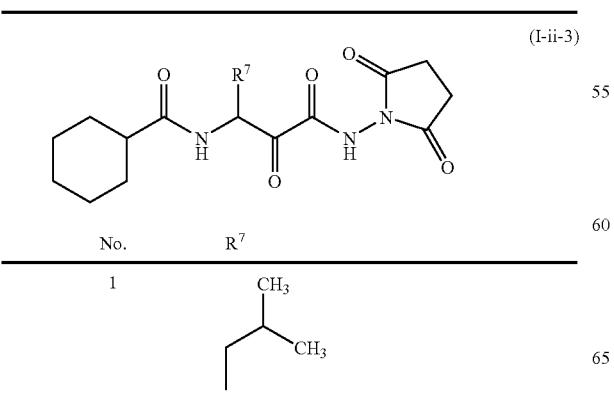
TABLE 9
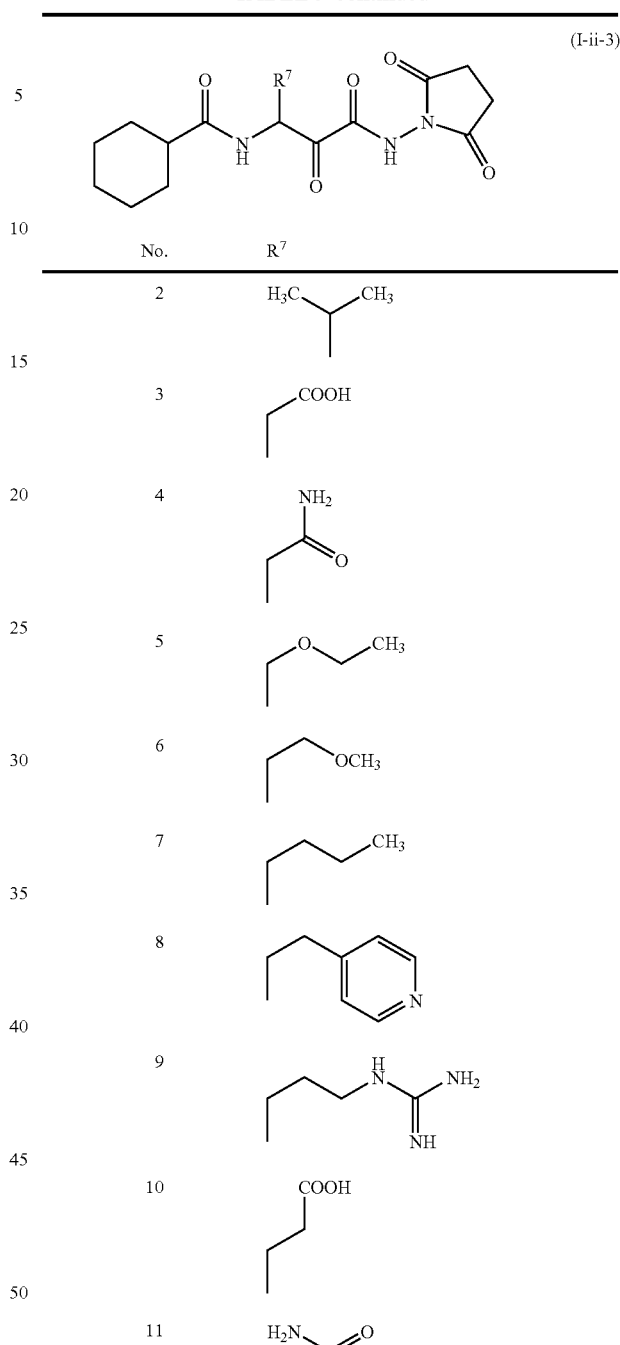
TABLE 9-continued
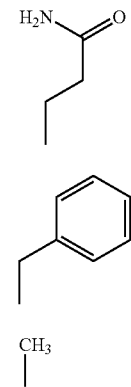

TABLE 9-continued
(I-ii-3)
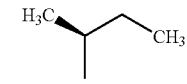
| No. | R⁷ |
|---|---|
| 14 | 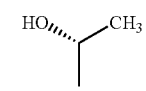 |
| 15 | H |
| 16 | 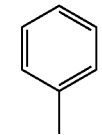 |
| 17 |  |
| 18 | 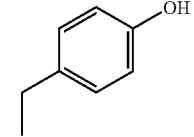 |
| 19 | 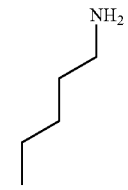 |
| 20 | 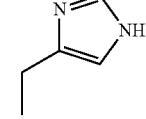 |
| 21 | 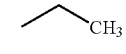 |
| 22 | 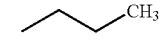 |
| 23 | 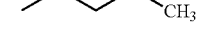 |
| 24 |  |
| 25 |  |
| 26 | 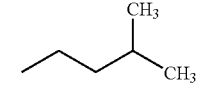 |
| 27 | 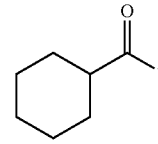 |
TABLE 9-continued
(I-ii-3)
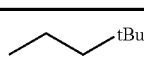
| No. | R⁷ |
|---|---|
| 28 | 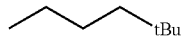 |
| 29 | 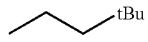 |
| 30 | 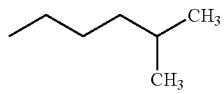 |
| 31 | 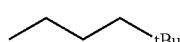 |
| 32 | 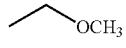 |
| 33 | 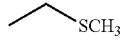 |
| 34 | 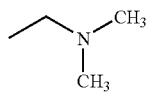 |
| 35 | 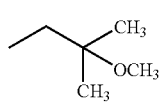 |
| 36 | 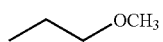 |
| 37 | 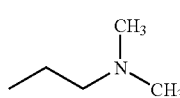 |
| 38 | 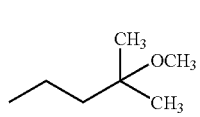 |
| 39 |  |
| 40 |  |
| 41 | 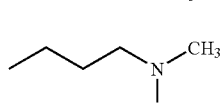 |
| 42 | 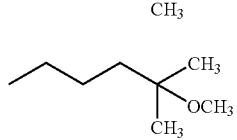 |

TABLE 9-continued
(I-ii-3)
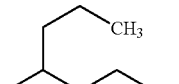
| No. | R⁷ |
|---|---|
| 43 |  |
| 44 |  |
| 45 |  |
| 46 |  |
| 47 |  |
| 48 |  |
| 49 |  |
| 50 |  |
| 51 |  |
| 52 |  |
| 53 |  |
| 54 | 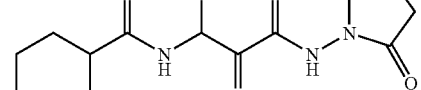 |
TABLE 9-continued
(I-ii-3)
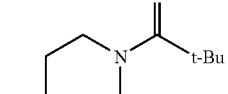
| No. | R⁷ |
|---|---|
| 55 | 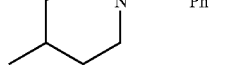 |
| 56 | 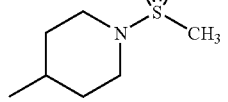 |
| 57 | 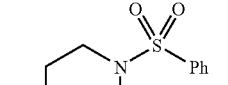 |
| 58 | 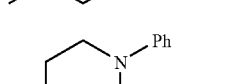 |
| 59 |  |
| 60 | 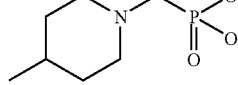 |
| 61 | 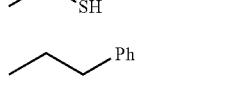 |
| 62 | 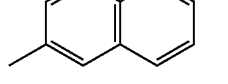 |
| 63 | 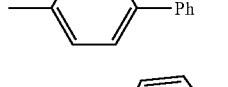 |
| 64 | 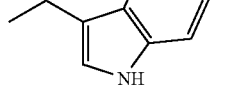 |
| 65 |  |

TABLE 9-continued
 (I-ii-3)
| No. | R⁷ |
|---|---|
| 66 | 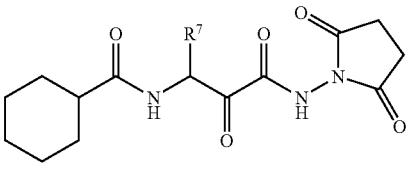 |
TABLE 10
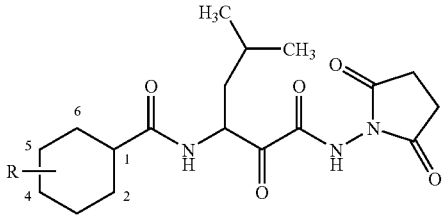 (I-ii-5)
| No. | R |
|---|---|
| 1 | 1- 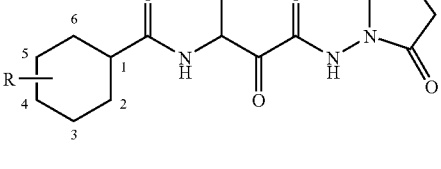 |
| 2 | 1- 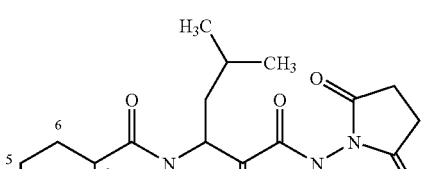 |
| 3 | 1- 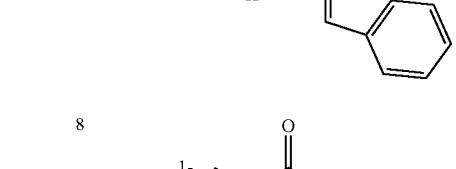 |
| 4 | 1- 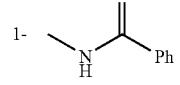 |
| 5 | 1- 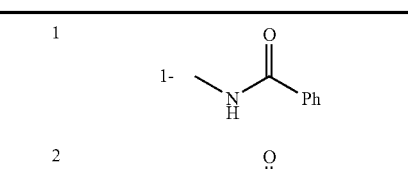 |
| 6 | 1- 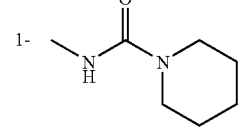 |
TABLE 10-continued
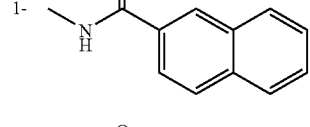 (I-ii-5)
| No. | R |
|---|---|
| 7 | 1- 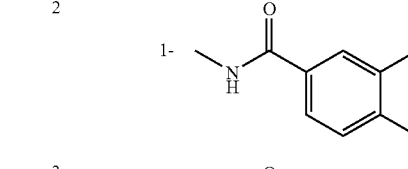 |
| 8 | 1- 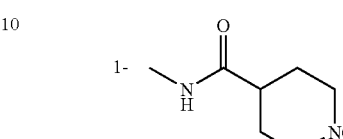 |
| 9 | 1- 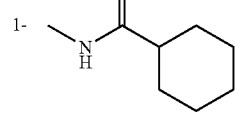 |
| 10 | 1- 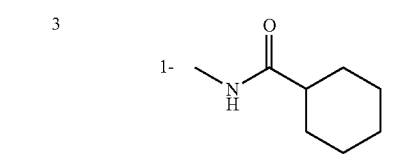 |
| 11 | 1- 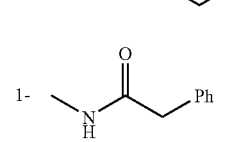 |
| 12 | 1- 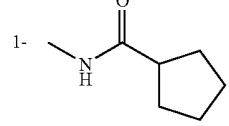 |
| 13 | 2- 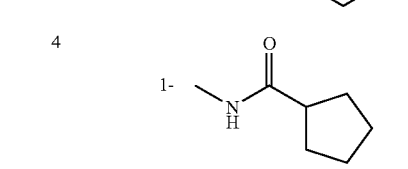 |
| 14 | 2- 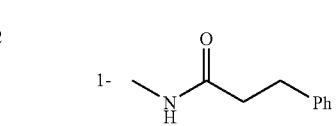 |

TABLE 10-continued
(I-ii-5)
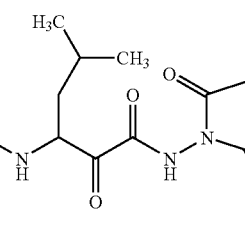
| No. | R |
|---|---|
| 15 | 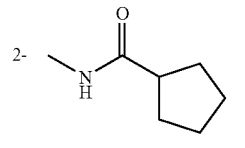 |
| 16 | 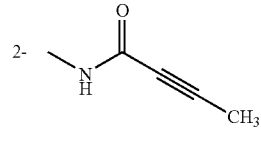 |
| 17 | 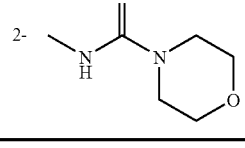 |
| 18 | 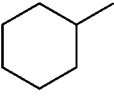 |
TABLE 11
(I-ii-6)
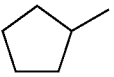
| No. | R$^{16}$ |
|---|---|
| 1 | 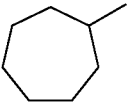 |
| 2 | 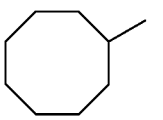 |
| 3 | 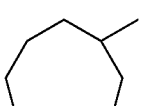 |
| 4 | 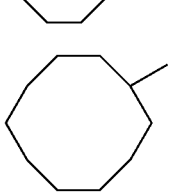 |
| 5 |  |
| 6 |  |
| 7 | 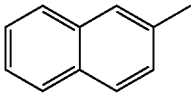 |
| 8 | 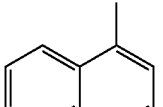 |
| 9 | 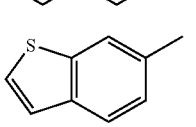 |
| 10 | 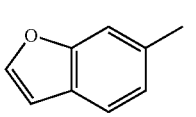 |
| 11 | 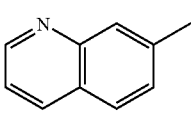 |
| 12 | 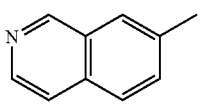 |
| 13 | |
| 14 | |

TABLE 11-continued (I-ii-6)

| No. | R^16 |
|-----|------|
| 15 | Ph-CH2- |
| 16 | tBu-O- |
| 17 | Ph-CH2-O- |
| 18 | H3CO- |
| 19 | cyclopentyl-O- |
| 20 | tBu-CH2-O- |
| 21 | 2-methyl-3-ethyl-4-oxo-pyrimidinyl |
| 22 | 2-phenyl-3-ethyl-4-oxo-pyrimidinyl |
| 23 | 2-(cyclohexylmethyl)-3-ethyl-4-oxo-pyrimidinyl |
| 24 | adamantyl-CH2- |
| 25 | adamantyl- |
| 26 | 2-thienyl-(CH2)3- |

TABLE 11-continued (I-ii-6)

| No. | R^16 |
|-----|------|
| 27 | piperidinyl-(CH2)2- |
| 28 | benzothiophen-2-yl |
| 29 | benzofuran-2-yl |
| 30 | Cl3C-CH2-O- |
| 31 | cyclopentyl-CH2-CH2- |
| 32 | (CH3)3C-CH=CH- |
| 33 | (CH3)2C(CH3)-CH2-CH2- |
| 34 | (CH3)2CH-CH(CH3)-O- |
| 35 | (CH3)3C-CH2-O- |

TABLE 12
(I-iii-1)
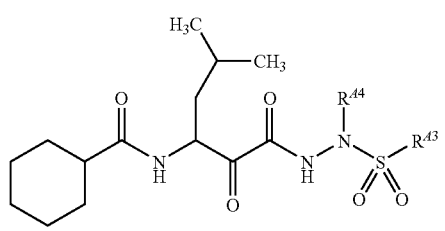
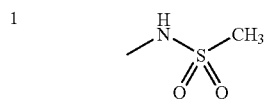
| No. | |
|---|---|
| 1 | 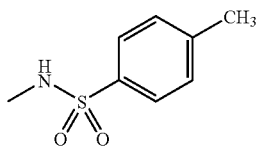 |
| 2 | 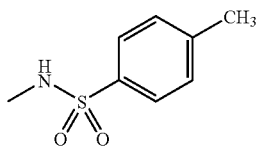 |
| 3 | 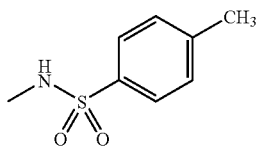 |
| 4 | 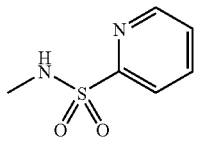 |
| 5 | 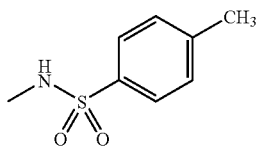 |
| 6 | 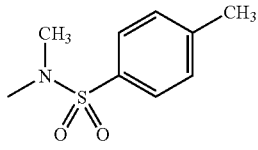 |
| 7 | 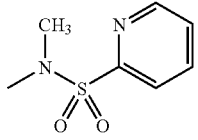 |
| 8 | 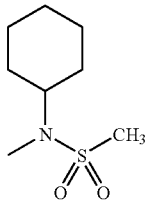 |
TABLE 12-continued
(I-iii-1)
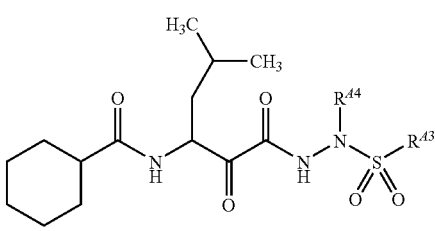
| No. | |
|---|---|
| 9 | 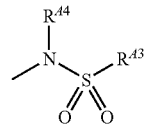 |
| 10 | 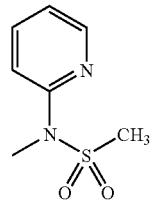 |
TABLE 13
(I-iii-2)
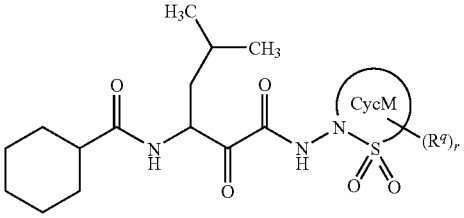
| No. | |
|---|---|
| 1 | 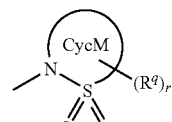 |
| 2 | 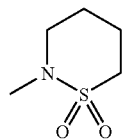 |
| 3 | 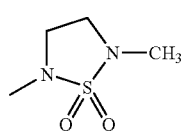 |

TABLE 13-continued
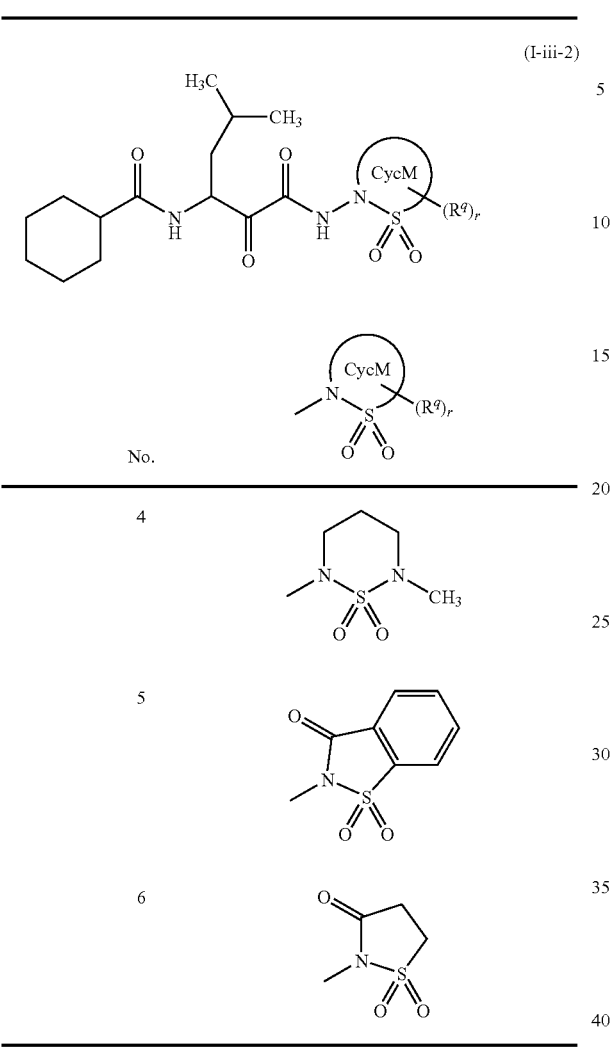
| No. | |
|---|---|
| 4 | |
| 5 | |
| 6 | |
TABLE 14
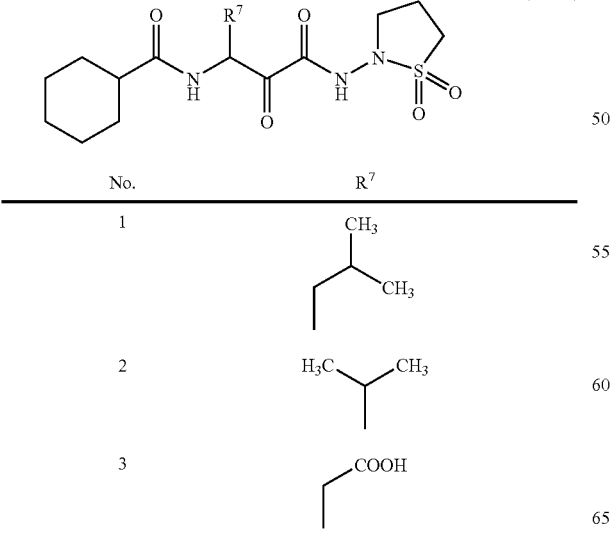
| No. | R⁷ |
|---|---|
| 1 | |
| 2 | |
| 3 | |
TABLE 14-continued
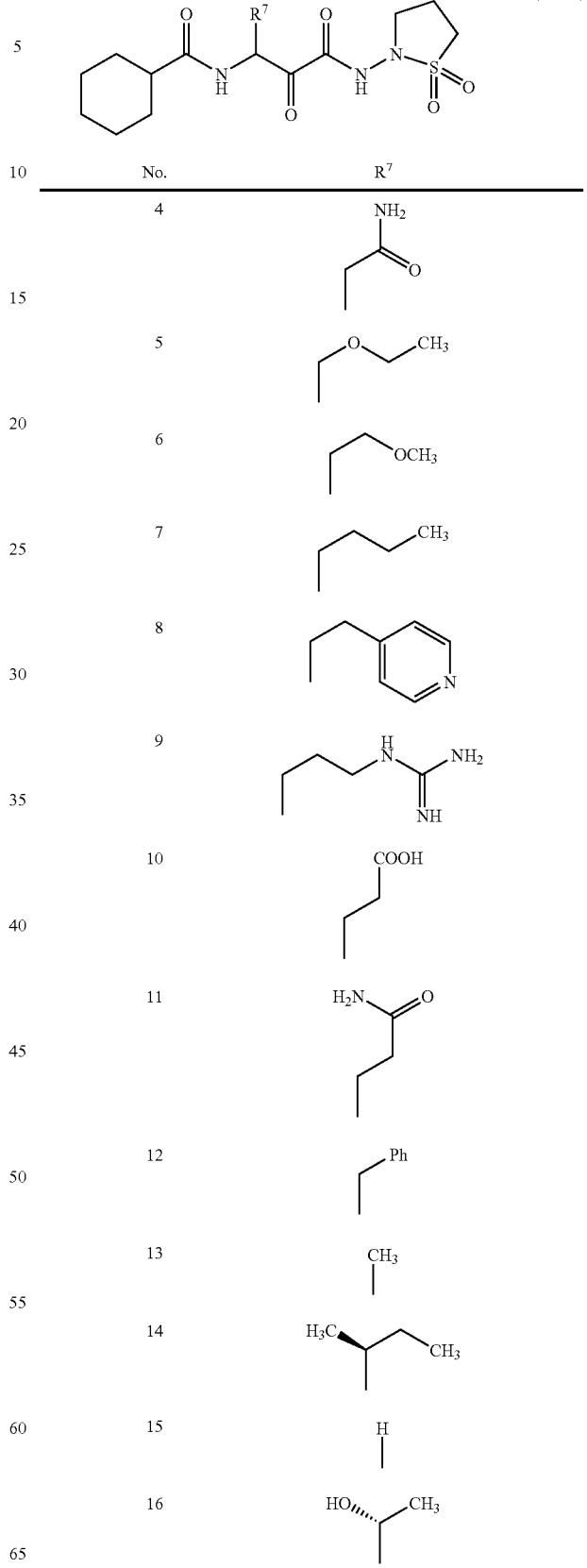
| No. | R⁷ |
|---|---|
| 4 | |
| 5 | |
| 6 | |
| 7 | |
| 8 | |
| 9 | |
| 10 | |
| 11 | |
| 12 | Ph |
| 13 | |
| 14 | |
| 15 | H |
| 16 | |

TABLE 14-continued (I-iii-3)

Structure: Cyclohexyl-C(=O)-NH-CH(R⁷)-C(=O)-C(=O)-NH-N(sulfonyl ring, isothiazolidine 1,1-dioxide)

| No. | R⁷ |
|---|---|
| 17 | CH₂-Ph |
| 18 | CH₂CH₂OH |
| 19 | CH₂-(4-hydroxyphenyl)-ethyl |
| 20 | (CH₂)₄NH₂ |
| 21 | CH₂-(1H-imidazol-4-yl) |
| 22 | CH₂CH₂CH₃ |
| 23 | (CH₂)₃CH₃ |
| 24 | (CH₂)₄CH₃ |
| 25 | (CH₂)₅CH₃ |
| 26 | CH₂CH(tBu) |
| 27 | CH₂CH(CH₃)CH₂CH₃ |
| 28 | CH₂CH₂CH₂tBu |
| 29 | CH₂CH₂CH(CH₃)CH₂CH₃ |
| 30 | CH₂CH₂CH₂CH₂tBu |
| 31 | CH₂CH₂OCH₃ |
| 32 | CH₂CH₂SCH₃ |
| 33 | CH₂CH₂N(CH₃)₂ |
| 34 | CH₂C(CH₃)(OCH₃)CH₂CH₃ |
| 35 | CH₂CH₂CH₂OCH₃ |
| 36 | CH₂CH₂CH₂N(CH₃)₂ |
| 37 | CH₂CH₂C(CH₃)₂OCH₃ |
| 38 | (CH₂)₄OCH₃ |
| 39 | (CH₂)₄SCH₃ |
| 40 | (CH₂)₄N(CH₃)₂ (propyl linker) |
| 41 | CH₂CH₂C(CH₃)(OCH₃)CH₂CH₂CH₃ |
| 42 | CH₂CH(CH₂CH₃)CH(CH₃)₂ |
| 43 | CH₂CH₂CH(CH₂CH₃)CH₂CH₂CH₃ |
| 44 | CH₂-cyclopropyl |
| 45 | CH₂-cyclobutyl |
| 46 | CH₂-cyclopentyl |

TABLE 14-continued
(I-iii-3)
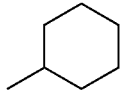
| No. | R⁷ |
|---|---|
| 47 | 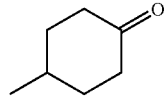 |
| 48 | 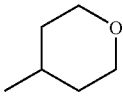 |
| 49 | 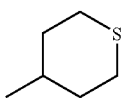 |
| 50 | 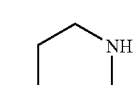 |
| 51 | 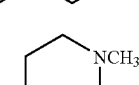 |
| 52 | 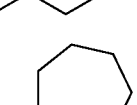 |
| 53 | 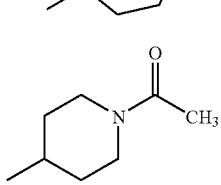 |
| 54 | 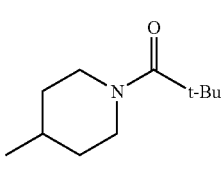 |
| 55 | 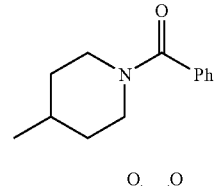 |
| 56 | 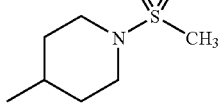 |
| 57 | 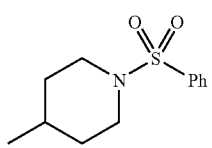 |
TABLE 14-continued
(I-iii-3)
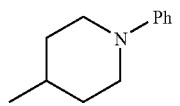
| No. | R⁷ |
|---|---|
| 58 | 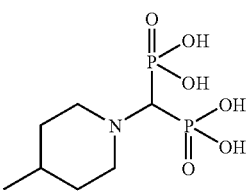 |
| 59 |  |
| 60 | 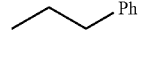 |
| 61 | 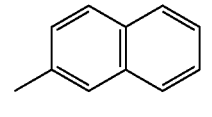 |
| 62 | 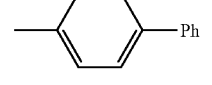 |
| 63 | 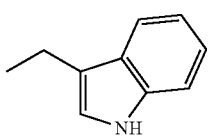 |
| 64 | 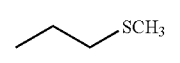 |
| 65 | |
| 66 | |

TABLE 15
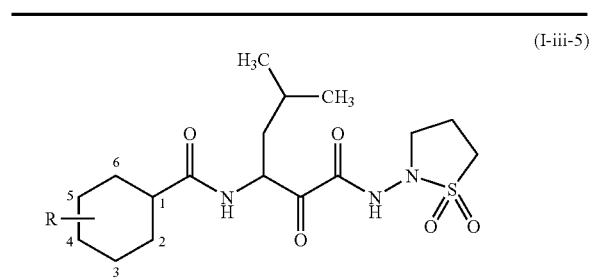
(I-iii-5)
| No. | R |
|---|---|
| 1 | 1- —NH—C(=O)—Ph |
| 2 | 1- —NH—C(=O)-(naphthalen-2-yl) |
| 3 | 1- —NH—C(=O)-cyclohexyl |
| 4 | 1- —NH—C(=O)-cyclopentyl |
| 5 | 1- —NH—C(=O)—C≡C—CH₃ |
| 6 | 1- —NH—C(=O)-morpholin-4-yl |
| 7 | 1- —NH—C(=O)-(benzothiophen-2-yl) |
| 8 | 1- —NH—C(=O)-(benzofuran-2-yl) |
TABLE 15-continued
(I-iii-5)
| No. | R |
|---|---|
| 9 | 1- —NH—C(=O)-piperidin-1-yl |
| 10 | 1- —NH—C(=O)-(1-methylpiperidin-4-yl) |
| 11 | 1- —NH—C(=O)—CH₂—Ph |
| 12 | 1- —NH—C(=O)—CH₂CH₂—Ph |
| 13 | 2- —NH—C(=O)—Ph |
| 14 | 2- —NH—C(=O)-(naphthalen-2-yl) |
| 15 | 2- —NH—C(=O)-cyclohexyl |
| 16 | 2- —NH—C(=O)-cyclopentyl |
| 17 | 2- —NH—C(=O)—C≡C—CH₃ |

TABLE 15-continued
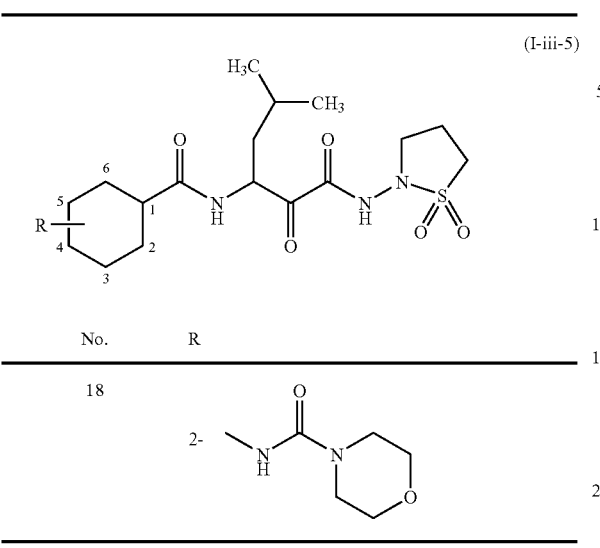
(I-iii-5)
| No. | R |
|---|---|
| 18 | 2- (N-methylcarbamoyl morpholine) |
TABLE 16
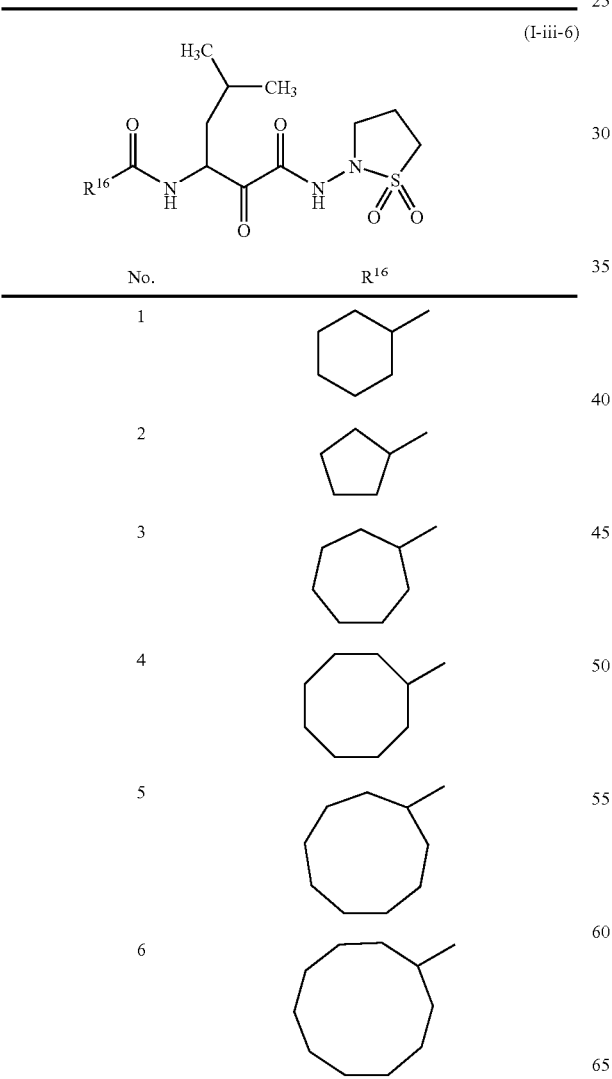
(I-iii-6)
| No. | R16 |
|---|---|
| 1 | cyclohexyl |
| 2 | cyclopentyl |
| 3 | cycloheptyl |
| 4 | cyclooctyl |
| 5 | cyclononyl |
| 6 | cyclodecyl |
TABLE 16-continued
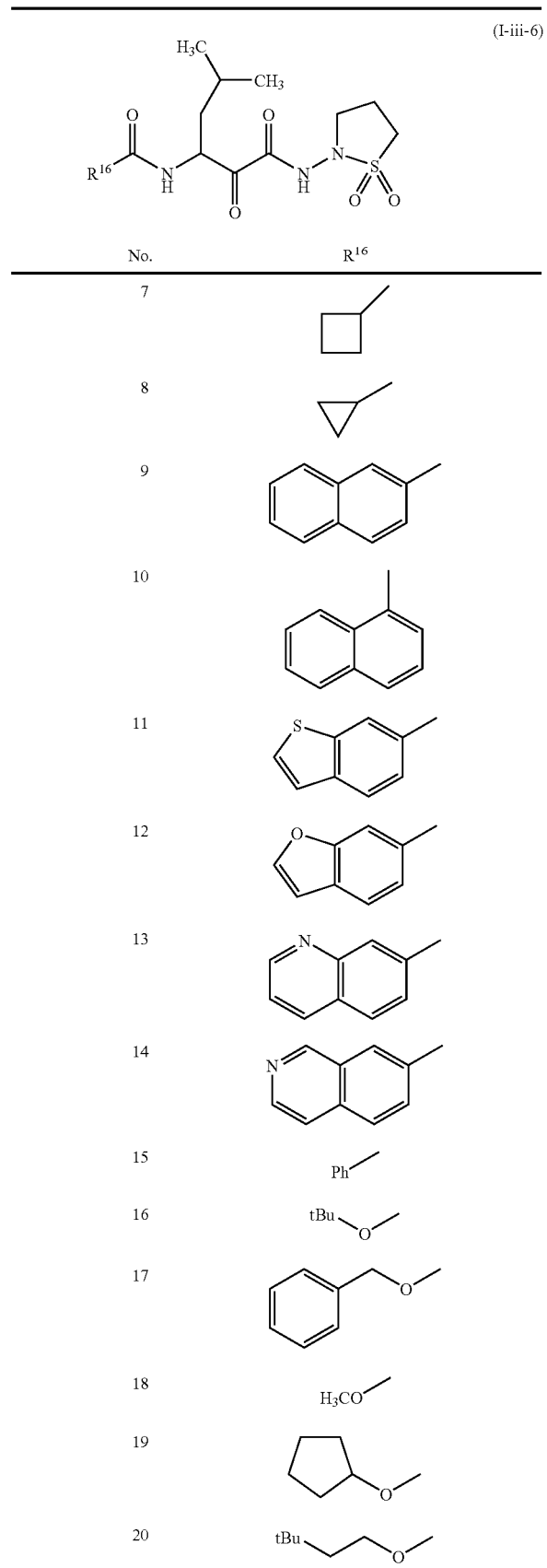
(I-iii-6)
| No. | R16 |
|---|---|
| 7 | cyclobutyl |
| 8 | cyclopropyl |
| 9 | 2-naphthyl |
| 10 | 1-naphthyl |
| 11 | benzothiophene |
| 12 | benzofuran |
| 13 | quinoline |
| 14 | isoquinoline |
| 15 | Ph |
| 16 | tBu—O |
| 17 | PhCH2—O |
| 18 | H3CO |
| 19 | cyclopentyl-O |
| 20 | tBu—CH2CH2—O |

TABLE 16-continued (I-iii-6)

[Structure: R16-NH-C(=O)-NH-CH(CH2CH(CH3)2)-C(=O)-C(=O)-NH-N(SO2-cyclic isothiazolidine 1,1-dioxide)]

| No. | R16 |
|---|---|
| 21 | 2-methyl-3-ethyl-4-oxo-3,4-dihydropyrimidin-(yl)methyl (pyrimidinone with CH3 at 2, ethyl on N, =O at 4) |
| 22 | 2-phenyl-3-ethyl-4-oxo-3,4-dihydropyrimidinyl |
| 23 | 2-(cyclohexylmethyl)-3-ethyl-4-oxo-3,4-dihydropyrimidinyl |
| 24 | adamantylethyl |
| 25 | adamantylmethyl |
| 26 | 2-thienylbutyl |
| 27 | 3-(piperidin-1-yl)propyl |
| 28 | 2-methylbenzothiophen-3-yl-methyl |
| 29 | 2-methylbenzofuran-3-yl-methyl |
| 30 | $CCl_3CH_2OCH_3$ related (trichloro methoxy) |
| 31 | 2-cyclopentylethyl |
| 32 | 3-methylbut-1-en-... (H3C)2C-CH=CH- |
| 33 | (CH3)2C(CH3)-CH2CH2- |
| 34 | (CH3)2CH-CH(OCH3)- |
| 35 | (CH3)2C(CH3)-CH2-O- |

In the present invention, isomers are included unless specified. For example, alkyl, alkoxy, alkylthio, alkenyl, alkynyl, and alkylene and alkenylene include straight and branched ones. Furthermore, the present invention includes isomers in double bond, ring, fused ring (E, Z, cis, trans), isomers by the presence of asymmetric carbon etc. (R, S, α, β, enantiomer, diastereomer), optical isomers having optical rotation (D, L, d, l, +, −), polars by chromatography separation (more polar, less polar), equilibrium compound, a compound of arbitrary ratios of those and racemic mixture.

[Salts]

The compounds of formula (I) of the present invention may be converted into corresponding pharmaceutically acceptable salts by conventional methods. In the present specification, pharmaceutically acceptable salts include alkali metal salts, alkaline earth metal salts, amine salts, acid-addition salts, etc. and corresponding quaternary ammonium salts when the compound of formula (I) contains amino acid residues.

Non-toxic and water-soluble salts are preferable as pharmaceutically acceptable salts. Appropriate pharmaceutically acceptable salts include salts of alkali metals (potassium, sodium, etc.), salts of alkaline earth metals (calcium, magnesium, etc.), ammonium salts and salts of pharmaceutically acceptable organic amines (tetramethyl ammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc. and preferably alkali metal salts.

Non-toxic, water-soluble acid-addition salts are preferable. Appropriate acid-addition salts are, inorganic salts such as hydrochloride, hydrobromide, sulfate, phosphate, nitrate, or organic salts such as acetate, trifluoroacetate, lactate, tartrate, oxalate, fumarate, malate, citrate, benzoate, methanesulfonate, ethanesulfonate, benzenesulfonate, toluenesulfonate, isethionate, glucuronate, gluconate.

The compounds of formula (I) of the present invention or a salt thereof may be converted into a solvate of water, ethanol, etc. by a conventional method.

The compounds of formula (I) of the present invention may also be converted into N-oxide compounds or S-oxide compounds by a conventional method.

[Methods for the Preparation of the Compound of the Present Invention]

[1] In the compound of formula (I), the compound wherein none of R, $AA^1$, $AA^2$, $R^7$, $R^8$ $R^9$, $R^{10}$, $R^X$ or $R^Y$ includes carboxy, hydroxy, amino, mercapto, guanidino, phosphono, i.e. the compound of formula (IA)

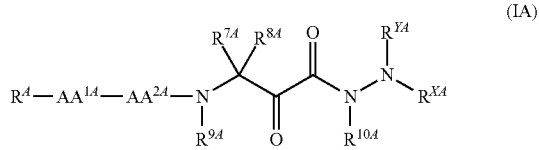

(IA)

(wherein $R^A$, $AA^{1A}$, $AA^{2A}$, $R^{7A}$, $R^{8A}$, $R^{9A}$, $R^{10A}$, $R^{XA}$, $R^{YA}$ are each the same meaning as R, $AA^1$, $AA^2$, $R^7$, $R^8$, $R^9$, $R^{10}$, $R^X$, $R^Y$ but none of them includes carboxy, hydroxy, amino, mercapto, guanidino, amidino, phosphono) may be prepared according to the method of the following (A), (B) and (C).

(A) The compound of formula (IA) may be prepared by subjecting to oxidation reaction the compound of formula (II)

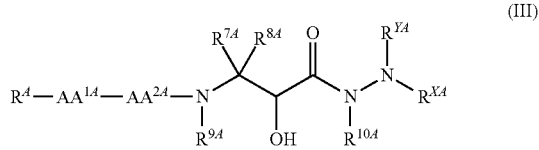

(III)

(wherein all symbols have the same meaning as described hereinbefore).

This oxidation reaction is known, for example,
(1) a method of Swern oxidation,
(2) a method utilizing Dess-Martin reagent, and
(3) a method utilizing TEMPO reagent, etc. may be included.

To describe them concretely,
(1) the method of Swern oxidation is, for example, carried out in an inert organic solvent (chloroform, methylene chloride, etc.) subjecting to a reaction oxalyl chloride and dimethylsulfoxide at −78° C. and then subjecting to a reaction the obtained solution with an alcohol compound, and then subjecting to a reaction with a tertiary amine (triethyl amine etc.) at a temperature of −78 to 20° C.

(2) the method utilizing Dess-Martin reagent is, for example, carried out in an inert organic solvent (chloroform, dichloromethane, etc.) in the presence of Dess-Martin reagent (1,1,1-triacetoxy-1,1-dihydro-1,2-benzoiodoxol-3-(1H)-one) at a temperature of 0 to 40° C.

(3) the method utilizing TEMPO reagent is, for example, carried out in an inert organic solvent (chloroform, dichloromethane, etc.), in the presence of TEMPO reagent (2,2,6,6-tetramethyl-1-piperidinyloxy, free radical) at a temperature of 20 to 60° C.

These reactions of (1), (2) and (3) are desirably carried out under the atmosphere of an inert gas (argon, nitrogen, etc.).

The present invention further includes other oxidation reactions which oxidizes alcohol to ketone easily and selectively. For example, Jones oxidation, oxidation by pyridinium chlorochromate (PCC), sulfur trioxide-pyridine complex or ones described in "Comprehensive Organic Transformations" (Richard C. Larock, VCH Publishers, Inc., (1989) 604-614) may be used.

(B) The compound of formula (IA) may be prepared by subjecting to amidation reaction the compound of formula (III)

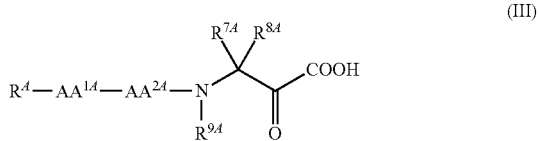

(III)

(wherein all symbols have the same meaning as described hereinbefore) and the compound of formula (IV)

(IV)

(wherein all symbols have the same meaning as described hereinbefore).

Amidation reaction is known, for example,
(1) a method using acid halide,
(2) a method using mixed anhydride,
(3) a method using a condensing agent etc.

To explain these methods concretely,
(1) the method using acid halide is carried out, for example, by subjecting to a reaction carboxylic acid and acid-halogenating agent (oxalyl chloride, thionyl chloride, etc.) in an organic solvent (chloroform, methylene chloride, diethyl ether, tetrahydrofuran, etc.) or without a solvent, between −20° C. and refluxing temperature, and then subjecting thus obtained acid halide to a reaction with amine in the presence of base (pyridine, triethylamine, dimethylaniline, dimethylaminopyridine, etc.) in an inert organic solvent (chloroform, methylene chloride, diethyl ether, tetrahydrofuran, etc.) at a temperature of 0 to 40° C. Alternatively, it may be carried out by subjecting to a reaction with acid halide in an organic solvent (dioxane, tetrahydrofuran, etc.) using an aqueous alkali solution (an aqueous solution of sodium bicarbonate or sodium hydroxide, etc.) at a temperature of 0 to 40° C.

(2) In a method where mixed anhydride is used, for example, carboxylic acid is subjected to a reaction with acid halide (pivaloyl chloride, tosyl chloride, mesylchloride, etc.) or acid derivative (chloroethyl formate, chloroisobutyl formate, etc.) in an organic solvent (chloroform, methylene chloride, diethyl ether, tetrahydrofuran, etc.) or without a solvent, in the presence of a base (pyridine, triethylamine, dimethylaniline, dimethylaminopyridine, diisopropylethylamine, etc.), at a temperature of 0 to 40° C., and then thus obtained mixed anhydride is subjected to a reaction with amine in an organic solvent (chloroform, methylene chloride, diethyl ether, tetrahydrofuran, etc.) at a temperature of 0 to 40° C.

(3) In a method where a condensing agent is used, for example, carboxylic acid is subjected to a reaction with amine in an organic solvent (chloroform, methylene chloride, dimethylformamide, diethyl ether, tetrahydrofuran, etc.) or without a solvent, in the presence or absence of a base (pyridine, triethylamine, dimethylaniline, dimethylaminopyridine, etc.), using a condensing agent (1,3-dicyclohexylcarbodiimide (DCC), 1-ethyl-3-[3-(dimethyl amino)propyl]carbodiimide (EDC), 1,1'-carbonyldiimidazole (CDI), 2-chloro-1-methylpyridinium iodide, 1-propanephosphonic acid cyclic anhydride (PPA), etc.) in the presence or absence of 1-hydroxybenzotriazole (1-HOBt), at a temperature of 0 to 40° C.

The reactions (1), (2) and (3) are desirably carried out under atmosphere of inert gas (argon, nitrogen, etc.) and anhydrous conditions.

(C) In the compound of formula (IA), the compound of formula (IA-i)

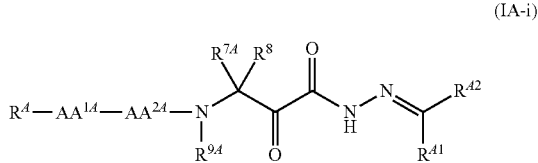

(IA-i)

(wherein all symbols have the same meaning as described hereinbefore) may be prepared according to the method described in the following reaction scheme 1.

Reaction Scheme 1

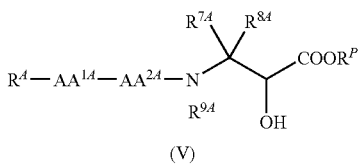

(V)

↓ oxidation

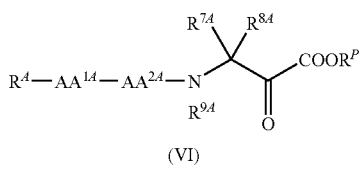

(VI)

deprotection ↙   ↘ $H_2N-NH_2$

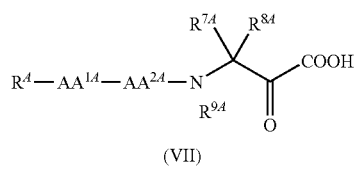     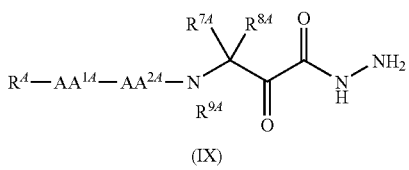

(VII)                    (IX)

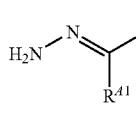     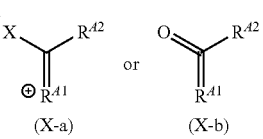

(VIII)                  (X-a)   (X-b)

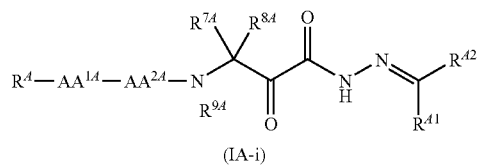

(IA-i)

In the reaction scheme 1, X is a eliminating group (halogen, methylthio, ethylthio, methanesulfonyloxy, toluenesulfonyloxy, trifluoromethylsulfonyl, etc.), and $R^P$ is a protective group of esters.

The compound of formula (IA-ii)

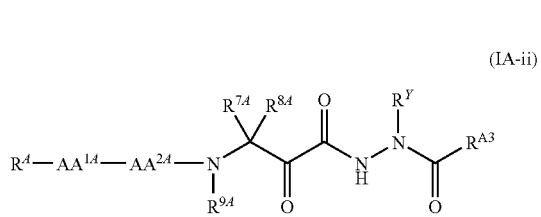

(IA-ii)

(wherein all symbols have the same meaning as described hereinbefore) and the compound of formula

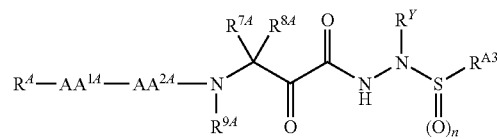

(IA-iii)

(wherein all symbols have the same meaning as described hereinbefore) may be prepared according to the method described in reaction scheme 2.

Reaction scheme 2

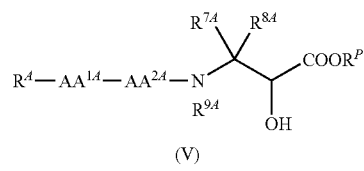

(V)

↓ oxidation

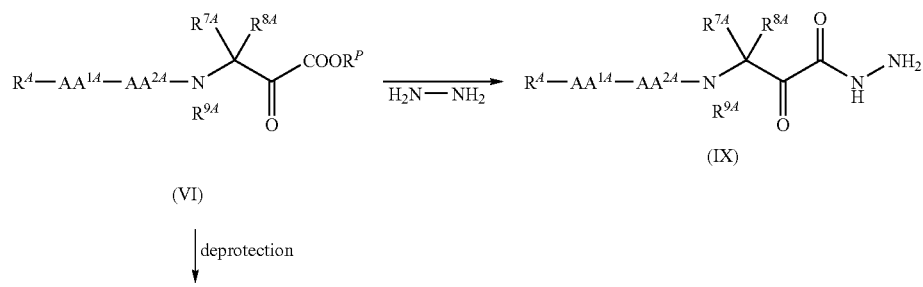

(VI)    (IX)

↓ deprotection

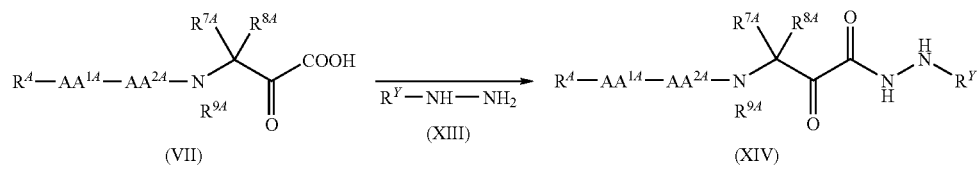

(VII)    (XIII)    (XIV)

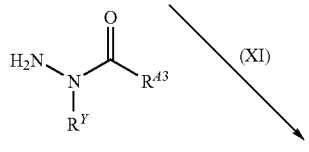 (XI)    (XV) 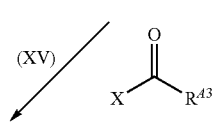

-continued

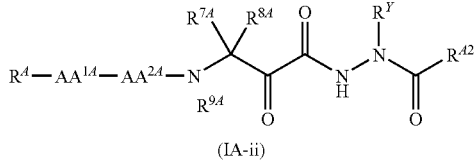

(IA-ii)

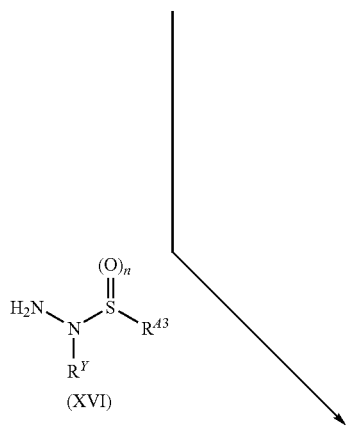

(XVI)

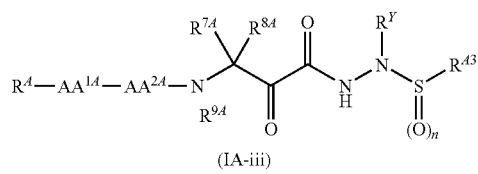

(XVII)

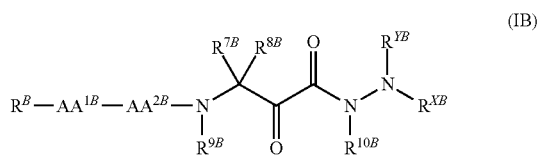

(IA-iii)

In the reaction scheme 2, all symbols have the same meaning as described hereinbefore.

[2] In the compound of formula (I). the compound wherein at least one of R, $AA^1$, $AA^2$, $R^7$, $R^8$, $R^9$, $R^{10}$, $R^X$ or $R^Y$ includes carboxy, hydroxy, amino, mercapto, guanidino, amidino or phosphono, i.e. the compound of formula (IB)

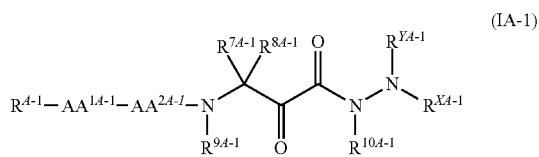

(IB)

(wherein $R^B$, $AA^{1B}$, $AA^{2B}$, $R^{7B}$, $R^{8B}$, $R^{9B}$, $R^{10B}$, $R^{XB}$ and $R^{YB}$ have the same meaning as R, $AA^1$, $AA^2$, $R^7$, $R^8$, $R^9$, $R^{10}$, $R^X$ and $R^Y$ respectively, and among them at least one group includes carboxy, hydroxy, amino, mercapto, guanidino, amidino or phosphono) may be prepared by subjecting to deprotection reaction the compound of formula (IA), in which at least one group of R, $AA^1$, $AA^2$, $R^7$, $R^8$, $R^9$, $R^{10}$, $R^X$, $R^Y$ includes a protective group of carboxy, hydroxy, amino, mercapto, guanidino, amidino or phosphono, i.e. the compound of formula (IA-1)

(IA-1)

(wherein $R^{A-1}$, $AA^{1A-1}$, $AA^{2A-1}$, $R^{7A-1}$, $R^{8A-1}$, $R^{9A-1}$, $R^{10A-1}$, $R^{XA-1}$ and $R^{YA-1}$ has the same meaning as $R^A$, $AA^{1A}$, $AA^{2A}$, $R^{7A}$, $R^{8A}$, $R^{9A}$, $R^{10A}$, $R^{XA}$ and $R^{YA}$ respectively, among which at least one group includes a protective group of carboxy, hydroxy, amino, mercapto, guanidino, amidino or phosphono).

Protective groups for carboxy include, for example, methyl, ethyl, t-butyl, benzyl, etc.

Protective groups for hydroxy include, for example, methoxymethyl, 2-tetrahydropyranyl, t-butyldimethylsilyl, t-butyldiphenylsilyl, acetyl, benzyl, etc.

Protective groups for amino include, for example, benzyloxycarbonyl, t-butoxycarbonyl, trifluoroacetyl, 9-fluorenylmethoxycarbonyl, etc.

Protective groups for mercapto include, for example, benzyl, methoxybenzyl, methoxymethyl, 2-tetrahydropyranyl, diphenylmethyl, acetyl, etc.

Protective groups for guanidino and amidino include, for example, benzyloxycarbonyl, t-butoxycarbonyl, 9-fluorenylmethoxycarbonyl, etc.

Protective groups for carboxy, hydroxy, amino, mercapto, guanidino or amidino are not limited to the above groups, but those groups eliminated easily and selectively are also allowed. For example, the ones described in T. W. Greene, Protective Groups in Organic Synthesis, Wiley, New York, 1991 are used.

Protective groups for phosphono include, for example, C1-2 alkyl, phenyl, benzyl, 2,2,2-trichloroethyl and cyanoethyl.

Deprotection reactions of the protective groups of carboxy, hydroxy, amino, mercapto, guanidino, amidino or phosphono are well known, for example,
1) a deprotection reaction under alkaline conditions,
2) a deprotection reaction under acidic conditions,
3) a deprotection reaction by hydration,
4) a deprotection reaction of silyl-containing groups, etc. may be included.

To explain these methods concretely;
1) A deprotection reaction under alkaline conditions is carried out, for example, in an organic solvent (methanol, tetrahydrofuran, dioxane, dimethylformamide, etc.) using a hydroxide of alkali metals (sodium hydroxide, potassium hydroxide, lithium hydroxide, etc.), hydroxide of alkaline earth metals (barium hydroxide, calcium hydroxide, etc.), organic amine (triethylamine, N-methylmorpholine, diisopropylethylamine, piperidine, etc.) or a quaternary ammonium salt (tetrabutyl ammonium fluoride etc.) or a solution thereof or a mixture thereof at a temperature of 0 to 40° C.;
2) A deprotection reaction under acidic conditions is carried out, for example, in an organic solvent (methylene chloride, chloroform, dioxane, ethyl acetate, anisole, etc.), using organic acid (acetic acid, trifluoroacetic acid, methanesulfonic acid, etc.) or inorganic acid (hydrochloric acid, sulfuric acid, etc.) or a mixture thereof (hydrobromic acid/acetic acid, etc.) at a temperature of 0 to 100° C.;
3) A deprotection reaction by hydration is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles such as acetonitrile, amides such as dimethylformamide, water, ethyl acetate, acetic acid or a mixture of more than two from above, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

As easily understood by those skilled in the art, the compounds of the present invention may be easily prepared by selecting these reactions.
4) A deprotection reaction of silyl-containing group is carried out, for example, in a water-miscible organic solvent (tetrahydrofuran, acetonitrile, etc.) using tetrabutylammonium fluoride at a temperature of 0 to 40° C.

Deprotection reaction of protective groups of phosphono is well-known, for example,
(a) Elimination of C1-2 alkyl is carried out by subjecting to a reaction in an organic solvent (chloroform etc.), using halogenated trimethylsilyl (e.g. trimethylsilyl chloride, trimethylsilyl bromide, trimethylsilyl iodide, etc.) as a reagent, in the presence or absence of alkali metal iodide (e.g. sodium iodide, potassium iodide, etc.) at a temperature of 0 to 40° C.
(b) Elimination of phenyl is carried out by subjecting to a reaction under atmosphere of hydrogen, in an organic solvent (methanol, ethanol, tetrahydrofuran, etc.) or without a solvent, in the presence or absence of a catalyst (platinum oxide etc.) and an organic acid (acetic acid etc.) or inorganic acid (hydrochloric acid etc.) at a temperature of 0 to 50° C. for 24 hours to 3 days.
(c) Elimination of benzyl is carried out by subjecting to a reaction under atmosphere of hydrogen, in an organic solvent (methanol, ethanol, tetrahydrofuran, pyridine, acetic acid, etc.) in the presence or absence of a catalyst (palladium-carbon, palladium black, palladium hydroxide, etc.) at a temperature of 0 to 50° C.
(d) Elimination of 2,2,2-trichloroethyl is carried out in an organic solvent (methanol, ethanol, tetrahydrofuran, etc.) or without a solvent, using fine powder of zinc etc. and an organic acid (acetic acid etc.) or an inorganic acid (hydrochloric acid etc.) at a temperature of 0 to 50° C.
(e) Elimination of cyanoethyl is carried out in a solvent (water, methanol, ethanol, tetrahydrofuran, pyridine, etc.) or without a solvent in the presence of a base (trimethylamine, dimethylamine, t-butylamine, etc.) at a temperature of 0 to 100° C.

The compound of formula (II), an intermediate of the compound of the present invention may be prepared according to the method described in reaction scheme 3.

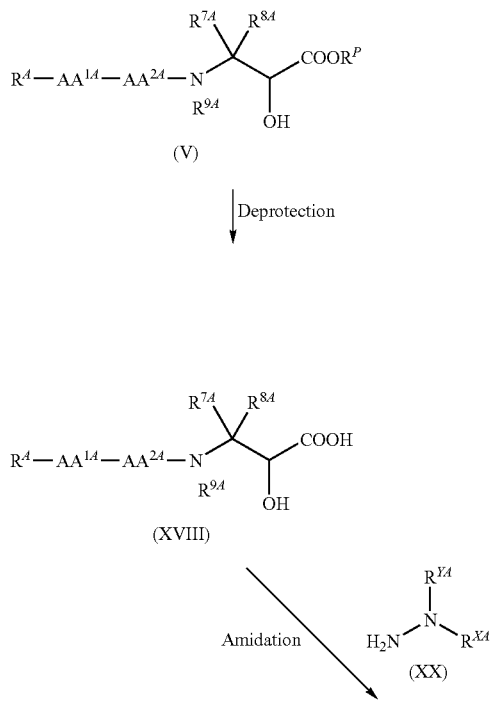

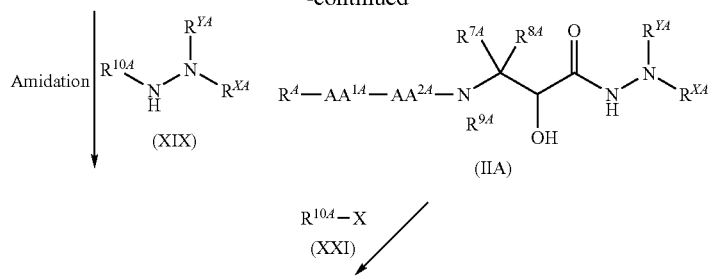
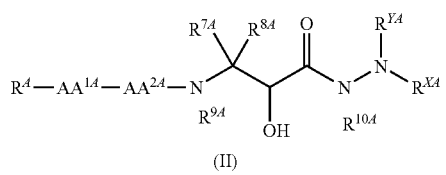
In the reaction scheme 3, all symbols have the same meaning as described hereinbefore.
In the compound of formula (IIA), the compound of formula (IIA-i)
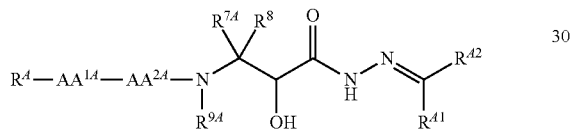
(wherein all symbols have the same meaning as described hereinbefore) may be prepared by the method described in reaction scheme 4.
Reaction scheme 4
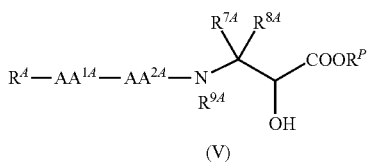
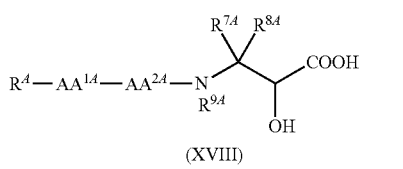
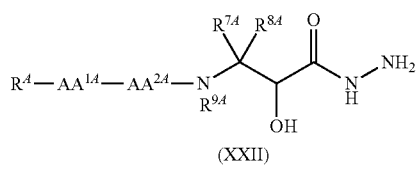
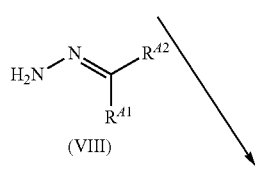
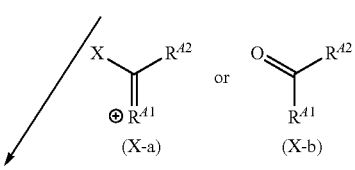

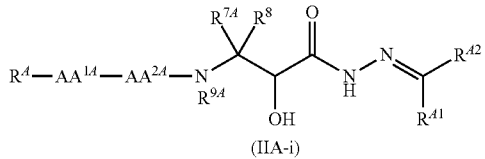

(IIA-i)

In the reaction scheme 4, all symbols have the same meaning as described hereinbefore.

As the method for the preparation of the compound of formula (IIA-i) from the compound of formula (XXII), for example, in the compound of formula (IIA-i), the compound wherein $R^{A1}$ and $R^{A2}$ are taken together with the adjacent carbon to form thiazolidine ring, may be prepared by the method described in the reaction scheme 5.

Reaction scheme 5

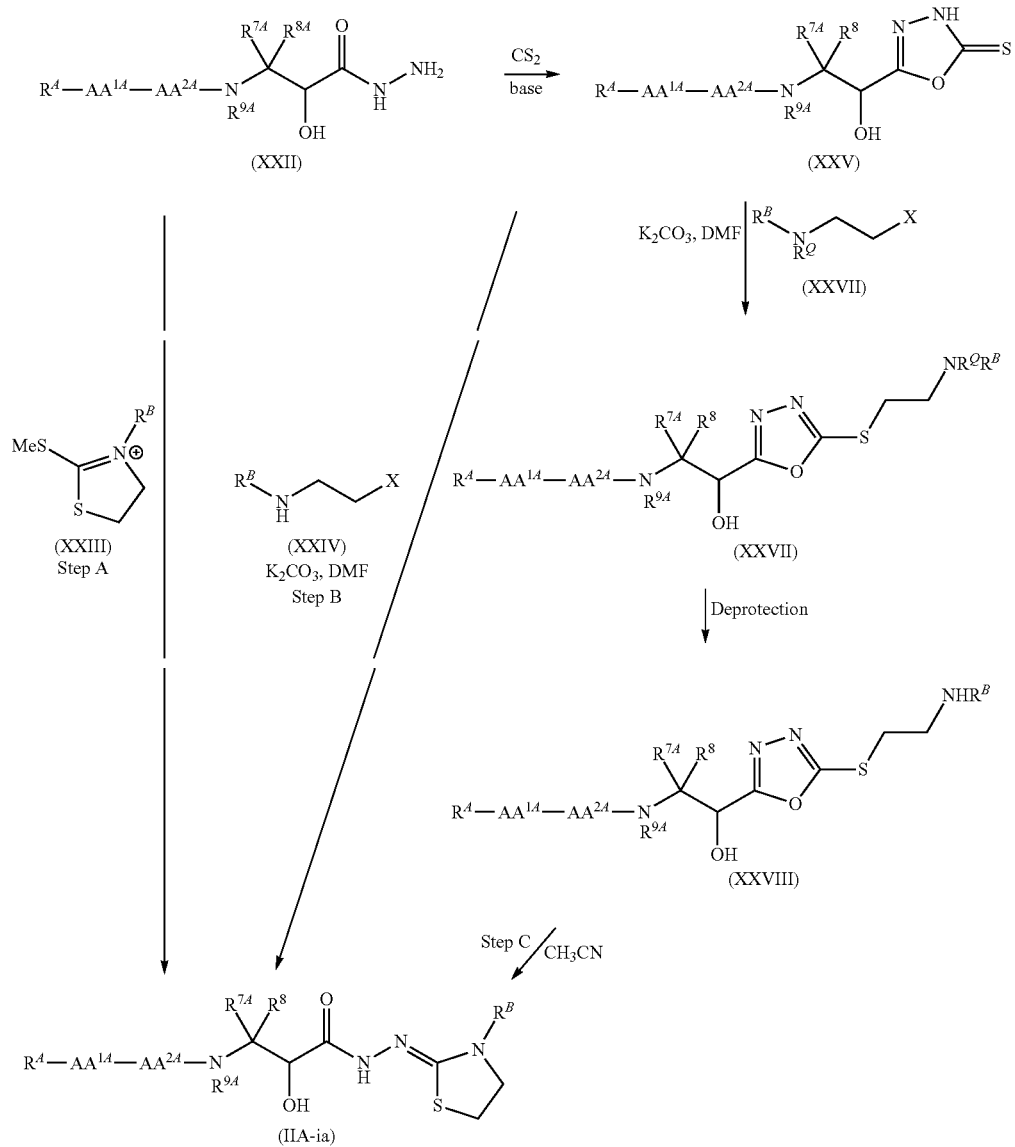

In the reaction scheme 5, all symbols have the same meaning as described hereinbefore.

As is easily understood by those skilled in the art, those compounds whose structures are similar to the compound of formula (IIA-ia), for example, the compounds having tetrahydrothiazine or thiazetidine structures may also be prepared according to the steps A, B or C.

As is also understood by those skilled in the art, in the compound of formula (I), the compound wherein $R^{A1}$ and $R^{A2}$ are taken together with the adjacent carbon to form thiazolidine ring, i.e. the compound of formula (IA-ia)

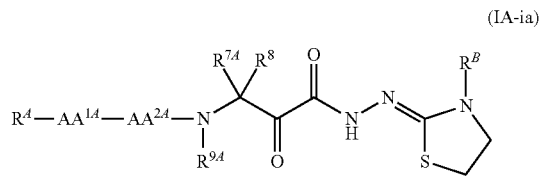

(IA-ia)

may also be prepared by the same procedure as described in step A, B or C using the compound of formula (XXIX)

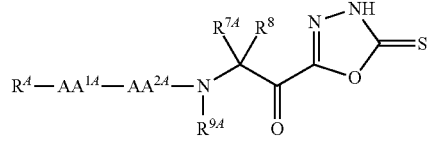

(XXIX)

in place of the compound (XXV).

In the compound of formula (IIA), the compound of formula (IIA-ii)

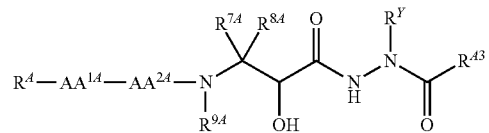

(IIA-ii)

(wherein all symbols have the same meaning as described hereinbefore) and the compound of formula (IIA-iii)

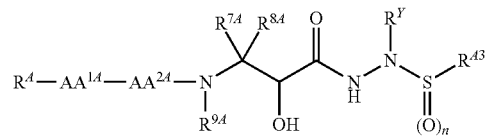

(IIA-iii)

(wherein all symbols have the same meaning as described hereinbefore) may be prepared according to the method described in reaction scheme 6.

Reaction scheme 6

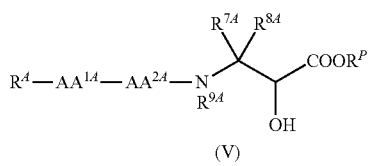

(V)

| Deprotection

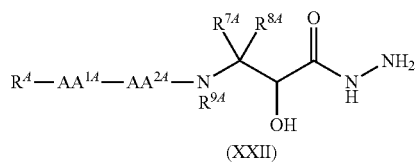

(XXII)

| $R^Y$—X
  (XII)

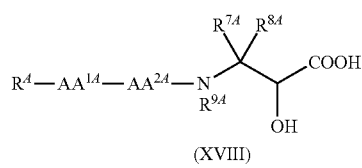
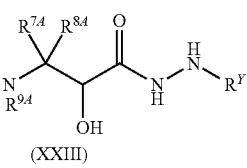
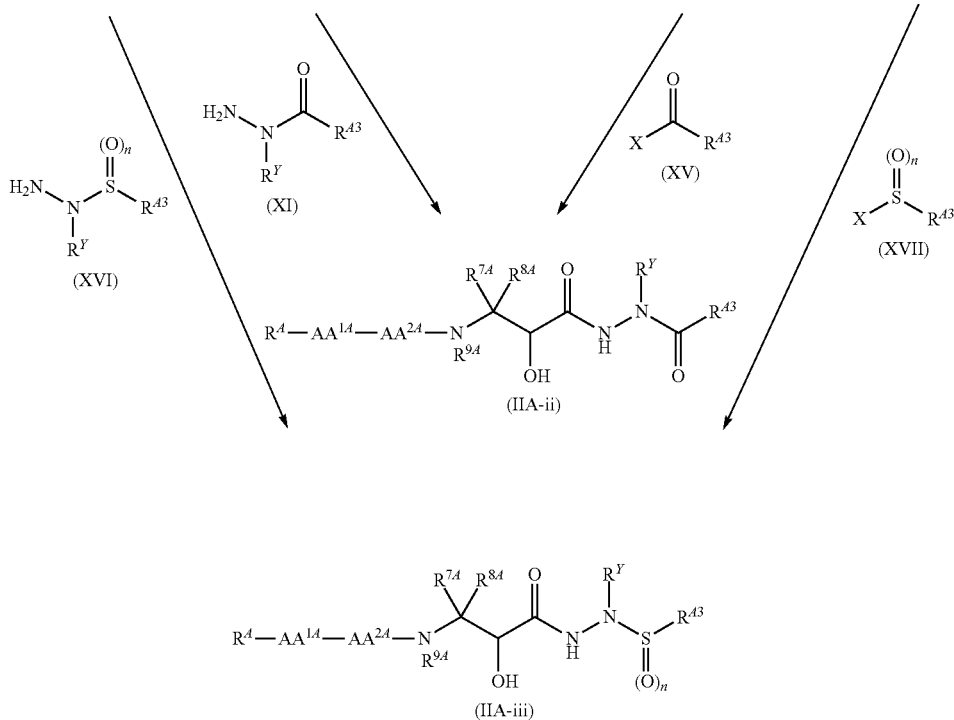
In the reaction scheme 6, all symbols have the same meaning as described hereinbefore.
The compound of formula (VI), which is used as a starting material in the reaction scheme 5 and 6, may be prepared by the method described in the following reaction scheme 7.
Reaction scheme 7
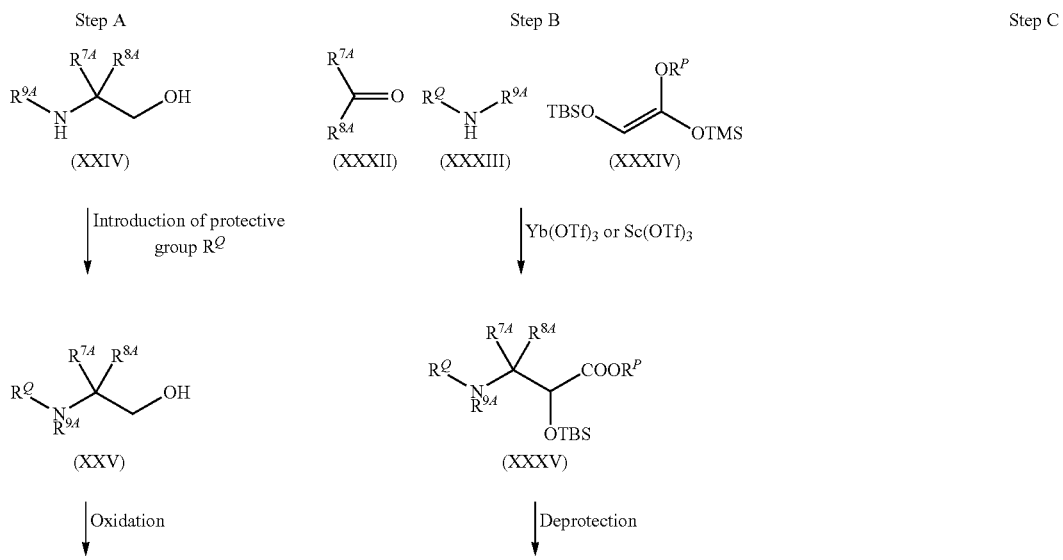

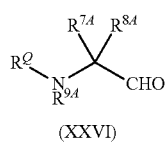
(XXVI)

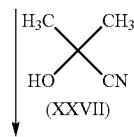
(XXVII)

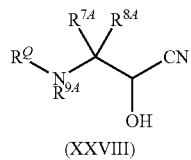
(XXVIII)

| Hydrolysis

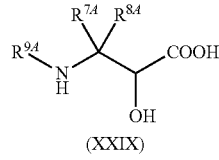
(XXIX)

Esterification →

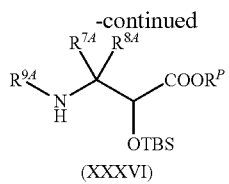
(XXXVI)

| $R^A$—$AA^{1A}$—$AA^{2A}$—OH
(XXXI)

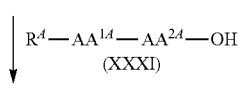
(XXXVII)

Deprotection

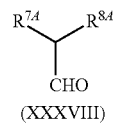
(XXXVIII)

| ClCOOR$^P$
(XXXIX)

(XL)

| $R^B$—CN
(XLI)

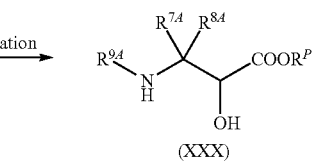
(XXX)

$R^A$—$AA^{1A}$—$AA^{2A}$—OH
(XXXI)

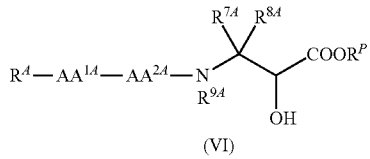
(VI)

In the reaction scheme 7, $R^Q$ is a protective group of amino group, e.g. t-butoxycarbonyl, benzyloxycarbonyl, etc. TBS is t-butyldimethylsilyl, TMS is trimethylsilyl, and the other symbols have the same meaning as described hereinbefore. $R^B$ is $R^A$-$AA^{1A}$-$AA^{2A}$- group whose —CO— group in the right is missing, and the other symbols have the same meaning as described hereinbefore.

In the compound of formula (VI), when R-$AA^{1A}$-$AA^{2A}$- has carbonyl in the right, the compound of formula (VI) may be prepared according to the method described in step C of the reaction scheme 7.

The compounds of formula (III) and (XXIX) may be prepared according to the method described in the reaction scheme 8.

Reaction scheme 8

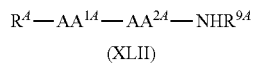
(XLII)

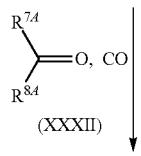
(XXXII)

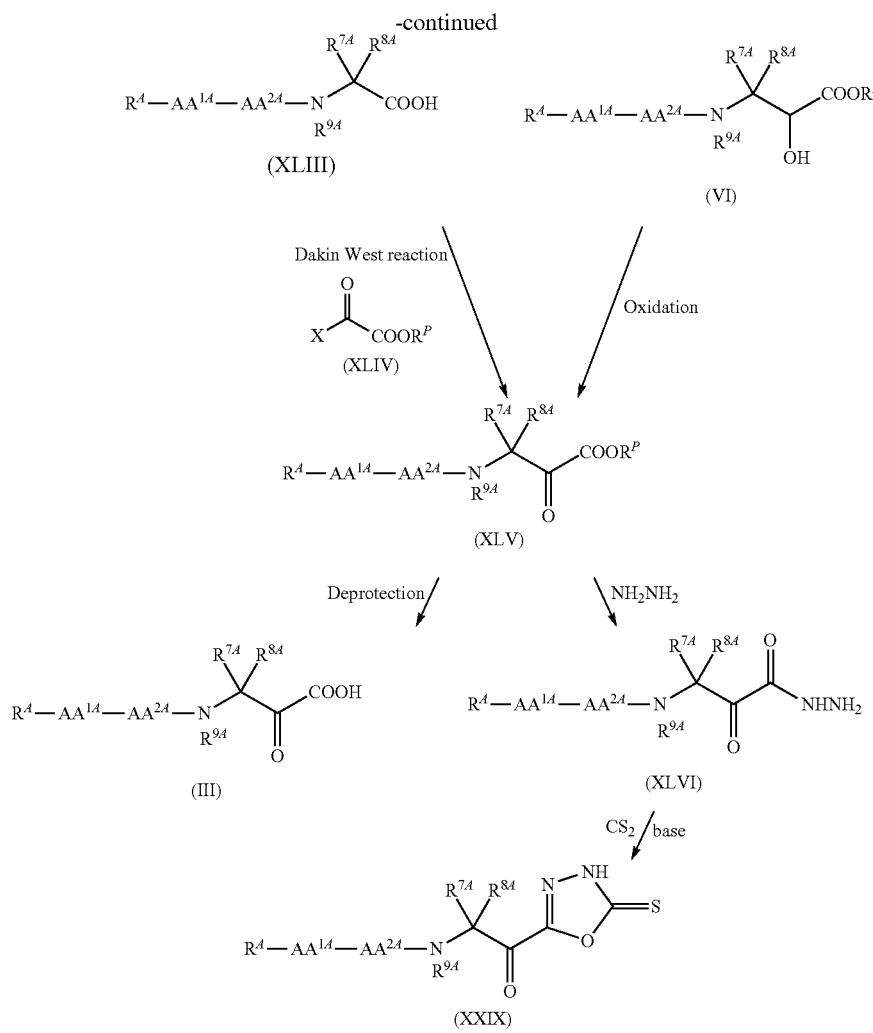

In the reaction scheme 8, $R^B$ represents a group $R^A$-$AA^{1A}$-$AA^{2A}$- whose —CO— group in the right is missing. The other symbols have the same meaning as described hereinbefore.

The compounds of formula (III) to (XLVI) may be known per se or they may be prepared by known methods.

The reactions in the reaction schemes may be carried out by known methods. In the present invention, other starting materials and reagents are known per se or they may be prepared by known methods.

For example, in the reaction scheme 5, the compounds of formula (XXV), (XXVII) and (XXVIII) and the compound of formula (XXDC) are known; for example, they may be prepared by the methods described in WO02/96892.

In each reaction of the present specification, reaction products may be purified by conventional techniques, for example, distillation under atmospheric or reduced pressure, high performance liquid chromatography, thin layer chromatography or column chromatography using silica gel or magnesium silicate, washing or recrystallization, etc. Purification may be carried out after each reaction, or after a series of reactions.

[Pharmacological Activities of the Compounds of the Present Invention]

The pharmacological activities of the compound of formula (I) of the present invention was confirmed by the following experiments.

(i) Measurement of Cathepsin K Inhibitory Activity

65 FL of cathepsin K enzyme reaction buffer (50 mmol/L of 2-(N-morpholino)ethanesulfonate, 2 mmol/L of ethylenediaminetetraacetate (EDTA) and 4 mmol/L of dithiothreitol (DTT) were mixed to adjust to pH 5.5), 5 μL of cysteine protease inhibitor solution of several concentrations, 20 μL of synthesized substrate (t-butyloxycarbonyl-L-alanyl-glycyl-L-prolyl-L-arginine-4-methyl-chromanyl-7-amide) solution of several concentrations and 10 μL of cathepsin K enzyme solution were mixed and the increase of fluorescence intensity when reacted at 37° C. was measured (λex (excitation wavelength)=355 nm, λem (fluorescence wavelength)=460 nm). As to the substrate and the compound of the present invention, enzyme reactions were carried out in combination of several appropriate concentrations and Dixon plotting was prepared, to define the absolute value of X-coordinate of the intersection point of the graph as Ki value.

It was confirmed that the compound of formula (I) of the present invention showed an inhibitory activity of more than 50%. For example, the Ki value of the compound of example 8(1) was 2.5 nM, that of the compound of example 2(6) was 14 nM, that of the compound of example 5 was 4 nM, and that of the compound of example 8(5) was 4.9 nM.

(ii) Measurement of Cathepsin B Inhibitory Activity

10 μL of synthesized substrate (carbobenzoxy-L-arginyl-L-arginine-4-methyl-chromanyl-7-amide or carbobenzoxy- L-phenylalanyl-L-arginine-4-methyl-chromanyl-7-amide) solution of several concentrations, 10 µl of cysteine protease inhibitor solution of several concentrations, 70 µl of cathepsin B enzyme reaction buffer (mixture of 400 mmol/L in acetic acid, 4 mmol/L EDTA, 8 mmol/L DDT to adjust to pH 5.5) and 10 µl of cathepsin B enzyme solution were mixed and the increase of fluorescence intensity was measured ($\lambda$ex (excitation wavelength)=355 nm, $\lambda$em (fluorescence wavelength)= 460 nm) when reacted at 37° C.

It was confirmed that the compound of formula (I) of the present invention had an inhibitory activity more than 50% at 10 µM. For example, IC50 value of the compound of example 8(5) was 60 nM.

(iii) Measurement of Cathepsin S Inhibitory Activity

10 µl of synthesized substrate (carbobenzoxy-L-leucyl-L-leucyl-L-arginine-4-methyl-chromanyl-7-amide) solution and 5 µl of cysteine protease inhibitor solution of several concentrations, 75 µl of cathepsin S enzyme reaction buffer (100 mmol/L of sodium phosphate, 2 mmol/L of EDTA, 2 mmol/L of DTT were mixed to adjust to pH 6.5) and 10 µl of cathepsin S enzyme solution were mixed and the increase of fluorescence intensity was measured ($\lambda$ex(excitation wavelength)=355 nm, $\lambda$em (fluorescence wavelength)=460 nm) when reacted at 37° C.

It was confirmed that the compound of formula (I) of the present invention has an inhibitory effect more than 50% at 10 µM. For example, 1050 value of the compound of example 8(5) was 30 nM.

(iv) Measurement of Cathepsin L Inhibitory Activity

5 µl of Synthesized substrate (carbobenzoxy-L-phenylalanyl-L-arginine-4-methyl-chromanyl-7-amide or L-prolyl-L-phenyl alanyl-L-arginine-4-methyl-chromanyl-7-amide) solution and 5 µl of cysteine protease inhibitor solution of several concentrations, 80 µl of cathepsin L enzyme reaction buffer (400 mmol/L acetic acid, 4 mmol/L EDTA, 8 mmol/L DTT were mixed to adjust to pH 5.5) and 10 µl of cathepsin L enzyme solution were mixed and the increase of fluorescence intensity was measured ($\lambda$ex (excitation wavelength)=355 nm, $\lambda$em (fluorescence wavelength)=460 nm) when reacted at 37° C.

It was confirmed that the compound of formula (I) of the present invention had an inhibitory activity of more than 50% at 10 µM. For example, IC50 value of the compound of example 8(5) was 79 nM.

(v) Measurement of Calpain Inhibitory Activity

The activity was measured according to the method described in Calcium-depending protease, Seibutsukagaku-Jikkenhou (Biochemistry Experimental Method) Tanpakubunkaikouso (Protease) I, 57 (1993).

(vi) Measurement of Caspase-1 Inhibitory Activity

50 µl of caspase-1 enzyme reaction solution (20 mmol/L of 4-(2-hydroxyethyl)-1-piperazinethanesulfonate-sodium hydroxide buffer pH 7.4, 10 mmol/L of potassium chloride, 1.5 mmol/L of magnesium chloride, 0.1 mmol/L EDTA, 10% glycerol) and 50 µl of cysteine protease inhibitor solution of several concentrations, 50 µl of caspase-1 enzyme solution and 100 µl of synthesized substrate (acetyl-L-tyrosinyl-L-valinyl-L-alanyl-L-aspartic acid-4-methyl-chromanyl-7-amide) solution of several concentrations were reacted at 37° C. and the fluorescence intensity was measured ($\lambda$ex (excitation wavelength)=355 nm, $\lambda$em (fluorescence wavelength)= 460 nm).

(vii) Investigation in Bone Resorption Inhibitory Activity Using Mouse Calvaria Cultivation System Mouse neonatal calvaria was cultured in D-minimum essential medium containing cysteine protease inhibitor (mixture of Penicillin G potassium (final concentration 100 U/ml), streptomycin sulfate (final concentration 0.1 mg/ml), bovine serum albumin (final concentration 0.1%), glutamine (final concentration 0.3 mg/ml) in D-minimal essential medium) with incitant (parathyroid hormone (PTH) or arotinoid) at 37° C. and the calcium concentration in the culture medium was measured.

(viii) Bone Resorption Pit Formation Test Using Rabbit Osteoclast Cells

Osteoclast cells collected from rabbit bones were sowed over slices of bovine cortical bone, dentine or teeth of toothed whale and were cultured at 37° C. in $\alpha$-minimal essential medium containing final concentration 5% of fetal bovine serum and various concentrations of cysteine protease inhibitor. The pits formed on the slices by the osteoclast cells were observed and at the same time type-I collagen C-terminal telopeptide (CTx) concentration in culture medium was measured.

(ix) Investigation of Immune Reaction Inhibitory Effect Using Antigen-Sensitized Mouse Spleen Cells Spleen cells were collected from mice sensitized by ovalbumin (OVA) several times. Inhibitory effect of cysteine protease inhibitors against immune response induced by OVA stimulus was investigated, using cytokine concentration and immunoglobulin concentration in culture solution as indicators.

(x) Investigation in Inhibitory Effect Against Bone Resorption Using the Rat PTH Hypercalcemia Model The effect of cysteine protease inhibitor (compulsory oral administration, intraperitoneal administration) on bone resorption which was promoted by intravenous administration of parathyroid hormone (PTH) solution (30 µg/ml) was investigated in rats, using calcium concentration in blood as an indicator.

(xi) Studies on Bone Resorption Inhibitory Effect Using TPTx Rat PTHrP-Induced Hypercalcemia Model The effect of cysteine protease inhibitor (compulsory oral administration, intraperitoneal administration) on bone resorption, promoted by subcutaneous administration of parathyroid hormone related peptide (PTHrP) to a fasting rat (thyroparathyroidectomized; TPTx) was investigated, using calcium concentration in blood as an indicator.

(xii) Inhibitory Effects on Human Neutrophil Elastase

A mixture of HEPS buffer (0.2 M, pH 8.0, 0.5 ml), an aqueous solution of sodium chloride (2.5 M, 0.2 ml), polyethyleneglycol 6000 (1%, 0.1 ml), distilled water (0.04 ml), a solution of the test compound in DMSO (0.05 ml), MeO-Suc-Ala-Ala-Pro-Val-pNA (10, 20 and 40 mM, each 0.01 ml) were preincubated for 5 minutes at 37° C. To the above mixture was added human neutrophil elastase (TINE) (2 U/ml, 0.1 ml) and the reaction was started. The rate of absorbance at 405 nM was measured at 37° C. every 30 seconds for 10 minutes. Elastase activity was regarded as generating rate (V) of liberated p-nitroaniline (pNA) and rate of absorbance per minute ($\Delta$mO.D./min, wavelength=405 nm) was calculated. Inhibition constant (Ki value) was calculated from the Dixon plot of the given rate of absorbance.

(xiii) Inhibitory Effects on Human Neutrophil Elastase Induced Lung Hemorrhage in Hamster To male Syrian hamsters was administered orally a test compound suspended in polyethyleneglycol 400:ethanol:distilled water=51:16:33. At 60 min after the administration, to the exposed trachea under pentobarbital anesthesia (60 mg/kg, i.p.) was administered 10 U/0.1 mL/lung of human neutrophil elastase (HNE) to induce pulmonary hemorrhage. 60 minutes after the administration, hamsters were bled to sacrifice and subjected to bronchioalveolar lavage with saline (2.5 mL) and recovered lavage solution (BALF). The recovered BALF (0.2 mL) was diluted by 10 times with distilled water and sonicated for 10 minutes. The given supernatant was subjected to the measure, and the amount of blood in BALF was calculated from absorbance at 412 nm using standard curve.

(xiv) Inhibitory Effects on Elevation of Elastase Activity in Hamster Whole Blood Induced by Opsonized Zymosan To a male Syrian hamster was administered a test compound (a suspension or a solution in a mixture of polyethyleneglycol 400:ethanol:distilled water=51:16:33 or another appropriate solvent) orally. 60 minutes after administration, under ether anesthesia blood (0.9 ml) was drawn from the artery in the abdomen (3.8% sodium citrate solution (0.1 ml) was used).

540 µl of the blood was incubated at 37° C. 5 minutes after incubation to the mixture was added opsonized zymosan (60 µl) and the mixture was incubated for 30 minutes at 37° C. The reaction was terminated by cooling with ice. After termination the mixture was centrifuged (3,000 rpm, 4° C.) for 10 minutes. The supernatant was collected and it was subjected to measurement of elastase activity.

To a mixture of Tris-HCl buffer solution (pH8.0, 0.2M, 100 µl), an aqueous solution of sodium chloride (2.5 M, 40 µl), distilled water (36 µl) and MeO-Suc-Ala-Ala-Pro-Val-pNA (50 mM, 4 µl) was added the above supernatant (20 µl) and the mixture was incubated for 24 hours at 37° C. Liberated p-nitroaniline (pNA) was subjected to the measurement of rate of absorbance (405 nm) and the inhibition rate was given by the following equation.

Inhibition rate(%)=[1−(value of the test compound−value of blank)/(value of control−value of blank)]×100

By the above experiments, it was confirmed that the compound of the present invention has a serine protease inhibitory effect, particularly elastase inhibitory effect by oral administration.

(xv) Measurement of Cathepsin H Inhibitory Activity

According to the method described in FEBS Lett. 280(2) 307-310/1991, Methods Enzymol. 80, 535-561/1981, the activity was measured.

(xvi) Measurement of Cathepsin C Inhibitory Activity

According to the method described in J. Immunol. 150, 4733-4742, 1993, the activity was measured.

[Toxicity]

The toxicity of the compound of the present invention was very low and it was confirmed that it was safe enough for pharmaceutical use.

INDUSTRIAL APPLICABILITY

[Application to Pharmaceuticals]

The compound of formula (I) of the present invention has an inhibitory activity against cysteine proteases (cathepsins such as K, L, S, B, F, C, H, etc., caspase, calpain, etc.), and therefore it is useful as an agent for the prophylaxis and/or treatment of inflammatory diseases (periodontitis, arthritis, inflammatory bowel diseases, infectious diseases, pancreatitis, hepatitis, glomerular nephritis, endocarditis, myocarditis, ulcerative colitis, etc.), immune diseases (diseases by disorder of immune response (graft versus host diseases, rejection of an organ transplantation, allergic diseases (bronchial asthma, atopic dermatitis, allergic rhinitis, hay fever, diseases induced by house dusts, irritable pneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), acquired immune deficiency syndrome (AIDS, AIDS-related complex (ARC)), etc.), ischemic diseases (brain ischemia, brain disorder by ischemic reperfusion, cardiac infarction, ischemic liver damage, etc.). respiratory diseases (adult acute respiratory distress syndrome, lung disorder, fibroid lungs, decomposition of alveolus elastica (emphysema etc.), circulatory diseases (arterosclerosis, restenosis after PTCA (percutaneous transluminal coronary angioplasty), hyperlipidemia, etc.), blood diseases (thrombocytopenic purpura, hemolytic uremic syndrome, myelodysplastic syndrome, cyclic thrombocytopenia, aplastic anemia, spontaneous thrombocytopenia, disseminated intravascular coagulation (DIC), spontaneous thrombocytopenic purpura, autoimmune hemolytic anemia, hyperlipidemia, etc.), neuronal diseases (dementia such as Alzheimer's disease, Alzheimer-type senile dementia, cerebrovascular injury, peripheral nerve injury, neurodegenerative disease (Huntington's chorea, Parkinson's disease, multiple sclerosis, traumatic encephalopathy, traumatic spondylopathy, etc.), etc.), hepatic and biliary diseases (primary biliary cirrhosis, viral hepatitis (A, B, C, F, etc.) or hepatitis medicamentosa and cirrhosis, etc.), bone and biliary diseases (osteoporosis, rheumatoid arthritis, arthritis, osteoarthritis, hypocalcaemia, osteometastasis of cancer, bone fracture, etc.), metabolic diseases (osteoporosis, rheumatoid arthritis, arthritis, osteoarthritis, hypocalcaemia, bone metastasis of cancer, endocrinesthenia (hyperthyroidism etc.), diseases induced by apoptosis (graft versus host diseases, rejection during transplantation, acquired immunodeficiency syndrome (AIDS), AIDS-related complex (ARC), adult T cell leukemia, hairy cells leukemia, spondylopathy, disorders of respiratory apparatus, arthritis, HIV or HTLV-1 related diseases (uveitis etc.), virus related diseases (hepatitis C etc.), cancer, collagenosis (systemic lupus erythematosus, rheumatoid arthritis, etc.), Sjoegren syndrome, myasthenia gravis, autoimmune diseases (insulin dependent (type I) diabetes, etc.), infectious diseases, prostatomegaly, hysteromyoma, bronchial asthma, nephritis, senile cataract, chronic fatigue syndrome, myodystrophy, etc.), diseases induced by decomposition of proteins which compose a body (myodystrophy, cataract, periodontitis, hepatocyte injury by bile acid (cholestatic cirrhosis etc.), etc., shock (septic shock, systemic inflammatory responsive syndrome, endotoxin shock, acidosis, etc.), malignant tumor, AIDS-related complex, parasitic diseases (malaria etc.).

Cysteine protease which the compound of the present invention inhibits is all preferable, for example, cathepsin K, cathepsin L, cathepsin S, cathepsin B, cathepsin H, cathepsin F, cathepsin C, calpain, caspase-1. Of course, cysteine proteases other than them are included in the scope of the present invention and naturally so are those cysteine proteases to be discovered in the future.

The compound of formula (I) of the present invention and a pharmaceutically acceptable salt and acid addition salt thereof also inhibits elastase and it is useful for the treatment and/or prophylaxis of diseases induced by an abnormal enhancement of degradation of elastin, collagen fiber and/or proteoglycans by elastase in mammals, particularly in humans, for example, chronic obstructive pulmonary disease (COPD) such as pulmonary emphysema, rheumatoid arthritis, arteriosclerosis, adult respiratory distress syndrome (ARDS), glomerular nephritis, myocardial infarction, ulcerative colitis and gingivitis, etc.

The compound of formula (I) of the present invention or a pharmaceutically acceptable salt thereof, an acid-addition salt thereof or a hydrate thereof may normally be administered orally or parenterally.

The compound of formula (I) or a pharmaceutically acceptable salt thereof may also be administered as a concomitant agent in combination with other agents for
1) supplementing and/or reinforcement of preventive and/or treating effect(s) of the compound,
2) improvement in kinetics and absorption of the compound and reduction of dose and/or
3) reduction of side effect of the compound.

A concomitant agent of the compound of formula (I) with other agents may be administered in a mode of compounded agent in which both components are compounded in a single preparation or in a mode of separate preparations. When administration is conducted using separate preparations, a simultaneous administration and administrations with time difference is included. In the case of administrations with time difference, the compound of formula (I) may be firstly administered and then other drug may be administered, or the other drug may be firstly administered and then the compound of formula (I) may be administered. Each of the methods for the administration may be the same or different.

There is no particular limitation for the diseases for which the above-mentioned concomitant agent achieves the preventive and/or the treating effect but any disease will be acceptable so far as it supplements and/or enforces the preventive and/or treating effect of the compound of formula (I).

For example, examples of the other drug for supplementing and/or reinforcing the preventive and/or treating effect of the compound of formula (I) to osseous or articular diseases include, for example, bisphosphonates, steroids, vitamin K derivative, vitamin D derivative, caspase-1 inhibitor, PTHrP derivatives, PG ligands, metalloprotease inhibitor, farnesoid X receptor agonist, estrogen agonist, progesterone agonists, etc.

Bisphosphonates include, olpadronate, alendronate sodium hydrate, ibandronate, etidronate disodium, zoledronate, KCO-692 (clodronate sodium hydrate), incadronate disodium, pamidronate disodium, YM175, YM529 (ONO-5920), tiludronate disodium (ME3737, SR41319B), risedronate sodium hydrate (NE-58095), etc.

Steroids include, KB-889 (OD14, tibolone), Osaterone acetate (TZP-4238), etc.

Vitamin K derivatives include menatetrenone, etc.

Vitamin D derivatives include, alfacalcidol, falecalcitriol, calcitriol, 1α,25 dihydroxycholecalciferol, dihydrotachysterol, ST-630, KDR, ST-630, ED-71, rocaltrol (Ro44-7190), etc.

Calcitonin formulations include, calcitonin salmon (STH-32, SMC20-51), calcitonin chicken (MC1-536), secalciferol, elcatonin, TJN-135, etc.

Caspase-1 inhibitor include, pralnacasan, nitroflubiprofen, etc.

PTHrP derivatives include, RS-66271, hPTHrP, etc.

Bone Morphogenetic Protein include YM484 (BMP-2), etc.

PG ligands include, for example, ONO-4819, nitroflubiprofen, etc.

PG ligands include, ONO-4819, nitroflubiprofen, etc.

Farnesoid X receptor agonists include, SR-45023A, etc.

Estrogen agonists include, TSE-424, WJ-713/MPA, raloxifene tartarate, Estradiol, teriparatide acetate, osaterone acetate, etc.

Progesterone agonists include, trimegestone, etc.

There is no limitation for the ratio by weight of the compound of formula (I) to other agents.

With regard to other agents, two or more members of any agent may be administered in combination.

Such other agents which supplement and/or reinforce the preventive and/or treating effect of the compound of formula (I) include not only those which have been found on the basis of the above-mentioned mechanism but also those which will be found in future.

The compound of formula (I) of the present invention, a combination of the compound of formula (I) of the present invention and other drug is generally administered systemically or topically and orally or parenterally when it is used for the above objects.

The dosages are determined depending on age, body weight, symptom, therapeutic effect, administration route, duration of the treatment and the like. Generally, 1 mg to 1000 mg per adult is orally administered once to several times per day, or 1 mg to 100 mg per adult is parenterally administered (preferably by intravenous administration) once to several times per day, or continuously administered from vein for 1 to 24 hours per day.

Since the dose changes depending on various conditions as described above, there are cases in which doses lower than or greater than the above ranges may be used.

The compound of formula (I) of the present invention and concomitant agent of the compound of formula (I) of the present invention and other agent(s) may be administered in the form of solid compositions, liquid compositions and other compositions for oral administration, and injections, liniments, suppositories, eye lotions, inhalants and the like for parenteral administration.

Solid compositions for oral administration include tablets, pills, capsules, dispersible powders, granules and the like.

Capsules include hard capsules and soft capsules.

In such solid compositions, one or more active compound(s) are mixed with at least one inert diluent such as lactose, mannitol, glucose, hydroxypropyl cellulose, microcrystalline cellulose, starch, polyvinyl pyrrolidone or magnesium metasilicate aluminate. The composition may also contain additional substances other than the inert diluent, e.g., lubricants such as magnesium stearate, disintegrating agents such as cellulose calcium glycolate, stabilizing agents such as lactose, and assisting agents for dissolving such as glutamic acid and aspartic acid according to usual methods. If necessary, the tablets or pills may be coated with film of gastric- or enteric-coating agents such as sugar, gelatin, hydroxypropyl cellulose and hydroxypropyl cellulose phthalate, or be coated with two or more films. Furthermore, capsules of absorbable materials such as gelatin are included.

Liquid compositions for oral administration include pharmaceutically acceptable emulsions, solutions, syrups, elixirs and the like. In such liquid compositions, one or more active compound(s) are contained in an inert diluent commonly used (e.g., purified water, ethanol). Furthermore, such compositions may also contain auxiliary material such as wetting agents or suspending agents, sweetening agents, flavoring agents, flavoring agents, and preserving agents.

Injections for parenteral administration in the present invention include solutions, suspensions and emulsions, and also solid injections which are to be dissolved or suspended in solvents upon use. Such an injection is prepared by dissolving, suspending or emulsifying one or more active substances in a solvent and then put to use. Examples of the solvent include distilled water for injection, physiological saline, plant oil, alcohols such propylene glycol, polyethylene glycol and ethanol, and combinations thereof. Further, the injection may contain a stabilizer, a solubilizing auxiliary agent such as glutamic acid, aspartic acid and POLYSORBATE 80 (registered trade mark) etc.), suspending agent, emulsifying agent, soothing agent, buffering agent, preservative agent and the like. The injection may be sterilized in the final step of the preparation process or the whole preparation process may be operated under sterile conditions. Alternatively, the sterile product, for example a sterile freeze-dried product may be prepared, and upon use, the product may be dissolved in sterilized or aseptic distilled water for injection or other sterilized or aseptic solvents.

Other compositions for parenteral administration include liquids for external use, ointments, endemic liniments, inhalants, spray compositions, suppositories for intrarectal administration, and pessaries for intravaginal administration and the like containing one or more active compound(s) which can be prepared by known methods.

Spray compositions may contain stabilizing agents such as sodium hydrogen sulfate, buffering agents to give isotonicity, isotonic solutions such as sodium chloride, sodium citrate or citric acid, in addition to inert diluents. For preparation of such spray compositions, for example, the method described in the U.S. Pat. No. 2,868,691 and the method described in the U.S. Pat. No. 3,095,355 explain it in detail.

BEST MODE FOR CARRYING OUT THE INVENTION

The present invention is explained below in detail based on Examples; but the present invention is not limited thereto.

The solvents in the parentheses show the developing or eluting solvents and the ratios of the solvents used are by volume in chromatographic separations or TLC. The solvents in the parentheses in NMR show the solvents for measurement.

In the measurement of NMR, unless specified, DMSO-$d_6$ is used as a solvent, measurement was done at ordinary temperature, and the example compounds represent free compounds.

In the formuli, TBS is t-butyldimethylsilyl, Boc is t-butoxycarbonyl, Ph is phenyl, Bn is benzyl, Ac is acetyl, tBu is t-butyl.

Example 1

Preparation of N'-(3-t-butyl-1,3-thiazolidin-2-ylidene)-[3-cyclohexylcarbonylamino-2-oxo-3-(tetrahydropyran-4-yl)propionohydrazide]hydrochloride

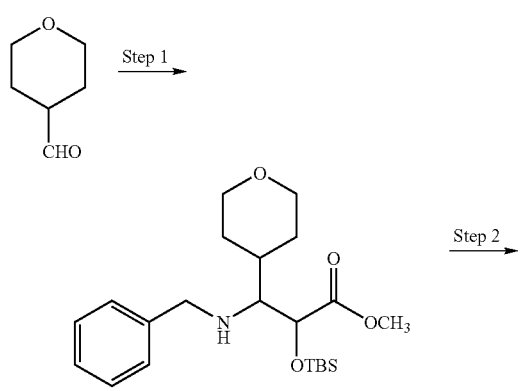

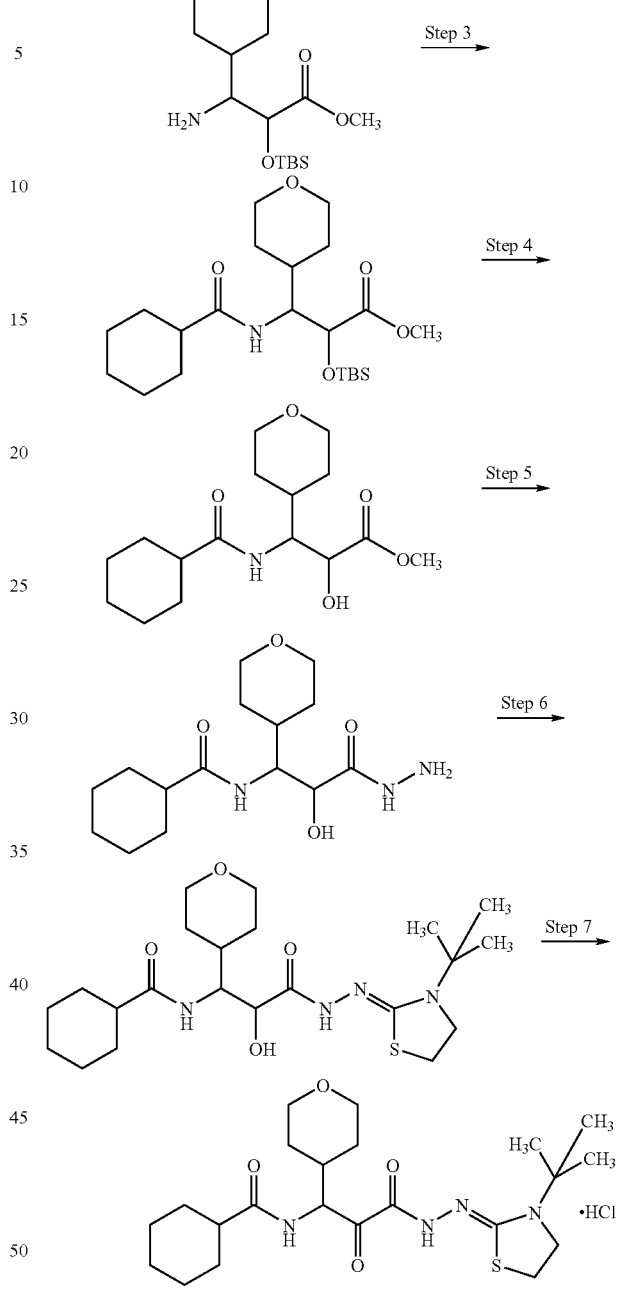

Step 1: To a solution of 4-formyltetrahydropyran (16.5 g) in toluene (150 ml) was added benzylamine (15.5 g) and the mixture was stirred for 20 minutes at room temperature. The precipitate was collected, and the filtrate was concentrated and azeotroped with toluene twice. The residue was dissolved in toluene (150 ml) and to the mixture were added 1-methoxy-1-trimethylsiloxy-2-t-butyldimethylsiloxy ethene (*Tetrahedron Lett.*, 2001, 42, 4025-4028 (48.0 g)) and scandium trifluoromethanesulfonate (III) salt (1.43 g) and the mixture was stirred for 2 hours at room temperature. To the reaction mixture was added acetic acid (30 ml) and stirred for 2 hours and the mixture was concentrated. To the residue was added saturated aqueous sodium bicarbonate and the mixture was extracted with ethyl acetate. The organic layer was washed with brine, dried over anhydrous sodium sulfate and concentrated to give 3-benzylamino-3-(tetrahydropyran-4-yl)-2-(t-butyldimethylsilyloxy)propanoic acid methyl ester (crude product, 64.6 g).

TLC: Rf 0.43 and 0.21 (n-hexane:ethyl acetate=7:3).

Step 2: To the compound prepared in step 1 (64.0 g) were added 5% palladium carbon and methanol (150 ml) and under the atmosphere of hydrogen the mixture was stirred vigorously for 4 hours at 40° C. The reaction mixture was filtered and the filtrate was concentrated. The residue was azeotroped with acetonitrile to give 3-amino-3-(tetrahydropyran-4-yl)-2-(t-butyldimethylsilyloxy)propanoic acid methyl ester (crude, 49.0 g).

TLC: Rf 0.12 (n-hexane:ethyl acetate=1:1).

Step 3: To a solution of the compound prepared in step 2 (49.0 g) in acetonitrile (150 ml) was added N-methylmorpholine (19.1 ml) and the mixture was cooled to 0° C. and to the mixture was added cyclohexanecarbonyl chloride (19.4 ml) and the mixture was stirred for 30 minutes at the same temperature. To the reaction mixture was added N,N-dimethylethylenediamine (2.55 g) and it was extracted with water and ethyl acetate. The organic layer was washed with 1N hydrochloric acid, a saturated aqueous solution of sodium bicarbonate and brine successively, dried over anhydrous sodium sulfate and concentrated to give 3-cyclohexylcarbonylamino-3-(tetrahydro pyran-4-yl)-2-(t-butyldimethylsilyloxy)propanoic acid methyl ester (crude, 60.3 g).

TLC: Rf 0.74 and 0.75 (n-hexane:ethyl acetate=1:1).

Step 4: To a solution of the compound prepared in step 3 (60 g) in methanol (80 ml) was added 10% hydrochloric acid-methanol (70 ml) at room temperature and the mixture was stirred for 40 minutes. The reaction mixture was concentrated and to the residue was added a saturated aqueous solution of sodium bicarbonate and extracted with ethyl acetate. The organic layer was washed with a saturated aqueous solution of sodium bicarbonate and brine successively, dried over anhydrous magnesium sulfate and concentrated. The residue was washed with t-butylmethyl ether and dried to give 3-cyclohexylcarbonylamino-3-(tetrahydropyran-4-yl)-2-hydroxypropanoic acid methyl ester (28.2 g).

TLC: Rf 0.31 (n-hexane:ethyl acetate=1:1).

Step 5: To a solution of the compound prepared in step 4 (12.2 g) in methanol (40 ml) was added hydrazine monohydrate (9.7 g) and the mixture was stirred for 2 hours at room temperature. To the reaction mixture was added methanol (20 ml) and it was stirred for another 20 hours. The reaction mixture was concentrated and to the residue was added diisopropyl ether and it was filtered, washed with diisopropyl ether and dried to give 3-cyclohexylcarbonylamino-3-(tetrahydropyran-4-yl)-2-hydroxypropanohydrazide (11.4 g).

TLC: Rf 0.30 (methylene chloride:methanol=9:1).

Step 6: To a suspension of the compound prepared in step 5 (626 mg) in DMSO (8 ml) were added N-methylmorpholine (0.22 ml) and 2-methylthio-3-t-butylthiazolinium iodide (1.14 g) and the mixture was stirred for 20 hours at room temperature. To the reaction mixture was added water and extracted with ethyl acetate three times. The organic layers were combined and washed with brine, dried over anhydrous sodium sulfate and concentrated to give N'-(3-t-butyl-1,3-thiazolidin-2-ylidene)-[3-cyclohexylcarbonylamino-2-hydroxy-3-(tetrahydropyran-4-yl)propanohydrazine] (885 mg).

TLC: Rf 0.71 and 0.70 (methylene chloride:methanol=9:1).

Step 7: To a solution of the compound prepared in step 6 (620 mg) in dimethylsulfoxide (5 ml) were added triethylamine (0.95 ml) and sulfur trioxide-pyridine complex (869 mg) and the mixture was stirred for 30 minutes. To the reaction mixture was added water and extracted with ethyl acetate. The organic layer was washed with brine, dried over anhydrous sodium sulfate and concentrated. The residue was washed with t-butylmethyl ether and dried to give free compound of N'-(3-t-butyl-1,3-thiazolidin-2-ylidene)-[3-cyclohexylcarbonylamino-2-oxo-3-(tetrahydropyran-4-yl)propionohydrazide]. To the free compound was added 4N hydrochloric acid-ethyl acetate solution and concentrated. The residue washed with ethyl acetate and dried to give hydrochloride of the title compound (303 mg).

Free Compound

NMR: δ 1.00-1.76 (m, 23H), 2.14 (m, 1H), 2.28 (m, 1H), 3.01 (t, J=6.6 Hz, 2H), 3.22 (m, 2H), 3.67 (t, J=6.6 Hz, 2H), 3.82 (m, 2H), 5.02 (m, 1H), 7.96 (d, J=8.0 Hz, 1H), 10.64 (s, 1H).

Hydrochloride

TLC: Rf 0.69 (methylene chloride:methanol=9:1);

NMR: δ 0.96-1.83 (m, 23H), 2.12 (m, 1H), 2.29 (m, 1H), 3.08 (t, J=7.0 Hz, 2H), 3.24 (m, 2H), 3.73-3.91 (m, 4H), 4.98 (m, 1H), 6.95-7.68 (broad, 1H), 8.04 (d, J=7.4 Hz, 1H), 10.94 (s, 1H).

Example 1(1)-Example 1(8)

By the same method as described in example 1 using corresponding compounds (optionally followed by subjecting to deprotection reaction by known methods), the following compounds were given.

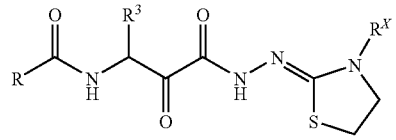

| Example | R | $R^3$ | $R^x$ |
|---|---|---|---|
| 1(1) | cyclohexyl | (S)-isobutyl | phenyl |
| | TLC:Rf 0.64 (methylene chloride:isopropanol = 9:1) | | |
| | NMR (100° C.): δ 10.16 (br-m, 1H), 7.55-7.50 (m, 3H), 7.36-7.31 (m, 2H), 7.13-7.08 (m, 1H), 4.99 (br-m, 1H), 4.13 (t, J = 6.0 Hz, 2H), 3.31 (t, J = 6.0 Hz, 2H), 2.23-2.14 (m, 1H), 1.71-1.20 (m, 13H), 0.89 (d, J = 6.0 Hz, 3H), 0.87 (d, J = 6.0 Hz, 3H) | | |
| 1(2) hydro- chloride | cyclohexyl | benzoylpiperidin-4-yl | methyl |
| | TLC:Rf 0.71 (methylene chloride:methanol = 9:1) | | |
| | NMR: δ 1.00-1.45 (m, 7H), 1.45-1.80 (m, 7H), 2.05-2.35 (m, 2H), 3.09 (s, 3H), 317 (m, 1H), 3.38 (t, J = 7.69 Hz, 2H), 3.59 (m, 1H), 3.90-4.20 (m, 3H), 4.47 (m, 1H), 4.88 (d, J = 6.32 Hz, 2H), 7.41 (m, 5H), 8.22 (d, J = 5.77 Hz, 1H), 11.48 (s, 1H) | | |
| 1(3) hydro- chloride | cyclohexyl | N-pivaolylpiperidin-4-yl | methyl |
| | TLC:Rf 0.37 (methylene chloride:methanol = 9:1) | | |
| | NMR: δ 1.00-1.40 (m, 16H), 1.40-1.70 (m, 7H), 2.00-2.40 (m, 2H), 2.51-2.80 (m, 2H), 3.06 (s, 3H), 3.36 (t, J = 7.28 Hz, 2H), 3.70-4.20 (m, 3H), 4.27 (m, 2H), 4.89 (m, 1H), 8.17 (d, J = 6.59 Hz, 11H), 11.38 (s, 1H) | | |
| 1(4) hydro- chloride | cyclohexyl | N-toluenesulfonyl- piperidin-4-yl | methyl |
| | TLC:Rf 0.56 (methylene chloride:methanol = 9:1) | | |
| | NMR: δ 0.93-1.82 (m, 15H), 1.93-2.31 (m, 3H), 2.39 (s, 3H), 2.97-3.06 (m, 3H), 3.23-3.38 (m, 2H), | | |

135
-continued

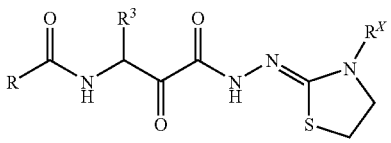

| Example | R | R³ | Rˣ |
|---|---|---|---|
| | | 3.61 (m, 2H), 3.88 (m, 2H), 4.00-4.80 (broad, 1H), 4.82 (m, 1H), 7.43 (d, J = 8.0 Hz, 2H), 7.59 (d, J = 8.0 Hz, 2H), 8.14 (m, 1H), 11.25 (brs, 1H) | |

Example 1(5)

N'-(3-methyl-1,3-thiazolidin-2-ylidene)-[N-(3-cyclo-hexylcarbonyl)-N-methylamino-4-methyl-2-oxopentanohydrazide]hydrochloride TLC: Rf 0.39 (ethyl acetate:methanol=9:1);
NMR: δ 11.39 (br-s, 1H), 4.12 (d, J=6.6 Hz, 1H), 4.04 (t, J=7.5 Hz, 2H), 3.40 (t, J=7.5 Hz, 2H), 3.13 (s, 3H), 3.11 (s, 3H), 2.63-2.44 (m, 1H), 2.41-2.26 (m, 1H), 1.80-1.52 (m, 5H), 1.41-1.10 (m, 5H), 0.97 (d, J=6.9 Hz, 3H), 0.81 (d, J=6.9 Hz, 3H).

Example 1(6)

N'-(1,3-dimethylimidazolidin-2-ylidene)-3-cyclo-hexyl-3-cyclohexylcarbonylamino-2-oxopropanohydrazide]dihydrochloride TLC: Rf 0.56 (methylene chloride:methanol=9:1);
NMR: δ 0.90-1.82 (m, 21H), 2.25 (m, 1H), 2.97 (s, 6H), 3.65 (s, 4H), 4.64 (m, 1H), 8.27 (d, J=5.5 Hz, 1H), 10.14 (s, 1H), 11.33 (s, 1H).

Example 1(7)-Example 1(8)

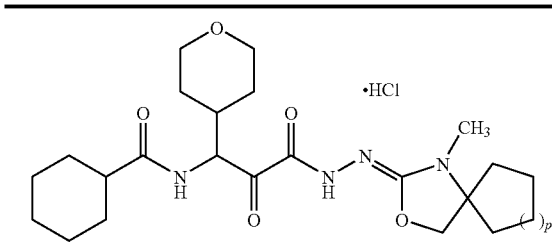

| 1(7) | p = 1 | TLC:Rf 0.60 (methylene chloride:methanol 9:1) NMR: δ 11.06 (s, 1H,), 8.23 (d, J = 6.3 Hz, 1H), 4.77 (t, J = 6.3 Hz, 1H), 4.59 (s, 2H), 3.95-3.70 (m, 2H), 3.34-3.10 (m, 2H), 3.00 (s, 3H), 2.33-2.17 (m, 1H), 2.15-1.00 (m, 23H) |
| 1(8) | p = 2 | TLC:Rf 0.62 (methylene chloride:methanol = 9:1) NMR: δ 11.06 (s, 1H), 8.23 (d, J = 6.3 Hz, 1H), 4.78 (t, J = 6.3 Hz, 1H), 4.61 (s, 2H), 3.90-3.75 (m, 2H), 3.35-3.12 (m, 2H), |

136
-continued

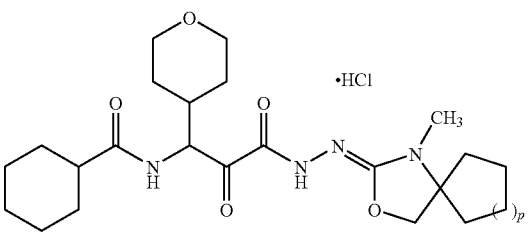

2.98 (s, 3H), 2.33-2.18 (m, 1H), 2.15-2.00 (m, 1H), 1.90-1.00 (m, 24H)

Example 2

Preparation of 2-[(3S)-3-cyclohexylcarbonylamino-2-hydroxy-5-methyl-hexanohydrazono]-1-methylpyrrolidine hydrochloride

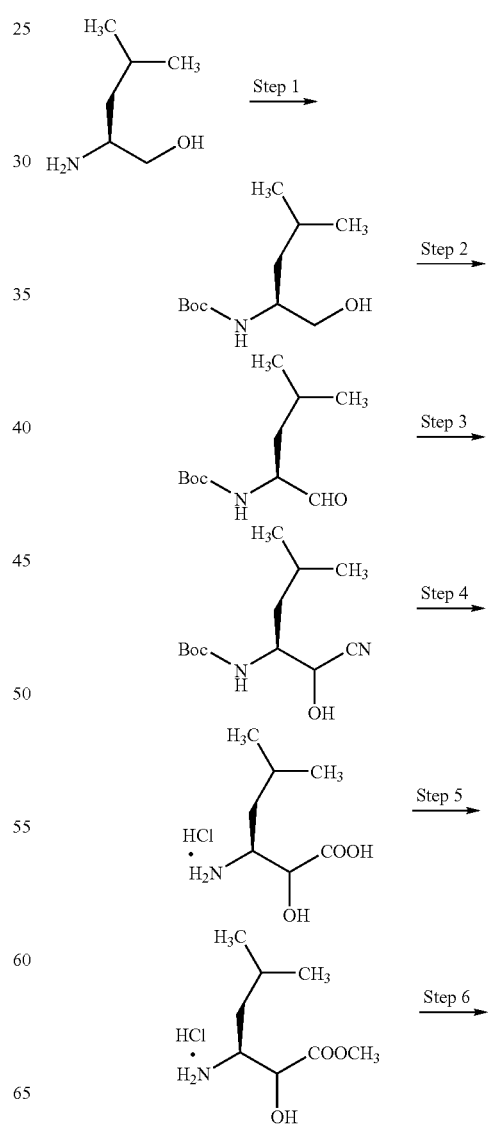

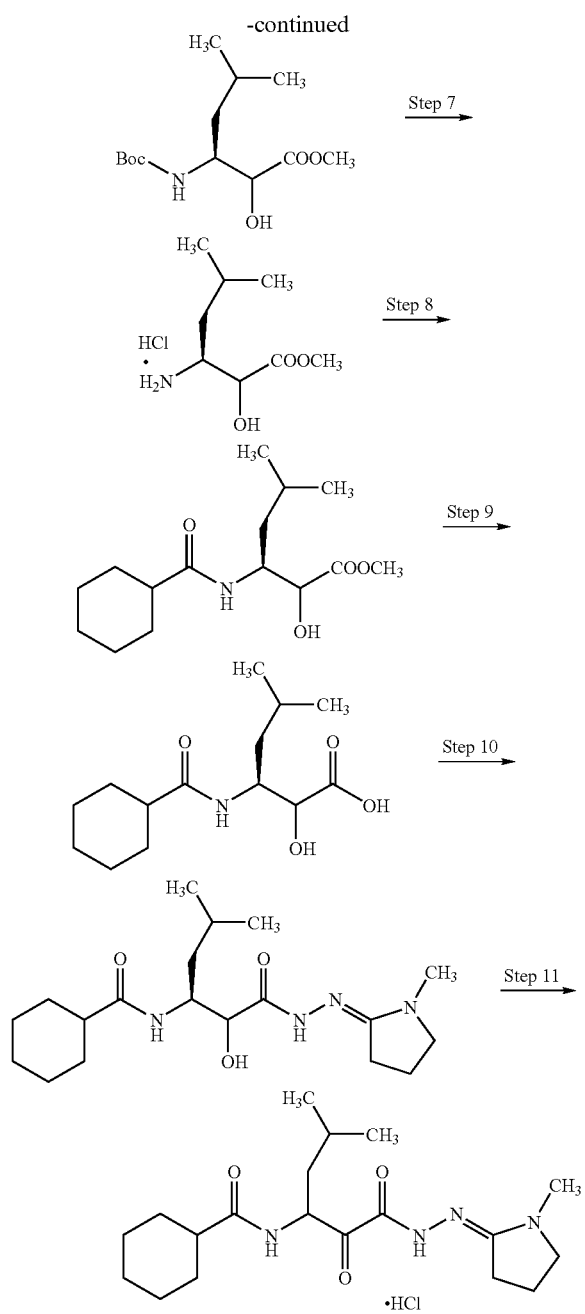

Step 1: To a solution of (2S)-2-amino-4-methylpentanol ((L)-leucinol) (20 g) in THF (1000 ml) was added di-t-butyl carbonate (43 ml) at 0° C. dropwise and the mixture was stirred for 90 minutes at room temperature. The reaction mixture was concentrated to give a crude product of (2S)-2-(t-butoxycarbonylamino)-4-methylpentanol.

TLC: Rf 0.50 (chloroform:methanol=10:1).

Step 2: To a solution of the compound prepared in step 1 in DMSO (344 ml) were added triethylamine (72 ml) and a solution of sulfur trioxide-pyridine complex (82 g) in DMSO (280 ml) at 10° C. and the mixture was stirred for 1 hour. The reaction mixture was poured into ice-water and extracted by ethyl acetate. The organic layer was washed by 10% aqueous solution of citric acid, water and a saturated aqueous solution of sodium chloride successively, and dried over anhydrous sodium sulfate and concentrated to give a crude product of (2S)-2-(t-butoxycarbonylamino)-4-methylpentanal.

TLC: Rf 0.45 (chloroform:methanol=10:1).

Step 3: To a solution of the compound prepared in step 2 in methanol (180 ml) were added acetone cyanohydrine (19 ml) and potassiumcarbonate (4.7 g) at 0° C. and the mixture was stirred for 1 hour at room temperature. The reaction mixture was concentrated and the residue was extracted by ethyl acetate and water. The organic layer was washed by water and a saturated aqueous solution of sodium chloride successively, dried over anhydrous sodium sulfate and concentrated. The residue was purified by column chromatography on silica gel (n-hexane:ethyl acetate=3:1) to give (3S)-3-(t-butoxycarbonylamino)-2-hydroxy-5-methylhexanenitrile (33.6 g).

TLC: Rf 0.40 (n-hexane:ethyl acetate=3:1).

Step 4: To the compound prepared in step 3 (33.6 g) was added a concentrated hydrochloric acid (300 ml) and the mixture was stirred for 5 hours at 80° C. The reaction mixture was concentrated to give a crude product of (3S)-3-amino-2-hydroxy-5-methylhexanoic acid hydrochloride.

TLC: Rf 0.30 (chloroform:methanol:water=6:4:1).

Step 5: To methanol (1000 ml) was added thionyl chloride (92 ml) at −40° C. dropwise and the mixture was stirred for 10 minutes. The solution was added to a solution of the compound prepared in step 4 in methanol (250 ml) at −10° C. dropwise and the mixture was stirred for 4 hours at room temperature. The reaction mixture was concentrated to give a crude product of methyl (3S)-3-amino-2-hydroxy-5-methylhexanoate hydrochloride.

TLC: Rf 0.50 (chloroform:methanol:water=6:4:1).

Step 6: To a solution of the crude compound prepared in step 5 (32 g) in methylene chloride (300 ml) were added triethylamine (20 ml) and di-t-butyl-dicarbonate (34 ml) at 0° C. and the mixture was stirred for 4 hours at room temperature. To the reaction mixture was added water and was extracted by ethyl acetate. The organic layer was washed by 10% aqueous solution of citric acid, a saturated aqueous solution of sodium bicarbonate, water and a saturated aqueous solution of sodium chloride successively, dried over anhydrous sodium sulfate and concentrated. The residue was purified by column chromatography on silica gel (n-hexane:ethyl acetate=3:1) to give (3S)-3-(t-butoxycarbonylamino)-2-hydroxy-5-methylhexanoic acid methyl ester (28 g).

TLC: Rf 0.40 and 0.35 (n-hexane:ethyl acetate=3:1).

Step 7: To a solution of the compound prepared in step 6 (825 mg) in ethyl acetate (6 ml) was added 4N hydrochloric acid-ethyl acetate (9 ml) and the mixture was stirred for 40 minutes at room temperature. The reaction mixture was concentrated to give (3S)-3-amino-2-hydroxy-5-methylhexanoic acid methyl ester hydrochloride.

TLC: Rf 0.26 (ethyl acetate:methanol=4:1).

Step 8: To a solution of the compound prepared in step 7 in acetonitrile (15 ml) were added N-methylmorpholine (0.49 ml) and cyclohexanecarbonyl chloride (484 mg) and the mixture was stirred overnight at room temperature. The reaction mixture was poured into 1N hydrochloric acid and extracted with ethyl acetate. The organic layer was washed with a saturated aqueous solution of sodium bicarbonate and brine successively and dried over anhydrous magnesium sulfate to give (3S)-3-cyclohexylcarbonylamino-2-hydroxy-5-methylhexanoic acid methyl ester (682 mg).

TLC: Rf 0.53 and 0.39 (n-hexane:ethyl acetate=1:1).

Step 9: To a solution of the compound prepared in step 8 (670 mg) in methanol (2.4 ml) was added 1N aqueous solution of sodium hydroxide (2.4 ml) and the mixture was stirred for 30 minutes at room temperature. The reaction mixture was poured into 1N hydrochloric acid and was extracted with ethyl acetate. The organic layer was washed with brine, dried over anhydrous magnesium sulfate and concentrated to give (3S)-3-cyclohexylcarbonylamino-2-hydroxy-5-methylhexanoic acid (676 mg).

TLC: Rf 0.56 (ethyl acetate:methanol=4:1).

Step 10: To a solution of the compound prepared in step 9 (271 mg) and N-methylpyrrolidine-2-ylidenehydrazine (186 mg) in DMF (2 ml) were added 1-hydroxybenzotriazole (150 mg), triethylamine (0.34 ml) and 1-ethyl-3-[3-(dimethylamino)propyl]carbodiimide hydrochloride (230 mg) and the mixture was stirred for 17 hours. To the reaction mixture was added brine, and extracted with ethyl acetate twice. The organic layer was dried over anhydrous sodium sulfate and concentrated. The residue was washed with diisopropyl ether and dried to give 2-[(3S)-3-cyclohexylcarbonylamino-2-hydroxy-5-methylhexanohydrazono]-1-methylpyrrolidine hydrochloride (243 mg).

TLC: Rf 0.78 (methylene chloride:methanol=8:2).

Step 11: To a suspension of the compound prepared in step 10 (219 mg) in DMSO (0.42 ml) were added ethyl acetate (0.5 ml), triethylamine (0.42 ml) and sulfur trioxide-pyridine complex (286 mg) and the mixture was stirred for 1 hour. To the reaction mixture was added brine and extracted with ethyl acetate. The organic layer was washed with brine, dried over anhydrous sodium sulfate and concentrated. The residue was purified by column chromatography on silica gel (ethyl acetate:methanol=20:1->1:1). The product was dissolved in ethyl acetate and thereto was added hydrochloric acid-ethyl acetate (0.1 ml) and concentrated to give N'-(1-methylpyrrolidine-2-ylidene)-(3-cyclohexylcarbonylamino-5-methyl-2-oxohexanohydrazide) hydrochloride (107 mg).

TLC: Rf 0.51 (ethyl acetate:methanol=9:1);

NMR: δ 11.8-11.4 (broad, 1H), 11.6 (brs, 1H), 8.35 (m, 1H), 4.78 (m, 1H), 3.80 (m, 2H), 3.14 (s, 3H), 2.83 (m, 2H), 2.18 (m, 1H), 2.04 (m, 2H), 1.80-1.00 (m, 13H), 1.00-0.70 (m, 6H).

Example 2(1)-Example 2(17)

By the same procedures as described in example 2 using a corresponding compound, the following compounds were given. Unless specified, free compounds are shown.

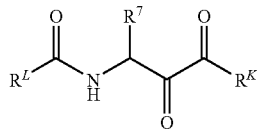

| Example | $R^L$ | $R^7$ | $R^K$ |
|---|---|---|---|
| 2(1) | cyclohexyl | isopropyl | ![structure] |

TLC:Rf 0.52 (ethyl acetate:methanol = 9:1)
NMR: δ 10.52 (s, 1H), 7.92 (d, J = 7.2 Hz, 1H), 4.84 (t-like, J = 6.9 Hz,
1H), 3.43-3.27 (m, 4H), 2.68 (s, 3H), 2.35-2.24 (m, 1H), 2.22-2.10 (m,
1H), 1.67-1.58 (m, 5H), 1.37-1.07 (m, 5H),
0.87 (d, J = 6.9 Hz, 3H),
0.82 (d, J = 6.9 Hz, 3H)

| Example | $R^L$ | $R^7$ | $R^K$ |
|---|---|---|---|
| 2(2) | cyclohexyl | isopropyl | ![structure] |

TLC:Rf 0.29 (n-hexane:ethyl acetate = 1:3)
NMR: δ 10.91 (s, 1H), 8.10 (d, J = 6.9 Hz, 1H), 4.74 (t-like, J = 6.9 Hz,
1H), 4.39 (dt, J = 2.4, 7.5 Hz, 2H),
3.64 (t, J = 7.5 Hz, 2H), 2.34-2.23
(m, 1H), 2.21-2.09 (m, 1H), 1.67-1.58
(m, 5H), 1.37-1.10 (m, 5H),
0.88 (d, J = 6.9 Hz, 3H), 0.84
(d, J = 6.9 Hz, 3H)

| 2(3) | cyclohexyl | neopentyl | ![structure] |

TLC:Rf 0.59 (methylene chloride:methanol = 9:1)
NMR: δ 10.52 (brs, 1H), 8.06 (d, J =
7.2 Hz, 1H), 5.02-4.92 (m, 1H),
3.45-3.20 (m, 4H), 2.69 (s, 3H),
2.23-2.09 (m, 1H), 1.80-1.03 (m,
12H), 0.89 (s, 9H)

| 2(4) | cyclohexyl | isobutyl | ![structure] |

TLC:Rf 0.56 (methylene chloride:methanol = 9:1)
NMR: δ 10.52 (brs, 1H), 8.08 (d,
J = 7.2 Hz, 1H), 4.96-4.85 (m, 1H),
3.43-3.20 (m, 4H), 2.69 (s, 3H),
2.24-2.11 (m, 1H), 1.83-1.04 (m,
13H), 0.88 and 0.85 (each d, J =
6.6 Hz, total 6H)

| 2(5) | cycloheptyl | neopentyl | ![structure] |

TLC:Rf 0.59 (methylene chloride:methanol = 9:1)
NMR: δ 10.4 (broad, 1H), 7.69 (broad,
1H), 4.95 (m, 1H), 3.43 (t,
J = 7.2 Hz, 2H), 2.38 (m, 1H), 2.28 (t,
J = 7.2 Hz, 2H), 2.03 (m, 2H),
1.85-1.33 (m, 14H), 0.93 (s, 9H)

| 2(6) | cycloheptyl | neopentyl | ![structure] |

TLC:Rf 0.65 (methylene chloride:methanol = 9:1)
NMR: δ 10.6 (brs, 1H), 8.08
(brd, J = 7.2 Hz, 1H), 4.91 (m, 1H), 3.47
(m, 2H), 3.24 (t, J = 7.2 Hz, 2H), -continued

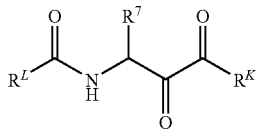

| Example | $R^L$ | $R^7$ | $R^K$ |
|---|---|---|---|

2.38-2.25 (m, 3H), 1.75-1.32 (m, 14H), 0.90 (s, 9H)

2(7) cyclohexyl

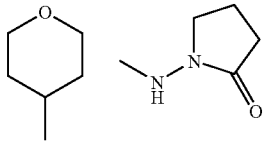

TLC:Rf 0.49 (methylene chloride:methanol = 9:1)
NMR: δ 1.01-1.76 (m, 14H),
1.92-2.14 (m, 3H), 2.19-2.33 (m, 3H),
3.23 (m, 2H), 3.41 (t, J = 7.14 Hz, 2H), 3.82 (m, 2H), 4.77 (m, 1H),
8.17 (d, J = 7.42 Hz, 1H), 10.72 (s, 1H)

2(8) cyclohexyl neopentyl 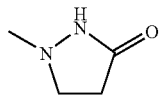

TLC:Rf 0.38 (methylene chloride:methanol = 9:1)
NMR: δ 11.50 (s, 1H), 8.43 (d, J = 6.6 Hz, 1H), 4.54-4.46 (m, 1H),
4.15-3.95 (m, 2H), 2.60 (t, J = 8.4 Hz, 2H), 2.22-2.07 (m, 1H),
1.78-1.03 (m, 12H), 0.90 (s, 9H)

2(9) hydro-chloride cyclohexyl cyclohexyl

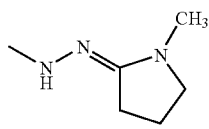

TLC:Rf 0.56 (methylene chloride:methanol = 9:1)
NMR: δ 0.90-1.90 (m, 2H), 2.05 (m, 2H), 2.26 (m, 1H), 2.82 (t, J = 7.5 Hz, 2H), 3.14 (s, 3H), 3.81 (t, J = 7.5 Hz, 2H), 4.66 (m, 1H), 8.27 (d, J = 5.7 Hz, 1H), 11.7-11.4 (broad, 1H), 11.55 (brs, 1H)

2(10) cyclohexyl

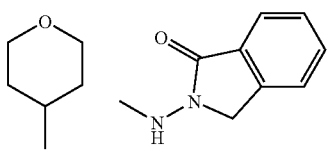

TLC:Rf 0.59 (methanol:ethyl acetate = 1:9)
NMR: δ 1.00-1.80 (m, 14H), 2.00-2.40 (m, 2H), 3.27 (m, 2H), 3.83 (m, 2H), 4.55 (s, 2H), 4.79 (t, J = 6.46 Hz, 1H), 7.45-7.80 (m, 4H), 8.22 (d, J = 6.87 Hz, 1H), 11.10 (s, 1H)

2(11) cyclohexyl

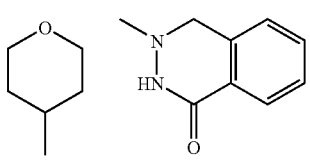

TLC:Rf 0.49 (ethyl acetate)
NMR(CDCl$_3$): δ 0.90-1.90 (m, 14H),

-continued

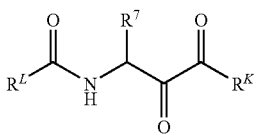

| Example | $R^L$ | $R^7$ | $R^K$ |
|---|---|---|---|

1.95-2.15 (m, 1H), 2.15-2.60 (m, 1H), 3.38 (m, 2H), 3.96 (m, 2H), 4.11 (m, 1H), 5.07 (m, 2H), 7.07 (m, 1H), 7.31 (m, 1H), 7.40-7.70 (m, 2H), 8.10 (m, 1H), 9.35 (m, 1H)

2(12) cycloheptyl

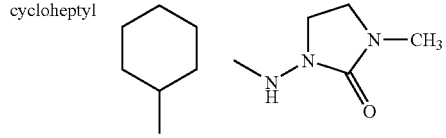

TLC:Rf 0.65 (ethyl acetate:methanol = 9:1)
NMR: δ 1.43 (m, 23H), 2.43 (m, 1H), 2.69 (s, 3H), 3.34 (m, 4H), 4.80 (t-like, J = 6.59 Hz, 1H), 7.98 (d, J = 7.14 Hz, 1H), 10.47 (s, 1H)

2(13) cyclohexyl

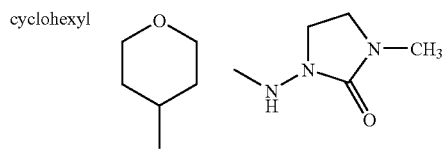

TLC:Rf 0.41 (ethyl acetate:methanol = 9:1)
NMR: δ 1.27 (m, 9H), 1.65 (m, 5H), 2.09 (m, 1H), 2.26 (m, 1H), 2.69 (s, 3H), 3.29 (m, 6H), 3.80 (m, 2H), 4.81 (t-like, J = 6.73 Hz, 1H), 8.11 (d, J = 7.14 Hz, 1H), 10.50 (s, 1H)

2(14) cycloheptyl

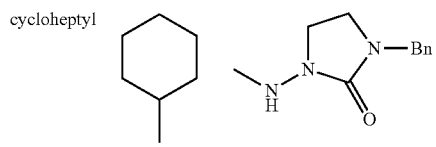

TLC:Rf 0.40 (n-hexane:ethyl acetate = 1:2)
NMR: δ 1.44 (m, 23H), 2.44 (m, 1H), 3.22 (m, 2H), 3.41 (t, J = 8.10 Hz, 2H), 4.28 (d, J = 15.11 Hz, 1H), 4.35 (m, 1H), 4.82 (t, J = 6.59 Hz, 1H), 7.26 (m, 5H), 8.00 (d, J = 7.14 Hz, 1H), 10.55 (s, 1H)

2(15) cyclohexyl

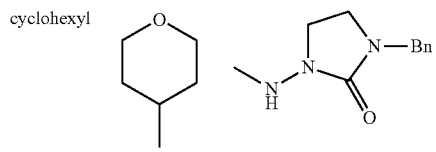

TLC:Rf 0.52 (ethyl acetate:methanol = 9:1)
NMR: δ 1.45 (m, 14H), 2.10 (m, 1H), 2.28 (m, 1H), 3.22 (m, 4H), 3.41 (t, J = 7.97 Hz, 2H), 3.81 (m, 2H), 4.28 (d, J = 15.11 Hz, 1H), 4.34 (m, 1H), 4.82 (t, J = 6.73 Hz, 1H), 7.28 (m, 5H), 8.14 (d, J = 7.14 Hz, 1H), 10.57 (s, 1H)

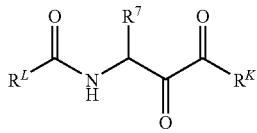

| Example | $R^L$ | $R^7$ | $R^K$ |
|---|---|---|---|
| 2(16) | cyclohexyl | | |

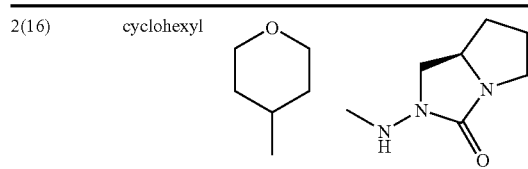

TLC:Rf 0.55 (ethyl acetate:methanol = 9:1)
NMR: δ 1.57 (m, 20H), 3.14 (m, 1H),
3.65 (m, 8H), 5.18 (m, 1H), 6.20
(d, J = 8.24 Hz, 1H), 8.65 (s, 1H)

2(17) cycloheptyl

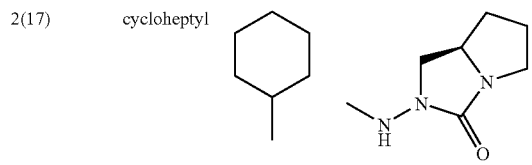

TLC:Rf 0.57 (ethyl acetate)
NMR: δ 1.50 (m, 27H), 2.30 (m, 1H),
3.14 (m, 1H), 3.67 (m, 4H), 5.11
(m, 1H), 6.02 (d, J = 7.97 Hz, 1H),
8.58 (s, 1H)

Example 3

Preparation of N'-benzylidene-[(3S)-3-cyclohexyl-carbonylamino-5-methyl-2-oxo hexanohydrazide]

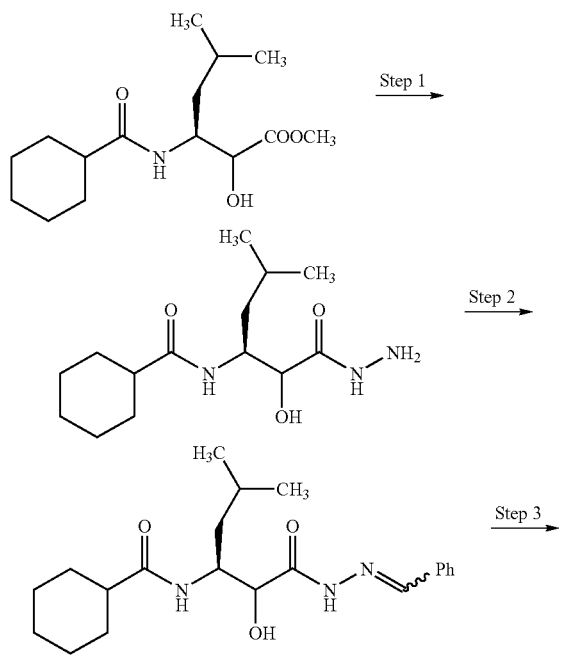

Step 1: To a solution of the compound prepared in step 8 of example 2 (11.4 g) in methanol (40 ml) was added hydrazine monohydrate (10.2 g) and the mixture was stirred overnight at room temperature. The precipitate was collected and washed with methanol and dried to give (3S)-3-cyclohexylcarbonylamino-2-hydroxy-5-methylhexanohydrazide (11.0 g).

TLC: Rf 0.39 (methylene chloride:methanol=9:1).

Step 2: To a suspension of the compound prepared in step 1 (300 mg) in ethanol (3 ml) was added benzaldehyde (0.66 ml) and the mixture was refluxed for 6 hours. The reaction mixture was concentrated and the residue was washed with t-butyl methyl ether and dried to give N'-benzylidene-[(3S)-3-cyclohexylcarbonyl amino-2-hydroxy-5-methylhexanohydrazide] (340 mg).

TLC: Rf 0.77 (ethyl acetate).

Step 3: To a solution of the compound prepared in step 2 (233 mg) in DMSO (2 ml) were added triethylamine (0.2 ml) and sulfur trioxide-pyridine complex (2.96 mg) at 0° C. and the mixture was stirred for 30 minutes. To the reaction mixture was added water and extracted with ethyl acetate. The aqueous layer was reextracted with chloroform. The organic layers were combined and washed with brine, dried over anhydrous sodium sulfate and concentrated. The residue was washed with diisopropylether and dried to give N'-benzylidene-[(3S)-3-cyclohexylcarbonylamino-5-methyl-2-oxohexanohydrazide] (182 mg).

TLC: Rf 0.56 (ethyl acetate:n-hexane=1:1);

NMR: δ 12.18 and 12.09 (each brs, totally 1H), 8.49 and 7.99 (each s, totally 1H), 8.17 and 8.07 (each brd, J=6.3 Hz, totally 1H), 7.70-7.60 (m, 2H), 7.50-7.35 (m, 3H), 5.00 and 4.89 (each m, totally 1H), 2.30-2.10 (m, 1H), 1.81-1.02 (m, 13H), 1.00-0.80 (m, 6H).

Example 3(1)-Example 3(12)

By the same procedure as described in example 3 using the compound prepared in step 9 of example 2 or a corresponding compound, the following compounds were given. Unless specified, free compounds are shown.

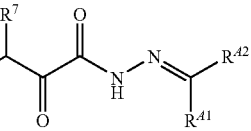

| Example | $R^L$ | $R^7$ | $R^{A1}$ $R^{A2}$ |
|---|---|---|---|
| 3(1) | cyclohexyl | (S)-isobutyl | isopropylidene |

TLC:Rf 0.49 (ethyl acetate)
NMR: δ 11.02 and 10.61 (each brs,

-continued

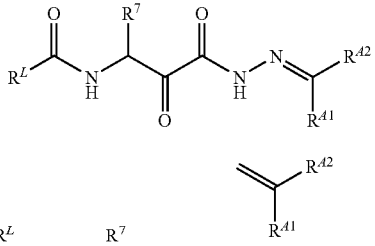

| Example | $R^L$ | $R^7$ | (structure) |
|---|---|---|---|
| | | | totally 1H), 8.10 and 7.90 (each brd, J = 7.2 Hz, and J = 9.0 Hz, totally 1H), 4.98 and 4.80 (each m, totally 1H), 2.30-1.00 (m, 20H), 1.00-0.80 (m, 6H) |
| 3(2) | cyclohexyl | (S)-isobutyl | 1-phenylethylidene |
| | | | TLC:Rf 0.80 (ethyl acetate) |
| | | | NMR: δ 11.40 and 10.50 (each br, totally 1H), 8.13 and 8.02 (each brd, J = 7.5 Hz, and J = 9.0 Hz, totally 1H), 7.81 and 7.69 (each m, totally 2H), 7.48-7.37 (m, 3H), 5.03-4.80 (m, 1H), 2.30-2.10 (m, 4H), 1.80-1.00 (m, 13H), 1.00-0.78 (m, 6H) |
| 3(3) | cyclohexyl | (S)-isobutyl | cyclopentylidene |
| | | | TLC:Rf 0.51 (ethyl acetate) |
| | | | NMR: δ 10.92 and 10.43 (each brs, totally 1H), 8.06 and 7.89 (each brd, J = 7.2 Hz, and J = 9.0 Hz, totally 1H), 4.96 and 4.73 (each m, totally 1H), 2.40-2.10 (m, 5H), 1.80-1.00 (m, 17H), 1.00-0.78 (m, 6H) |
| 3(4) hydro- chloride | cyclohexyl | isobutyl | pyridin-2-ylmethylidene |
| | | | TLC:Rf 0.38 (ethyl acetate) |
| | | | NMR: δ 12.60 and 12.40 (each brs, totally 1H), 8.66 and 8.25 (each brd, J = 5.1 Hz, and J = 6.6 Hz, totally 1H), 8.57 and 8.11 (each brs, totally 1H), 8.20-8.00 (m, 2H), 7.70-7.50 (m, 2H), 6.90-6.30 (m, 1H), 5.00-4.80 (m, 1H), 2.30-2.10 (m, 1H), 1.80-1.00 (m, 13H), 1.00-0.78 (m, 6H) |
| 3(5) | cyclohexyl | (S)-isobutyl | furan-3-ylmethylidene |
| | | | TLC:Rf 0.78 (ethyl acetate) |
| | | | NMR: δ 12.03 and 11.98 (each brs, totally 1H), 8.41 and 7.98 (each s, totally 1H), 8.20-7.70 (m, 3H), 6.75 (m, 1H), 5.01-4.83 (m, 1H), 2.30-2.10 (m, 1H), 1.80-1.00 (m, 13H), 1.00-0.78 (m, 6H) |
| 3(6) | cyclohexyl | (S)-isobutyl | 3-methyl-1-butylidene |
| | | | TLC:Rf 0.84 (ethyl acetate) |
| | | | NMR: δ 11.70 and 10.60 (each brs, totally 1H), 8.20 and 7.90 (each brd, J = 7.2 Hz, and J = 9.0 Hz, totally 1H), 7.77 and 7.31 (each t, J = 5.1 Hz, 1H), 4.98-4.80 (each m, totally 1H), 2.30-1.95 (m, 3H), 1.90-1.00 (m, 14H), 1.00-0.80 (m, 12H) |
| 3(7) | cyclohexyl | (S)-isobutyl | tetrahydropyran-4-yl methylidene |
| | | | TLC:Rf 0.83 (ethyl acetate) |
| | | | NMR: δ 11.73 and 11.60 (each brs, totally 1H), 8.13 and 7.93 (each brd, J = 7.2 Hz, and J = 9.0 Hz, totally 1H), 7.71 and 7.30 (each brd, J = 5.1 Hz, totally 1H), 4.92-4.70 (m, 1H), 3.90-3.70 (m, 2H), 3.43-3.20 (m, 2H), 2.60-2.05 (m, 2H), 1.80-1.00 (m, 17H), 1.00-0.80 (m, 6H) |
| 3(8) | cyclohexyl | (S)-isobutyl | tetrahydropyran-4-ylidene |
| | | | TLC:Rf 0.44 (methanol:ethyl acetate = 1:19) |
| | | | NMR: δ 11.73 and 11.60 (each brs, totally 1H), 8.13 and 7.93 (each brd, J = 7.2 Hz, and J = 9.0 Hz, totally 1H), 7.71 and 7.30 (each brd, J = 5.1 Hz, totally 1H), 4.92-4.70 (m, 1H), 3.90-3.70 (m, 2H), 3.43-3.20 (m, 2H), 2.60-2.05 (m, 2H), 1.80-1.00 (m, 17H), 1.00-0.80 (m, 6H) |
| 3(9) | cyclohexyl | neopentyl | 1-(pyridin-2-yl)ethylidene |
| | | | free compound |
| | | | NMR (100° C.): δ 8.59 (brd, J = 3.9 Hz, 1H), 7.98 (br, 2H), 7.80 (m, 1H), 7.40 (m, 1H), 4.92 (m, 1H), 2.38 (s, 3H), 2.19 (m, 1H), 1.90-1.50 (m, 7H), 1.40-1.03 (m, 5H), 1.00-0.78 (m, 9H) |
| | | | hydrochloride |
| | | | TLC:Rf 0.47 (methylene chloride:methanol = 9:1) |
| | | | NMR: δ 11.71 and 11.02 (each brs, totally 1H), 8.60 (m, 1H), 8.30-7.81 (m, 3H), 7.60-7.40 (m, 1H), 5.10 and 4.87 (each m, totally 1H), 2.40 and 2.31 (each s, totally 3H), 2.21-2.03 (m, 1H), 1.80-1.00 (m, 12H), 0.91 and 0.82 (each s, totally 9H) |
| 3(10) hydro- chloride | cyclohexyl | neopentyl | 1-(pyridin-4-yl)ethylidene |
| | | | TLC:Rf 0.70 (methylene chloride:methanol = 9:1) |
| | | | NMR: δ 12.10 and 11.37 (each brs, totally 1H), 8.92-8.82 (m, 2H), 8.30-7.90 (m, 3H), 5.03-4.78 (m, totally 1H), 2.60-2.21 (m, 3H), 2.30-2.00 (m, 1H), 1.80-1.40 (m, 6H), 1.40-1.00 (m, 6H), 1.00-0.70 (m, 9H) |
| 3(11) | cyclohexyl | neopentyl | 1-(3-trifluoromethyl- phenyl)ethylidene |
| | | | TLC:Rf 0.66 (n-hexane:ethyl acetate = 1:1) |
| | | | NMR: δ 11.60 and 11.02 (each brs, each 1H), 8.20-8.10 (m, 2H), 8.02-7.90 (brs, 1H), 7.83-7.60 (m, 2H), 5.04 and 4.82 (each t, J = 9.0 Hz, totally 1H), 2.38 and 2.27 (each s, totally 3H), 2.20-2.00 (m, 1H), 1.80-1.00 (m, 12H), 0.91 and 0.82 (each s, totally 9H) |
| 3(12) | cyclohexyl | neopentyl | 1-(4-trifluorophenyl) ethylidene |
| | | | TLC:Rf 0.55 (n-hexane:ethyl acetate = 1:1) |
| | | | NMR: δ 11.61 and 11.20 (each m, totally 1H), 8.20-7.90 (m, 5H), 5.05 and 4.85 (each t, J = 9.0 Hz, totally 1H), 2.37 and 2.26 (each s, totally 3H), 2.20-2.00 (m, 1H), 1.90-1.00 (m, 12H), 0.91 and 0.82 (each s, totally 9H) |

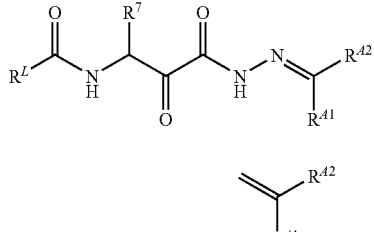

Example 4

Preparation of N'-acetyl-N'-phenyl-[(3S)-3-cyclohexylcarbonylamino-5-methyl-2-oxohexanohydrazide]

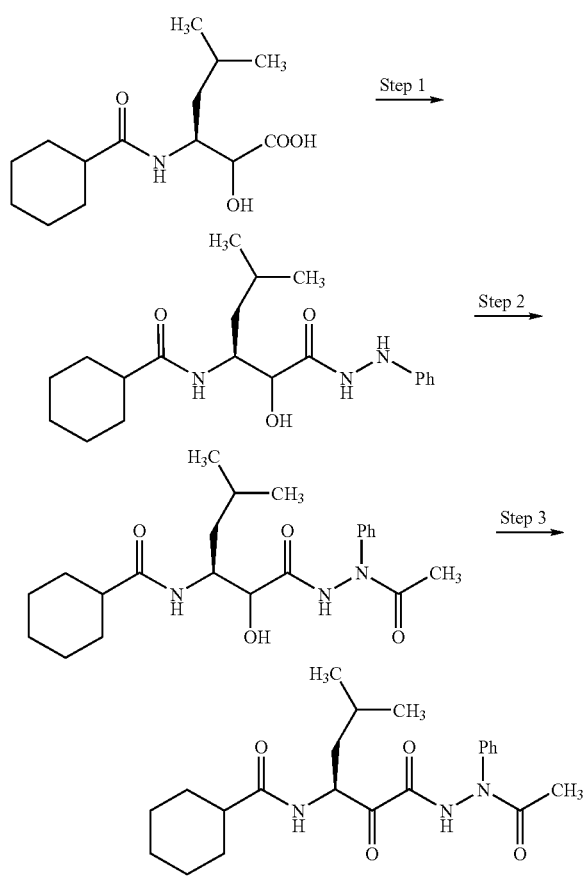

Step 1: To a solution of the compound prepared in step 9 of example 2 (620 mg) and phenylhydrazine (246 mg) in N,N-dimethyldormamide (5 ml) were added 1-hydroxybenzotriazole (342 mg) and 1-ethyl-3-[3-(dimethylamino)propyl]carbodiimide hydrochloride (524 mg) and the mixture was stirred for 3 hours at room temperature. To the reaction mixture were added water and ethyl acetate and the mixture was filtered. The filtrate was extracted and the organic layer was washed with brine, dried over sodium sulfate and concentrated. The residue was combined with the above given precipitate and washed with diisopropyl ether and dried to give N'-phenyl-[(3S)-3-cyclohexylcarbonylamino-2-hydroxy-5-methylhexanohydrazide] (635 mg).

TLC: Rf 0.51 (ethyl acetate).

Step 2: To a solution of the compound prepared in step 1 (510 mg) in pyridine (5 ml) was added acetic anhydride (0.40 ml) at room temperature and the mixture was stirred for 15 hours. To the reaction mixture was added 2N hydrochloric acid and extracted with ethyl acetate. The organic layer was washed with a saturated aqueous solution of sodium bicarbonate and brine successively, dried over anhydrous sodium sulfate and concentrated. The residue was dissolved in methanol (5 ml) and thereto was added potassium carbonate (195 mg) and the mixture was stirred for 2 hours at room temperature. The organic layer was washed with brine, dried over anhydrous sodium sulfate and concentrated. The residue was washed with ethyl acetate and filtered and crystallized. The filtrate was concentrated and the residue was washed with t-butyl methyl ether and collected. It was combined with the above crystals and dried to give N'-acetyl-N'-phenyl-[(3S)-3-cyclohexylcarbonyl amino-2-hydroxy-5-methylhexanohydrazide] (335 mg).

TLC: Rf 0.60 (ethyl acetate).

Step 3: To a solution of the compound prepared in step 2 (202 mg) in acetonitrile (5 ml) was added 1,1,1-triacetoxy-1,1-dihydro-1,2-benzoiodoxol-3-(1H)-one (Dess-Martin reagent) (254 mg) at room temperature and the mixture was stirred for 15 minutes. To the reaction mixture were added ethyl acetate and a saturated aqueous solution of sodium thiosulfate and the mixture was stirred vigorously for 5 minutes. Extracted organic layer was washed with a saturated aqueous solution of sodium bicarbonate twice, and brine once successively, dried over anhydrous sodium sulfate and concentrated. The residue was suspended in ethyl acetate (2 ml) and collected by filtration and dried to give N'-acetyl-N'-phenyl-[(3S)-3-cyclohexylcarbonylamino-5-methyl-2-oxohexanohydrazide] (89 mg).

TLC: Rf 0.65 (n-hexane:ethyl acetate=2:8);

NMR (100° C.): δ 11.2 (brs, 1H), 7.81 (brd, J=5.8 Hz, 1H), 7.54-7.14 (m, 5H), 4.75 (m, 1H), 2.15 (m, 1H), 2.04 (s, 3H), 1.70-1.00 (m, 13H), 0.90 (d, J=6.3 Hz, 3H), 0.88 (d, J=6.3 Hz, 3H).

Example 4(1)

N'-acetyl-N'-cyclohexyl-[3-cyclohexylcarbonylamino-3-(tetrahydropyran-4-yl)-2-oxopropanohydrazide]

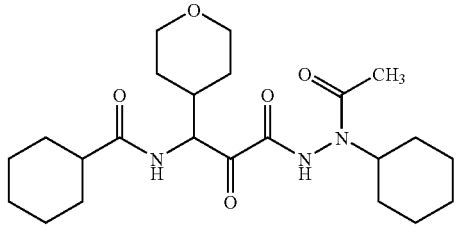

By the same procedure as described in example 4 using a corresponding compound, the following compound was given.

TLC: Rf 0.63 (ethyl acetate:methanol=9:1);

NMR: δ 1.00-1.40 (m, 12H), 1.40-1.75 (m, 12H), 1.78 and 1.81 (each s, total 3H), 2.00-2.35 (m, 2H), 3.22 (m, 2H), 3.83 (m, 2H), 4.09 (m, 1H), 4.55 (m, 1H), 8.30 (d, 1=6.04 Hz, 1H), 10.82 and 10.89 (each brs, total 1H).

Example 5

Preparation of 1-(3-cyclohexylcarbonylamino-5,5-dimethyl-2-oxohexanoylamino)-2,5-dioxopyrrolidine

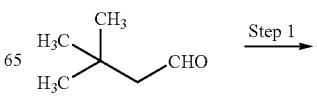

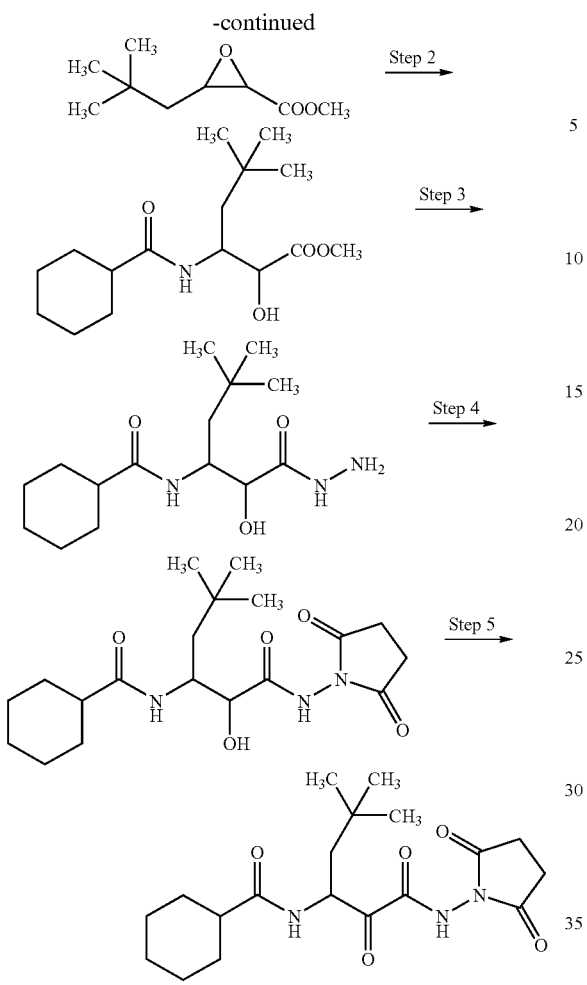

Step 1: To a solution of 3,3-dimethylbutylaldehyde (4.1 g) and methyl chloroacetate (4.44 g) in acetonitrile (60 ml) was added sodium hydride (1.57 g) at 60° C. over a period of 75 minutes and the mixture was refluxed for 0.5 hours. The reaction mixture was poured into ice-water and extracted with t-butyl methyl ether, the organic layer was washed with brine and dried over anhydrous magnesium sulfate and concentrated. The residue was purified by column chromatography on silica gel (n-hexane:ethyl acetate=19:1) to give 5,5-dimethyl-2,3-epoxyhexanoic acid methyl ester (3.68 g).

TLC: Rf 0.53 (n-hexane:ethyl acetate=4:1).

Step 2: To a mixture of the compound prepared in step 1 (2.75 g) and cyclohexanecarbonitrile (3.8 ml) was added borane trifluoride ether complex (2.1 ml) at 0° C. and the mixture was stirred for 2 hours at room temperature. To the reaction mixture were added water, methanol and hydrochloric acid and the mixture was stirred for 4 hours at room temperature. The reaction mixture was poured into water and extracted with ethyl acetate. The organic layer was washed with a saturated aqueous solution of sodium bicarbonate and brine successively, dried over anhydrous magnesium sulfate and concentrated. The residue was washed with hexane and dried. The mother liquor was purified by column chromatography on silica gel (n-hexane:ethyl acetate=2:1) and it was combined with the above residue to give 3-cyclohexylcarbonylamino-5,5-dimethyl-2-hydroxyhexanoic acid methyl ester (2.76 g).

TLC: Rf 0.34 and 0.23 (n-hexane:ethyl acetate=2:1).

Step 3: To a solution of the compound prepared in step 2 (2.73 g) in methanol (10 ml) was added hydrazine monohydrate (2.33 g) and the mixture was stirred overnight at room temperature. The precipitate was collected and the mother liquor was washed with brine, and the given solid product was washed with t-butylmethyl ether and dried to give 3-cyclohexylcarbonylamino-5,5-dimethyl-2-hydroxyhexanohydrazide (2.73 g).

TLC: Rf 0.32 (ethyl acetate:methanol=9:1).

Step 4: To a solution of the compound prepared in step 3 (299 mg) in acetic acid (2 ml) was added succinic anhydride (110 mg) and the mixture was refluxed for 1 hour. The reaction mixture was concentrated to give 1-(3-cyclohexylcarbonylamino-5,5-dimethyl-2-hydroxyhexanoylamino)-2,5-dioxopyrrolidine (433 mg).

TLC: Rf 0.52 (methylene chloride:methanol=9:1).

Step 5: To a solution of the compound prepared in step 4 (420 mg) in DMSO (2 ml) were added triethylamine (0.42 ml) and sulfur trioxide-pyridine complex (477 mg) and the mixture was stirred overnight at room temperature. The reaction mixture was poured into 1N hydrochloric acid and extracted with ethyl acetate. The organic layer was washed with water, a saturated aqueous solution of sodium bicarbonate and brine successively, dried over anhydrous magnesium sulfate and concentrated. The residue was purified by column chromatography on silica gel (ethyl acetate) to give 1-(3-cyclohexylcarbonylamino-5,5-dimethyl-2-oxohexanoylamino)-2,5-dioxopyrrolidine (160 mg).

TLC: Rf 0.56 (methylene chloride:methanol=9:1);

NMR: δ 0.89 (s, 9H), 1.40 (m, 12H), 2.17 (m, 1H), 2.82 (s, 4H), 4.95 (m, 1H), 8.12 (d, J=7.14 Hz, 1H), 11.37 (s, 1H).

Example 5(1)-Example 5(21)

By the same procedure as described in example 5, the following compounds were given.

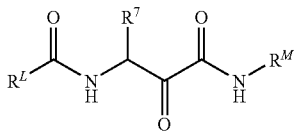

| Example | $R^L$ | $R^7$ | $R^M$ |
|---|---|---|---|
| 5(1) | cyclohexyl | 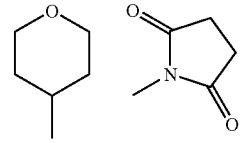 | |
| | TLC:Rf 0.49 (ethyl acetate:methanol = 9:1) NMR: δ 11.35 (s, 1H), 8.19 (d, J = 6.6 Hz, 1H), 4.78 (t, J = 6.6 Hz, 1H), 3.93-3.70 (m, 2H), 3.30-3.10 (m, 2H), 2.81 (s, 4H), 2.32-2.19 (m, 1H), 2.19-2.02 (m, 1H), 1.81-1.00 (m, 14H) | | |
| 5(2) | cyclohexyl | cyclohexyl | 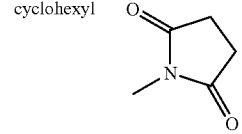 |

| Example | R^L | R^7 | R^M |
|---|---|---|---|
| | | | TLC:Rf 0.56 (methylene chloride:methanol = 9:1)<br>NMR: δ 11.31 (s, 1H), 8.07 (d, J = 7.2 Hz, 1H), 4.81 (t, J = 6.6 Hz, 1H), 2.81 (s, 4H), 2.32-2.21 (m, 1H), 1.89-1.73 (m, 1H), 1.73-0.97 (m, 20H) |
| 5(3) | cyclohexyl | phenyl | (N-methylsuccinimide) |
| | | | TLC:Rf 0.54 (methylene chloride:methanol = 9:1)<br>NMR: δ 11.36 (s, 1H), 8.68 (d, J = 5.7 Hz, 1H), 7.50-7.30 (m, 5H), 6.05 (t, J = 5.7 Hz, 1H), 2.78 (s, 4H), 2.36-2.24 (m, 1H), 1.84-1.03 (m, 10H) |
| 5(4) | cyclohexyl | (4-methyltetrahydropyran-4-yl) | (1,4,4-trimethylpiperidine-2,6-dione) |
| | | | TLC:Rf 0.33 (methylene chloride:methanol = 10:1)<br>NMR: δ 1.80-0.98 (m, 20H), 2.20-2.02 (m, 1H), 2.38-2.21 (m, 1H), 2.80-2.60 (m, 4H), 3.30-3.18 (m, 2H), 3.86-3.78 (m, 2H), 4.91 (t, J = 6.87 Hz, 1H), 8.10 (d, J = 7.42 Hz, 1H), 11.02 (s, 1H) |
| 5(5) | cyclohexyl | (4-methyltetrahydropyran-4-yl) | (1,3,3-trimethylpiperidine-2,6-dione) |
| | | | TLC:Rf 0.33 (methylene chloride:methanol = 10:1)<br>NMR: δ 1.90-1.00 (m, 22H), 2.20-2.02 (m, 1H), 2.38-2.21 (m, 1H), 2.90-2.78 (m, 2H), 3.30-3.16 (m, 2H), 3.86-3.75 (m, 2H), 4.98-4.82 (m, 1H), 8.08 (d, J = 7.50 Hz, 1H), 10.99 and 10.96 (each s, total 1H) |
| 5(6) | cyclohexyl | cyclohexyl | (4-methylmorpholine-3,5-dione) |
| | | | TLC:Rf 0.57 (n-hexane:ethyl acetate = 1:2)<br>NMR: δ 1.00-1.79 (m, 20H), 1.80-1.95 (m, 1H), 2.20-2.38 (m, 1H), 4.62 (s, 4H), 4.80-4.92 (m, 1H), 8.04 (d, J = 6.87 Hz, 1H), 11.26 (s, 1H) |
| 5(7) | cyclohexyl | (4-methyltetrahydropyran-4-yl) | (N-methylphthalimide) |
| | | | TLC:Rf 0.61 (methylene chloride:methanol = 9:1)<br>NMR: δ 11.51 (s, 1H), 8.27 (d, J = 6.6 Hz, 1H), 8.08-7.87 (m, 4H), 4.74 (t, J = 6.6 Hz, 1H), 3.92-3.73 (m, 2H), 3.27-3.15 (m, 2H), 2.34-2.22 (m, 1H), 2.22-2.05 (m, 1H), 1.83-1.03 (m, 14H) |
| 5(8) | cyclohexyl | (S)-isopropyl | (N-methylsuccinimide) |
| | | | TLC:Rf 0.53 (ethyl acetate)<br>NMR: δ 11.34 (s, 1H), 8.07 (d, J = 7.2 Hz, 1H), 4.81 (t-like, J = 7.2 Hz, 1H), 2.81 (s, 4H), 2.35-2.25 (m, 1H), 2.20-2.07 (m, 1H), 1.69-1.59 (m, 5H), 1.38-1.05 (m, 5H), 0.89 (d, J = 6.0 Hz, 3H), 0.86 (d, J = 6.9 Hz, 3H) |
| 5(9) | cyclohexyl | cyclohexyl | (1,3,3-trimethylpyrrolidine-2,5-dione) |
| | | | TLC:Rf 0.58 (n-hexane:ethyl acetate = 1:2)<br>NMR: δ 11.31 (s, 1H), 8.08 (d, J = 6.6 Hz, 1H), 4.79 (t, J = 6.6 Hz, 1H), 2.75 (s, 2H), 2.32-2.20 (m, 1H), 1.93-0.95 (m, 21H), 1.26 (s, 6H) |
| 5(10) | cyclohexyl | neopentyl | (1,3,3-trimethylpyrrolidine-2,5-dione) |
| | | | TLC:Rf 0.42 (n-hexane:ethyl acetate = 1:2)<br>NMR: δ 11.35 (s, 1H), 8.13 (d, J = 7.2 Hz, 1H), 4.92 (m, 1H), 2.76 (s, 2H), 2.23-2.10 (m, 1H), 1.80-1.08 (m, 12H), 1.26 (s, 6H), 0.89 (s, 9H) |
| 5(11) | 3,3-dimethylbut-1-enyl | cyclohexyl | (N-methylsuccinimide) |

-continued

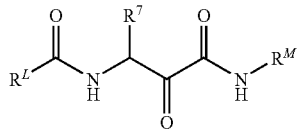

| Example | $R^L$ | $R^7$ | $R^M$ |
|---|---|---|---|

TLC:Rf 0.59 (ethyl acetate)
NMR: δ 11.36 (s, 1H), 8.26 (d, J = 6.9 Hz, 1H), 6.63 (d, J = 15.6 Hz, 1H), 6.04 (d, J = 15.6 Hz, 1H), 5.01 (t-like, J = 6.6 Hz, 1H), 2.82 (s, 4H), 1.93-1.50 (m, 6H), 1.27-0.99 (m, 5H), 1.03 (s, 9H)

5(12) cycloheptyl 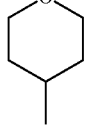 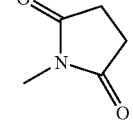

TLC:Rf 0.48 (ethyl acetate:methanol = 9:1)
NMR (CDCl$_3$): δ 1.54 (m, 16H), 2.29 (m, 2H), 2.87 (s, 4H), 3.38 (m, 2H), 3.98 (m, 2H), 5.06 (m, 1H), 6.18 (d, J = 7.97 Hz, 1H), 9.20 (m, 1H)

5(13) cycloheptyl 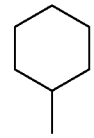 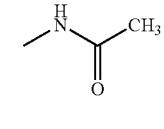

TLC:Rf 0.61 (ethyl acetate)
NMR: δ 1.40 (m, 23H), 2.49 (m, 1H), 2.81 (s, 4H), 4.80 (t, J = 6.59 Hz, 1H), 8.05 (d, J = 6.59 Hz, 1H), 11.29 (s, 1H)

5(14) cycloheptyl 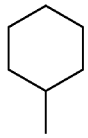 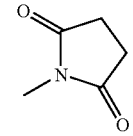

TLC:Rf 0.61 (ethyl acetate)
NMR (CDCl$_3$): δ 1.55 (m, 23H), 2.31 (m, 1H), 2.86 (s, 4H), 5.01 (dd, J = 7.83, 6.18 Hz, 1H), 6.03 (d, J = 7.97 Hz, 1H), 8.97 (s, 1H)

5(15) cycloheptyl 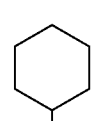 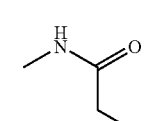

TLC:Rf 0.55 (ethyl acetate)
NMR (CDCl$_3$): δ 1.44 (m, 23H), 2.29 (m, 1H), 2.87 (s, 4H), 5.03 (dd, J = 7.97, 6.32 Hz, 1H), 6.00 (d, J = 7.97 Hz, 1H), 8.86 (s, 1H)

5(16) (1S)-1-(t-butoxycarbonyl-amino)-3-methyl-butyl 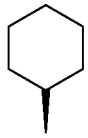 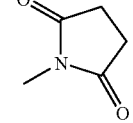

-continued

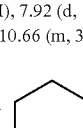

| Example | $R^L$ | $R^7$ | $R^M$ |
|---|---|---|---|

TLC:Rf 0.48 (n-hexane:ethyl acetate 1:3)
NMR : δ 0.84 (m, 6H), 1.37 (m, 22H), 1.84 (m, 1H), 2.82 (s, 4H), 4.04 (m, 1H), 4.96 (t, J = 6.22 Hz, 1H), 6.87 (m, 1H), 8.03 (m, 1H), 11.39 (m, 1H)

5(17) cycloheptyl 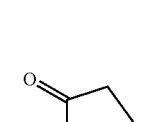 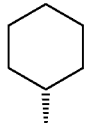

TLC:Rf 0.45 (ethyl acetate)
NMR (CDCl$_3$): δ 1.54 (m, 23H), 2.12 (s, 3H), 2.32 (m, 1H), 5.25 (dd, J = 8.24, 5.49 Hz, 1H), 6.08 (d, J = 8.52 Hz, 1H), 8.93 (s, 1H), 9.46 (s, 1H)

5(18) cycloheptyl 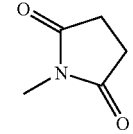 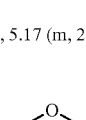

TLC:Rf 0.51 (ethyl acetate:methanol:water = 40:10:1)
NMR: δ 1.34 (m, 23H), 2.41 (m, 5H), 4.92 (t, J = 6.59 Hz, 1H), 7.92 (d, J = 7.42 Hz, 1H), 10.66 (m, 3H)

5(19) (1S)-1-methoxycarbonyl-amino-3-methyl-butyl 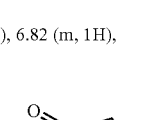

TLC:Rf 0.45 (ethyl acetate)
NMR (CDCl$_3$): δ 1.26 (m, 19H), 1.99 (m, 1H), 2.80 (m, 4H), 3.68 (s, 3H), 4.21 (m, 1H), 5.17 (m, 2H), 6.82 (m, 1H), 9.21 (s, 1H)

5(20) (1S)-1-(t-butoxycarbonyl-amino)-3-methyl-butyl 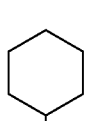 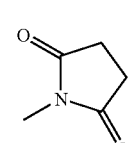

TLC:Rf 0.35 (chloroform:methanol = 19:1)
NMR: δ 0.87 (m, 6H), 1.35 (m, 15H), 1.58 (m, 1H), 2.12 (m, 1H), 2.80 (m, 4H), 3.26 (m, 2H), 3.82 (m, 2H), 4.05 (m, 1H), 4.97 (m, 1H), 6.87 (m, 1H), 8.19 (m, 1H), 11.41 (m, 1H)

Example 5(21)

3-(3-cycloheptylcarbonylamino-3-cyclohexyl-2-oxo-propanoyl)-1,2,3,4-tetrahydrophthalazin-1,4-dione TLC: Rf 0.29 (ethyl acetate);
NMR: δ 1.39 (m, 22H), 1.90 (m, 1H), 2.43 (m, 1H), 2.78 (t, J=6.96 Hz, 2H), 3.14 (t, J=6.77 Hz, 2H), 4.88 (t, J=6.32 Hz, 1H), 8.26 (d, J=5.68 Hz, 1H), 12.36 (br. s., 1H).

Example 6

Preparation of N-methyl-N'-(3-methyl-1,3-thiazolidin-2-ylidene)-[3-cyclohexylcarbonylamino-5-methyl-2-oxohexanohydrazide]hydrochlorde

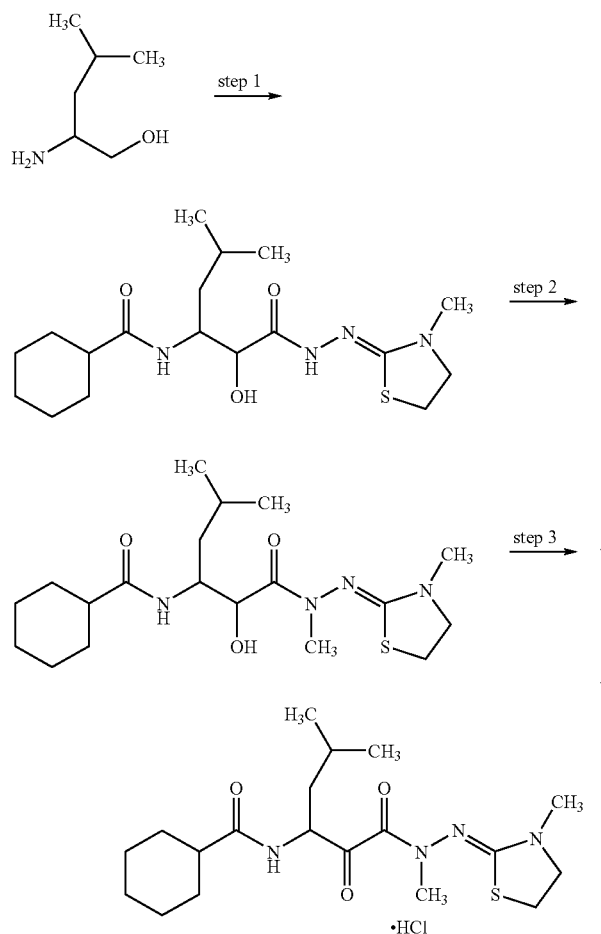

Step 1: By the same procedure as described in step 1->step 2->step 3->step 4->step 5->step 6 of example 1, N'-(3-methyl-1,3-thiazolidin-2-ylidene)-[3-cyclohexylcarbonylamino-2-hydroxy-5-methylhexanohydrazide] was given.
TLC: Rf 0.55 (methylene chloride:methanol=9:1).
Step 2: To a solution of the compound prepared in step 1 (600 mg) in DMF (5 ml) were added potassium carbonate (258 mg) and methyl iodide (0.116 ml) and the mixture was stirred for 2 hours at the same temperature and for 6 hours at room temperature. To the reaction mixture was added and extracted with ethyl acetate. The organic layer was washed with water twice and brine once successively, dried over anhydrous sodium sulfate and concentrated. The residue was purified by column chromatography on silica gel (ethyl acetate:methanol=20:1) to give N-methyl-N'-(3-methyl-1,3-thiazolidin-2-ylidene)-[3-cyclohexylcarbonylamino-2-hydroxy-5-methylhexanohydrazide] (400 mg).

Free Compound
NMR: δ 8.20 and 7.78 (each d, J=9.0 Hz, total 1H), 4.82 and 4.52 (each m, total 1H), 3.70-3.60 (m, 2H), 3.28-118 (m, 2H), 2.95 and 2.94 (each s, total 3H), 2.85 and 2.80 (each s, total 3H), 2.28-2.12 (m, 1H), 1.80-1.00 (m, 13H), 0.92-0.77 (m, 6H).

Hydrochloride
TLC: Rf 0.19 (ethyl acetate);
NMR: δ 7.27 and 6.94 (each brd, J=9.3 Hz, total 1H), 4.42-3.96 (m, 3H), 3.19 (t, J=6.9 Hz, 2H), 3.19 (t, J=6.9 Hz, 2H), 2.88 (s, 6H), 2.10-1.98 (m, 1H), 1.70-1.00 (m, 13H), 0.90-0.75 (m, 6H).

Step 3: By the same procedure as described in example 1 using a hydrochloride of the compound prepared in step 2, N-methyl-N'-(3-methyl-1,3-thiazolidin-2-ylidene) [3-cyclohexylcarbonylamino-5-methyl-2-oxohexanohydrazide]hydrochloride was given.
TLC: Rf 0.70 (ethyl acetate:methanol=9:1);
NMR: δ 8.36 and 7.92 (each m, total 1H), 7.40-6.00 (broad, 1H), 4.80 and 4.87 (each in, total 1H), 3.88 and 3.78 (each m, total 2H), 3.40-126 (m, 2H), 3.09 and 3.03 (each s, total 3H), 3.05 and 2.91 (each s, total 3H), 2.28-2.12 (m, 1H), 1.80-1.00 (m, 13H), 0.93-0.78 (m, total 6H).

Example 7

Preparation of N'-(3-methyl-4-oxo-1,3-thiazolidin-2-ylidene)-[3-cyclohexylcarbonylamino-3-(tetrahydropyran-4-yl)-2-oxopropanohydrazide]

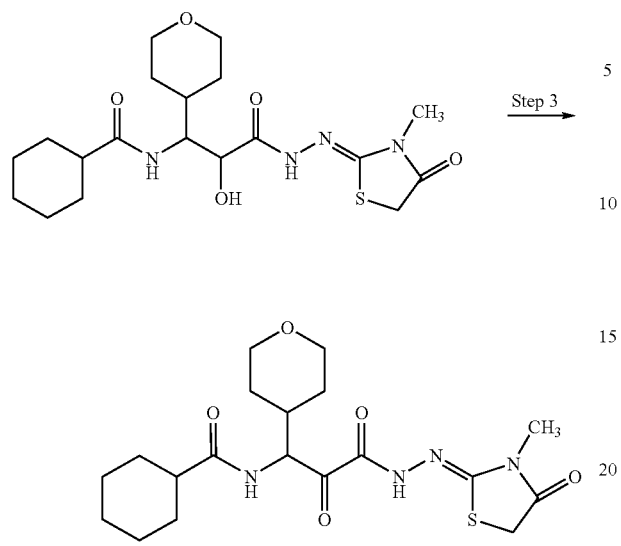

Step 1: To a solution of 1-hydroxybenzotriazole (77 mg) in DMF (2 ml) were added 3-cyclohexylcarbonylamino-3-(tetrahydropyran-4-yl)-2-hydroxypropanoic acid (given by the same procedure as described in step 9 of example 2 using the compound prepared in step 4 of example 1; 125 mg) and thereto was added thiosemicarbazide (48 mg) and then thereto was added 1-ethyl-3-[3-(dimethylamino)propyl]carbodiimide hydrochloride (96 mg) at 0° C. and the mixture was stirred at room temperature. The reaction mixture was poured into a saturated aqueous solution of sodium bicarbonate and extracted with ethyl acetate. The organic layer was washed with brine and dried and the residue was washed with ethyl acetate to give N'-methylaminothiocarbonyl-3-cyclohexylcarbonyl amino-3-(tetrahydropyran-4-yl)-2-hydroxypropanoazide (69 mg).

TLC: Rf 0.28 ($CHCl_3$:methanol=9:1).

Step 2: To a solution of the compound prepared in step 1 (65 mg) and sodium acetate (21 mg) in ethanol (1.2 ml) was added ethylbromoacetate (31 mg) and the mixture was refluxed. To the reaction mixture was added 2N hydrochloric acid (0.15 ml) and the mixture was concentrated. The residue was washed with ethyl acetate and dried to give N'-(3-methyl-4-oxo-1,3-thiazolidin-2-ylidene)-[3-cyclohexylcarbonyl amino-2-hydroxy-3-(tetrahydropyran-4-yl)propanohydrazide] (76 mg).

TLC: Rf 0.38 (chloroform:methanol=9:1).

Step 3: By the same procedure as described in example 1 using the compound prepared in step 2, N'-(3-methyl-4-oxo-1,3-thiazolidin-2-ylidene)-[3-cyclohexyl carbonylamino-3-(tetrahydropyran-4-yl)-2-oxopropanohydrazide].

TLC: Rf 0.41 (methylene chloride:methanol=9:1);

NMR: δ 11.14 (s, 1H), 8.06 (d, J=7.2 Hz, 1H), 4.99 (t, J=6.6 Hz, 1H), 3.89-3.77 (m, 2H), 3.29-3.13 (m, 2H), 3.10 (s, 3H), 2.38-2.22 (m, 1H), 2.20-2.04 (m, 1H), 1.80-1.06 (m, 14H).

Example 7(1)-Example 7(3)

By the same procedure as described in example 7 using a corresponding compound, the compound of the present invention were given as follows.

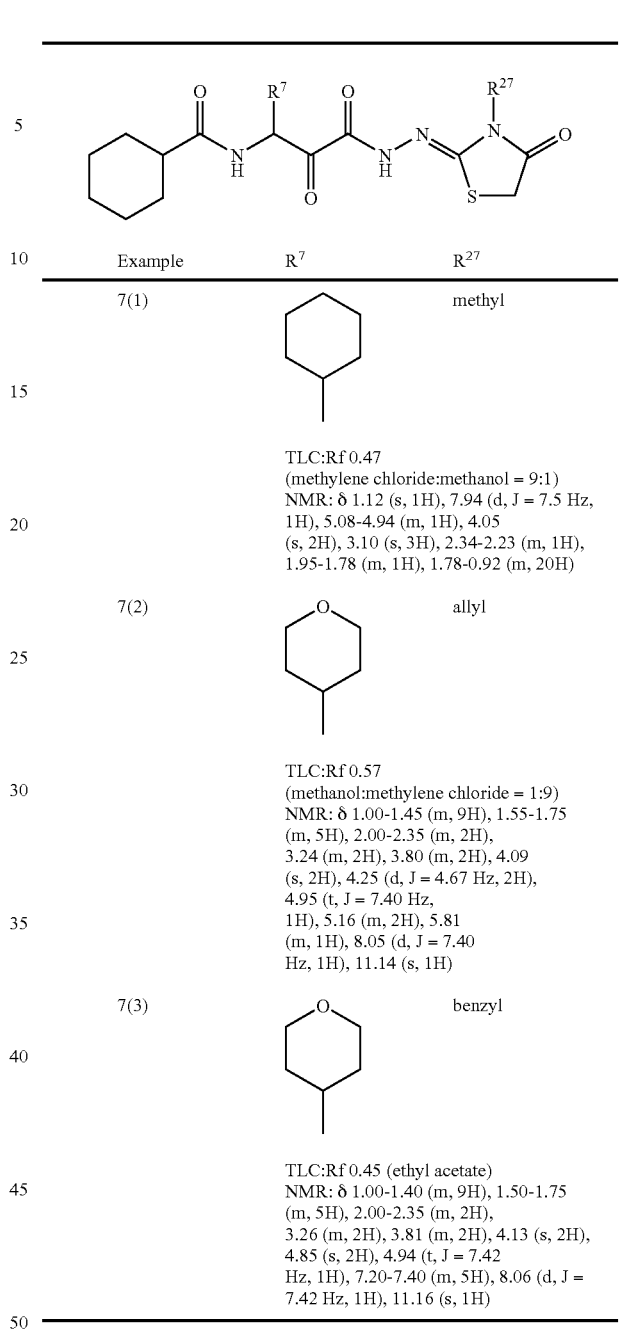

| Example | $R^7$ | $R^{27}$ |
|---|---|---|
| 7(1) | cyclohexyl | methyl |
| | TLC:Rf 0.47 (methylene chloride:methanol = 9:1) NMR: δ 1.12 (s, 1H), 7.94 (d, J = 7.5 Hz, 1H), 5.08-4.94 (m, 1H), 4.05 (s, 2H), 3.10 (s, 3H), 2.34-2.23 (m, 1H), 1.95-1.78 (m, 1H), 1.78-0.92 (m, 20H) | |
| 7(2) | tetrahydropyran-4-yl | allyl |
| | TLC:Rf 0.57 (methanol:methylene chloride = 1:9) NMR: δ 1.00-1.45 (m, 9H), 1.55-1.75 (m, 5H), 2.00-2.35 (m, 2H), 3.24 (m, 2H), 3.80 (m, 2H), 4.09 (s, 2H), 4.25 (d, J = 4.67 Hz, 2H), 4.95 (t, J = 7.40 Hz, 1H), 5.16 (m, 2H), 5.81 (m, 1H), 8.05 (d, J = 7.40 Hz, 1H), 11.14 (s, 1H) | |
| 7(3) | tetrahydropyran-4-yl | benzyl |
| | TLC:Rf 0.45 (ethyl acetate) NMR: δ 1.00-1.40 (m, 9H), 1.50-1.75 (m, 5H), 2.00-2.35 (m, 2H), 3.26 (m, 2H), 3.81 (m, 2H), 4.13 (s, 2H), 4.85 (s, 2H), 4.94 (t, J = 7.42 Hz, 1H), 7.20-7.40 (m, 5H), 8.06 (d, J = 7.42 Hz, 1H), 11.16 (s, 1H) | |

Example 8

Preparation of N'-(3-propyl-1,3-thiazolidin-2-ylidene)-(3-cyclohexylcarbonylamino-3-(tetrahydropyran-4-yl)-2-opropanohydrazide)hydrochloride

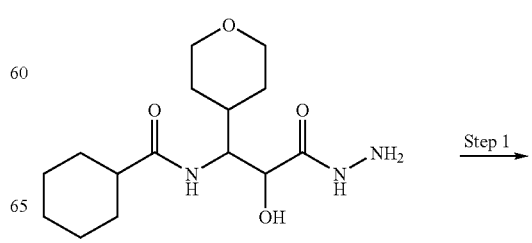

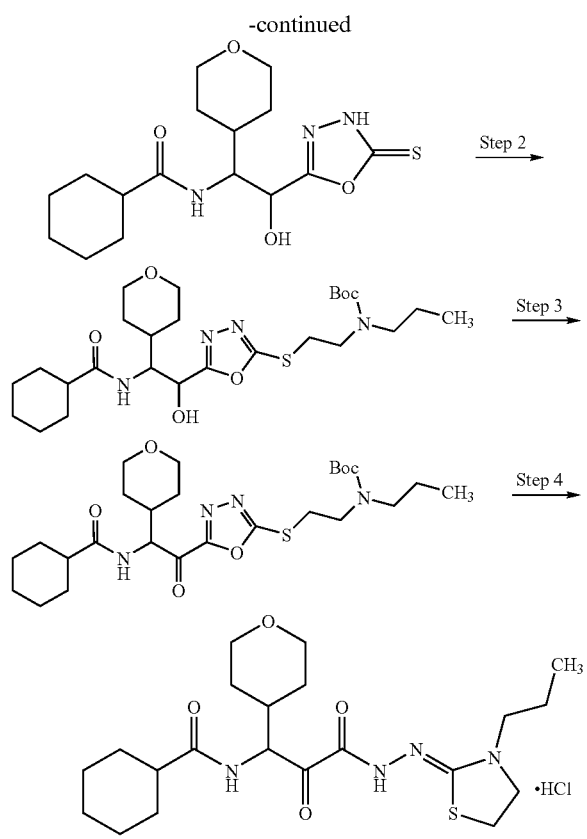

Step 1: To a solution of potassium hydroxide in methanol (1.0 M, 8.0 ml) was suspended 3-cyclohexylcarbonylamino-3-(tetrahydropyran-4-yl)-2-hydroxypropanohydrazide (prepared in step 5 in example 1; 2.0 g) and thereto were added methanol (16 ml) and carbon disulfide (0.46 ml) and the mixture was stirred for 3 hours at room temperature and followed by refluxing for 24 hours. The reaction mixture was poured into iced aqueous solution of citric acid and extracted with ethyl acetate. The organic layer was washed by water and brine successively, dried over magnesium sulfate and concentrated to give 5-(1-hydroxy-2-cyclohexyl carbonylamino-2-tetrahydropyran-4-ylethyl)-2-thioxo-1,3,4-oxadiazoline (2.41 g).

TLC: Rf 0.61 (ethyl acetate:methanol=9:1).

Step 2: To a solution of the compound prepared in step 1 (650 mg) in N,N-dimethylformamide (10 ml) were added N-(t-butoxycarbonyl)-N-(2-chloro ethyl)-N-propylamine (763 mg), sodium iodide (518 mg) and potassium carbonate (477 mg) and the mixture was stirred overnight at 60° C. The reaction mixture was poured into ice-water and was extracted with ethyl acetate. The organic layer was washed with water and brine successively, dried over anhydrous magnesium sulfate and concentrated. The residue was purified by column chromatography on silica gel (n-hexane:ethyl acetate=1:1) to give 1-[5-(N-t-butoxycarbonyl-N-propyl-aminoethylthio)-1,3,4-oxadiazol-2-yl]-2-(tetrahydropyran-4-yl)-2-cyclohexylcarbonylaminoethanol (572 mg).

TLC: Rf 0.44 and 0.35 (ethyl acetate).

Step 3: By the same procedure as described in step 3 of example 4 using the compound prepared in step 2 oxidized compound thereof (355 mg) (TLC: Rf 0.37 (n-hexane:ethyl acetate=1:1) was given. The oxidized compound (350 mg) was dissolved in ethyl acetate (2 ml) and thereto was added 4N hydrochloric acid/ethyl acetate (4 ml) and the mixture was stirred for 1 hour at room temperature. The reaction mixture was concentrated to give 1-[5-(N-t-butoxycarbonyl-N-propylamino ethylthio)-1,3,4-oxadiazol-2-yl]-2-(tetrahydropyran-4-yl)-2-cyclohexylcarbonylamino-1-oxoethane (315 mg).

NMR: δ 0.90 (t, J=7.42 Hz, 3H), 1.47 (m, 16H), 2.20 (m, 2H), 2.89 (m, 2H), 3.23 (m, 4H), 3.65 (t, J=7.14 Hz, 2H), 3.82 (m, 2H), 4.90 (t, J=6.46 Hz, 1H), 8.43 (d, J=6.32 Hz, 1H), 9.07 (m, 2H).

Step 4: A suspension of the compound prepared in step 3 (315 mg) in acetonitrile was stirred for 1 hour at 80° C. The precipitated powder was collected to give N'-(3-propyl-1,3-thiazolidin-2-ylidene)-(3-cyclohexylcarbonylamino-3-(tetrahydropyran-4-yl)-2-oxopropanohydrazide) hydrochloride (240 mg).

TLC: Rf 0.54 (methylene chloride:methanol=9:1);

NMR: δ 11.47 (br-s, 1H), 8.21 (d, J=6.6 Hz, 1H), 4.83 (t-like, J=6.0 Hz, 1H), 4.01 (t, J=7.2 Hz, 21-1), 3.83 (t-like, J=6.3 Hz, 21-1), 3.49 (t, J=7.2 Hz, 2H), 3.42 (t, J=7.2 Hz, 2H), 3.24 (t, J=9.9 Hz, 2H), 2.33-2.21 (m, 1H), 2.16-2.02 (m, 1H), 1.69-1.57 (m, 7H), 1.50-1.04 (m, 9H), 0.89 (t, J=7.5 Hz, 3H).

Example 8(1)~Example 8(75)

By the same procedure as described in example 8 using corresponding compounds, the following compounds were given.

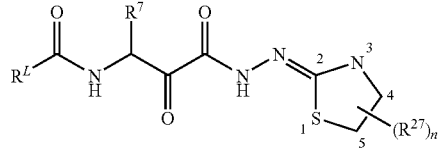

| Example | $R^L$ | $R^7$ | $R^{27}$ |
|---|---|---|---|
| 8(1) hydrochloride | cyclohexyl | (S)-isobutyl | 3-methyl |
| | TLC:Rf 0.60 (methylene chloride:methanol:acetic acid = 9:1:0.1) NMR: δ 11.6 (brs, 1H), 8.20 (brd, J = 5.7 Hz, 1H), 6.40-5.20 (broad, 1H), 4.89 (m, 1H), 4.01 (brt, J = 7.8 Hz, 2H), 3.41 (brt, J = 7.8 Hz, 2H), 3.13 (s, 3H), 2.19 (m, 1H), 1.80-1.00 (m, 13H), 0.89 and 0.86 (each d, J = 6.6 Hz, total 6H) | | |
| 8(2) hydrochloride | 4-bromophenyl | (S)-isobutyl | 3-methyl |
| | TLC:Rf 0.55 (methylene chloride:methanol:acetic acid = 9:1:0.1) NMR: δ 11.7 (brs, 1H), 9.04 (brd, J = 6.0 Hz, 1H), 7.84 (d, J = 8.7 Hz, 2H), 7.70 (d, J = 8.7 Hz, 2H), 6.00-5.20 (broad, 1H), 5.10 (m, 1H), 4.03 (brt, J = 7.5 Hz, 2H), 3.41 (brt, J = 7.5 Hz, 2H), 3.16 (s, 3H), 1.80-1.50 (m, 3H), 0.93 and 0.91 (each d, J = 6.0 Hz, total 6H) | | |
| 8(3) hydrochloride | cyclohexyl | (S)-isopropyl | 3-methyl |
| | TLC:Rf 0.43 (methylene chloride:methanol = 9:1) NMR: δ 11.5 (brs, 1H), 8.11 (brd, J = 6.6 Hz, 1H), 7.20-6.00 (broad, 1H), 4.83 (t, J = 6.6 Hz, 1H), 3.99 (brt, J = 7.5 Hz, 2H), 3.39 (brt, J = 7.5 Hz, 2H), 3.11 (s, 3H), 2.29 (m, 1H), 2.15 (m, 1H), 1.80-1.55 (m, 5H), 1.40-1.00 (m, 5H), 0.88 and 0.86 (each d, J = 6.3 Hz, total 6H) | | |
| 8(4) hydrochloride | cycloheptyl | (S)-neopentyl | 3-methyl |
| | TLC:Rf 0.39 (methylene chloride:methanol = 20:1) NMR: δ 11.46 (s, 1H), 8.12 (d, J = 6.9 Hz, 1H), 5.00-4.92 (m, 1H), 3.97 | | |

-continued

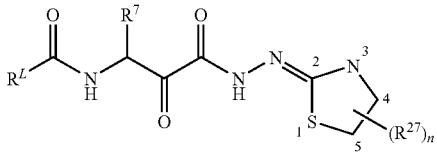

| Example | $R^L$ | $R^7$ | $R^{27}$ |
|---|---|---|---|
| 8(5) hydrochloride | 1-benzoylaminocyclo hexyl free compound NMR: δ 10.62 (t, 1H), 8.00-7.40 (m, 7H), 5.17-5.02 (m, 1H), 3.58 (t, J = 6.9 Hz, 2H), 3.17 (t, J = 6.9 Hz, 2H), 2.86 (s, 3H), 1.80-1.20 (m, 13H), 0.95-0.75 (m, 6H) hydrochloride TLC:Rf 0.63 (methylene chloride:methanol = 10:1) NMR: δ 11.42 (s, 1H), 7.80-7.38 (m, 7H), 5.00-4.88 (m, 1H), 3.94 (t, J = 6.9 Hz, 2H), 3.37 (t, J = 6.9 Hz, 2H), 3.08 (s, 3H), 2.30-2.00 (m, 2H), 1.82-1.15 (m, 11H), 0.95-0.70 (m, 6H) | isobutyl (t, J = 6.9 Hz, 2H), 3.39 (t, J = 6.9 Hz, 2H), 3.10 (s, 3H), 2.40-2.24 (m, 1H), 1.78-1.33 (m, 14H), 0.90 (s, 9H) | 3-methyl |
| 8(6) hydrochloride | cyclohexyl TLC:Rf 0.77 (methylene chloride:methanol = 9:1) NMR: δ 11.5 (brs, 1H), 8.09 (brd, J = 6.0 Hz, 1H), 6.00-5.20 (broad, 1H), 4.89 (m, 1H), 3.97 (brt, J = 7.5 Hz, 2H), 3.39 (brt, J = 7.5 Hz, 2H), 3.09 (s, 3H), 2.28 (m, 1H), 1.90 (m, 1H), 1.80-1.00 (m, 12H), 0.85 (d, J = 6.9 Hz, 3H), 0.83 (t, J = 7.5 Hz, 3H) | (S,S)-s-butyl | 3-methyl |
| 8(7) hydrochloride | cyclohexyl TLC:Rf 0.48 (methylene chloride:methanol = 9:1) NMR: δ 11.46 (s, 1H), 8.29 (d, 15.7 Hz, 1H), 7.30-7.17 (m, 5H), 5.03 (br-m, 1H), 3.96 (t, J = 6.6 Hz, 2H), 3.38 (t, J = 6.6 Hz, 2H), 3.22-3.00 (m, 1H), 3.09 (s, 3H), 2.89-2.71 (m, 1H), 2.20-2.05 (m, 1H), 1.64-1.56 (m, 5H), 1.25-1.01 (m, 5H) | (S)-benzyl | 3-methyl |
| 8(8) hydrochloride | cyclohexyl TLC:Rf 0.39 (ethyl acetate:methanol = 9:1) NMR: δ 11.49 (s, 1H), 8.08 (d, J = 5.7 Hz, 1H), 4.97 (td, J = 5.7 Hz, 1H), 4.02 (t, J = 7.8 Hz, 2H), 3.40 (t, J = 7.8 Hz, 2H), 3.13 (s, 3H), 2.42-2.30 (m, 1H), 1.67-1.58 (m, 5H), 1.34-1.06 (m, 5H), 0.94 (s, 9H) | (S)-t-butyl | 3-methyl |
| 8(9) hydrochloride | cyclohexyl TLC:Rf 0.58 (methylene chloride:methanol = 9:1) NMR: δ 11.42 (s, 1H), 8.19 (d, J = 5.7 Hz, 1H), 4.86-4.77 (m, 1H), 3.96 (t, J = 7.2 Hz, 2H), 3.38 (t, J = 7.2 Hz, 2H), 3.08 (s, 3H), 2.27-2.13 (m, 1H), 1.80-1.45 (m, 7H), 1.29-1.02 (m, 9H), 0.85 (t, J = 6.3 Hz, 3H) | (S)-butyl | 3-methyl |
| 8(10) hydrochloride | cyclohexyl TLC:Rf 0.50 (methylene chloride:methanol = 9:1) NMR: δ 11.57 (brs, 1H), 8.16 (d, J = 6.3 Hz, 1H), 5.02-4.92 (m, 1H), 4.01 (t, J = 7.5 Hz, 2H), 3.41 (t, J = 7.5 Hz, 2H), 3.13 (s, 3H), 2.22-2.08 (m, 1H), 1.85-1.00 (m, 12H), 0.90 (s, 9H) | neopentyl | 3-methyl |
| 8(11) hydrochloride | cyclohexyl TLC:Rf 0.50 (methylene chloride:methanol = 9:1) NMR: δ 11.28 (brs, 1H), 8.16 (d, J = 3.6 Hz, 1H), 5.02-4.92 (m, 1H), 4.01 (t, J = 7.5 Hz, 2H), 3.42 (t, J = 7.5 Hz, 2H), 3.13 (s, 3H), 2.92 (s, 3H), 2.22-2.07 (m, 1H), 2.05-1.02 (m, 12H), 1.19 and 1.08 (each s, total 6H) | 2-methyl-2-methoxy-propyl | 3-methyl |

-continued

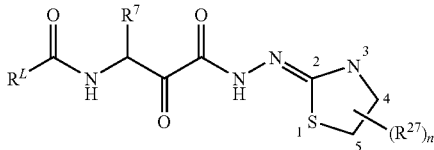

| Example | $R^L$ | $R^7$ | $R^{27}$ |
|---|---|---|---|
| 8(12) hydrochloride | methyl TLC:Rf 0.46 (methylene chloride:methanol = 10:1) NMR: δ 11.53 (s, 1H), 8.41 (d, J = 6.0 Hz, 1H), 4.94-4.82 (m, 1H), 4.00 (t, J = 7.5 Hz, 2H), 3.40 (t, J = 7.5 Hz, 2H), 3.12 (s, 3H), 1.85 (s, 3H), 1.78-1.60 (m, 1H), 1.54-1.36 (m, 2H), 0.90 and 0.87 (each d, J = 6.6 Hz, total 6H) | (S)-isobutyl | 3-methyl |
| 8(13) hydrochloride | ![tetrahydropyranyl] TLC:Rf 0.46 (methylene chloride:methanol = 10:1) NMR: δ 11.39 (s, 1H), 7.26 (d, J = 6.0 Hz, 1H), 5.02-4.85 (m, 1H), 4.02-3.88 (m, 2H), 3.87-3.76 (m, 2H), 3.44-3.32 (m, 2H), 3.31-3.21 (m, 2H), 3.07 (s, 3H), 2.48-2.30 (m, 1H), 1.75-1.38 (m, 7H), 0.91-0.75 (m, 6H) | (S)-isobutyl | 3-methyl |
| 8(14) hydrochloride | t-butyl TLC:Rf 0.56 (methylene chloride:methanol = 10:1) NMR: δ 11.60 (s, 1H), 7.27 (d, J = 9.6 Hz, 1H), 4.94-4.78 (m, 1H), 4.14-3.96 (m, 2H), 3.54-3.36 (m, 2H), 3.17 (s, 3H), 1.80-1.40 (m, 3H), 1.10 (s, 9H), 0.97-0.70 (m, 6H) | (S)-isobutyl | 3-methyl |
| 8(15) hydrochloride | phenyl TLC:Rf 0.51 (methylene chloride:methanol = 10:1) NMR: δ 11.59 (s, 1H), 8.90 (d, J = 6.3 Hz, 1H), 8.00-7.40 (m, 5H), 5.18-5.04 (m, 1H), 3.99 (t, J = 7.5 Hz, 2H), 3.38 (t, J = 7.5 Hz, 2H), 3.12 (s, 3H), 1.80-1.52 (m, 3H), 1.05-0.80 (m, 6H) | (S)-isobutyl | 3-methyl |
| 8(16) hydrochloride | cycloheptyl TLC:Rf 0.54 (methylene chloride:methanol = 10:1) NMR: δ 11.52 (s, 1H), 8.19 (d, J = 6.0 Hz, 1H), 4.85-4.82 (m, 1H), 4.00 (t, J = 7.5 Hz, 2H), 3.41 (t, J = 7.5 Hz, 2H), 3.12 (s, 3H), 2.40-2.30 (m, 1H), 1.90-1.30 (m, 15H), 0.98-0.78 (m, 6H) | (S)-isobutyl | 3-methyl |
| 8(17) hydrochloride | cyclohexyl TLC:Rf 0.48 (methylene chloride:methanol = 9:1) NMR (100° C.): δ 7.67 (br, 1H), 5.02-4.91 (m, 1H), 3.92-3.82 (m, 2H), 3.61-3.48 (m, 2H), 3.31 (t, J = 7.2 Hz, 2H), 2.26-2.17 (m, 1H), 1.73-1.16 (m, 13H), 1.18 (t, J = 7.2 Hz, 3H), 0.91 (d, J = 6.3 Hz, 3H), 0.89 (d, J = 6.3 Hz, 3H) | isobutyl | 3-methyl |
| 8(18) hydrochloride | cyclohexyl TLC:Rf 0.57 (methylene chloride:methanol = 9:1) NMR (100° C.): δ 7.64 (br, 1H), 5.02-4.91 (m, 1H), 3.93-3.83 (m, 2H), 3.48 (t, J = 6.9 Hz, 2H), 3.32 (t, J = 7.2 Hz, 2H), 2.26-2.18 (m, 1H), 1.73-1.12 (m, 15H), 0.92 (t, J = 7.5 Hz, 3H), 0.92 (d, J = 5.4 Hz, 3H), 0.90 (d, J = 5.4 Hz, 3H) | (S)-isobutyl | 3-methyl |
| 8(19) hydrochloride | cycloheptyl TLC:Rf 0.63 (methylene chloride:methanol = 9:1) NMR: δ 11.5 (brs, 1H), 8.13 (brd, J = | neopentyl | 3-methyl |

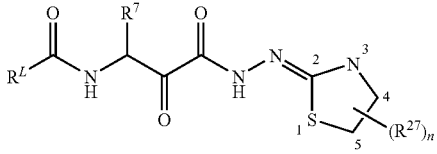
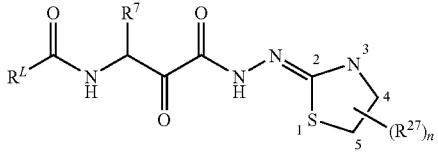

| Example | R<sup>L</sup> | R<sup>7</sup> | R<sup>27</sup> |
|---|---|---|---|

6.3 Hz, 1H), 6.00-5.00 (broad, 1H), 4.95 (m, 1H), 4.00 (brt, J = 7.5 Hz, 2H), 3.41 (brt, J = 7.5 Hz, 2H), 3.11 (s, 3H), 2.33 (m, 1H), 1.90-1.30 (m, 14H), 0.90 (s, 9H)

8(20) hydro-chloride — benzyl — (S)-isobutyl — 3-methyl
TLC:Rf 0.63 (methylene chloride:methanol = 10:1)
NMR: δ 11.63 (s, 1H), 8.70 (d, J = 5.1 Hz, 1H), 7.38-7.15 (m, 5H), 5.00-4.86 (m, 1H), 4.02 (t, J = 7.8 Hz, 2H), 3.49 (s, 2H), 3.40 (t, J = 7.8 Hz, 2H), 3.14 (s, 3H), 1.78-1.60 (m, 1H), 1.58-1.42 (m, 2H), 0.95-0.75 (m, 6H)

8(21) hydro-chloride — phenoxymethyl — (S)-isobutyl — 3-methyl
TLC:Rf 0.60 (methylene chloride:methanol = 10:1)
NMR: δ 11.63 (s, 1H), 8.67 (d, J = 6.9 Hz, 1H), 7.38-6.85 (m, 5H), 5.18-4.98 (m, 1H), 4.56 (s, 2H), 4.00 (t, J = 7.5 Hz, 2H), 3.39 (t, J = 7.5 Hz, 2H), 3.13 (s, 3H), 1.70-1.40 (m, 3H), 0.95-0.78 (m, 6H)

8(22) hydro-chloride — cyclohexyl — (S)-isobutyl — 3-benzyl
TLC:Rf 0.69 (methylene chloride:methanol = 9:1)
NMR: δ 11.30 (br-s, 1H), 8.13 (d, J = 7.2 Hz, 1H), 7.42-7.39 (m, 5H), 5.02-4.90 (m, 1H), 4.76 (s, 2H), 3.78 (t, J = 7.2 Hz, 2H), 3.33 (t, J = 7.2 Hz, 2H), 2.23-2.16 (m, 1H), 1.69-1.18 (m, 13H), 0.89 (d, J = 6.9 Hz, 3H), 0.87 (d, J = 6.9 Hz, 3H)

8(23) hydro-chloride — cyclohexyl — (S)-isobutyl — 3-isopropyl
TLC:Rf 0.63 (methylene chloride:methanol = 9:1)
NMR (100° C.): δ 7.60 (br-m, 1H), 5.00 (br-m, 1H), 4.43-4.27 (m, 1H), 3.75 (t, J = 6.9 Hz, 2H), 3.23 (t, J = 6.9 Hz, 2H), 2.28-2.17 (m, 1H), 1.73-1.15 (m, 19H), 0.91 (d, J = 6.6 Hz, 3H), 0.90 (d, J = 6.6 Hz, 3H)

8(24) hydro-chloride — cyclohexyl — (tetrahydropyran-4-yl) — 3-methyl
TLC:Rf 0.56 (methanol:methylene chloride = 1:9)
NMR: δ 11.37 (brs, 1H), 8.17 (brd, J = 6.3 Hz, 1H), 4.85 (m, 1H), 4.80-4.10 (br, 1H), 3.97 (t, J = 7.5 Hz, 2H), 3.79 (m, 2H), 3.37 (t, J = 7.5 Hz, 2H), 3.21 (m, 2H), 3.06 (s, 3H), 2.25 (m, 1H), 2.10 (m, 1H), 1.80-1.00 (m, 14H)

8(25) hydro-chloride — cyclohexyl — cyclohexyl — 3-methyl
TLC:Rf 0.61 (methanol:methylene chloride = 1:9)
NMR: δ 11.41 (brs, 1H), 8.07 (brd, J = 6.3 Hz, 1H), 4.85 (m, 1H), 5.30-4.70 (br, 1H), 3.95 (t, J = 6.0 Hz, 2H), 3.38 (t, J = 6.0 Hz, 2H), 3.08 (s, 3H), 2.30 (m, 1H), 1.90-1.00 (m, 21H)

8(26) hydro-chloride — (CH<sub>3</sub>)<sub>3</sub>C-CH=CH- (tert-butyl vinyl) — (S)-isobutyl — 3-methyl
TLC:Rf 0.68 (methylene chloride:methanol = 10:1)
NMR: δ 11.49 (s, 1H), 8.45 (d, J = 5.7 Hz, 1H), 6.63 (d, J = 15.6 Hz, 1H), 5.91 (d, J = 15.6 Hz, 1H), 5.02-4.92 (m, 1H), 4.02-3.88 (m, 2H), 3.39 (t, J = 7.2 Hz, 2H), 3.09 (s, 3H), 1.80-1.40 (m, 3H), 1.02 (s, 9H), 0.94-0.74 (m, 6H)

8(27) hydro-chloride — cyclohexyl — (S)-isobutyl — 3-(2-hydroxyethyl)
TLC:Rf 0.48 (ethyl acetate:methanol:water = 40:10:1)
NMR (100° C.): δ 7.60 (br-m, 1H), 4.97 (br-m, 1H), 3.89 (t, J = 6.0 Hz, 2H), 3.72-3.63 (m, 1H), 3.57-3.50 (m, 2H), 3.27 (t, J = 6.0 Hz, 2H), 2.25-2.16 (m, 1H), 1.77-1.16 (m, 13H), 0.90 (d, J = 6.0 Hz, 3H), 0.88 (d, J = 6.0 Hz, 3H)

8(28) hydro-chloride — cyclohexyl — cyclopropyl — 3-methyl
TLC:Rf 0.53 (methylene chloride:methanol = 9:1)
NMR: δ 11.55 (brs, 1H), 8.45 (d, J = 4.8 Hz, 1H), 4.18 (dd, J = 9.0, 4.8 Hz, 1H), 4.02 (t, J = 7.2 Hz, 2H), 3.41 (t, J = 7.2 Hz, 2H), 3.15 and 3.14 (each s, total 3H), 2.30-2.13 (m, 1H), 1.78-1.02 (m, 10H), 1.02-0.87 (m, 1H), 0.60-0.20 (m, 4H)

8(29) hydro-chloride — cyclohexyl — cyclopentyl — 3-methyl
TLC:Rf 0.56 (methylene chloride:methanol = 9:1)
NMR: δ 11.4 (brs, 1H), 8.20 (brd, J = 5.7 Hz, 1H), 7.00-6.00 (broad, 1H), 4.83 (m, 1H), 3.97 (t, J = 7.8 Hz, 2H), 3.38 (t, J = 7.8 Hz, 2H), 3.09 (s, 3H), 2.30-2.10 (m, 2H), 1.80-1.00 (m, 18H)

8(30) hydro-chloride — cyclohexyl — 2-propylbutyl — 3-methyl
TLC:Rf 0.37 (methylene chloride:isopropanol = 19:1)
NMR: δ 11.49 (s, 1H), 7.88 (d, J = 7.5 Hz, 1H), 5.21-5.18 (m, 1H), 3.95 (t, J = 7.2 Hz, 2H), 3.38 (t, J = 7.2 Hz, 2H), 3.09 (s, 3H), 2.40-2.37 (m, 1H), 2.03-1.90 (m, 1H), 1.77-1.55 (m, 5H), 1.43-1.02 (m, 13H), 0.86-0.79 (m, 6H)

8(31) hydro-chloride — cyclohexyl — phenyl — 3-methyl
TLC:Rf 0.41 (methylene chloride:methanol = 9:1)
NMR: δ 11.42 (brs, 1H), 8.60 (brd, J = 5.7 Hz, 1H), 7.41-7.27 (m, 5H), 6.10 (brd, J = 5.7 Hz, 1H), 3.90 (t, J = 7.5 Hz, 2H), 3.31 (t, J = 7.5 Hz, 2H), 3.02 (s, 3H), 2.40-2.23 (m, 1H), 1.80-1.50 (m, 5H), 1.40-1.00 (m, 5H)

8(32) hydro-chloride — 2-methylpropyloxy — (S)-isobutyl — 3-methyl
TLC:Rf 0.71 (methylene chloride:methanol = 10:1)
NMR: δ 0.78-0.95 (m, 12H), 1.40-1.90 (m, 4H), 2.99 (s, 3H), 3.24-3.30 (m, 2H), 3.75 (d, J = 6.59 Hz, 4H), 4.60-5.20 (m, 1H), 6.80-7.02 (m, 1H)

-continued

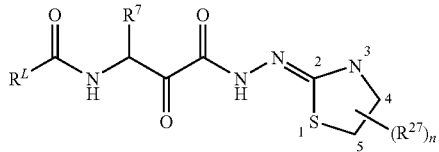

| Example | $R^L$ | $R^7$ | $R^{27}$ |
|---|---|---|---|
| 8(33) dihydrochloride | cyclohexyl | 4-piperidinyl (NH) | 3-methyl |

TLC:Rf 0.25 (ethyl acetate:acetic acid:water = 3:1:1)
NMR: δ 1.01-1.80 (m, 14H), 2.11 (m, 1H), 2.23 (m, 1H), 2.81 (m, 2H), 3.09 (s, 3H), 3.21 (m, 2H), 3.37 (t, J = 7.2 Hz, 2H), 3.94 (t, J = 7.2 Hz, 2H), 4.78 (m, 1H), 5.10-5.90 (broad, 1H), 8.39 (d, J = 5.5 Hz, 1H), 8.75 (brs, 1H), 9.11 (brs, 1H), 11.39 (brs, 1H)

| 8(34) hydrochloride | cyclohexyl | tetrahydropyran-4-yl | 3-benzyl |

TLC:Rf 0.50 (methylene chloride:methanol = 9:1)
NMR: δ 1.04-1.44 (m, 9H), 1.09-1.58 (m, 5H), 2.04-2.20 (m, 1H), 2.25-2.32 (m, 1H), 3.20-3.30 (m, 4H), 3.72 (t, J = 6.9 Hz, 2H), 3.80-3.85 (m, 2H), 4.71 (s, 2H), 4.94 (t-like, J = 6.6 Hz, 1H), 7.30-7.42 (m, 5H), 8.22 (d, J = 6.6 Hz, 1H), 11.20 (br-s, 1H)

| 8(35) | cyclohexyl | 1-acetylpiperidin-4-yl | 3-methyl | free compound
NMR: δ 1.04-1.79 (m, 10H), 1.95 (s, 3H), 2.12 (m, 1H), 2.26 (m, 1H), 2.43 (m, 2H), 2.86 (s, 3H), 2.95 (m, 2H), 3.17 (t, J = 7.0 Hz, 2H), 3.58 (t, J = 7.0 Hz, 2H), 3.80 (m, 2H), 4.35 (m, 2H), 5.08 (m, 1H), 7.92 (d, J = 7.7 Hz, 1H), 10.65 (s, 1H)
hydrochloride
TLC:Rf 0.46 (methylene chloride:methanol = 9:1)
NMR: δ 0.98-1.81 (m, 14H), 1.95 (s, 3H), 2.08 (m, 1H), 2.26 (m, 1H), 2.42 (m, 1H), 2.95 (m, 1H), 3.05 (s, 3H), 3.35 (t, J = 7.2 Hz, 2H), 3.81 (m, 1H), 3.91 (m, 2H), 4.35 (m, 1H), 4.69-5.09 (m, 2H), 8.15 (m, 1H), 11.33 (brs, 1H)

| 8(36) hydrochloride | (1R,2S)-2-benzoylaminocyclohexyl | (S)-isobutyl | 3-methyl |

TLC:Rf 0.74 (methylene chloride:methanol = 10:1)
NMR: δ 0.64 (d, J = 6.32 Hz, 3H), 0.72 (d, J = 6.32 Hz, 3H), 1.26-2.05 (m, 11H), 2.70-2.80 (m, 1H), 3.00 (s, 3H), 3.26-3.35 (m, 2H), 3.80-3.90 (m, 2H), 4.25-4.60 (m, 2H), 4.95-5.05 (m, 1H), 7.37-7.56 (m, 3H), 7.73-7.80 (m, 3H), 8.20 (d, J = 7.14 Hz, 1H), 11.22 (s, 1H)

-continued

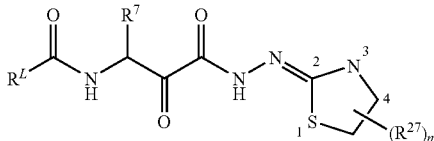

| Example | $R^L$ | $R^7$ | $R^{27}$ |
|---|---|---|---|
| 8(37) hydrochloride | 3,4-dihydro-5-methoxycarbonylamino-4-oxo-2-phenylpyrimidine-3-ylmethyl | (S)-isopropyl | 3-methyl |

TLC:Rf 0.41 (methylene chloride:methanol = 9:1)
NMR: δ 0.77 (d, J = 6.6 Hz, 3H), 0.85 (d, J = 6.6 Hz, 3H), 2.14 (m, 1H), 3.09 (s, 3H), 3.37 (t, J = 7.2 Hz, 2H), 3.68 (s, 3H), 3.96 (t, J = 7.2 Hz, 2H), 4.56 (s, 2H), 5.01 (m, 1H), 6.00-5.30 (broad, 1H), 7.32-7.70 (m, 5H), 8.42 (s, 1H), 8.57 (d, J = 7.4 Hz, 1H), 8.79 (s, 1H), 11.57 (brs, 1H)

| 8(38) hydrochloride | cyclohexyl | 2-ethylpropyl | 3-methyl |

TLC:Rf 0.73 (methylene chloride:methanol = 10:1)
NMR: δ 0.75-0.90 (m, 6H), 1.05-1.85 (m, 15H), 2.23-2.40 (m, 1H), 3.10 (s, 3H), 3.32-3.45 (m, 2H), 3.90-4.05 (m, 2H), 5.12-5.24 (m, 1H), 7.92 (d, J = 7.42Hz, 1H), 11.53 (s, 1H)

| 8(39) | cyclohexyl | N-Boc-piperidin-4-yl | 3-methyl | free compound
NMR: δ 1.22 (m, 23H), 2.07 (m, 1H), 2.26 (m, 1H), 2.63 (m, 2H), 2.86 (s, 3H), 3.17 (t, J = 6.8 Hz, 2H), 3.58 (t, J = 6.8 Hz, 2H), 3.91 (m, 2H), 5.10 (m, 1H), 7.92 (d, J = 5.8 Hz, 1H), 10.65 (brs, 1H)
hydrochloride
TLC:Rf 0.51 (methylene chloride:methanol = 9:1)
NMR: δ 0.98-1.81 (m, 23H), 2.05 (m, 1H), 2.26 (m, 1H), 2.65 (m, 2H), 3.06 (s, 3H), 3.36 (t, J = 7.6 Hz, 2H), 3.86-3.96 (m, 4H), 4.89 (m, 1H), 5.90-5.10 (broad, 1H), 8.16 (d, J = 6.59 Hz, 1H), 1.38 (s, 1H)

| 8(40) free compound | cyclohexyl | 4-(trifluoromethyl)phenyl | 3-methyl |

TLC:Rf 0.44 (ethyl acetate:methanol = 9:1)
NMR: δ 1.40-1.03 (m, 5H), 1.72-1.01 (m, 5H), 2.29 (t-like, J = 6.9 Hz, 1H), 2.82 (s, 3H), 3.12 (t, J = 6.3 Hz, 2H), 3.54 (t, J = 6.3 Hz, 2H), 6.31 (d, J = 6.9 Hz, 1H), 7.54 (d, J =

-continued

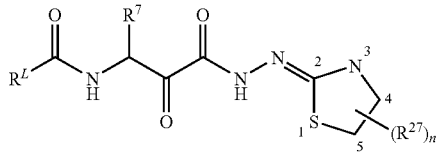

| Example | $R^L$ | $R^7$ | $R^{27}$ |
|---|---|---|---|
| | | 8.4 Hz, 2H), 7.75 (d, J = 8.4 Hz, 2H), 8.62 (d, J = 6.9 Hz, 1H), 1..68 (s, 1H) | |
| 8(41) | cyclohexyl | OCH₃-phenyl (4-methoxyphenyl) | 3-methyl |
| | | free compound NMR: (CDCl₃): δ 7.38 (d, J = 9.0 Hz, 2H), 6.87 (d, J = 9.0 Hz, 2H), 6.43-6.38 (m, 2H), 3.77 (s, 3H), 3.61 (t, J = 7.2 Hz, 2H), 3.50-3.35 (m, 2H), 2.91 (s, 3H), 2.19 (m, 1H), 2.00-1.19 (m, 10H) hydrochloride TLC:Rf 0.33 (methylene chloride:methanol = 9:1) NMR: δ 1.00-1.40 (m, 5H), 1.50-1.80 (m, 5H), 2.27 (m, 1H), 3.05 (s, 3H), 3.34 (t, J = 7.69 Hz, 2H), 3.73 (s, 3H), 3.97 (m, 2H), 4.42 (m, 1H), 6.05 (d, J = 5.49 Hz, 1H), 6.94 (d, J = 8.52 Hz, 1H), 7.26 (d, J = 8.52 Hz, 2H), 8.57 (d, J = 5.49 Hz, 1H), 11.47 (s, 1H) | |
| 8(42) | cyclohexyl | Ms-N-piperidin-4-yl (4-methyl) | 3-methyl |
| | | TLC:Rf 0.51 (methylene chloride:methanol = 9:1) NMR: δ 1.39 (m, 14H), 1.96 (m, 1H), 2.27 (m, 1H), 2.64 (m, 2H), 2.83 (s, 3H), 3.04 (s, 3H), 3.35 (t, J = 7.3 Hz, 2H), 3.55 (m, 2H), 3.90 (t, J = 7.3 Hz, 2H), 4.90 (m, 1H), 4.90-5.50 (brd, 1H), 8.22 (d, J = 5.5 Hz, 1H), 11.31 (brs, 1H) | |
| 8(43) hydrochloride | cyclohexyl | 2-methylphenyl | 3-methyl |
| | | TLC:Rf 0.36 (methylene chloride:methanol = 9:1) NMR: δ 1.05-1.41 (m, 5H), 1.59-1.72 (m, 5H), 2.26-2.32 (m, 1H), 2.39 (s, 3H), 3.02 (m, 3H), 3.32 (t, J = 7.5 Hz, 2H), 3.90 (t, J = 7.5 Hz, 2H), 6.34 (d, J = 6.6 Hz, 1H), 7.00 (d, J = 7.2 Hz, 1H), 7.17-7.26 (m, 3H), 8.43 (d, J = 6.6 Hz, 1H), 11.56 (br-s, 1H) | |
| 8(44) hydrochloride | 2-methylpropyloxy | 2-methylphenyl | 3-methyl |
| | | TLC:Rf 0.52 (methylene chloride:methanol = 9:1) NMR (100° C.): δ 0.88 (d, J = 6.8 Hz, 6H), 1.79-1.92 (m, 1H), 2.43 (s, 3H), 2.91 (s, 3H), 3.19 (t, J = 7.1 Hz, 2H), 3.66 (t, J = 7.1 Hz, 2H), 3.78 (d, J = 6.4 Hz, 2H), 6.26-6.32 (m, 1H), 7.03-7.29 (m, 5H) | |
| 8(45) hydrochloride | methoxy | 2-methylphenyl | 3-methyl |
| | | TLC:Rf 0.50 (methylene chloride:methanol = 9:1) NMR (100° C.): δ 2.43 (s, 3H), 2.91 (s, 3H), | |

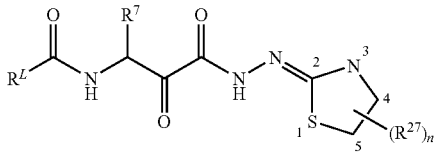

| Example | $R^L$ | $R^7$ | $R^{27}$ |
|---|---|---|---|
| | | 3.21 (t, J = 7.3 Hz, 2H), 3.59 (s, 3H), 3.68 (t, J = 7.3 Hz, 2H), 6.28 (d, J = 6.6 Hz, 1H), 7.03-7.24 (m, 4H), 7.30-7.41 (m, 1H) | |
| 8(46) hydrochloride | 2-methylpropyloxy | 2,5-dimethylphenyl | 3-methyl |
| | | TLC:Rf 0.55 (methylene chloride:methanol = 9:1) NMR: δ 0.85 (d, J = 6.6 Hz, 6H), 1.74-1.89 (m, 1H), 2.27 (s, 6H), 2.96 (s, 3H), 3.17-3.30 (m, 2H), 3.75 (d, J = 6.6 Hz, 2H), 3.85 (t, J = 7.4 Hz, 2H), 6.27 (d, J = 7.1 Hz, 1H), 6.99-7.11 (m, 3H), 7.75 (br-s, 1H), 11.58 (br-s, 1H) | |
| 8(47) hydrochloride | cyclohexyl | 2-chlorophenyl | 3-methyl |
| | | TLC:Rf 0.53 (methylene chloride:methanol = 9:1) NMR: δ 11.62 (s, 1H), 8.69 (d, J = 6.3 Hz, 1H), 7.56-7.14 (m, 4H), 6.38 (d, J = 6.3 Hz 1H), 3.96 (t, J = 7.2 Hz, 2H), 3.36 (t, J = 7.2 Hz, 2H), 3.08 (s, 3H), 2.32-2.17 (m, 1H), 1.83-1.02 (m, 10H) | |
| 8(48) hydrochloride | cyclohexyl | 2-methoxyphenyl | 3-methyl |
| | | TLC:Rf 0.69 (methylene chloride:methanol = 10:1) NMR: δ 1.05-1.85 (m, 10H), 2.20-2.35 (m, 1H), 3.03 (s, 3H), 3.34 (t, J = 7.55 Hz, 2H), 3.76 (s, 3H), 3.92 (t, J = 7.28 Hz, 2H), 6.29 (d, J = 6.59 Hz, 1H), 6.90-7.40 (m, 4H), 8.31 (d, J = 7.14 Hz, 1H), 11.42 (s, 1H) | |
| 8(49) hydrochloride | 2-methylpropyloxy | 2-methoxyphenyl | 3-methyl |
| | | TLC:Rf 0.61 (methylene chloride:methanol = 10:1) NMR: δ 0.87 (d, J = 6.32 Hz, 6H), 1.73-1.90 (m, 1H), 3.04 (s, 3H), 3.20-3.45 (m, 2H), 3.60-1.83 (m, 5H), 3.85-4.00 (m, 2H), 6.18 (d, J = 7.97 Hz, 1H), 6.82-7.40 (m, 4H), 7.76 (d, J = 7.69 Hz, 1H), 11.53 (s, 1H) | |
| 8(50) hydrochloride | cyclohexyl | (S)-isobutyl | 3,5,5-trimethyl |
| | | TLC:Rf 0.65 (methylene chloride:methanol = 9:1) NMR: δ 11.45 (brs, 1H), 8.21 (d, J = 6.0 Hz, 1H), 4.93-4.78 (m, 1H), 3.84 (s, 2H), 3.16 (brs, 3H), 2.27-2.10 (m, 1H), 1.83-1.02 (m, 13H), 1.51 (s, 6H), 0.89 and 0.86 (each d, J = 6.6 Hz, total 6H) | |
| 8(51) hydrochloride | cyclohexyl | tetrahydropyran-4-yl | 3,5,5-trimethyl |
| | | TLC:Rf 0.47 (methylene chloride:methanol = 9:1) NMR: δ 11.40 (brs, 1H), 8.23 (d, J = 6.0 Hz, 1H), 4.84-4.72 (m, 1H), 3.93-3.70 (m, 2H), 3.82 (s, 2H), 3.33-3.16 (m, 2H), 3.14 (s, 3H), 2.33-2.20 (m, 1H), 2.17-2.00 (m, 1H), 1.78-1.05 (m, 14H), 1.51 (s, 6H) | |

-continued

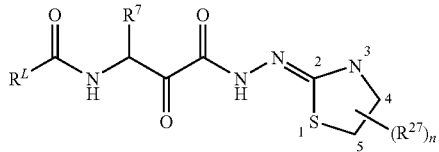

| Example | R<sup>L</sup> | R<sup>7</sup> | R<sup>27</sup> |
|---|---|---|---|

8(52) cycloheptyl 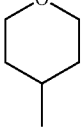 3-methyl free compound
TLC:Rf 0.38 (methylene chloride:methanol = 9:1)
NMR: δ 11.44 (s, 1H), 8.20 (d, J =
6.3 Hz, 1H), 4.83 (t-like, J = 5.4 Hz,
1H), 3.96 (t, J = 7.5 Hz, 2H),
3.89-3.77 (m, 2H), 3.38 (t, J = 7.5 Hz, 2H),
3.24 (t, J = 10.5 Hz,
2H), 3.09 (s, 3H), 2.57-2.41 (m, 1H), 2.16-2.00 (m,
1H), 1.77-1.29 (m, 16H)
hydrochloride
TLC:Rf 0.37 (methylene chloride:methanol = 9:1)
NMR (CDCl₃): δ 1.67 (m, 16H), 2.36 (m, 2H),
3.04 (s, 3H), 3.25 (t,
J = 6.87 Hz, 2H), 3.35 (m, 2H), 3.65 (t, J =
6.87 Hz, 2H), 3.95 (m,
J = 10.71 Hz, 2H), 5.15 (m, 1H), 6.44 (d,
J = 9.07 Hz, 1H), 8.73 (s, 1H)

8(53) cyclohexyl (S)-isopropyl 3-propyl
hydro-
chloride
TLC:Rf 0.47 (methylene chloride:methanol = 9:1)
NMR: δ 11.56 (br-s, 1H), 8.12 (d, J =
6.9 Hz, 1H), 4.82 (t-like, J = 6.0
Hz, 1H), 4.04 (t, J = 7.2 Hz, 2H), 3.53 (t, J =
7.2 Hz, 2H), 3.14 (t, J = 7.2
Hz, 2H), 2.33-2.27 (m, 1H), 2.21-2.09
(m, 1H), 1.65-1.58 (m, 7H),
1.37-1.08 (m, 5H), 0.92-0.85 (m, 9H)

8(54) cyclohexyl (S)-isopropyl 3-benzyl
hydro-
chloride
TLC:Rf 0.57 (n-hexane:ethyl acetate = 1:3)
NMR: δ 11.32 (br-s, 1H), 8.05 (d, J =
7.5 Hz, 1H), 7.43-7.33 (m, 5H),
4.91 (t-like, J = 6.0 Hz, 1H), 4.80-4.70
(m, 2H), 3.77 (t, J = 7.2 Hz, 2H),
3.33 (t, J = 7.2 Hz, 2H), 2.36-2.12
(m, 2H), 1.70-1.58 (m, 5H),
1.38-1.05 (m, 5H), 0.89 (d, J =
6.9 Hz, 3H), 0.85 (d, J = 6.9 Hz, 3H)

8(55) cyclohexyl 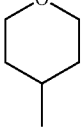 3-methyl
hydro-
chloride

TLC:Rf 0.52 (methylene chloride:methanol = 9:1)
NMR: δ 0.88-1.96 (m, 21H), 2.28 (m, 1H),
3.10 (s, 3H), 3.39 (t, J = 7.5
Hz, 2H), 3.98 (t, J = 7.5 Hz,
2H), 4.86 (m, 1H), 4.91-6.15 (broad, 1H),
8.09 (d, J = 6.0 Hz, 1H), 11.47 (brs, 1H)

8(56) cycloheptyl 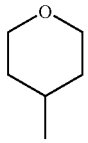 3-benzyl

-continued

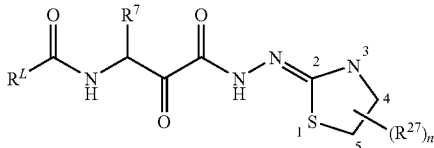

| Example | R<sup>L</sup> | R<sup>7</sup> | R<sup>27</sup> |
|---|---|---|---|

TLC:Rf 0.53 (ethyl acetate)
NMR: δ 11.23 (s, 1H), 8.13 (d, J =
7.2 Hz, 1H), 7.47-7.31 (m, 5H),
4.98-4.87 (m, 1H), 4.79-4.65 (m, 2H), 3.85-3.81
(m, 2H), 3.74 (t,
J = 7.5 Hz, 2H), 3.31 (t, J =
7.5 Hz, 2H), 3.29-3.21 (m, 2H), 2.50-2.43
(m, 1H), 2.20-2.03 (m, 1H), 1.78-1.38 (m, 16H)

8(57) 3,3- 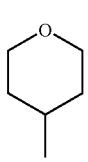 3-benzyl
hydro- dimethylbut-1-enyl
chloride

TLC:Rf 0.45 (n-hexane:ethyl acetate = 1:3)
NMR: δ 1.03 (s, 9H), 1.35-1.50 (m, 4H),
2.10-2.22 (m, 1H), 3.18-3.37
(m, 4H), 3.80-3.94 (m, 4H), 4.63 (s, 2H),
5.04-5.13 (m, 1H), 6.05 (d,
J = 15.66 Hz, 1H), 6.63 (d, J =
15.66 Hz, 1H), 7.24-7.58 (m, 5H), 8.27
(d, J = 5.49 Hz, 1H), 11.00 (s, 1H)

8(58) 3,3- 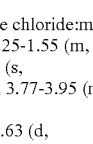 3-methyl
hydro- dimethylbut-1-enyl
chloride

TLC:Rf 0.56 (methylene chloride:methanol = 9:1)
NMR: δ 1.03 (s, 9H), 1.25-1.55 (m, 4H),
2.04-2.21 (m, 1H), 2.99 (s,
3H), 3.20-3.40 (m, 4H), 3.77-3.95 (m, 4H),
4.98-5.08 (m, 1H), 6.03
(d, J = 15.66 Hz, 1H), 6.63 (d,
J = 15.66 Hz, 1H), 8.34 (d, J = 8.52 Hz,
1H), 11.15 (s, 1H)

8(59) 3,3- 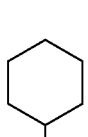 3-methyl
hydro- dimethylbut-1-enyl
chloride

TLC:Rf 0.36 (methylene chloride:methanol = 9:1)
NMR: δ 1.02 (s, 9H), 1.02 (m, 5H),
1.67 (m, 6H), 3.11 (s, 3H), 3.39 (t,
J = 7.55 Hz, 2H), 3.98 (t,
J = 7.55 Hz, 2H), 4.94 (t, J = 6.18 Hz, 1H), 6.04
(d, J = 15.66 Hz, 1H), 6.61 (d, J =
15.66 Hz, 1H), 8.33 (d, J = 6.32 Hz,
1H), 11.50 (s, 1H)

8(60) 3,3- 3-(2-
hydro- dimethylbut-1-enyl hydroxy-
chloride ethyl)

TLC:Rf 0.50 (methylene chloride:methanol = 9:1)
NMR: δ 1.11 (m, 14H), 1.67 (m, 6H), 3.38 (t,
J = 7.42 Hz, 2H), 3.62 (s, -continued

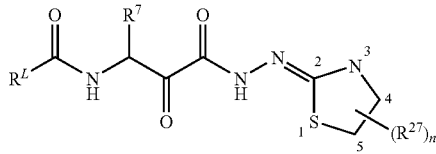

| Example | R^L | R^7 | R^27 |
|---|---|---|---|
| | | 4H), 4.06 (t, J = 7.42 Hz, 2H), 4.95 (t, J = 6.18 Hz, 1H), 6.04 (d, J = 15.66 Hz, 1H), 6.61 (d, J = 15.66 Hz, 1H), 8.30 (d, J = 6.04 Hz, 1H), 11.43 (s, 1H) | |
| 8(61) hydrochloride | cyclohexyl | [cyclohexyl] TLC:Rf 0.50 (methylene chloride:methanol 9:1) NMR: δ 1.07 (m, 10H), 1.63 (m, 11H), 2.26 (m, 1H), 3.40 (t, J = 7.55 Hz, 2H), 3.62 (s, 4H), 4.08 (t, J = 7.55 Hz, 2H), 4.86 (t, J = 6.18 Hz, 1H), 8.08 (d, J = 6.04 Hz, 1H), 11.46 (s, 1H) | 3-(2-hydroxyethyl) |
| 8(62) hydrochloride | cyclohexyl | [cyclohexyl] TLC:Rf 0.54 (methylene chloride:methanol = 9:1) NMR: δ 1.43 (m, 21H), 2.27 (m, 1H), 3.09 (s, 3H), 3.38 (t, J = 7.55 Hz, 2H), 3.96 (t, J = 7.42 Hz, 2H), 4.86 (m, 2H), 8.08 (d, J = 6.32 Hz, 1H), 11.42 (s, 1H) | 3-methyl |
| 8(63) 2hydrochloride | cyclohexyl | [cyclohexyl] TLC:Rf 0.51 (methylene chloride:methanol:ammonia water = 90:10:1) NMR: δ 1.31 (m, 21H), 2.27 (m, 1H), 2.65 (s, 3H), 2.67 (s, 3H), 3.29 (t, J = 7.28 Hz, 2H), 3.68 (t, J = 7.28 Hz, 2H), 4.25 (m, 2H), 4.72 (s, 2H), 4.98 (m, 2H), 7.46 (d, J = 7.97 Hz, 2H), 7.58 (d, J = 8.24 Hz, 2H), 7.97 (d, J = 6.87 Hz, 1H), 10.83 (s, 1H), 11.07 (s, 1H) | 3-(4-dimethylaminomethylbenzyl) |
| 8(64) hydrochloride | cycloheptyl | [cyclohexyl] TLC:Rf 0.40 (methylene chloride:methanol = 9.1) NMR: δ 1.43 (m, 23H), 2.49 (m, 1H), 3.11 (s, 3H), 3.40 (t, J = 7.55 Hz, 2H), 3.98 (t, J = 7.55 Hz, 2H), 4.83 (t, J = 6.18 Hz, 1H), 8.08 (d, J = 6.04 Hz, 1H), 11.46 (s, 1H) | 3-methyl |

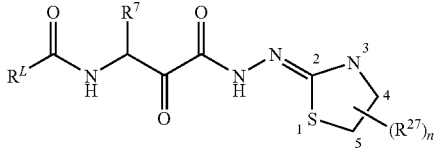

| Example | R^L | R^7 | R^27 |
|---|---|---|---|
| 8(65) hydrochloride | cycloheptyl | [tetrahydropyran] TLC:Rf 0.60 (methylene chloride:methanol = 9:1) NMR: δ 1.52 (m, 16H), 2.08 (m, 1H), 2.48 (m, 1H), 3.08 (s, 3H), 3.24 (m, 2H), 3.38 (t, J = 7.55 Hz, 2H), 3.88 (m, 4H), 4.84 (t, J = 6.18 Hz, 2H), 8.18 (d, J = 6.04 Hz, 1H), 11.40 (s, 1H) | 3-methyl |
| 8(66) hydrochloride | cycloheptyl | [tetrahydropyran] TLC:Rf 0.56 (methylene chloride:methanol = 9:1) NMR: δ 1.53 (m, 16H), 2.09 (m, 1H), 2.45 (m, 1H), 3.11 (s, 3H), 3.24 (m, 2H), 3.40 (t, J = 7.69 Hz, 2H), 3.83 (m, 2H), 3.99 (t, J = 7.55 Hz, 2H), 4.80 (m, 2H), 8.21 (d, J = 6.32 Hz, 1H), 11.49 (s, 1H) | 3-methyl |
| 8(67) hydrochloride | cyclohexyl | (R)-isopropyl TLC:Rf 0.46 (methylene chloride:methanol = 9:1) NMR: δ 0.88 (m, 6H), 1.22 (m, 5H), 1.67 (m, 5H), 2.15 (m, 1H), 2.31 (m, 1H), 3.12 (s, 3H), 3.40 (t, J = 7.55 Hz, 2H), 4.00 (m, 2H), 4.83 (t, J = 6.18 Hz, 1H), 8.10 (d, J = 6.32 Hz, 1H), 11.52 (s, 1H) | 3-methyl |
| 8(68) hydrochloride | cyclohexyl | (R)-butyl TLC:Rf 0.58 (methylene chloride:methanol = 9:1) NMR: δ 0.84 (t, J = 6.87 Hz, 3H), 1.42 (m, 16H), 2.20 (m, 1H), 3.09 (s, 3H), 3.38 (t, J = 7.42 Hz, 2H), 3.96 (t, J = 7.42 Hz, 2H), 4.83 (s, 1H), 8.18 (d, J = 5.49 Hz, 1H), 11.41 (s, 1H) | 3-methyl |
| 8(69) hydrochloride | cyclohexyl | (R)-neopentyl TLC:Rf 0.50 (methylene chloride:methanol = 9:1) NMR: δ 0.90 (s, 9H), 1.41 (m, 12H), 2.16 (m, 1H), 3.08 (s, 3H), 3.37 (t, J = 7.55 Hz, 2H), 3.95 (t, J = 7.55 Hz, 2H), 4.24 (m, 1H), 4.99 (m, 1H), 8.11 (d, J = 6.04 Hz, 1H), 11.40 (s, 1H) | 3-methyl |
| 8(70) hydrochloride | cyclohexyl | (R)-cyclopropyl TLC:Rf 0.56 (methylene chloride:methanol = 9:1) NMR: δ 0.41 (m, 4H), 1.11 (m, 6H), 1.63 (m, 5H), 2.22 (m, 1H), 3.08 (s, 3H), 3.38 (t, J = 7.55 Hz, 2H), 3.62 (m, 1H), 3.96 (t, J = 7.55 Hz, 2H), 4.20 (dd, J = 8.79, 5.49 Hz, 1H), 8.40 (d, J = 4.67 Hz, 1H), 11.40 (s, 1H) | 3-methyl |

Example 8(71)

N'-[3-methyl-1,3-thiazolidin-2-ylidene]-[3-(N-phenylsulfonyl-N-methylamino)-2-oxo-4-methylpentanohydrazide]hydrochloride TLC: Rf 0.45 (ethyl acetate:methanol=9:1);
NMR: δ 11.28 (br-s, 1H), 7.73 (d, J=7.2 Hz, 2H), 7.66-7.55 (m, 3H), 5.04 (d, J=9.9 Hz, 1H), 3.86 (t, J=7.5 Hz, 2H), 3.32 (t, J=7.5 Hz, 2H), 3.04 (s, 3H), 2.84 (s, 3H), 2.20-2.02 (m, 1H), 0.83 (d, J=6.9 Hz, 3H), 0.79 (d, J=6.9 Hz, 3H).

Example 8(72)

N'-(3-methyl-1,3-perhydrothiazin-2-ylidene)-[3-cyclohexylcarbonylamino-2-oxo-3-(tetrahydropyran-4-yl)hexanohydrazide]hydrochloride TLC: Rf 0.36 (ethyl acetate:acetic acid:water=3:1:1);
NMR: δ 1.00-1.80 (m, 15H), 2.09 (m, 2H), 2.27 (m, 1H), 3.20-3.40 (m, 7H), 3.59 (t, J=5.22 Hz, 2H), 3.84 (m, 2H), 4.80 (t, J=6.18 Hz, 1H), 8.27 (d, J=6.04 Hz, 1H), 11.37 (s, 1H).

Example 8(73)

N'-(3-methyl-1,3-thiazolidin-2-ylidene)-[3-cyclohexylcarbonylamino-3-methyl-2-oxobutanohydrazide]hydrochloride TLC: Rf 0.52 (methylene chloride:methanol=9:1);
NMR: δ 11.10 (br, 1H), 8.52 (s, 1H), 4.03 (t, J=7.2 Hz, 2H), 3.40 (t, J=7.2 Hz, 2H), 2.16-2.04 (m, 1H), 1.68-1.57 (m, 5H), 1.36 (s, 6H), 1.29-1.03 (m, 5H).

Example 8(74)

N'-(3-methyl-1,3-perhydrothiazin-2-ylidene)-(3-cyclohexylcarbonylamino-2-oxo-5-methylhexanohydrazide)

Free Compound:
NMR: δ 10.20 (brs, 1H), 7.90-7.78 (m, 3H), 7.60-7.40 (m, 3H), 5.11 (m, 1H), 3.31 (m, 2H), 2.98 (s, 3H), 2.92 (m, 2H), 2.31-2.10 (m, 2H), 2.10-1.90 (m, 1H), 1.90-1.20 (m, 13H), 1.00-0.70 (m, 6H).
Hydrochloride:
TLC: Rf 0.58 (methylene chloride:methanol=9:1);
NMR: δ 11.45 (brs, 1H), 8.20-7.20 (m, 7H), 4.89 (q, J=6.0 Hz, 1H), 3.69 (m, 2H), 3.25 (s, 3H), 3.23 (m, 2H), 2.40-2.00 (m, 4H), 1.97-1.05 (m, 11H), 1.00-0.70 (m, 6H).

Example 8(75)

N'-(3-methyl-1,3-perhydrothiazin-2-ylidene)-[3-(1-benzoylamino cyclohexylcarbonylamino)-5-methyl-2-oxohexanohydrazide]

Free Compound:
NMR: δ 10.62 (s, 1H), 8.00-7.40 (m, 7H), 5.17-5.02 (m, 1H), 3.58 (t, J=6.9 Hz, 2H), 3.17 (t, J=6.9 Hz, 2H), 2.86 (s, 3H), 1.80-1.20 (m, 13H), 0.95-0.75 (m, 6H).

Hydrochloride:
TLC: Rf 0.63 (methylene chloride:methanol=10:1);
NMR: δ 11.42 (s, 1H), 7.80-7.38 (m, 7H), 5.00-4.88 (m, 1H), 3.94 (t, J=6.9 Hz, 2H), 3.37 (t, J=6.9 Hz, 2H), 3.08 (s, 3H), 230-2.00 (m, 2H), 1.82-1.15 (m, 11H), 0.95-0.70 (m, 6H).

Example 9

Preparation of N'-(3,4,4-trimethyl-1,3-thiazolidin-2-ylidene)-[3-cyclohexylcarbonyl amino-3-(tetrahydropyran-4-yl)-2-oxopropanohydrzide]hydrochloride

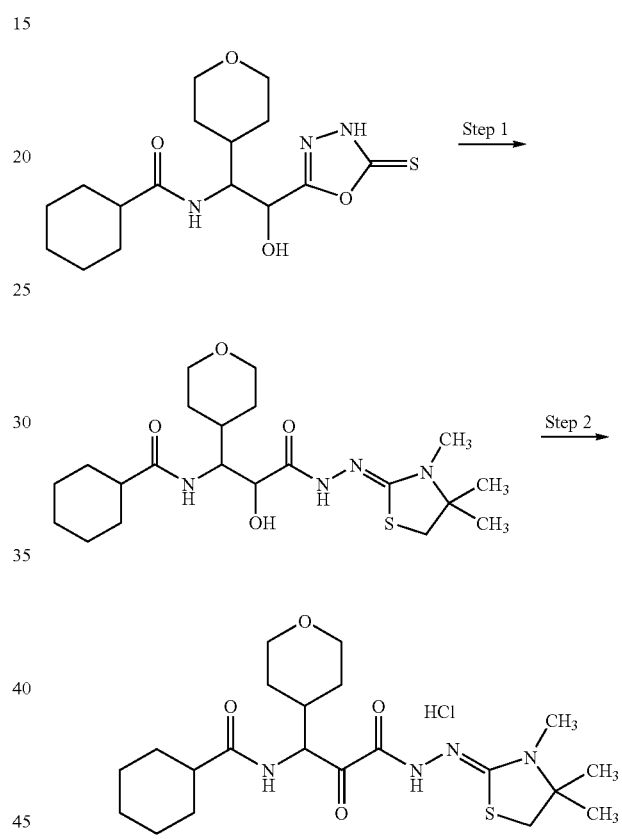

Step 1: To a solution of 1:5-(1-hydroxy-2-cyclohexylcarbonylamino-2-tetrahydropyran-4-ylethyl)-2-thioxo-1,3,4-oxadiazoline (prepared in step 1 of example 8; 281 mg) in N,N-dimethylformamide (2 ml) were added N-methyl-N-(1,1-dimethyl-2-chloroethyl)amine (125 mg) and potassium carbonate (328 mg) and the mixture was stirred for 3 hours at 70° C. The reaction mixture was poured into brine and was extracted with ethyl acetate, dried over anhydrous magnesium sulfate and concentrated. The residue was purified by column chromatography on silica gel (ethyl acetate:methanol=9:1) to give N'-(3,4,4-trimethyl-1,3-thiazolidin-2-ylidene)-[3-cyclohexylcarbonylamino-3-(tetrahydropyran-4-yl)-2-hydroxypropanohydrazide] (279 mg).
TLC: Rf 0.51 and 0.44 (methylene chloride:methanol=9:1).

Step 2: By the same procedure as described in step 7 of example 1 using the compound prepared in step 1, a free compound of N'-(3,4,4-trimethyl-1,3-thiazolidin-2-ylidene)-[3-cyclohexylcarbonylamino-3-(tetrahydro pyran-4-yl)-2-oxopropanohydrazide] was given. To the free compound was added 4N hydrochloric acid-ethyl acetate solution and the mixture was stirred for 1 hour at room temperature and the mixture was concentrated. The residue was washed with ethyl acetate to give N'-(3,4,4-trimethyl-1,3-thiazolidin-2-ylidene)-[3-cyclohexylcarbonylamino-3-(tetrahydropyran-4-yl)-2-oxopropanohydrazide]hydrochloride (140 mg).

Free Compound:

NMR: δ 1.25 (s, 3H), 1.26 (s, 3H), 1.29 (m, 14H), 2.10 (d, J=6.59 Hz, 1H), 2.29 (m, 1H), 2.74 (s, 3H), 3.04 (s, 2H), 3.26 (m, J=29.67 Hz, 2H), 3.82 (m, 2H), 5.06 (dd, J=8.10, 5.91 Hz, 1H), 7.95 (d, J=7.69 Hz, 1H), 10.55 (s, 1H).

Hydrochloride:

TLC: Rf 0.46 (methylene chloride:methanol=9:1);

NMR (CDCl$_3$): δ 1.35 (s, 6H), 1.56 (m, 14H), 2.16 (m, 1H), 2.39 (m, 1H), 2.90 (s, 3H), 3.07 (s, 2H), 3.34 (m, 2H), 3.94 (m, 2H), 5.15 (dd, J=9.20, 6.46 Hz, 1H), 6.57 (d, J=9.07 Hz, 1H), 8.76 (s, 1H).

Example 9(1)-Example 9(9)

By the same procedure as described in example 9 using corresponding compounds, the following compounds were given.

| Example | R$^L$ | R$^7$ |
|---|---|---|
| 9(1) hydrochloride | cyclohexyl | isobutyl |
| | TLC: Rf 0.66 (methylene chloride:methanol = 9:1) NMR(100° C.): δ 7.68-7.56 (br, 1H), 5.04-4.92 (m, 1H), 3.15 (s, 2H), 2.87 (brs, 3H), 2.29-2.15 (m, 1H), 1.82-1.08 (m, 13H), 1.33 (s, 6H), 0.91 and 0.90 (each d, J = 6.3 Hz, total 6H) | |
| 9(2) hydrochloride | cyclohexyl | neopentyl |
| | TLC: Rf 0.65 (methylene chloride:methanol = 9:1) NMR(100° C.): δ 7.69-7.50 (m, 1H), 5.10-4.90 (m, 1H), 3.18 (s, 2H), 2.90 (s, 3H), 2.27-2.12 (m, 1H), 1.88-1.10 (m, 12H), 1.35 (s, 6H), 0.94 (s, 9H) | |
| 9(3) hydrochloride | 3,3-dimethylbut-1-enyl | tetrahydropyran-4-yl |
| | TLC: Rf 0.54 (methylene chloride:methanol = 10:1) NMR: δ 1.02 (s, 9H), 1.40 (m, 10H), 2.12 (m, 1H), 2.92 (s, 3H), 3.24 (m, 4H), 3.88 (m, 2H), 4.98 (m, 1H), 6.02 (d, J = 15.66 Hz, 1H), 6.62 (d, J = 15.66 Hz, 1H), 8.38 (d, J = 7.42 Hz, 1H), 11.22 (s, 1H) | |
| 9(4) | cycloheptyl | tetrahydropyran-4-yl |
| | free compound TLC: Rf 0.37 (methylene chloride:methanol = 9:1) NMR (CDCl$_3$): δ 1.33 (m, 6H), 1.66 (m, 16H), 2.36 (m, 2H), 2.90 (s, 3H), 3.06 (s, 2H), 3.35 (m, 2H), 3.95 (m, 2H), 5.14 (dd, J = 9.61, 6.32 Hz, 1H), 6.47 (d, J = 9.61 Hz, 1H), 8.75 (s, 1H) hydrochloride TLC: Rf 0.43 (methylene chloride:methanol = 9:1) NMR: δ 1.52 (m, 22H), 2.07 (m, 1H), 2.49 (m, 1H), 3.03 (s, 3H), 3.24 (m, 2H), 3.32 (s, 2H), 3.83 (m, 2H), 4.80 (t, J = 6.18 Hz, 1H), 8.24 (d, J = 6.32 Hz, 1H), 11.49 (s, 1H) | |
| 9(5) hydrochloride | cyclohexyl | cyclohexyl |
| | TLC: Rf 0.33 (n-hexane:ethyl acetate = 1:10) NMR: δ 1.41 (m, 27H), 2.26 (m, 1H), 2.99 (s, 3H), 3.29 (s, 2H), 4.86 (m, 1H), 8.09 (d, J = 6.32 Hz, 1H), 11.38 (s, 1H) | |

-continued

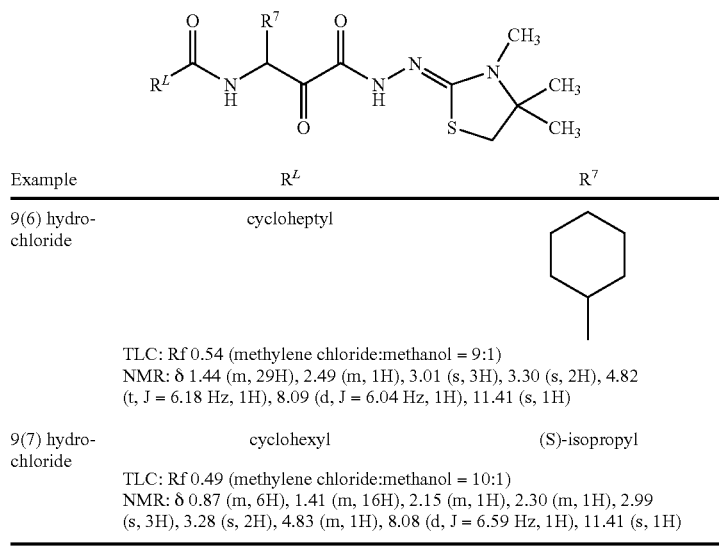

| Example | $R^L$ | $R^7$ |
|---|---|---|
| 9(6) hydro-chloride | cycloheptyl | cyclohexyl (shown) |

TLC: Rf 0.54 (methylene chloride:methanol = 9:1)
NMR: δ 1.44 (m, 29H), 2.49 (m, 1H), 3.01 (s, 3H), 3.30 (s, 2H), 4.82 (t, J = 6.18 Hz, 1H), 8.09 (d, J = 6.04 Hz, 1H), 11.41 (s, 1H)

| 9(7) hydro-chloride | cyclohexyl | (S)-isopropyl |

TLC: Rf 0.49 (methylene chloride:methanol = 10:1)
NMR: δ 0.87 (m, 6H), 1.41 (m, 16H), 2.15 (m, 1H), 2.30 (m, 1H), 2.99 (s, 3H), 3.28 (s, 2H), 4.83 (m, 1H), 8.08 (d, J = 6.59 Hz, 1H), 11.41 (s, 1H)

Example 9(8)

N'-(4,4-dimethyl-3-ethyl-1,3-thiazolidin-2-ylidene)-[3-cyclohexyl carbonylamino-3-(tetrahydropyran-4-yl)-2-oxopropanohydrazide]-hydrochloride TLC: Rf 0.51 (ethyl acetate:methanol=15:1);
NMR: δ 1.35 (m, 23H), 2.09 (m, 1H), 2.28 (m, 1H), 3.25 (s, 2H), 3.44 (m, 4H), 3.84 (m, 2H), 4.87 (m, 1H), 8.17 (m, 1H), 11.27 (s, 1H).

Example 9(9)

N'-[1-aza-1-methyl-3-thiaspiro[4.4]non-2-ylidene)-[3-cyclohexyl-3-cyclohexylcarbonylamino-2-oxo-propionohydrazide]hydrochloride TLC: Rf 0.67 (methylene chloride:methanol=9:1);
NMR: δ 1.45 (m, 22H), 2.08 (m, 1H), 2.27 (m, 1H), 3.00 (s, 3H), 3.23 (m, 2H), 3.34 (s, 2H), 3.81 (m, 2H), 4.84 (t, J=6.32 Hz, 1H), 8.20 (d, J=6.32 Hz, 1H), 11.39 (s, 1H).

Example 10

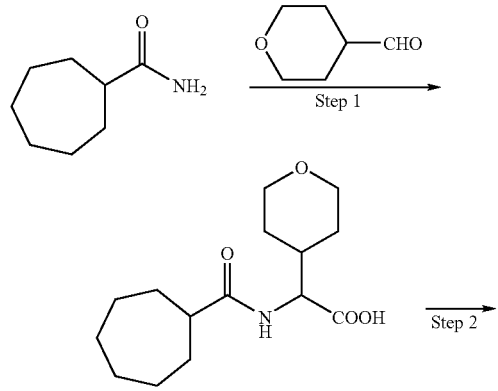

Step 1: To a solution of 4-formyltetrahydropyran (1.14 g), cycloheptylcarboxyamide (1.41 g) in N-methylpyrrolidone (8 ml) were added lithium bromide (304 mg), conc. sulfic acid (10 mg) and dibromobis(triphenylphosphine) palladium (II) (20 mg) and the mixture was stirred at 120° C. for 10 hours in an autoclave under atmosphere of carbon monoxide at a pressure of 57 kg/cm². The reaction mixture was extracted with ethyl acetate and a saturated aqueous solution of sodium bicarbonate. The aqueous layer was neutralized with conc. hydrochloric acid and extracted with ethyl acetate twice, washed with diisopropyl ether to give 2-cycloheptylcarbonyl amino-2-(tetrahydropyran-4-yl)acetic acid (2.33 g).

TLC: Rf 0.60 (methylene chloride:methanol=10:1).

Step 2: To a solution of the compound prepared in step 1 (1.13 g), pyridine (0.97 ml) and dimethylaminopyridine (24.4 mg) in tetrahydrofuran (4 ml) was added 2-cycloheptylcarbonylamino-2-(tetrahydropyran-4-yl)acetic acid (prepared in step 1; 0.89 ml) and the mixture was refluxed for 6 hours. To the mixture was added 2-cycloheptylcarbonylamino-2-(tetrahydropyran-4-yl)acetic acid (0.089 ml) again and the mixture was stirred for 1 hour. To the reaction mixture was extracted with ethyl acetate and ice-water. The organic layer was washed with an aqueous solution of citric acid, a saturated aqueous solution of sodium bicarbonate, water and brine successively, dried over anhydrous sodium sulfate and concentrated. The residue was dissolved in methanol (4 ml) and thereto was added sodium bicarbonate (136 mg) and the mixture was refluxed for 150 minutes. The precipitate was collected, and the filtrate was concentrated, and the residue was washed with diisopropyl ether 3-cycloheptylcarbonylamino-3-(tetrahydropyran-4-yl)-2-oxopropanoic acid methyl ester (542 mg).

TLC: Rf 0.36 (n-hexane:ethyl acetate=1:1).

Step 3: To a suspension of the compound prepared in step 2 (325 mg) in methanol (1 ml) was added hydrazine monohydrate (60 mg) and the mixture was stirred for 3 hours. To the mixture was added hydrazine monohydrate (6 mg) again and the mixture was stirred for 30 minutes. To the reaction mixture was added methanol (4 ml) and the precipitate was collected and washed with methanol to give 3-cycloheptylcarbonylamino-2-oxo-3-(tetrahydropyran-4-yl)propanohydrazide (142 mg).

TLC: Rf 0.44 (methylene chloride:methanol=10:1).

Step 4: By the same procedure as described in step 6 of example 1 using the compound prepared in step 3 and a corresponding compound, followed by recrystallization from isopropanol to give N'-(3-ethyl-4-methyl-1,3-thiazolidin-2-ylidene)-[3-cycloheptylcarbonylamino-3-[(3S)-tetrahydropyran-4-yl]-2-oxopropanohydrazide].

TLC: Rf 0.54 (methylene chloride:methanol=9:1);

NMR (CDCl$_3$): δ 1.19 (t, J=7.14 Hz, 3H), 1.33 (d, J=6.22 Hz, 3H), 1.67 (m, 16H), 2.30 (m, 1H), 2.40 (m, 1H), 2.86 (dd, J=10.80, 6.41 Hz, 1H), 3.22 (td, J=14.10, 6.96 Hz, 1H), 3.35 (m, 3H), 3.79 (td, J=14.46, 7.32 Hz, 1H), 3.98 (m, 3H), 5.14 (dd, J=9.15, 6.22 Hz, 1H), 6.46 (d, J=9.15 Hz, 1H), 8.73 (s, 1H).

Example 10(1)-Example 10(66)

By the same procedure as described in example 10 using corresponding compounds, the following compounds were given.

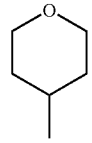

| Example | R$^L$ | R$^7$ | R$^{27}$ |
|---|---|---|---|
| 10(1) | cyclohexyl | 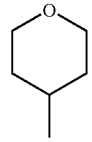 | 3-(4-methoxybenzyl) |

TLC: Rf 0.55 (ethyl acetate)
NMR (CDCl$_3$): δ 1.59 (m, 14H), 2.17 (m, 1H), 2.40 (m, 1H), 3.18 (t, J = 6.87 Hz, 2H), 3.35 (m, 2H), 3.51 (t, J = 7.00 Hz, 2H), 3.80 (s, 3H), 3.95 (m, 2H), 4.56 (d, J = 14.56 Hz, 1H), 4.62 (d, J = 14.50 Hz, 1H), 5.19 (dd, J = 9.07, 6.04 Hz, 1H), 6.50 (d, J = 9.07 Hz, 1H), 6.88 (d, J = 8.79 Hz, 2H), 7.26 (d, J = 8.79 Hz, 2H), 8.79 (s, 1H)

| | | | |
|---|---|---|---|
| 10(2) | cycloheptyl | 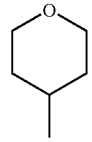 | (4S)-3,4-dimethyl |

TLC: Rf 0.53 (ethyl acetate:methanol:water = 40:10:1)
NMR (CDCl$_3$): δ 1.33 (d, J = 6.32 Hz, 3H), 1.66 (m, 16H), 2.30 (m, 2H), 2.88 (dd, J = 10.71, 6.04 Hz, 1H), 2.98 (s, 3H), 3.35 (m, 3H), 3.90 (m, 3H), 5.15 (dd, J = 9.07, 6.04 Hz, 1H), 6.45 (d, J = 9.89 Hz, 1H), 8.73 (s, 1H)

| | | | |
|---|---|---|---|
| 10(3) | cycloheptyl | 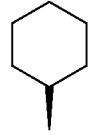 | 3-methyl |

TLC: Rf 0.52 (methylene chloride:methanol = 9:1)
NMR (CDCl$_3$): δ 1.55 (m, 23H), 2.29 (m, 1H), 3.03 (s, 3H), 3.24 (t, J = 6.87 Hz, 2H), 3.64 (t, J = 7.00 Hz, 2H), 5.04 (dd, J = 8.93, 6.73 Hz, 1H), 6.38 (d, J = 8.52 Hz, 1H), 8.72 (s, 1H)

-continued

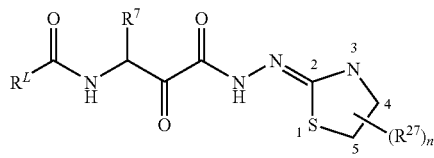

| Example | R$^L$ | R$^7$ | R$^{27}$ |
|---|---|---|---|
| 10(4) | (1S)-1-(t-butoxycarbonylamino)-3-methylbutyl | 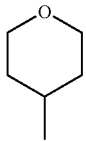 | 3-methyl |

TLC: Rf 0.50 (chloroform:methanol = 9:1)
NMR: δ 0.84 (m, 6H), 1.34 (m, 15H), 1.61 (m, 1H), 2.15 (m, 1H), 2.87 (s, 3H), 3.24 (m, 4H), 3.57 (m, 2H), 3.81 (m, 2H), 4.07 (m, 1H), 5.16 (m, 1H), 6.91 (m, 1H), 7.91 (m, 1H), 10.70 (s, 1H)

| 10(5) | cycloheptyl | 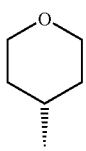 | (4S)-3,4-dimethyl |

TLC: Rf 0.43 (methylene chloride:methanol = 9:1)
NMR (CDCl$_3$): δ 1.33 (d, J = 6.32 Hz, 3H), 1.66 (m, 16H), 2.33 (m, 2H), 2.88 (dd, J = 10.71, 6.32 Hz, 1H), 2.98 (s, 3H), 3.35 (m, 3H), 3.91 (m, 3H), 5.15 (dd, J = 9.07, 6.32 Hz, 1H), 6.46 (d, J = 9.07 Hz, 1H), 8.74 (s, 1H)

| 10(6) | cycloheptyl | 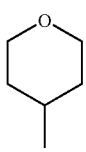 | (4R)-3,4-dimethyl |

TLC: Rf 0.43 (methylene chloride:methanol = 9:1)
NMR (CDCl$_3$): δ 1.33 (d, J = 6.32 Hz, 3H), 1.66 (m, 16H), 2.33 (m, 2H), 2.88 (dd, J = 10.71, 6.04 Hz, 1H), 2.98 (s, 3H), 3.35 (m, 3H), 3.91 (m, 3H), 5.15 (dd, J = 9.07, 6.04 Hz, 1H), 6.45 (d, J = 9.07 Hz, 1H), 8.73 (s, 1H)

| 10(7) | cycloheptyl | 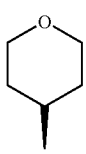 | (4R)-3,4-dimethyl |

TLC: Rf 0.43 (methylene chloride:methanol = 9:1)
NMR (CDCl$_3$): δ 1.33 (d, J = 6.32 Hz, 3H), 1.65 (m, 16H), 2.34 (m, 2H), 2.88 (dd, J = 10.85, 6.18 Hz, 1H), 2.98 (s, 3H), 3.35 (m, 3H), 3.91 (m, 3H), 5.15 (dd, J = 9.07, 6.32 Hz, 1H), 6.45 (d, J = 9.07 Hz, 1H), 8.73 (s, 1H)

| 10(8) | (1S)-1-methoxycarbonylamino-3-methylbutyl |  | 3-methyl |

TLC: Rf 0.50 (chloroform:methanol = 9:1)
NMR: δ 0.87 (m, 6H), 1.35 (m, 6H), 1.61 (m, 1H), 2.16 (m, 1H), 2.87 (s, 3H), 3.23 (m, 4H), 3.51 (s, 3H), 3.58 (t, J = 6.87 Hz, 2H), 3.80 (m, 2H), 4.21 (m, 1H), 5.12 (m, 1H), 7.24 (m, 1H), 8.10 (m, 1H), 10.67 (s, 1H)

-continued

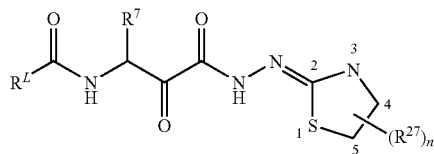

| Example | R$^L$ | R$^7$ | R$^{27}$ |
|---|---|---|---|
| 10(9) | (1S)-1-(t-butoxycarbonylamino)-3-methylbutyl | cyclohexyl | 3-methyl |

TLC: Rf 0.51 (chloroform:methanol = 10:1)
NMR (CDCl$_3$): δ 1.31 (m, 28H), 2.13 (m, 1H), 3.01 (s, 3H), 3.22 (t, J = 6.73 Hz, 2H), 3.61 (t, J = 6.87 Hz, 2H), 4.11 (m, 1H), 4.85 (m, 1H), 5.21 (m, 1H), 6.89 (m, 1H), 8.71 (s, 1H)

| 10(10) | cyclohexyl | tetrahydropyran-4-yl | (4R)-3,4-dimethyl |

TLC: Rf 0.47 (methylene chloride:methanol = 9:1)
NMR (CDCl$_3$): δ 1.33 (d, J = 6.04 Hz, 3H), 1.55 (m, 14H), 2.15 (m, 1H), 2.38 (m, 1H), 2.88 (dd, J = 10.85, 6.18 Hz, 1H), 2.98 (s, 3H), 3.36 (m, 3H), 3.90 (m, 3H), 5.15 (dd, J = 9.07, 6.32 Hz, 1H), 6.54 (d, J = 9.07 Hz, 1H), 8.73 (s, 1H)

| 10(11) | (1S)-1-methoxycarbonylamino-3-methylbutyl | cyclohexyl | 3-methyl |

TLC: Rf 0.48 (ethyl acetate:methanol = 10:1)
NMR (CDCl$_3$): δ 1.28 (m, 19H), 2.13 (m, 1H), 3.02 (s, 3H), 3.23 (t, J = 6.87 Hz, 2H), 3.62 (t, J = 6.87 Hz, 2H), 3.68 (s, 3H), 4.21 (m, 1H), 5.11 (m, 2H), 6.79 (m, 1H), 8.70 (s, 1H)

| 10(12) | cycloheptyl | tetrahydropyran-4-yl | (4R)-4-isopropyl-3-methyl |

TLC: Rf 0.60 (ethyl acetate:methanol = 9:1)
NMR: δ 0.86 (m, 6H), 1.51 (m, 16H), 2.17 (m, 2H), 2.46 (m, 1H), 2.86 (s, 3H), 2.97 (m, 1H), 3.26 (m, 3H), 3.77 (m, 3H), 5.02 (m, 1H), 7.93 (d, J = 7.69 Hz, 1H), 10.55 (s, 1H)

| 10(13) | cycloheptyl | tetrahydropyran-4-yl | (4R)-4-isobutyl-3-methyl |

TLC: Rf 0.69 (ethyl acetate:methanol = 9:1)
NMR: δ 0.91 (m, 6H), 1.52 (m, 19H), 2.09 (m, 1H), 2.47 (m, 1H), 2.84 (s, 3H), 2.91 (m, 1H), 3.29 (m, 3H), 3.80 (m, 3H), 5.05 (m, 1H), 7.93 (d, J = 6.96 Hz, 1H), 10.56 (s, 1H)

| 10(14) | cyclohexyl | tetrahydropyran-4-yl | (4R)-4-isopropyl-3-methyl |

TLC: Rf 0.56 (ethyl acetate:methanol = 9:1)
NMR: δ 0.86 (m, 6H), 1.39 (m, 14H), 2.19 (m, 3H), 2.85 (s, 3H), 2.97

-continued

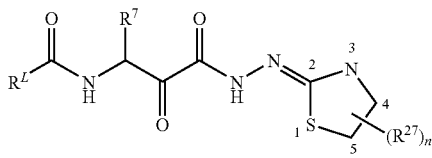

| Example | R^L | R^7 | R^27 |
|---|---|---|---|

(m, 1H), 3.29 (m, 3H), 3.70 (m, 1H), 3.83 (m, 2H), 5.06 (m, 1H), 7.94 (d, J = 8.06 Hz, 1H), 10.56 (s, 1H)

10(15)   cyclohexyl   tetrahydropyran-4-yl   (4R)-4-isobutyl-3-methyl

TLC: Rf 0.65 (ethyl acetate:methanol = 9:1)
NMR: δ 0.90 (m, 6H), 1.40 (m, 17H), 2.11 (m, 1H), 2.29 (m, 1H), 2.84 (s, 3H), 2.91 (m, 1H), 3.27 (m, 3H), 3.77 (m, 3H), 5.06 (m, 1H), 7.93 (d, J = 7.32 Hz, 1H), 10.56 (s, 1H)

10(16)   cycloheptyl   cyclohexyl   (4R)-4-isopropyl-3-methyl

TLC: Rf 0.50 (ethyl acetate)
NMR: δ 0.85 (m, 6H), 1.45 (m, 23H), 2.20 (m, 1H), 2.47 (m, 1H), 2.85 (s, 3H), 2.96 (m, 1H), 3.16 (m, 1H), 3.70 (m, 1H), 5.01 (m, 1H), 7.81 (d, J = 6.96 Hz, 1H), 10.52 (s, 1H)

10(17)   cycloheptyl   cyclohexyl   (4R)-4-isobutyl-3-methyl

TLC: Rf 0.60 (ethyl acetate)
NMR: δ 0.91 (m, 6H), 1.48 (m, 26H), 2.45 (m, 1H), 2.84 (s, 3H), 2.91 (m, 1H), 3.34 (m, 1H), 3.77 (m, 1H), 5.01 (m, 1H), 7.81 (d, J = 7.69 Hz, 1H), 10.53 (s, 1H)

10(18)   cycloheptyl   tetrahydropyran-4-yl   (5R)-3,5-dimethyl

TLC: Rf 0.58 (methylene chloride:methanol = 9:1)
NMR (CDCl$_3$): δ 1.47 (d, J = 6.59 Hz, 3H), 1.47 (m, J = 6.59 Hz, 16H), 2.30 (m, 1H), 2.39 (m, 1H), 3.03 (s, 3H), 3.32 (m, 3H), 3.71 (m, 1H), 3.82 (m, 1H), 3.95 (m, 2H), 5.14 (dd, J = 8.06, 6.59 Hz, 1H), 6.45 (d, J = 9.15 Hz, 1H), 8.69 (s, 1H)

10(19)   cyclohexyl   tetrahydropyran-4-yl   (5R)-3,5-dimethyl

TLC: Rf 0.55 (methylene chloride:methanol = 9:1)
NMR (CDCl$_3$): δ 1.47 (d, J = 6.59 Hz, 3H), 1.47 (m, J = 6.59 Hz, 14H), 2.16 (m, 1H), 2.37 (m, 1H), 3.03 (s, 3H), 3.32 (m, 3H), 3.72 (m, 1H), 3.82 (m, 1H), 3.96 (m, 2H), 5.15 (dd, J = 9.15, 6.59 Hz, 1H), 6.54 (d, J = 8.79 Hz, 1H), 8.70 (s, 1H)

-continued

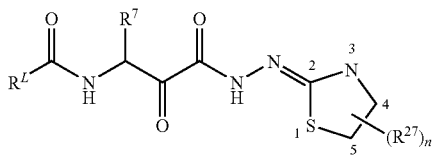

| Example | R^L | R^7 | R^27 |
|---|---|---|---|
| 10(20) | cycloheptyl | cyclohexyl | (5R)-3,5-dimethyl |

TLC: Rf 0.58 (methylene chloride:methanol = 9:1)
NMR (CDCl$_3$): δ 1.46 (d, J = 6.59 Hz, 22H), 1.46 (d, J = 6.59 Hz, 3H), 2.10 (m, 1H), 2.29 (m, 1H), 3.03 (s, 3H), 3.27 (dd, J = 9.34, 6.41 Hz, 1H), 3.71 (m, 1H), 3.81 (m, 1H), 5.04 (m, 1H), 6.40 (d, J = 8.79 Hz, 1H), 8.69 (s, 1H)

| 10(21) | cycloheptyl | tetrahydropyran-4-yl | (4R)-3,4-diethyl |

TLC: Rf 0.57 (methylene chloride:methanol = 9:1)
NMR: (CDCl$_3$): δ 0.97 (t, J = 7.51 Hz, 3H), 1.19 (t, J = 7.14 Hz, 3H), 1.63 (m, 18H), 2.30 (m, 1H), 2.42 (m, 1H), 2.96 (dd, J = 10.98, 6.22 Hz, 1H), 3.20 (m, 1H), 3.34 (m, 3H), 3.81 (m, 2H), 3.97 (m, 2H), 5.16 (m, 1H), 6.46 (m, 1H), 8.72 (s, 1H)

| 10(22) | cycloheptyl | cyclohexyl | (4R)-3,4-diethyl |

TLC: Rf 0.58 (methylene chloride:methanol = 9:1)
NMR (CDCl$_3$): δ 0.97 (t, J = 7.51 Hz, 3H), 1.49 (m, 27H), 2.11 (m, 1H), 2.29 (m, 1H), 2.95 (dd, J = 10.98, 6.22 Hz, 1H), 3.21 (m, 1H), 3.30 (dd, J = 10.80, 6.77 Hz, 1H), 3.81 (m, 2H), 5.03 (m, 1H), 6.42 (m, 1H), 8.72 (s, 1H)

| 10(23) | cyclohexyl | tetrahydropyran-4-yl | (4R)-3,4-diethyl |

TLC: Rf 0.56 (methylene chloride:methanol = 9:1)
NMR (CDCl$_3$): δ 0.97 (t, J = 7.51 Hz, 3H), 1.54 (m, 19H), 2.15 (m, 1H), 2.38 (m, 1H), 2.96 (dd, J = 10.98, 6.22 Hz, 1H), 3.20 (m, 1H), 3.35 (m, 3H), 3.81 (m, 2H), 3.94 (m, 2H), 5.14 (dd, J = 9.15, 6.22 Hz, 1H), 6.55 (d, J = 8.79 Hz, 1H), 8.73 (s, 1H)

| 10(24) | cycloheptyl | tetrahydropyran-4-yl | (4R)-3-ethyl-4-methyl |

TLC: Rf 0.46 (ethyl acetate:methanol = 20:1)
NMR: δ 1.07 (t, J = 7.05 Hz, 3H), 1.22 (d, J = 6.22 Hz, 3H), 1.54 (m, 17H), 2.12 (m, 1H), 2.79 (dd, J = 10.89, 6.87 Hz, 1H), 3.17 (m, 4H), 3.55 (m, 1H), 3.81 (m, 2H), 3.93 (m, 1H), 5.02 (dd, J = 7.69, 6.04 Hz, 1H), 7.93 (d, J = 7.69 Hz, 1H), 10.56 (s, 1H)

| 10(25) | cycloheptyl | tetrahydropyran-4-yl | (4R)-4-ethyl-3-methyl |

-continued

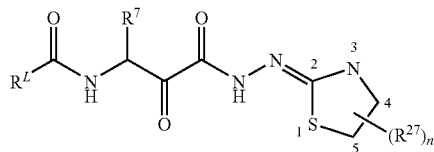

| Example | $R^L$ | $R^7$ | $R^{27}$ |
|---|---|---|---|

TLC: Rf 0.45 (ethyl acetate:methanol = 9:1)
NMR: δ 0.87 (t, J = 7.05 Hz, 3H), 1.42 (m, 18H), 2.12 (m, 1H), 2.30 (m, 1H), 2.84 (s, 3H), 2.93 (m, 1H), 3.26 (m, 3H), 3.74 (m, 3H), 5.05 (m, 1H), 7.94 (d, J = 8.06 Hz, 1H), 10.57 (s, 1H)

10(26)　　cyclohexyl　　(tetrahydropyran-4-yl)　　(4R)-4-ethyl-3-methyl

TLC: Rf 0.45 (ethyl acetate:methanol = 9:1)
NMR: δ 0.87 (t, J = 6.87 Hz, 3H), 1.52 (m, 17H), 2.12 (m, 1H), 2.84 (s, 3H), 2.93 (m, 1H), 3.26 (m, 3H), 3.67 (m, 1H), 3.82 (m, 2H), 4.98 (m, 1H), 7.94 (d, J = 8.06 Hz, 1H), 10.56 (s, 1H)

10(27)　　cycloheptyl　　(cyclohexyl)　　(4R)-4-ethyl-3-methyl

TLC: Rf 0.47 (ethyl acetate)
NMR: δ 0.87 (m, 3H), 1.48 (m, 25H), 2.47 (m, 1H), 2.84 (s, 3H), 2.94 (m, 1H), 3.29 (m, 1H), 3.69 (m, 1H), 5.03 (m, 1H), 7.82 (d, J = 7.69 Hz, 1H), 10.53 (s, 1H)

10(28)　　cycloheptyl　　(tetrahydropyran-4-yl)　　3-[(1R)-1-phenylethyl]

TLC: Rf 0.57 (chloroform:methanol = 9:1)
NMR (CDCl$_3$): δ 1.66 (m, 19H), 2.37 (m, 2H), 3.12 (m, 2H), 3.34 (m, 3H), 3.57 (m, 1H), 3.96 (m, 2H), 5.18 (dd, J = 8.97, 6.22 Hz, 1H), 5.70 (m, 1H), 6.43 (d, J = 8.97 Hz, 1H), 7.33 (m, 5H), 8.81 (s, 1H)

10(29)　　cyclohexyl　　(tetrahydropyran-4-yl)　　3-[(1R)-1-phenylethyl]

TLC: Rf 0.55 (chloroform:methanol = 9:1)
NMR (CDCl$_3$): δ 1.54 (m, 17H), 2.17 (m, 1H), 2.42 (m, 1H), 3.11 (m, 2H), 3.34 (m, 3H), 3.57 (m, 1H), 3.94 (m, 2H), 5.19 (dd, J = 9.15, 6.41 Hz, 1H), 5.69 (m, 1H), 6.52 (d, J = 9.15 Hz, 1H), 7.34 (m, 5H), 8.81 (s, 1H)

10(30)　　cyclohexyl　　(tetrahydropyran-4-yl)　　(4R)-3-ethyl-4-methyl

TLC: Rf 0.47 (ethyl acetate)
NMR: δ 1.07 (t, J = 7.14 Hz, 3H), 1.23 (d, J = 6.22 Hz, 3H), 1.51 (m, 14H), 2.13 (m, 1H), 2.29 (m, 1H), 2.80 (dd, J = 10.98, 6.96 Hz, 1H), 3.24 (m, 4H), 3.56 (m, 1H), 3.81 (m, 2H), 3.93 (m, 1H), 5.05 (dd, J = 7.69, 5.86 Hz, 1H), 7.94 (d, J = 8.06 Hz, 1H), 10.57 (s, 1H)

-continued

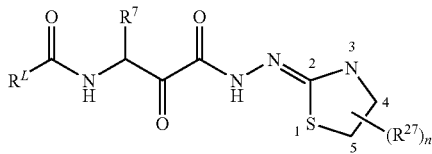

| Example | $R^L$ | $R^7$ | $R^{27}$ |
|---|---|---|---|
| 10(31) | cyclohexyl | tetrahydropyran-4-yl | (4S)-3-ethyl-4-methyl |

TLC: Rf 0.53 (methylene chloride:methanol = 9:1)
NMR (CDCl$_3$): δ 1.54 (m, 20H), 2.15 (m, 1H), 2.38 (m, 1H), 2.86 (dd, J = 10.80, 6.41 Hz, 1H), 3.22 (td, J = 14.28, 6.96 Hz, 1H), 3.35 (m, 3H), 3.79 (td, J = 14.37, 7.14 Hz, 1H), 3.99 (m, 3H), 5.15 (dd, J = 8.97, 6.41 Hz, 1H), 6.54 (d, J = 9.15 Hz, 1H), 8.73 (s, 1H)

| 10(32) | cycloheptyl | tetrahydropyran-4-yl | (4R)-4-benzyl-3-methyl |

TLC: Rf 0.50 (ethyl acetate:methanol = 9:1)
NMR (CDCl$_3$): δ 1.65 (m, 16H), 2.36 (m, 2H), 2.76 (dd, J = 12.45, 9.89 Hz, 1H), 2.97 (dd, J = 10.98, 3.66 Hz, 1H), 3.07 (s, 3H), 3.07 (m, 2H), 3.36 (m, 2H), 3.97 (m, 3H), 5.15 (m, 1H), 6.45 (d, J = 9.52 Hz, 1H), 7.27 (m, 5H), 8.74 (s, 1H)

| 10(33) | cyclohexyl | tetrahydropyran-4-yl | (4R)-4-benzyl-3-methyl |

TLC: Rf 0.39 (ethyl acetate:methanol = 9:1)
NMR (CDCl$_3$): δ 1.53 (m, 14H), 2.16 (m, 1H), 2.39 (m, 1H), 2.76 (dd, J = 13.36, 9.70 Hz, 1H), 2.97 (dd, J = 10.98, 3.66 Hz, 1H), 3.07 (s, 3H), 3.16 (m, 2H), 3.34 (m, 2H), 3.95 (m, 3H), 5.15 (m, 1H), 6.54 (d, J = 7.69 Hz, 1H), 7.27 (m, 5H), 8.74 (s, 1H)

| 10(34) | cycloheptyl | cyclohexyl | (4R)-3-ethyl-4-methyl |

TLC: Rf 0.53 (methylene chloride:methanol = 30:1)
NMR: δ 1.37 (m, 29H), 1.87 (m, 1H), 2.80 (m, 1H), 3.13 (m, 1H), 3.32 (m, 1H), 3.56 (m, 1H), 3.94 (m, 1H), 4.99 (m, 1H), 7.82 (d, J = 8.06 Hz, 1H), 10.52 (m, 1H)

| 10(35) | cycloheptyl | tetrahydropyran-4-yl | (4R)-3-benzyl-4-methyl |

TLC: Rf 0.70 (methylene chloride:methanol = 9:1)
NMR (CDCl$_3$): δ 1.28 (d, J = 6.22 Hz, 3H), 1.67 (m, 16H), 2.31 (m, 1H), 2.40 (m, 1H), 2.87 (dd, J = 10.80, 5.68 Hz, 1H), 3.35 (m, 3H), 3.85 (m, 1H), 3.96 (m, 2H), 4.16 (d, J = 15.38 Hz, 1H), 5.18 (m, 2H), 6.42 (d, J = 9.15 Hz, 1H), 7.32 (m, 5H), 8.79 (s, 1H)

| 10(36) | cyclohexyl | tetrahydropyran-4-yl | (4R)-3-benzyl-4-methyl |

-continued

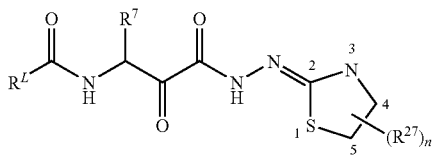

| Example | R^L | R^7 | R^27 |
|---|---|---|---|

TLC: Rf 0.69 (methylene chloride:methanol = 9:1)
NMR (CDCl$_3$): δ 1.55 (m, 17H), 2.16 (m, 1H), 2.40 (m, 1H), 2.87 (dd, J = 10.62, 5.49 Hz, 1H), 3.36 (m, 3H), 3.84 (m, 1H), 3.96 (m, 2H), 4.16 (d, J = 15.38 Hz, 1H), 5.19 (m, 2H), 6.51 (d, J = 9.15 Hz, 1H), 7.32 (m, 5H), 8.79 (s, 1H)

10(37) cycloheptyl cyclohexyl (4R)-4-benzyl-3-methyl

TLC: Rf 0.43 (ethyl acetate)
NMR (CDCl$_3$): δ 1.42 (m, 22H), 2.10 (m, 1H), 2.30 (m, 1H), 2.75 (dd, J = 13.36, 10.07 Hz, 1H), 2.96 (dd, J = 11.17, 3.11 Hz, 1H), 3.07 (m, 3H), 3.14 (m, 2H), 3.97 (m, 1H), 5.03 (m, 1H), 6.39 (d, J = 9.15 Hz, 1H), 7.24 (m, 5H), 8.74 (s, 1H)

10(38) cycloheptyl tetrahydropyran (4R)-3-benzyl-4-ethyl

TLC: Rf 0.72 (methylene chloride:methanol = 9:1)
NMR (CDCl$_3$): δ 0.89 (t, J = 7.51 Hz, 3H), 1.67 (m, 18H), 2.31 (m, 1H), 2.42 (m, 1H), 2.98 (dd, J = 10.80, 5.31 Hz, 1H), 3.33 (m, 3H), 3.66 (m, 1H), 3.96 (m, 2H), 4.17 (d, J = 15.38 Hz, 1H), 5.20 (m, 2H), 6.43 (d, J = 9.15 Hz, 1H), 7.33 (m, 5H), 8.79 (s, 1H)

10(39) cyclohexyl tetrahydropyran (4R)-3-benzyl-4-ethyl

TLC: Rf 0.71 (methylene chloride:methanol = 9:1)
NMR (CDCl$_3$): δ 0.89 (t, J = 7.51 Hz, 3H), 1.55 (m, 16H), 2.16 (m, 1H), 2.40 (m, 1H), 2.98 (dd, J = 10.98, 5.13 Hz, 1H), 3.32 (m, 3H), 3.66 (m, 1H), 3.95 (m, 2H), 4.17 (d, J = 15.38 Hz, 1H), 5.20 (m, 2H), 6.51 (d, J = 9.15 Hz, 1H), 7.31 (m, 5H), 8.79 (s, 1H)

10(40) cycloheptyl cyclohexyl 3-[(1R)-1-phenylethyl]

TLC: Rf 0.50 (chloroform:methanol = 40:1)
NMR (CDCl$_3$): δ 1.43 (m, 25H), 2.12 (m, 1H), 2.30 (m, 1H), 3.09 (m, 2H), 3.28 (m, 1H), 3.57 (m, 1H), 5.07 (dd, J = 8.79, 6.96 Hz, 1H), 5.71 (m, 1H), 6.38 (d, J = 8.79 Hz, 1H), 7.35 (m, 5H), 8.81 (s, 1H)

10(41) cyclohexyl tetrahydropyran 3-[(1S)-1-phenylethyl]

TLC: Rf 0.28 (chloroform:methanol = 40:1)
NMR (CDCl$_3$): δ 1.52 (m, 17H), 2.17 (m, 1H), 2.41 (m, 1H), 3.11 (m, 2H), 3.33 (m, 3H), 3.58 (m, 1H), 3.94 (m, 2H), 5.19 (dd, J = 9.15, 6.41 Hz, 1H), 5.69 (m, 1H), 6.52 (d, J = 9.15 Hz, 1H), 7.30 (m, 5H), 8.81 (s, 1H)

-continued

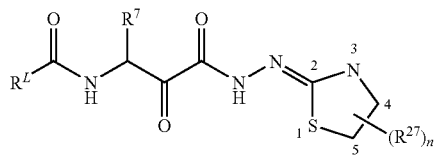

| Example | R$^L$ | R$^7$ | R$^{27}$ |
|---|---|---|---|
| 10(42) | cycloheptyl | tetrahydropyran-4-yl | (4R)-3-methyl-4-phenyl |

TLC: Rf 0.63 (ethyl acetate:methanol = 9:1)
NMR: δ 1.55 (m, 16H), 2.15 (m, 1H), 2.48 (m, 1H), 2.69 (s, 3H), 3.02 (m, 1H), 3.31 (m, 2H), 3.63 (m, 1H), 3.83 (m, 2H), 4.88 (m, 1H), 5.06 (m, 1H), 7.38 (m, 5H), 7.97 (d, J = 7.69 Hz, 1H), 10.73 (s, 1H)

| 10(43) | cyclohexyl | tetrahydropyran-4-yl | (4R)-3-methyl-4-phenyl |

TLC: Rf 0.60 (ethyl acetate:methanol = 9:1)
NMR: δ 1.44 (m, 14H), 2.14 (m, 1H), 2.31 (m, 1H), 2.69 (s, 3H), 3.03 (m, 1H), 3.25 (m, 2H), 3.63 (m, 1H), 3.83 (m, 2H), 4.88 (m, 1H), 5.08 (m, 1H), 7.34 (m, 5H), 7.98 (d, J = 8.06 Hz, 1H), 10.75 (s, 1H)

| 10(44) | cycloheptyl | tetrahydropyran-4-yl | (4R)-3-(2-methoxyethyl)-4-methyl |

TLC: Rf 0.43 (ethyl acetate:methanol = 9:1)
NMR (CDCl$_3$): δ 1.33 (d, J = 6.22 Hz, 3H), 1.67 (m, 16H), 2.35 (m, 2H), 2.86 (dd, J = 10.71, 5.77 Hz, 1H), 3.34 (m, 4H), 3.34 (s, 3H), 3.54 (m, 1H), 3.66 (m, 1H), 3.92 (m, 3H), 4.14 (m, 1H), 5.16 (dd, J = 8.88, 6.32 Hz, 1H), 6.43 (d, J = 8.60 Hz, 1H), 8.73 (s, 1H)

| 10(45) | cyclohexyl | tetrahydropyran-4-yl | (4R)-3-(2-methoxyethyl)-4-methyl |

TLC: Rf 0.43 (ethyl acetate:methanol = 9:1)
NMR (CDCl$_3$): δ 1.33 (d, J = 6.22 Hz, 3H), 1.33 (m, J = 6.22 Hz, 14H), 2.15 (m, 1H), 2.38 (m, 1H), 2.86 (dd, J = 10.71, 5.77 Hz, 1H), 3.34 (m, 4H), 3.34 (s, 3H), 3.54 (m, 1H), 3.66 (m, 1H), 3.92 (m, 3H), 4.15 (m, 1H), 5.16 (dd, J = 8.97, 6.22 Hz, 1H), 6.51 (d, J = 8.97 Hz, 1H), 8.73 (s, 1H)

| 10(46) | cycloheptyl | tetrahydropyran-4-yl | (4R)-4-ethyl-3-(2-methoxyethyl) |

TLC: Rf 0.64 (methylene chloride:methanol = 9:1)
NMR (CDCl$_3$): δ 0.95 (t, J = 7.32 Hz, 3H), 1.66 (m, 18H), 2.36 (m, 2H), 2.97 (dd, J = 11.23, 5.86 Hz, 1H), 3.36 (m, 7H), 3.53 (m, 1H), 3.67 (m, 1H), 3.97 (m, 4H), 5.16 (dd, J = 8.79, 6.35 Hz, 1H), 6.43 (d, J = 8.79 Hz, 1H), 8.72 (s, 1H)

| 10(47) | cyclohexyl | tetrahydropyran-4-yl | (4R)-4-ethyl-3-(2-methoxyethyl) |

-continued

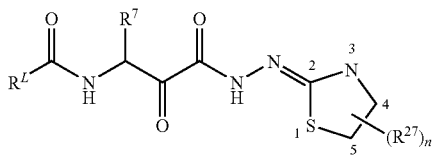

| Example | R$^L$ | R$^7$ | R$^{27}$ |
|---|---|---|---|

TLC: Rf 0.58 (methylene chloride:methanol = 9:1)
NMR (CDCl$_3$): δ 0.95 (t, J = 7.51 Hz, 3H), 1.56 (m, 16H), 2.15 (m, 1H), 2.39 (m, 1H), 2.97 (dd, J = 10.80, 5.31 Hz, 1H), 3.34 (m, 7H), 3.52 (m, 1H), 3.67 (m, 1H), 3.95 (m, 4H), 5.16 (dd, J = 9.15, 6.22 Hz, 1H), 6.51 (d, J = 9.15 Hz, 1H), 8.72 (s, 1H)

10(48)   cycloheptyl   (tetrahydropyran-4-yl)   (5R)-3-benzyl-5-methyl

TLC: Rf 0.62 (methylene chloride:methanol = 9:1)
NMR (CDCl$_3$): δ 1.69 (m, 19H), 2.31 (m, 1H), 2.41 (m, 1H), 3.15 (dd, J = 9.89, 6.22 Hz, 1H), 3.36 (m, 2H), 3.58 (dd, J = 9.89, 6.22 Hz, 1H), 3.76 (m, 1H), 3.95 (m, 2H), 4.61 (d, J = 14.65 Hz, 1H), 4.68 (m, 1H), 5.18 (dd, J = 9.15, 6.22 Hz, 1H), 6.42 (d, J = 9.15 Hz, 1H), 7.32 (m, 5H), 8.76 (s, 1H)

10(49)   cyclohexyl   (tetrahydropyran-4-yl)   (5R)-3-benzyl-5-methyl

TLC: Rf 0.60 (methylene chloride:methanol = 9:1)
NMR (CDCl$_3$): δ 1.55 (m, 17H), 2.16 (m, 1H), 2.40 (m, 1H), 3.15 (dd, J = 9.89, 6.41 Hz, 1H), 3.35 (m, 2H), 3.58 (dd, J = 9.79, 6.50 Hz, 1H), 3.77 (m, 1H), 3.96 (m, 2H), 4.61 (d, J = 14.83 Hz, 1H), 4.69 (m, 1H), 5.18 (dd, J = 9.15, 6.22 Hz, 1H), 6.51 (d, J = 9.15 Hz, 1H), 7.36 (m, 5H), 8.76 (s, 1H)

10(50)   cycloheptyl   (tetrahydropyran-4-yl)   (4R)-3-(4-fluorobenzyl)-4-methyl TLC: Rf 0.62 (methylene chloride:methanol = 9:1)
NMR (CDCl$_3$): δ 1.28 (d, J = 6.22 Hz, 3H), 1.67 (m, 16H), 2.31 (m, 1H), 2.41 (m, 1H), 2.88 (dd, J = 10.98, 5.86 Hz, 1H), 3.37 (m, 3H), 3.83 (m, 1H), 3.96 (m, 2H), 4.16 (d, J = 15.01 Hz, 1H), 5.11 (d, J = 15.38 Hz, 1H), 5.19 (dd, J = 9.15, 6.22 Hz, 1H), 6.39 (d, J = 8.79 Hz, 1H), 7.02 (m, 2H), 7.31 (m, 2H), 8.79 (s, 1H)

10(51)   cyclohexyl   (tetrahydropyran-4-yl)   (4R)-3-(4-fluorobenzyl)-4-methyl

TLC: Rf 0.56 (methylene chloride:methanol = 9:1)
NMR (CDCl$_3$): δ 1.55 (m, 17H), 2.16 (m, 1H), 2.40 (m, 1H), 2.88 (dd, J = 10.80, 5.86 Hz, 1H), 3.35 (m, 3H), 3.83 (m, 1H), 3.96 (m, 2H), 4.16 (d, J = 15.38 Hz, 1H), 5.11 (d, J = 15.38 Hz, 1H), 5.19 (dd, J = 8.97, 6.22 Hz, 1H), 6.47 (d, J = 8.97 Hz, 1H), 7.02 (m, 2H), 7.32 (m, 2H), 8.79 (s, 1H)

10(52)   cycloheptyl   (tetrahydropyran-4-yl)   (4S)-3-(2-methoxyethyl)-4-methyl)

-continued

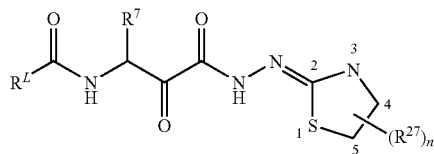

| Example | R$^L$ | R$^7$ | R$^{27}$ |
|---|---|---|---|

TLC: Rf 0.43 (ethyl acetate:methanol = 9:1)
NMR (CDCl$_3$): δ 1.32 (d, J = 6.22 Hz, 3H), 1.67 (m, 16H), 2.36 (m, 2H), 2.86 (dd, J = 10.62, 5.86 Hz, 1H), 3.34 (s, 3H), 3.34 (m, 4H), 3.53 (m, 1H), 3.66 (m, 1H), 3.92 (m, 3H), 4.16 (m, 1H), 5.16 (dd, J = 9.52, 6.13 Hz, 1H), 6.43 (d, J = 9.52 Hz, 1H), 8.73 (s, 1H)

10(53) cyclohexyl [tetrahydropyran-4-yl] (4S)-3-(2-methoxyethyl)-4-methyl)

TLC: Rf 0.43 (ethyl acetate:methanol = 9:1)
NMR (CDCl$_3$): δ 1.32 (d, J = 6.22 Hz, 3H), 1.32 (m, 14H), 2.15 (m, 1H), 2.39 (m, 1H), 2.86 (dd, J = 10.62, 5.86 Hz, 1H), 3.34 (s, 3H), 3.34 (m, 4H), 3.53 (m, 1H), 3.66 (m, 1H), 3.93 (m, 3H), 4.17 (m, 1H), 5.16 (dd, J = 9.15, 6.22 Hz, 1H), 6.51 (d, J = 9.15 Hz, 1H), 8.73 (s, 1H)

10(54) cycloheptyl [tetrahydropyran-4-yl] (4S)-3-benzyl-4-methyl

TLC: Rf 0.70 (methylene chloride:methanol = 9:1)
NMR (CDCl$_3$): δ 1.28 (d, J = 6.22 Hz, 3H), 1.65 (m, 16H), 2.31 (m, 1H), 2.40 (m, 1H), 2.87 (dd, J = 10.80, 5.68 Hz, 1H), 3.36 (m, 3H), 3.84 (m, 1H), 3.95 (m, 2H), 4.16 (d, J = 15.38 Hz, 1H), 5.19 (m, 2H), 6.42 (d, J = 9.15 Hz, 1H), 7.30 (m, 5H), 8.79 (s, 1H)

10(55) cyclohexyl [tetrahydropyran-4-yl] (4S)-3-benzyl-4-methyl

TLC: Rf 0.68 (methylene chloride:methanol = 9:1)
NMR (CDCl$_3$): δ 1.56 (m, 17H), 2.16 (m, 1H), 2.40 (m, 1H), 2.87 (dd, J = 10.62, 5.49 Hz, 1H), 3.34 (m, 3H), 3.91 (m, 3H), 4.16 (d, J = 15.74 Hz, 1H), 5.16 (m, 2H), 6.51 (d, J = 9.15 Hz, 1H), 7.30 (m, 5H), 8.80 (s, 1H)

10(56) cycloheptyl [tetrahydropyran-4-yl] (4S)-3-(4-fluorobenzyl)-4-methyl

TLC: Rf 0.62 (methylene chloride:methanol = 9:1)
NMR: (CDCl$_3$): δ 1.28 (d, J = 6.22 Hz, 3H), 1.66 (m, 16H), 2.31 (m, 1H), 2.40 (m, 1H), 2.88 (dd, J = 10.98, 5.86 Hz, 1H), 3.35 (m, 3H), 3.83 (m, 1H), 3.96 (m, 2H), 4.16 (d, J = 15.38 Hz, 1H), 5.11 (d, J = 15.38 Hz, 1H), 5.19 (dd, J = 9.15, 6.22 Hz, 1H), 6.39 (d, J = 9.15 Hz, 1H), 7.04 (m, 2H), 7.32 (m, 2H), 8.78 (s, 1H)

10(57) cyclohexyl [tetrahydropyran-4-yl] (4S)-3-(4-fluorobenzyl)-4-methyl

TLC: Rf 0.58 (methylene chloride:methanol = 9:1)
NMR (CDCl$_3$): δ 1.55 (m, 17H), 2.16 (m, 1H), 2.41 (m, 1H), 2.88 (dd, J = 10.62, 5.86 Hz, 1H), 3.35 (m, 3H), 3.84 (m, 1H), 3.96 (m, 2H), 4.16 (d, J = 15.38 Hz, 1H), 5.11 (d, J = 15.38 Hz, 1H), 5.19 (dd, J = 8.79, -continued

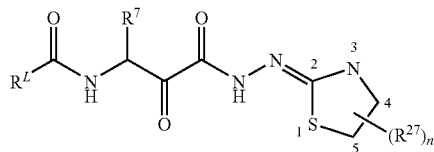

| Example | R^L | R^7 | R^27 |
|---|---|---|---|
| | | 6.22 Hz, 1H), 6.47 (d, J = 8.79 Hz, 1H), 7.03 (m, 2H), 7.32 (m, 2H), 8.79 (s, 1H) | |
| 10(58) | cycloheptyl | (tetrahydropyran-4-yl) | (4R)-4-ethyl-3-(4-fluorobenzyl) |

TLC: Rf 0.63 (methylene chloride:methanol = 10:1)
NMR (CDCl$_3$): δ 0.90 (t, J = 7.51 Hz, 3H), 1.65 (m, 18H), 2.30 (m, 1H), 2.43 (m, 1H), 2.98 (dd, J = 10.98, 5.68 Hz, 1H), 3.28 (dd, J = 10.98, 6.96 Hz, 1H), 3.37 (m, 2H), 3.64 (m, 1H), 3.95 (m, 2H), 4.17 (d, J = 15.38 Hz, 1H), 5.11 (d, J = 15.38 Hz, 1H), 5.18 (dd, J = 8.97, 6.04 Hz, 1H), 6.39 (d, J = 8.97 Hz, 1H), 7.02 (m, 2H), 7.30 (m, 2H), 8.77 (s, 1H)

| 10(59) | cycloheptyl | (tetrahydropyran-4-yl) | (5R)-3-ethyl-5-methyl |

TLC: Rf 0.14 (chloroform:methanol = 40:1)
NMR (CDCl$_3$): δ 1.20 (t, J = 7.14 Hz, 3H), 1.64 (m, 19H), 2.36 (m, 2H), 3.34 (m, 3H), 3.53 (m, 2H), 3.76 (m, 2H), 3.95 (m, 2H), 5.14 (m, 1H), 6.45 (d, J = 8.79 Hz, 1H), 8.69 (s, 1H)

| 10(60) | cyclohexyl | (tetrahydropyran-4-yl) | (5R)-3-ethyl-5-methyl |

TLC: Rf 0.17 (chloroform:methanol = 40:1)
NMR (CDCl$_3$): δ 1.48 (m, 20H), 2.14 (m, 1H), 2.39 (m, 1H), 3.31 (m, 3H), 3.53 (m, 2H), 3.75 (m, 2H), 3.96 (m, 2H), 5.15 (m, 1H), 6.55 (d, J = 9.15 Hz, 1H), 8.70 (s, 1H)

| 10(61) | cycloheptyl | (tetrahydropyran-4-yl) | (4S)-3-ethyl-4-methyl |

TLC: Rf 0.57 (methylene chloride:methanol = 9:1)
NMR (CDCl$_3$): δ 1.19 (t, J = 7.14 Hz, 3H), 1.33 (d, J = 6.22 Hz, 3H), 1.70 (m, 16H), 2.35 (m, 2H), 2.85 (m, 1H), 3.28 (m, 4H), 3.78 (m, 1H), 3.99 (m, 3H), 5.15 (m, 1H), 6.45 (d, J = 9.70 Hz, 1H), 8.73 (s, 1H)

| 10(62) | cycloheptyl | (tetrahydropyran-4-yl) | (4R)-3,4-dimethyl |

TLC: Rf 0.35 (methylene chloride:methanol = 9:1)
NMR (CDCl$_3$): δ 1.33 (d, J = 6.22 Hz, 3H), 1.68 (m, 16H), 2.36 (m, 2H), 2.88 (dd, J = 10.80, 6.04 Hz, 1H), 2.98 (m, 3H), 3.35 (m, 3H), 3.89 (m, 3H), 5.15 (dd, J = 9.15, 6.22 Hz, 1H), 6.46 (d, J = 9.15 Hz, 1H), 8.73 (s, 1H).

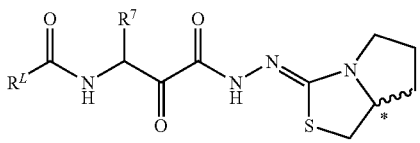

| Example | R^L | R^7 | Configuration at * |
|---|---|---|---|
| 10(63) | cycloheptyl | (tetrahydropyran-4-yl, dashed) | S |

TLC: Rf 0.53 (methylene chloride:methanol = 9:1);
H-NMR (CDCl$_3$): δ 1.89 (m, 22H), 3.08 (m, 1H), 3.36 (m, 4H), 3.57 (dt, J = 11.19, 7.86 Hz, 1H), 3.94 (m, 2H), 4.31 (m, 1H), 5.11 (dd, J = 8.93, 6.46 Hz, 1H), 6.48 (d, J = 9.34 Hz, 1H), 8.76 (s, 1H)

| 10(64) | cycloheptyl | (tetrahydropyran-4-yl, wedge) | R |

TLC: Rf 0.53 (methylene chloride:methanol = 9:1);
H-NMR (CDCl$_3$): δ 1.90 (m, 22H), 3.08 (m, 1H), 3.36 (m, 4H), 3.56 (dt, J = 11.26, 7.83 Hz, 1H), 3.95 (m, 2H), 4.31 (m, 1H), 5.11 (dd, J = 9.07, 6.59 Hz, 1H), 6.48 (d, J = 9.34 Hz, 1H), 8.77 (s, 1H)

| 10(65) | cyclohexyl | (tetrahydropyran-4-yl) | R |

TLC: Rf 0.65 (methylene chloride:methanol = 9:1);
H-NMR (CDCl$_3$): δ 1.56 (m, 15H), 2.24 (m, 5H), 3.08 (t, J = 10.30 Hz, 1H), 3.36 (m, 4H), 3.56 (dt, J = 11.26, 7.83 Hz, 1H), 3.95 (m, 2H), 4.31 (m, 1H), 5.11 (dd, J = 9.07, 6.59 Hz, 1H), 6.57 (d, J = 8.79 Hz, 1H), 8.77 (s, 1H)

| 10(66) | cycloheptyl | cyclohexyl | R |

TLC: Rf 0.70 (methylene chloride:methanol = 9:1);
H-NMR (CDCl$_3$): δ 1.42 (m, 23H), 2.18 (m, 5H), 3.07 (m, 1H), 3.37 (m, 2H), 3.56 (m, 1H), 4.31 (m, 1H), 5.02 (m, 1H), 6.42 (m, 1H), 8.77 (s, 1H)

Formulation Example 1

The following components were admixed in a conventional method and punched out to give 100 tablets each containing 50 mg of the active ingredient.

| | |
|---|---|
| N'-(3-methyl-1,3-thiazolidin-2-ylidene)-[(3S)-3-cyclohexylcarbonylamino-2-oxo-5-methylhexanohydrazide] hydrochloride | 5.0 g |
| carboxymethylcellulose calcium (disintegrating agent) | 0.2 g |
| magnesium stearate (lubricant) | 0.1 g |
| microcrystalline cellulose | 4.7 g |

Formulation Example 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| N'-(3-methyl-1,3-thiazolidin-2-ylidene)-[(3S)-3-cyclohexylcarbonylamino-2-oxo-5-methylhexanohydrazide] hydrochloride | 2.0 g |
| mannitol | 20 g |
| distilled water | 500 ml |

The invention claimed is:

1. A compound of formula (I)

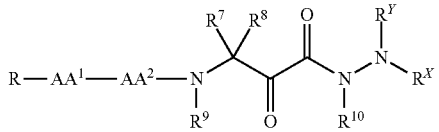

[wherein R is (1) hydrogen, (2) CycA, (3) $C_{1-8}$ alkyl optionally substituted with 1 to 5 groups selected from halogen, CycA, nitro, trifluoromethyl and cyano,

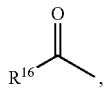 (4)

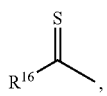 (5)

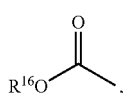 (6)

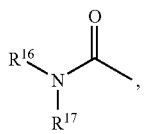 (7)

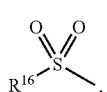 (8)

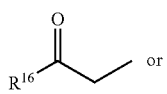 or (9)

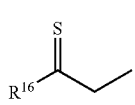 (10)

(wherein CycA is a $C_{3-15}$ mono-, bi- or tri-cyclic carboring or a 3-15 membered mono-, bi- or tri-cyclic heteroring comprising 1-4 of nitrogen, 1-2 of oxygen and/or 1-2 of sulfur;

$R^{16}$ is (1) $C_{1-8}$ alkyl, (2) $C_{2-8}$ alkenyl, (3) $C_{2-8}$ alkynyl, (4) CycA or (5) $C_{1-8}$ alkyl, $C_{2-8}$ alkenyl or $C_{2-8}$ alkynyl substituted with 1 to 5 groups selected from halogen, nitro, trifluoromethyl, cyano, CycA, —$NR^{18}R^{19}$, —$OR^{18}$, —$SR^{18}$, —NHC(O)-CycA and —NHC(O)—($C_{1-8}$ alkyl);

$R^{17}$, $R^{18}$ and $R^{19}$ are each independently, hydrogen, $C_{1-4}$ alkyl, CycA, $C_{1-4}$ alkyl substituted with CycA), $AA^1$ is (1) a bond, or

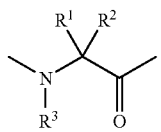 (2)

(wherein $R^1$ and $R^2$ are each independently, (i) hydrogen, (ii) $C_{1-8}$ alkyl, (iii) CycA or (iv) $C_{1-8}$ alkyl substituted with 1 to 5 groups selected from the following (a) to (j):
(a) —$NR^{21}R^{22}$, (b) —$OR^{23}$, (c) —$SR^{23}$, (d) —$COR^{24}$, (e) —$NR^{25}C(O)NR^{21}R^{22}$, (f) guanidino, (g) amidino, (h) CycA, and (j) —$NR^{25}SO_2R^{21}$; or $R^1$ and $R^2$ are taken together to form $C_{2-8}$ alkylene (wherein one carbon of the alkylene chain may be replaced by oxygen, sulfur or —$NR^{20}$— and the alkylene may be substituted with —$NR^{21}R^{22}$, —$OR^{23}$ or oxo), (wherein $R^{20}$ is hydrogen, $C_{1-4}$ alkyl, —C(O)O—($C_{1-4}$ alkyl), CycA or $C_{1-4}$ alkyl substituted with CycA; $R^{21}$, $R^{22}$, $R^{23}$ and $R^{25}$ are each independently, hydrogen, $C_{1-4}$ alkyl, CycA or $C_{1-4}$ alkyl substituted with CycA; $R^{24}$ is $C_{1-4}$ alkyl, CycA, —$NR^{21}R^{22}$, —$OR^{23}$, —$SR^{23}$ or $C_{1-4}$ alkyl substituted with CycA), $R^3$ is hydrogen, $C_{1-8}$ alkyl, CycA or $C_{1-8}$ alkyl substituted with CycA or $R^3$ may be taken together with $R^1$ to form $C_{2-6}$ alkylene (wherein one carbon of the alkylene chain may be replaced by oxygen, sulfur or —$NR^{20}$— and the alkylene may be substituted with —$NR^{21}R^{22}$, —$OR^{23}$, —$SR^{23}$ or oxo)) or R and $AA^1$ may be taken together to form

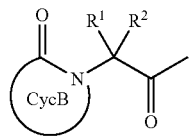

(wherein CycB is a 5-12 membered mono- or bi-cyclic heteroring and the other symbols have the same meaning as hereinbefore), $AA^2$ is (1) a bond,

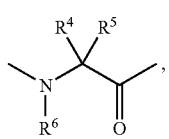 (2)

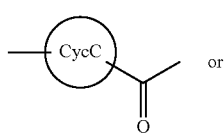 (3)

or

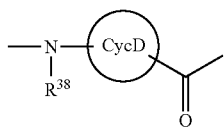 (4)

(wherein $R^4$ and $R^5$ are each independently, (i) hydrogen, (ii) $C_{1-8}$ alkyl, (iii) CycA or (iv) $C_{1-8}$ alkyl substituted with 1 to 5 groups selected from the following (a) to (h) and (j):
(a) —$NR^{31}R^{32}$, (b) —$OR^{33}$, (c) —$SR^{33}$, (d) —$COR^{34}$, (e) —$NR^{35}C(O)NR^{31}R^{32}$, (f) guanidino, (g) amidino, (h) CycA, and (j) —$NR^{35}SO_2R^{31}$; or $R^4$ and $R^5$ may be taken together to form $C_{2-8}$ alkylene (wherein one carbon of the alkylene chain may be replaced by oxygen, sulfur or —$NR^{30}$— and the alkylene may be substituted with —$NR^{31}R^{32}$, —$OR^{33}$, —$SR^{33}$ or oxo), (wherein $R^{30}$ is hydrogen, $C_{1-4}$ alkyl, —C(O)O—($C_{1-4}$ alkyl), CycA or $C_{1-4}$ alkyl substituted with CycA; $R^{31}$, $R^{32}$, $R^{33}$ and $R^{35}$ are each independently, hydrogen, $C_{1-4}$ alkyl, CycA or $C_{1-4}$ alkyl substituted with CycA; $R^{34}$ is $C_{1-4}$ alkyl, CycA, —$NR^{31}R^{32}$, —$OR^{33}$, —$SR^{33}$ or $C_{1-4}$ alkyl substituted with CycA), $R^6$ is hydrogen, $C_{1-8}$ alkyl, CycA or $C_{1-8}$ alkyl substituted with CycA or $R^6$ may be taken together with $R^4$ or R to form $C_{2-6}$ alkylene (wherein one carbon of the alkylene chain may be replaced by oxygen, sulfur or —$NR^{30}$— and the alkylene may be substituted with $NR^{31}R^{32}$, $OR^{33}$, $SR^{33}$ or oxo), $R^{38}$ is hydrogen, $C_{1-4}$ alkyl, CycA or $C_{1-4}$ alkyl substituted with CycA or when $AA^1$ is a bond, $R^{38}$ may be taken together with R to form $C_{2-6}$ alkylene (wherein one carbon of the alkylene chain may be replaced by oxygen, sulfur or —$NR^{37}$— (wherein $R^{37}$ is hydrogen or $C_{1-4}$ alkyl)), CycC is a 3-17 membered mono- or bi-cyclic heteroring,
CycD is a $C_{3-14}$ mono- or bi-cyclic carboring or a 3-14 membered mono- or bi-cyclic heteroring) or
$AA^2$ may be taken together with $AA^1$ to form

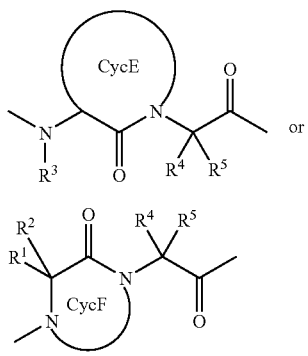

(wherein CycE is a 4-18 membered mono- or bi-cyclic heteroring, CycF is a 5-8 membered monocyclic heteroring, and the other symbols have the same meaning as hereinbefore), $R^7$ and $R^8$ are each independently (1) hydrogen, (2) $C_{1-8}$ alkyl, (3) CycA or (4) $C_{1-8}$ alkyl substituted with 1 to 5 groups selected from the following (i)~(x);
(i) —$NR^{41}R^{42}$, (ii) —$OR^{43}$, (iii) —$SR^{43}$, (iv) —$COR^{44}$, (v) —$NR^{45}C(O)NR^{41}R^{42}$, (vi) guanidino, (vii) amidino, (viii) CycA, (ix) —$NR^{45}SO_2R^{41}$, and (x) —P(O)($OR^{46}$)($OR^{47}$), or $R^7$ and $R^8$ may be taken together to form $C_{2-8}$ alkylene (wherein one carbon of the alkylene chain may be replaced by oxygen, sulfur or —$NR^{40}$— and the alkylene may be substituted with —$NR^{41}R^{42}$, —$OR^{43}$, —$SR^{43}$ or oxo), $R^{40}$ is hydrogen, $C_{1-4}$ alkyl, —C(O)O—($C_{1-4}$ alkyl), CycA or $C_{1-4}$ alkyl substituted with CycA, $R^{41}$, $R^{42}$, $R^{43}$ and $R^{45}$ are each independently hydrogen, $C_{1-4}$ alkyl, CycA or $C_{1-4}$ alkyl substituted with CycA, $R^{44}$ is $C_{1-4}$ alkyl, CycA, —$NR^{41}R^{42}$, —$OR^{43}$, —$SR^{43}$ or $C_{1-4}$ alkyl substituted with CycA, $R^{46}$ and $R^{47}$ are each independently, hydrogen or $C_{1-8}$ alkyl, $R^9$ is hydrogen, $C_{1-8}$ alkyl, CycA or $C_{1-8}$ alkyl substituted with CycA or $R^9$ may be taken together with $R^7$ or R to form $C_{2-6}$ alkylene (wherein one carbon of the alkylene chain may be replaced by oxygen, sulfur or —$NR^{40}$— and the alkylene may be substituted with —$NR^{41}R^{42}$, —$OR^{43}$, —$SR^{43}$ or oxo), (wherein all symbols have the same meaning as hereinbefore),

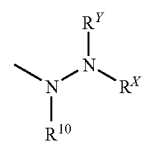

is a group selected from the following (1), (2) or (3);

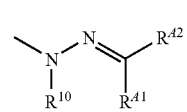
(1)

[wherein $R^{41}$ and $R^{42}$ are each independently, (i) hydrogen, (ii) $C_{1-8}$ alkyl, (iii) $C_{2-8}$ alkenyl, (iv) —$NR^{Z1}R^{Z2}$, (v) —$OR^{Z3}$, (vi) —$SR^{Z3}$, (vii) —$COR^{Z4}$, (viii) CycP or (ix) $C_{1-8}$ alkyl or $C_{2-8}$ alkenyl substituted with 1 to 5 groups selected from CycP, —$NR^{Z1}R^{Z2}$, —$OR^{Z3}$, —$SR^{Z3}$, —$COR^{Z4}$, —$SO_2R^{Z4}$, —$COOR^{Z3}$, —$CONR^{Z1}R^{Z2}$, —$SO_2NR^{Z1}R^{Z2}$ and —P(O)($OR^{Z5}$)($OR^{Z6}$)

(wherein $R^{Z1}$ and $R^{Z2}$ are each independently, hydrogen, $C_{1-8}$ alkyl, $C_{2-8}$ alkenyl, CycP, $C_{2-8}$ acyl, or $C_{1-8}$ alkyl substituted with CycP, $C_{2-8}$ acyl, $C_{1-8}$ alkoxy, $C_{1-8}$ alkylthio, $C_{1-8}$ monoalkylamino or di($C_{1-8}$ alkyl)amino;

$R^{Z3}$ is hydrogen, $C_{1-8}$ alkyl, $C_{2-8}$ alkenyl, CycP or $C_{1-8}$ alkyl substituted with 1 to 5 groups selected from CycP, $C_{1-8}$ alkoxy, $C_{1-8}$ alkylthio, amino, $C_{1-8}$ monoalkylamino, di($C_{1-8}$ alkyl)amino and $C_{2-8}$ acyl;

$R^{Z4}$ is $C_{1-8}$ alkyl, CycP or $C_{1-8}$ alkyl substituted with 1 to 5 groups selected from CycP, $C_{1-8}$ alkoxy, $C_{1-8}$ alkylthio, mono($C_{1-8}$ alkyl)amino, di($C_{1-8}$ alkyl)amino or $C_{2-8}$ acyl;

$R^{Z5}$ and $R^{Z6}$ are each independently, hydrogen or $C_{1-8}$ alkyl,

CycP is a $C_{4-10}$ carboring or 5-10 membered heteroring comprising 1-4 of nitrogen, 1-2 of oxygen and/or 1-2 of sulfur and $R^{10}$ is a hydrogen atom or $C_{1-4}$ alkyl) or $R^{41}$ and $R^{42}$ may be taken together with the adjacent carbon to represent CycH

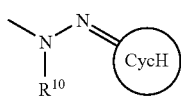

(wherein CycH is a $C_{4-10}$ mono- or bi-cyclic carboring or 4-10 membered mono- or bi-cyclic heteroring and $R^{10}$ has the same meaning as hereinbefore) or $R^{A1}$ and $R^{10}$ may be taken together with the adjacent carbon and nitrogen to represent

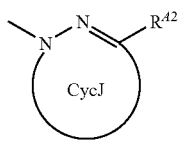

(wherein CycJ is a 5-10 membered mono- or bi-cyclic heteroring and $R^{A2}$ has the same meaning as hereinbefore)], (2)

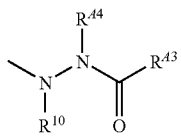

[wherein $R^{A3}$ is (i) $C_{1-8}$ alkyl, (ii) $C_{2-8}$ alkenyl, (iii) —$NR^{Z1}R^{Z2}$, (ix) —$OR^{Z3}$, (v) —$SR^{Z3}$, (vi) —$COR^{Z4}$, (vii) CycP or (viii) $C_{1-8}$ alkyl or $C_{2-8}$ alkenyl substituted with 1 to 5 groups selected from —$NR^{Z1}R^{Z2}$, —$OR^{Z3}$, —$SR^{Z3}$, —$COR^{Z4}$, —$SO_2R^{Z4}$, CycP and —$P(O)(OR^{Z5})(OR^{Z6})$ (wherein all symbols have the same meaning as hereinbefore), $R^{A4}$ is (i) hydrogen, (ii) $C_{1-8}$ alkyl, (iii) $C_{2-8}$ alkenyl, (iv) —$COR^{Z4}$, (v) CycP or (vi) $C_{1-8}$ alkyl or $C_{2-8}$ alkenyl substituted with 1 to 5 groups selected from CycP, —$NR^{Z1}R^{Z2}$, —$OR^{Z3}$, —$SR^{Z3}$, —$COR^{Z4}$, —$SO_2R^{Z4}$, —$COOR^{Z3}$, —$CONR^{Z1}R^{Z2}$, —$SO_2NR^{Z1}R^{Z2}$ and —$P(O)(OR^{Z5})(OR^{Z6})$ (wherein all symbols have the same meaning as hereinbefore), $R^{10}$ has the same meaning as hereinbefore, or $R^{A3}$ and $R^{A4}$ may be taken together with the adjacent carbon and nitrogen to represent

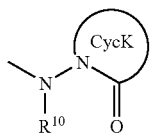

(wherein CycK is a 5-10 membered mono- or bi-cyclic heteroring and $R^{10}$ has the same meaning as hereinbefore), $R^{A3}$ and $R^{10}$ may be taken together with the adjacent carbon and nitrogens to represent

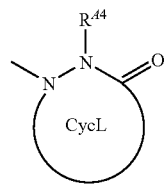

(wherein CycL is a 5-10 membered mono- or bi-cyclic heteroring and $R^{A4}$ has the same meaning as hereinbefore)), (3)

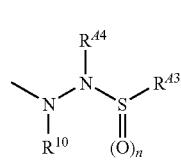

[wherein n is an integer of 1 or 2, and the other symbols have the same meaning as hereinbefore, and $R^{A3}$ and $R^{A4}$ may be taken together with the adjacent nitrogen and sulfur to represent

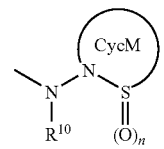

(wherein CycM is a 5-10 membered mono- or bi-cyclic heteroring and the other symbols have the same meaning as hereinbefore) or $R^{A3}$ and $R^{10}$ may be taken together with the nitrogens and sulfur to represent

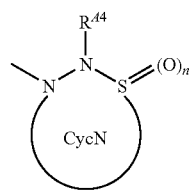

(wherein CycN is a 5-10 membered mono- or bi-cyclic heteroring and the other symbols have the same meaning as hereinbefore)], CycA's, CycB, CycC, CycD, CycE, CycF, CycH, CycJ, CycK, CycL, CycM, CycN and CycP may be each independently substituted with 1-5 of $R^{27}$, $R^{27}$ is (1) $C_{1-8}$ alkyl, (2) halogen, (3) —$NR^{11}R^{12}$, (4) —$OR^{13}$, (5) —$SR^{13}$, (6) CycG, (7) nitro, (8) cyano, (9) oxo, (10) —$COR^{14}$, (11) —$SO_2R^{14}$, (12) —$P(O)(OR^{15})(OR^{16})$, (13) guanidino, (14) amidino or (15) $C_{1-8}$ alkyl substituted with 1 to 5 groups selected from the following (i)-(xii):

(i) halogen, (ii) —$NR^{11}R^{12}$, (iii) —$OR^{13}$, (iv) —$SR^{13}$, (v) CycG, (vi) nitro, (vii) cyano, (viii) —$COR^{14}$, (ix) —$SO_2R^{14}$, (x) —$P(O)(OR^{15})(OR^{16})$, (xi) guanidino, and (xii) amidino (wherein $R^{11}$ and $R^{12}$ are each independently, hydrogen, $C_{1-4}$ alkyl, $C_{1-4}$ alkoxy, —C(O)O—($C_{1-4}$ alkyl), CycG or $C_{1-4}$ alkyl substituted with CycG, $R^{13}$ is hydrogen, $C_{1-4}$ alkyl, trifluoromethyl, CycG or $C_{1-4}$ alkyl substituted with CycG, CycG's are each independently, a $C_{4-10}$ mono- or bi-cyclic carboring or a 5-10 membered mono- or bi-cyclic heteroring comprising 1-4 of nitrogen, 1-2 of oxygen and/or 1-2 of sulfur, $R^{14}$ is $C_{1-8}$ alkyl, CycG, —$NR^{11}R^{12}$, —$OR^{13}$, —$SR^{13}$ or $C_{1-8}$ alkyl substituted with CycG, —$NR^{11}R^{12}$, —$OR^{13}$ or —$SR^{13}$, $R^{15}$'s are each independently, hydrogen or $C_{1-8}$ alkyl), when a saturated carbon atom exists in CycH, CycJ, CycK, CycL, CycM or CycN, the saturated carbon atom may form a spiro bond with CycQ (wherein CycQ is a C3-10 saturated or partially unsaturated mono-cyclic carboring or a 5-8 membered saturated or partially unsaturated monocyclic heteroring comprising 1 of —$NR^Q$— (wherein $R^Q$ is $C_{1-8}$ alkyl, $C_{2-8}$ acyl, —$SO_2$—($C_{1-8}$ alkyl), benzoyl, benzenesulfonyl, or toluenesulfonyl), 1 of oxygen and/or 1 of sulfur which may be oxidized)] or a pharmaceutically acceptable salt thereof.

2. The compound according to claim 1, wherein the compound of formula (I) is the compound of formula (I-i)

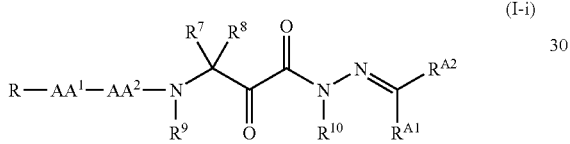

(I-i)

(wherein all symbols have the same meaning as claim 1) or a pharmaceutically acceptable salt thereof.

3. The compound according to claim 1, wherein the compound of formula (I) is the compound of formula (I-ii)

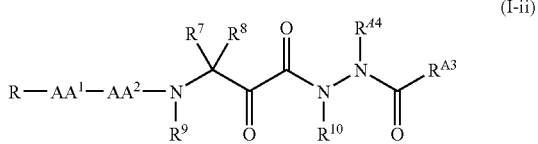

(I-ii)

(wherein all symbols have the same meaning as claim 1) or a pharmaceutically acceptable salt thereof.

4. The compound according to claim 1, wherein the compound of formula (I) is the compound of formula (I-iii)

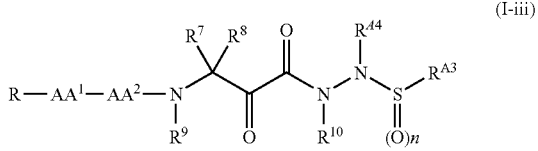

(I-iii)

(wherein all symbols have the same meaning as claim 1) or a pharmaceutically acceptable salt thereof.

5. A pharmaceutical composition comprising the compound of formula (I) or a pharmaceutically acceptable salt thereof which is described in claim 1, and a pharmaceutically acceptable carrier.

6. A medicinal formulation comprising the compound of formula (I) or a pharmaceutically acceptable salt thereof described in claim 1, combined with at least one member selected from a bisphosphonate, a steroidal agent, menatetrenone, alfacalcidol, falecalcitriol, calcitriol, 1α,25-dihydroxycholecalciferol, dihydrotachysterol, ST-630, KDR, ED-71, rocaltrol, a caspase-1 inhibitor, a PTHrP derivative, a PG ligand, a metalloprotease inhibitor, a farnesoid X receptor agonist, an estrogen agonist and a progesterone agonist.

7. A method for the treatment of lung cancer, bladder cancer, breast cancer, prostate cancer, myasthenia gravis, myodystrophy or malaria in a mammal characterized by administering to a mammal an effective amount of the compound of formula (I) or a pharmaceutically acceptable salt thereof described in claim 1.

8. A method for the treatment of osteoporosis, rheumatoid arthritis, arthritis, osteoarthritis, hypocalcaemia or osteometastasis of cancer in a mammal characterized by administering to a mammal an effective amount of the compound of formula (I) or a pharmaceutically acceptable salt thereof described in claim 1.

9. The compound according to claim 1, wherein the compound is selected from the group consisting of:

N'-(3-t-butyl-1,3-thiazolidin-2-ylidene)-[3-cyclohexylcarbonylamino-2-oxo-3-(tetrahydropyran-4-yl)propionohydrazide]hydrochloride;

N-((1S)-3-methyl-1-{oxo[(2Z)-2-(3-phenyl-1,3-thiazolidin-2-ylidene)hydrazino]acetyl}butyl)cyclohexanecarboxamide;

N-{1-(1-benzoylpiperidin-4-yl)-3-[(2Z)-2-(3-methyl-1,3-thiazolidin-2-ylidene)hydrazino]-2,3-dioxopropyl}cyclohexanecarboxamide hydrochloride;

N-{1-[1-(2,2-dimethylpropanoyl)piperidin-4-yl]-3-[(2Z)-2-(3-methyl-1,3-thiazolidin-2-ylidene)hydrazino]-2,3-dioxopropyl}cyclohexanecarboxamide hydrochloride;

N'-(3-methyl-1,3-thiazolidin-2-ylidene)-[N-(3-cyclohexylcarbonyl)-N-methylamino-4-methyl-2-oxopentanohydrazide]hydrochloride;

N'-(1,3-dimethyl imidazolidin-2-ylidene)-3-cyclohexyl-3-cyclohexylcarbonylamino-2-oxopropanohydrazide]dihydrochloride;

N-{3-[(2Z)-2-(1-methyl-3-oxa-1-azaspiro[4.4]non-2-ylidene)hydrazino]-2,3-dioxo-1-tetrahydro-2H-pyran-4-ylpropyl}cyclohexanecarboxamide hydrochloride;

N-{3-[(2Z)-2-(1-methyl-3-oxa-1-azaspiro[4.5]dec-2-ylidene)hydrazino]-2,3-dioxo-1-tetrahydro-2H-pyran-4-ylpropyl}cyclohexanecarboxamide hydrochloride;

N'-(1-methylpyrrolidine-2-ylidene)-(3-cyclohexylcarbonylamino-5-methyl-2-oxohexanohydrazide) hydrochloride;

N-{1-isopropyl-3-[(3-methyl-2-oxoimidazolidin-1-yl)amino]-2,3-dioxopropyl}cyclohexanecarboxamide;

N-{1-isopropyl-2,3-dioxo-3-[(2-oxo-1,3-oxazolidin-3-yl)amino]propyl}cyclohexanecarboxamide;

N-{3,3-dimethyl-1-[[(3-methyl-2-oxoimidazolidin-1-yl)amino](oxo)acetyl]butyl}cyclohexanecarboxamide;

N-{3-methyl-1-[[(3-methyl-2-oxoimidazolidin-1-yl)amino](oxo)acetyl]butyl}cyclohexanecarboxamide;

N-(3,3-dimethyl-1-{oxo[(2-oxopyrrolidin-1-yl)amino]acetyl}butyl)cycloheptanecarboxamide;

N-{1-[[(1,1-dioxidoisothiazolidin-2-yl)amino](oxo)acetyl]-3,3-dimethylbutyl}cycloheptanecarboxamide;

N-{2,3-dioxo-3-[(2-oxopyrrolidin-1-yl)amino]-1-tetrahydro-2H-pyran-4-ylpropyl}cyclohexanecarboxamide;

N-{3,3-dimethyl-1-[oxo(3-oxopyrazolidin-1-yl)acetyl]butyl}cyclohexanecarboxamide;

N-{1-cyclohexyl-3-[(2E)-2-(1-methylpyrrolidin-2-ylidene)hydrazino]-2,3-dioxopropyl}cyclohexanecarboxamide hydrochloride;

N-{2,3-dioxo-3-[(1-oxo-1,3-dihydro-2H-isoindol-2-yl)amino]-1-tetrahydro-2H-pyran-4-ylpropyl}cyclohexanecarboxamide;

N-[2,3-dioxo-3-(4-oxo-3,4-dihydrophthalazin-2(1H)-yl)-1-tetrahydro-2H-pyran-4-ylpropyl]cyclohexanecarboxamide;

N-{1-cyclohexyl-3-[(3-methyl-2-oxoimidazolidin-1-yl)amino]-2,3-dioxopropyl}cycloheptanecarboxamide;

N-{3-[(3-methyl-2-oxoimidazolidin-1-yl)amino]-2,3-dioxo-1-tetrahydro-2H-pyran-4-ylpropyl}cyclohexanecarboxamide;

N-{3-[(3-benzyl-2-oxoimidazolidin-1-yl)amino]-1-cyclohexyl-2,3-dioxopropyl}cycloheptanecarboxamide;

N-{3-[(3-benzyl-2-oxoimidazolidin-1-yl)amino]-2,3-dioxo-1-tetrahydro-2H-pyran-4-ylpropyl}cyclohexanecarboxamide;

N-(3-{[(7aR)-3-oxotetrahydro-1H-pyrrolo[1,2-c]imidazol-2(3H)-yl]amino}-2,3-dioxo-1-tetrahydro-2H-pyran-4-ylpropyl)cyclohexanecarboxamide;

N-(3-{[(7aR)-3-oxotetrahydro-1H-pyrrolo[1,2-c]imidazol-2(3H)-yl]amino}-1-cyclohexyl-2,3-dioxopropyl)cycloheptanecarboxamide;

N'-benzylidene-[(3S)-3-cyclohexylcarbonylamino-5-methyl-2-oxohexanohydrazide];

N-{(1S)-3-methyl-1-[[2-(1-methylethylidene)hydrazino](oxo)acetyl]butyl}cyclohexanecarboxamide;

N-((1S)-3-methyl-1-{oxo[(2E)-2-(1-phenylethylidene)hydrazino]acetyl}butyl)cyclohexanecarboxamide;

N-{(1S)-1-[2-cyclopentylidenehydrazino)(oxo)acetyl]-3-methylbutyl}cyclohexanecarboxamide;

N-(3-methyl-1-{oxo[(2E)-2-(pyridin-2-ylmethylene)hydrazino]acetyl}butyl)cyclohexanecarboxamide hydrochloride;

N-{(1S)-1-[[(2E)-2-(3-furylmethylene)hydrazino](oxo)acetyl]-3-methylbutyl}cyclohexanecarboxamide;

N-{(1S)-3-methyl-1-[[(2E)-2-(3-methylbutylidene)hydrazino](oxo)acetyl]butyl}cyclohexanecarboxamide;

N-((1S)-3-methyl-1-{oxo[(2E)-2-(tetrahydro-2H-pyran-4-ylmethylene)hydrazino]acetyl}butyl)cyclohexanecarboxamide;

N-{(1S)-3-methyl-1-[oxo(2-tetrahydro-4H-pyran-4-ylidenehydrazino)acetyl]butyl}cyclohexanecarboxamide;

N-(3,3-dimethyl-1-{oxo[2E]-2-(1-pyridin-2-ylethylidene)hydrazino]acetyl}butyl)cyclohexanecarboxamide hydrochloride;

N-(3,3-dimethyl-1-{oxo[(2E)-2-(1-pyridin-4-ylethylidene)hydrazino]acetyl}butyl)cyclohexanecarboxamide hydrochloride;

N-{3,3-dimethyl-1-[oxo((2E)-2-{1-[3-(trifluoromethyl)phenyl]ethylidene}hydrazino)acetyl]butyl}cyclohexanecarboxamide;

N-{3,3-dimethyl-1-[oxo((2E)-2-{1-[4-(trifluoromethyl)phenyl]ethylidene}hydrazino)acetyl]butyl}cyclohexanecarboxamide;

N'-acetyl-N'-phenyl-[(3S)-3-cyclohexylcarbonylamino-5-methyl-2-oxohexanohydrazide];

N'-acetyl-N'-cyclohexyl-[3-cyclohexylcarbonylamino-3-(tetrahydropyran-4-yl)-2-oxopropanohydrazide];

1-(3-cyclohexylcarbonylamino-5,5-dimethyl-2-oxohexanoylamino)-2,5-dioxopyrrolidine;

N-{3-[(2,5-dioxopyrrolidin-1-yl)amino]-2,3-dioxo-1-tetrahydro-2H-pyran-4-ylpropyl}cyclohexanecarboxamide;

N-{1-cyclohexyl-3-[(2,5-dioxopyrrolidin-1-yl)amino]-2,3-dioxopropyl}cyclohexanecarboxamide;

N-{3-[(2,5-dioxopyrrolidin-1-yl)amino]-2,3-dioxo-1-phenylpropyl}cyclohexanecarboxamide;

N-{3-[(4,4-dimethyl-2,6-dioxopiperidin-1-yl)amino]-2,3-dioxo-1-tetrahydro-2H-pyran-4-ylpropyl}cyclohexanecarboxamide;

N-{3-[(3,3-dimethyl-2,6-dioxopiperidin-1-yl)amino]-2,3-dioxo-1-tetrahydro-2H-pyran-4-ylpropyl}cyclohexanecarboxamide;

N-{1-cyclohexyl-3-[(3,5-dioxomorpholin-4-yl)amino]-2,3-dioxopropyl}cyclohexanecarboxamide;

N-{3-[(1,3-dioxo-1,3-dihydro-2H-isoindol-2-yl)amino]-2,3-dioxo-1-tetrahydro-2H-pyran-4-ylpropyl}cyclohexanecarboxamide;

N-{(1S)-3-[(2,5-dioxopyrrolidin-1-yl)amino]-1-isopropyl-2,3-dioxopropyl}cyclohexanecarboxamide;

N-{1-cyclohexyl-3-[(3,3-dimethyl-2,5-dioxopyrrolidin-1-yl)amino]-2,3-dioxopropyl}cyclohexanecarboxamide;

N-{1-[[(3,3-dimethyl-2,5-dioxopyrrolidin-1-yl)amino](oxo)acetyl]-3,3-dimethylbutyl}cyclohexanecarboxamide;

(2E)-N-{1-cyclohexyl-3-[(2,5-dioxopyrrolidin-1-yl)amino]-2,3-dioxopropyl}-4,4-dimethylpent-2-enamide;

N-{3-[(2,5-dioxopyrrolidin-1-yl)amino]-2,3-dioxo-1-tetrahydro-2H-pyran-4-ylpropyl}cycloheptanecarboxamide;

N-{1-cyclohexyl-3-[(2,5-dioxopyrrolidin-1-yl)amino]-2,3-dioxopropyl}cycloheptanecarboxamide;

N-{(1S)-1-cyclohexyl-3-[(2,5-dioxopyrrolidin-1-yl)amino]-2,3-dioxopropyl}cycloheptanecarboxamide;

N-{(1R)-1-cyclohexyl-3-[(2,5-dioxopyrrolidin-1-yl)amino]-2,3-dioxopropyl}cycloheptanecarboxamide;

$N^2$-(tert-butoxycarbonyl)-$N^1$-{1-cyclohexyl-3-[(2,5-dioxopyrrolidin-1-yl)amino]-2,3-dioxopropyl}-L-leucinamide;

N-[3-(2-acetylhydrazino)-1-cyclohexyl-2,3-dioxopropyl]cycloheptanecarboxamide;

4-(2-{3-[(cycloheptylcarbonyl)amino]-3-cyclohexyl-2-oxopropanoyl}hydrazino)-4-oxobutanoic acid;

$N^1$-{1-cyclohexyl-3-[(2,5-dioxopyrrolidin-1-yl)amino]-2,3-dioxopropyl}-$N^2$-(methoxycarbonyl)-L-leucinamide;

$N^2$-(tert-butoxycarbonyl)-$N^1$-{3-[(2,5-dioxopyrrolidin-1-yl)amino]-2,3-dioxo-1-tetrahydro-2H-pyran-4-ylpropyl}-L-leucinamide;

3-(3-cycloheptylcarbonylamino-3-cyclohexyl-2-oxopropanoyl)-1,2,3,4-tetrahydrophthalazin-1,4-dione;

N-methyl-N'-(3-methyl-1,3-thiazolidin-2-ylidene)-[3-cyclohexylcarbonylamino-5-methyl-2-oxohexanohydrazide]hydrochloride;

N'-(3-methyl-4-oxo-1,3-thiazolidin-2-ylidene)-[3-cyclohexylcarbonylamino-3-(tetrahydropyran-4-yl)-2-oxopropanohydrazide];

N-{1-cyclohexyl-3-[(2Z)-2-(3-methyl-4-oxo-1,3-thiazolidin-2-ylidene)hydrazino]-2,3-dioxopropyl}cyclohexanecarboxamide;

N-{3-[(2Z)-2-(3-benzyl-4-oxo-1,3-thiazolidin-2-ylidene)hydrazino]-2,3-dioxo-1-tetrahydro-2H-pyran-4-ylpropyl}cyclohexanecarboxamide;

N'-(3-propyl-1,3-thiazolidin-2-ylidene)-(3-cyclohexylcarbonylamino-3-(tetrahydropyran-4-yl)-2-oxopropanohydrazide)hydrochloride;

N-{(1S)-3-methyl-1-[[(2Z)-2-(3-methyl-1,3-thiazolidin-2-ylidene)hydrazino](oxo)acetyl]butyl}cyclohexanecarboxamide hydrochloride;

4-bromo-N-{(1S)-3-methyl-1-[[(2Z)-2-(3-methyl-1,3-thiazolidin-2-ylidene)hydrazino](oxo)acetyl]butyl}benzamide hydrochloride;

N-{(1S)-1-isopropyl-3-[(2Z)-2-(3-methyl-1,3-thiazolidin-2-ylidene)hydrazino]-2,3-dioxopropyl}cyclohexanecarboxamide hydrochloride;

N-{(1S)-3,3-dimethyl-1-[[(2Z)-2-(3-methyl-1,3-thiazolidin-2-ylidene)hydrazino](oxo)acetyl]butyl}cycloheptanecarboxamide hydrochloride;

N-{1-[({3-methyl-1-[[(2Z)-2-(3-methyl-1,3-thiazolidin-2-ylidene)hydrazino](oxo)acetyl]butyl}amino)carbonyl]cyclohexyl}benzamide hydrochloride;

N-{(1S)-2-methyl-1-[[(2Z)-2-(3-methyl-1,3-thiazolidin-2-ylidene)hydrazino](oxo)acetyl]butyl}cyclohexanecarboxamide hydrochloride;

N-{(1S)-1-benzyl-3-[(2Z)-2-(3-methyl-1,3-thiazolidin-2-ylidene)hydrazino]-2,3-dioxopropyl}cyclohexanecarboxamide hydrochloride;

N-{(1S)-1-tert-butyl-3-[(2Z)-2-(3-methyl-1,3-thiazolidin-2-ylidene)hydrazino]-2,3-dioxopropyl}cyclohexanecarboxamide hydrochloride;

N-{(1S)-1-[[(2Z)-2-(3-methyl-1,3-thiazolidin-2-ylidene)hydrazino](oxo)acetyl]pentyl}cyclohexanecarboxamide hydrochloride;

N-{3,3-dimethyl-1-[[(2Z)-2-(3-methyl-1,3-thiazolidin-2-ylidene)hydrazino](oxo)acetyl]butyl}cyclohexanecarboxamide hydrochloride;

N-{3-methoxy-3-methyl-1-[[(2Z)-2-(3-methyl-1,3-thiazolidin-2-ylidene)hydrazino](oxo)acetyl]butyl}cyclohexanecarboxamide hydrochloride;

N-{(1S)-3-methyl-1-[[(2Z)-2-(3-methyl-1,3-thiazolidin-2-ylidene)hydrazino](oxo)acetyl]butyl}acetamide hydrochloride;

N-{(1S)-3-methyl-1-[[(2Z)-2-(3-methyl-1,3-thiazolidin-2-ylidene)hydrazino](oxo)acetyl]butyl}tetrahydro-2H-pyran-4-carboxamide hydrochloride;

2,2-dimethyl-N-{(1S)-3-methyl-1-[[(2Z)-2-(3-methyl-1,3-thiazolidin-2-ylidene)hydrazino](oxo)acetyl]butyl}propanamide hydrochloride;

N-1-{(1S)-3-methyl-1-[[(2Z)-2-(3-methyl-1,3-thiazolidin-2-ylidene)hydrazino](oxo)acetyl]butyl}benzamide hydrochloride;

N-{(1S)-3-methyl-1-[[(2Z)-2-(3-methyl-1,3-thiazolidin-2-ylidene)hydrazino](oxo)acetyl]butyl}cycloheptanecarboxamide hydrochloride;

N-{(1S)-1-[[(2Z)-2-(3-ethyl-1,3-thiazolidin-2-ylidene)hydrazino](oxo)acetyl]-3-methylbutyl}cyclohexanecarboxamide hydrochloride;

N-((1S)-3-methyl-1-{oxo[(2Z)-2-(3-propyl-1,3-thiazolidin-2-ylidene)hydrazino]acetyl}butyl)cyclohexanecarboxamide hydrochloride;

N-{3,3-dimethyl-1-[[(2Z)-2-(3-methyl-1,3-thiazolidin-2-ylidene)hydrazino](oxo)acetyl]butyl}cycloheptanecarboxamide hydrochloride;

N-{(1S)-3-methyl-1-[[(2Z)-2-(3-methyl-1,3-thiazolidin-2-ylidene)hydrazino](oxo)acetyl]butyl}-2-phenylacetamide hydrochloride;

N-{(1S)-3-methyl-1-[[(2Z)-2-(3-methyl-1,3-thiazolidin-2-ylidene)hydrazino](oxo)acetyl]butyl}-2-phenoxyacetamide hydrochloride;

N-{(1S)-1-[[(2Z)-2-(3-benzyl-1,3-thiazolidin-2-ylidene)hydrazino](oxo)acetyl]-3-methylbutyl}cyclohexanecarboxamide hydrochloride;

N-{(1S)-1-[[(2Z)-2-(3-isopropyl-1,3-thiazolidin-2-ylidene)hydrazino](oxo)acetyl]-3-methylbutyl}cyclohexanecarboxamide hydrochloride;

N-{3-[(2Z)-2-(3-methyl-1,3-thiazolidin-2-ylidene)hydrazino]-2,3-dioxo-1-tetrahydro-2H-pyran-4-ylpropyl}cyclohexanecarboxamide hydrochloride;

N-{1-cyclohexyl-3-[(2Z)-2-(3-methyl-1,3-thiazolidin-2-ylidene)hydrazino]-2,3-dioxopropyl}cyclohexanecarboxamide hydrochloride;

(2E)-4,4-dimethyl-N-{(1S)-3-methyl-1-[[(2Z)-2-(3-methyl-1,3-thiazolidin-2-ylidene)hydrazino](oxo)acetyl]butyl}pent-2-enamide hydrochloride;

N-{(1S)-1-[{(2Z)-2-[3-(2-hydroxyethyl)-1,3-thiazolidin-2-ylidene]hydrazino}(oxo)acetyl]-3-methylbutyl}cyclohexanecarboxamide hydrochloride;

N-{1-cyclopropyl-3-[(2Z)-2-(3-methyl-1,3-thiazolidin-2-ylidene)hydrazino]-2,3-dioxopropyl}cyclohexanecarboxamide hydrochloride;

N-{1-cyclopentyl-3-[(2Z)-2-(3-methyl-1,3-thiazolidin-2-ylidene)hydrazino]-2,3-dioxopropyl}cyclohexanecarboxamide hydrochloride;

N-{1-[[(2Z)-2-(3-methyl-1,3-thiazolidin-2-ylidene)hydrazino](oxo)acetyl]-2-propylpentyl}cyclohexanecarboxamide hydrochloride;

N-{3-[(2Z)-2-(3-methyl-1,3-thiazolidin-2-ylidene)hydrazino]-2,3-dioxo-1-phenylpropyl}cyclohexanecarboxamide hydrochloride;

isobutyl(1S)-3-methyl-1-[[(2Z)-2-(3-methyl-1,3-thiazolidin-2-ylidene)hydrazino](oxo)acetyl]butylcarbamate hydrochloride;

N-{3-[(2Z)-2-(3-methyl-1,3-thiazolidin-2-ylidene)hydrazino]-2,3-dioxo-1-piperidin-4-ylpropyl}cyclohexanecarboxamide dihydrochloride;

N-{3-[(2Z)-2-(3-benzyl-1,3-thiazolidin-2-ylidene)hydrazino]-2,3-dioxo-1-tetrahydro-2H-pyran-4-ylpropyl}cyclohexanecarboxamide hydrochloride;

N-{1-(1-acetylpiperidin-4-yl)-3-[(2Z)-2-(3-methyl-1,3-thiazolidin-2-ylidene)hydrazino]-2,3-dioxopropyl}cyclohexanecarboxamide hydrochloride;

N-{(1S,2R)-2-[({(1S)-3-methyl-1-[[(2Z)-2-(3-methyl-1,3-thiazolidin-2-ylidene)hydrazino](oxo)acetyl]butyl}amino)carbonyl]cyclohexyl}benzamide hydrochloride;

methyl 1-[2-({(1S)-1-isopropyl-3-[(2Z)-2-(3-methyl-1,3-thiazolidin-2-ylidene)hydrazino]-2,3-dioxopropyl}amino)-2-oxoethyl]-6-oxo-2-phenyl-1,6-dihydropyrimidin-5-ylcarbamate hydrochloride;

N-{2-ethyl-1-[[(2Z)-2-(3-methyl-1,3-thiazolidin-2-ylidene)hydrazino](oxo)acetyl]butyl}cyclohexanecarboxamide hydrochloride;

tert-butyl 4-{1-[(cyclohexylcarbonyl)amino]-3-[(2Z)-2-(3-methyl-1,3-thiazolidin-2-ylidene)hydrazino]-2,3-dioxopropyl}piperidine-1-carboxylate hydrochloride;

N-{3-[(2Z)-2-(3-methyl-1,3-thiazolidin-2-ylidene)hydrazino]-2,3-dioxo-1-[4-(trifluoromethyl)phenyl]propyl}cyclohexanecarboxamide;

N-{1-(4-methoxyphenyl)-3-[(2Z)-2-(3-methyl-1,3-thiazolidin-2-ylidene)hydrazino]-2,3-dioxopropyl}cyclohexanecarboxamide hydrochloride;

N-{1-[1-(methylsulfonyl)piperidin-4-yl]-3-[(2Z)-2-(3-methyl-1,3-thiazolidin-2-ylidene)hydrazino]-2,3-dioxopropyl}cyclohexanecarboxamide hydrochloride;

N-{1-(2-methylphenyl)-3-[(2Z)-2-(3-methyl-1,3-thiazolidin-2-ylidene)hydrazino]-2,3-dioxopropyl}cyclohexanecarboxamide hydrochloride;

isobutyl 1-(2-methylphenyl)-3-[(2Z)-2-(3-methyl-1,3-thiazolidin-2-ylidene)hydrazino]-2,3-dioxopropylcarbamate hydrochloride;

methyl 1-(2-methylphenyl)-3-[(2Z)-2-(3-methyl-1,3-thiazolidin-2-ylidene)hydrazino]-2,3-dioxopropylcarbamate hydrochloride;

isobutyl 1-(2,6-dimethylphenyl)-3-[(2Z)-2-(3-methyl-1,3-thiazolidin-2-ylidene)hydrazino]-2,3-dioxopropylcarbamate hydrochloride;

N-{1-(2-chlorophenyl)-3-[(2Z)-2-(3-methyl-1,3-thiazolidin-2-ylidene)hydrazino]-2,3-dioxopropyl}cyclohexanecarboxamide hydrochloride;

N-{1-(2-methoxyphenyl)-3-[(2Z)-2-(3-methyl-1,3-thiazolidin-2-ylidene)hydrazino]-2,3-dioxopropyl}cyclohexanecarboxamide hydrochloride;

isobutyl 1-(2-methoxyphenyl)-3-[(2Z)-2-(3-methyl-1,3-thiazolidin-2-ylidene)hydrazino]-2,3-dioxopropylcarbamate hydrochloride;

N-((1S)-3-methyl-1-{oxo[(2Z)-2-(3,5,5-trimethyl-1,3-thiazolidin-2-ylidene)hydrazino]acetyl}butyl)cyclohexanecarboxamide hydrochloride;

N-{2,3-dioxo-1-tetrahydro-2H-pyran-4-yl-3-[(2Z)-2-(3,5,5-trimethyl-1,3-thiazolidin-2-ylidene)hydrazino]propyl}cyclohexanecarboxamide hydrochloride;

N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride;

N-{(1S)-1-isopropyl-2,3-dioxo-3-[(2Z)-2-(3-propyl-1,3-thiazolidin-2-ylidene)hydrazino]propyl}cyclohexanecarboxamide hydrochloride;

N-{(1S)-3-[(2Z)-2-(3-benzyl-1,3-thiazolidin-2-ylidene)hydrazino]-1-isopropyl-2,3-dioxopropyl}cyclohexanecarboxamide hydrochloride;

N-{(1S)-1-cyclohexyl-3-[(2Z)-2-(3-methyl-1,3-thiazolidin-2-ylidene)hydrazino]-2,3-dioxopropyl}cyclohexanecarboxamide hydrochloride;

N-{3-[(2Z)-2-(3-benzyl-1,3-thiazolidin-2-ylidene)hydrazino]-2,3-dioxo-1-tetrahydro-2H-pyran-4-ylpropyl}cycloheptanecarboxamide hydrochloride;

(2E)-N-{3-[(2Z)-2-(3-benzyl-1,3-thiazolidin-2-ylidene)hydrazino]-2,3-dioxo-1-tetrahydro-2H-pyran-4-ylpropyl}-4,4-dimethylpent-2-enamide hydrochloride;

(2E)-4,4-dimethyl-N-{3-[(2Z)-2-(3-methyl-1,3-thiazolidin-2-ylidene)hydrazino]-2,3-dioxo-1-tetrahydro-2H-pyran-4-ylpropyl}pent-2-enamide hydrochloride;

(2E)-N-{1-cyclohexyl-3-[(2Z)-2-(3-methyl-1,3-thiazolidin-2-ylidene)hydrazino]-2,3-dioxopropyl}-4,4-dimethylpent-2-enamide hydrochloride;

(2E)-N-(1-cyclohexyl-3-{(2Z)-2-[3-(2-hydroxyethyl)-1,3-thiazolidin-2-ylidene]hydrazino}-2,3-dioxopropyl)-4,4-dimethylpent-2-enamide hydrochloride;

N-(1-cyclohexyl-3-{(2Z)-2-[3-(2-hydroxyethyl)-1,3-thiazolidin-2-ylidene]hydrazino}-2,3-dioxopropyl)cyclohexanecarboxamide hydrochloride;

N-{(1R)-1-cyclohexyl-3-[(2Z)-2-(3-methyl-1,3-thiazolidin-2-ylidene)hydrazino]-2,3-dioxopropyl}cyclohexanecarboxamide hydrochloride;

N-{1-cyclohexyl-3-[(2Z)-2-(3-methyl-1,3-thiazolidin-2-ylidene)hydrazino]-2,3-dioxopropyl}cycloheptanecarboxamide hydrochloride;

N-{(1S)-3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride;

N-{(1R)-3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride;

N-{(1R)-1-isopropyl-3-[(2Z)-2-(3-methyl-1,3-thiazolidin-2-ylidene)hydrazino]-2,3-dioxopropyl}cyclohexanecarboxamide hydrochloride;

N-{(1R)-1-[[(2Z)-2-(3-methyl-1,3-thiazolidin-2-ylidene)hydrazino](oxo)acetyl]pentyl}cyclohexanecarboxamide hydrochloride;

N-{(1R)-3,3-dimethyl-1-[[(2Z)-2-(3-methyl-1,3-thiazolidin-2-ylidene)hydrazino](oxo)acetyl]butyl}cyclohexanecarboxamide hydrochloride;

N-{(1R)-1-cyclopropyl-3-[(2Z)-2-(3-methyl-1,3-thiazolidin-2-ylidene)hydrazino]-2,3-dioxopropyl}cyclohexanecarboxamide hydrochloride;

N'-[3-methyl-1,3-thiazolidin-2-ylidene]-[3-(N-phenylsulfonyl-N-methylamino)-2-oxo-4-methylpentanohydrazide]hydrochloride;

N'-(3-methyl-1,3-perhydrothiazin-2-ylidene)-[3-cyclohexylcarbonylamino-2-oxo-3-(tetrahydropyran-4-yl)hexanohydrazide]hydrochloride;

N'-(3-methyl-1,3-thiazolidin-2-ylidene)-[3-cyclohexylcarbonylamino-3-methyl-2-oxobutanohydrazide]hydrochloride;

N'-(3-methyl-1,3-perhydrothiazin-2-ylidene)-(3-cyclohexylcarbonylamino-2-oxo-5-methylhexanohydrazide);

N'-(3-methyl-1,3-perhydrothiazin-2-ylidene)-[3-(1-benzoylaminocyclohexylcarbonylamino)-5-methyl-2-oxohexanohydrazide];

N'-(3,4,4-trimethyl-1,3-thiazolidin-2-ylidene)-[3-cyclohexylcarbonylamino-3-(tetrahydropyran-4-yl)-2-oxopropanohydrazide]hydrochloride;

N-(3-methyl-1-{oxo[(2Z)-2-(3,4,4-trimethyl-1,3-thiazolidin-2-ylidene)hydrazino]acetyl}butyl)cyclohexanecarboxamide hydrochloride;

N-(3,3-dimethyl-1-{oxo[(2Z)-2-(3,4,4-trimethyl-1,3-thiazolidin-2-ylidene)hydrazino]acetyl}butyl)cyclohexanecarboxamide hydrochloride;

(2E)-N-{2,3-dioxo-1-tetrahydro-2H-pyran-4-yl-3-[(2Z)-2-(3,4,4-trimethyl-1,3-thiazolidin-2-ylidene)hydrazino]propyl}-4,4-dimethylpent-2-enamide hydrochloride;

N-{2,3-dioxo-1-tetrahydro-2H-pyran-4-yl-3-[(2Z)-2-(3,4,4-trimethyl-1,3-thiazolidin-2-ylidene)hydrazino]propyl}cycloheptanecarboxamide hydrochloride;

N-{1-cyclohexyl-2,3-dioxo-3-[(2Z)-2-(3,4,4-trimethyl-1,3-thiazolidin-2-ylidene)hydrazino]propyl}cyclohexanecarboxamide hydrochloride;

N-{1-cyclohexyl-2,3-dioxo-3-[(2Z)-2-(3,4,4-trimethyl-1,3-thiazolidin-2-ylidene)hydrazino]propyl}cycloheptanecarboxamide hydrochloride;

N-{(1S)-1-isopropyl-2,3-dioxo-3-[(2Z)-2-(3,4,4-trimethyl-1,3-thiazolidin-2-ylidene)hydrazino]propyl}cyclohexanecarboxamide hydrochloride;

N'-(3-ethyl-4-methyl-1,3-thiazolidin-2-ylidene)-[3-cycloheptylcarbonylamino-3-[(3S)-tetrahydropyran-4-yl]-2-oxopropanohydrazide];

N-(3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide;

N-{(1S)-1-cyclohexyl-3-[(2Z)-2-(3-methyl-1,3-thiazolidin-2-ylidene)hydrazino]-2,3-dioxopropyl}cycloheptanecarboxamide;

$N^2$-(tert-butoxycarbonyl)-$N^1$-{3-[(2Z)-2-(3-methyl-1,3-thiazolidin-2-ylidene)hydrazino]-2,3-dioxo-1-tetrahydro-2H-pyran-4-ylpropyl}-L-leucinamide;

N-((1R)-3-{(2Z)-2-[(4S)-3,4-dimethyl-1,3-thiazolidin-2-ylidene]hydrazino)-2,3-dioxo-1-tetrahydro-2H-pyran-4-ylpropyl)cycloheptanecarboxamide;

N-(3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide;

$N^2$-(methoxycarbonyl)-$N^1$-{3-[(2Z)-2-(3-methyl-1,3-thiazolidin-2-ylidene)hydrazino]-2,3-dioxo-1-tetrahydro-2H-pyran-4-ylpropyl}-L-leucinamide;

$N^2$-(tert-butoxycarbonyl)-$N^1$-{1-cyclohexyl-3-[(2Z)-2-(3-methyl-1,3-thiazolidin-2-ylidene)hydrazino]-2,3-dioxopropyl}-L-leucinamide;

N-(3-{(2Z)-2-[(4R)-3,4-dimethyl-1,3-thiazolidin-2-ylidene]hydrazino}-2,3-dioxo-1-tetrahydro-2H-pyran-4-ylpropyl)cyclohexanecarboxamide;

$N^1$-{1-cyclohexyl-3-[(2Z)-2-(3-methyl-1,3-thiazolidin-2-ylidene)hydrazino]-2,3-dioxopropyl}-$N^2$-(methoxycarbonyl)-L-leucinamide;

N-(3-{(2Z)-2-[(4R)-4-isopropyl-3-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-4-isobutyl-3-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-4-isopropyl-3-methyl-1,3-thiazolidin-2-ylidene]hydrazino}-2,3-dioxo-1-tetrahydro-2H-pyran-4-ylpropyl)cyclohexanecarboxamide;

N-(3-{(2Z)-2-[(4R)-4-isobutyl-3-methyl-1,3-thiazolidin-2-ylidene]hydrazino}-2,3-dioxo-1-tetrahydro-2H-pyran-4-ylpropyl)cyclohexanecarboxamide;

N-(1-cyclohexyl-3-{(2Z)-2-[(4R)-4-isopropyl-3-methyl-1,3-thiazolidin-2-ylidene]hydrazino}-2,3-dioxopropyl)cycloheptanecarboxamide;

N-(1-cyclohexyl-3-{(2Z)-2-[(4R)-4-isobutyl-3-methyl-1,3-thiazolidin-2-ylidene]hydrazino}-2,3-dioxopropyl)cycloheptanecarboxamide;

N-(3-{(2Z)-2-[(5R)-3,5-dimethyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(5R)-3,5-dimethyl-1,3-thiazolidin-2-ylidene]hydrazino}-2,3-dioxo-1-tetrahydro-2H-pyran-4-ylpropyl)cyclohexanecarboxamide;

N-(1-cyclohexyl-3-{(2Z)-2-[(5R)-3,5-dimethyl-1,3-thiazolidin-2-ylidene]hydrazino}-2,3-dioxopropyl)cycloheptanecarboxamide;

N-(3-{(2Z)-2-[(4R)-3,4-diethyl-1,3-thiazolidin-2-ylidene]hydrazino}-2,3-dioxo-1-tetrahydro-2H-pyran-4-ylpropyl)cycloheptanecarboxamide;

N-(1-cyclohexyl-3-{(2Z)-2-[(4R)-3,4-diethyl-1,3-thiazolidin-2-ylidene]hydrazino}-2,3-dioxopropyl)cycloheptanecarboxamide;

N-((1R)-3-{(2Z)-2-[(4R)-3,4-diethyl-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(4R)-3-ethyl-4-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-4-ethyl-3-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-4-ethyl-3-methyl-1,3-thiazolidin-2-ylidene]hydrazino}-2,3-dioxo-1-tetrahydro-2H-pyran-4-ylpropyl)cyclohexanecarboxamide;

N-(1-cyclohexyl-3-{(2Z)-2-[(4R)-4-ethyl-3-methyl-1,3-thiazolidin-2-ylidene]hydrazino}-2,3-dioxopropyl)cycloheptanecarboxamide;

N-[2,3-dioxo-3-((2Z)-2-{3-[(1R)-1-phenylethyl]-1,3-thiazolidin-2-ylidene}hydrazino)-1-tetrahydro-2H-pyran-4-ylpropyl]cycloheptanecarboxamide;

N-[2,3-dioxo-3-((2Z)-2-{3-[(1R)-1-phenylethyl]-1,3-thiazolidin-2-ylidene}hydrazino)-1-tetrahydro-2H-pyran-4-ylpropyl]cyclohexanecarboxamide;

N-((1R)-3-{(2Z)-2-[(4R)-3-ethyl-4-methyl-1,3-thiazolidin-2-ylidene]hydrazino}-2,3-dioxo-1-tetrahydro-2H-pyran-4-ylpropyl)cyclohexanecarboxamide;

N-((1S)-3-{(2Z)-2-[(4S)-3-ethyl-4-methyl-1,3-thiazolidin-2-ylidene]hydrazino}-2,3-dioxo-1-tetrahydro-2H-pyran-4-ylpropyl)cyclohexanecarboxamide;

N-(3-{(2Z)-2-[(4R)-4-benzyl-3-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-4-benzyl-3-methyl-1,3-thiazolidin-2-ylidene]hydrazino}-2,3-dioxo-1-tetrahydro-2H-pyran-4-ylpropyl)cyclohexanecarboxamide;

N-(1-cyclohexyl-3-{(2Z)-2-[(4R)-3-ethyl-4-methyl-1,3-thiazolidin-2-ylidene]hydrazino}-2,3-dioxopropyl)cycloheptanecarboxamide;

N-((1R)-3-{(2Z)-2-[(4S)-3-benzyl-4-methyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-3-benzyl-4-methyl-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(4R)-4-benzyl-3-methyl-1,3-thiazolidin-2-ylidene]hydrazino}-1-cyclohexyl-2,3-dioxopropyl)cycloheptanecarboxamide;

N-((1R)-3-{(2Z)-2-[(4R)-3-benzyl-4-ethyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-3-benzyl-4-ethyl-1,3-thiazolidin-2-ylidene]hydrazino}-2,3-dioxo-1-tetrahydro-2H-pyran-4-ylpropyl)cyclohexanecarboxamide;

N-[1-cyclohexyl-2,3-dioxo-3-((2Z)-2-{3-[(1R)-1-phenylethyl]-1,3-thiazolidin-2-ylidene}hydrazino)propyl]cycloheptanecarboxamide;

N-[2,3-dioxo-3-((2Z)-2-{3-[(1S)-1-phenylethyl]-1,3-thiazolidin-2-ylidene}hydrazino)-1-tetrahydro-2H-pyran-4-ylpropyl]cyclohexanecarboxamide;

N-(3-{(2Z)-2-[(4R)-3-methyl-4-phenyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(4R)-3-methyl-4-phenyl-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(4R)-3-(2-methoxyethyl)-4-methyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-3-(2-methoxyethyl)-4-methyl-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(4R)-4-ethyl-3-(2-methoxyethyl)-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-4-ethyl-3-(2-methoxyethyl)-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(5R)-3-benzyl-5-methyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(5R)-3-benzyl-5-methyl-1,3-thiazolidin-2-ylidene]hydrazino}-2,3-dioxo-1-tetrahydro-2H-pyran-4-ylpropyl)cyclohexanecarboxamide;

N-((1S)-3-{(2Z)-2-[(4S)-3-(2-methoxyethyl)-4-methyl-1,3-thiazolidin-2-ylidene]hydrazino}-2,3-dioxo-1-tetrahydro-2H-pyran-4-ylpropyl)cycloheptanecarboxamide;

N-((1S)-3-{(2Z)-2-[(4S)-3-(2-methoxyethyl)-4-methyl-1,3-thiazolidin-2-ylidene]hydrazino}-2,3-dioxo-1-tetrahydro-2H-pyran-4-ylpropyl)cyclohexanecarboxamide;

N-((1S)-3-{(2Z)-2-[(4S)-3-benzyl-4-methyl-1,3-thiazolidin-2-ylidene]hydrazino}-2,3-dioxo-1-tetrahydro-2H-pyran-4-ylpropyl)cycloheptanecarboxamide;

N-((1S)-3-{(2Z)-2-[(4S)-3-benzyl-4-methyl-1,3-thiazolidin-2-ylidene]hydrazino}-2,3-dioxo-1-tetrahydro-2H-pyran-4-ylpropyl)cyclohexanecarboxamide;

N-(3-{(2Z)-2-[(5R)-3-ethyl-5-methyl-1,3-thiazolidin-2-ylidene]hydrazino}-2,3-dioxo-1-tetrahydro-2H-pyran-4-ylpropyl)cycloheptanecarboxamide;

N-(3-{(2Z)-2-[(5R)-3-ethyl-5-methyl-1,3-thiazolidin-2-ylidene]hydrazino}-2,3-dioxo-1-tetrahydro-2H-pyran-4-ylpropyl)cyclohexanecarboxamide;

N-(3-{(2Z)-2-[(4S)-3-ethyl-4-methyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(7aS)-tetrahydro-1H-pyrrolo[1,2-c][1,3]thiazol-3-ylidene]hydrazino}-2,3-dioxo-1-tetrahydro-2H-pyran-4-ylpropyl)cycloheptanecarboxamide;

N-((1S)-3-{(2Z)-2-[(7aR)-tetrahydro-1H-pyrrolo[1,2-c][1,3]thiazol-3-ylidene]hydrazino}-2,3-dioxo-1-tetrahydro-2H-pyran-4-ylpropyl)cycloheptanecarboxamide;

N-((1S)-3-{(2Z)-2-[(7aR)-tetrahydro-1H-pyrrolo[1,2-c][1,3]thiazol-3-ylidene]hydrazino}-2,3-dioxo-1-tetrahydro-2H-pyran-4-ylpropyl)cyclohexanecarboxamide; and N-(3-{(2Z)-2-[(7aR)-tetrahydro-1H-pyrrolo[1,2-c][1,3]thiazol-3-ylidene]hydrazino}-1-cyclohexyl-2,3-dioxopropyl)cycloheptanecarboxamide; or a pharmaceutically acceptable salt thereof.

10. A compound selected from the group consisting of:

N-{1-{1-[(4-methylphenyl)sulfonyl]piperidin-4-yl}-3-[(2Z)-2-(3-methyl-1,3-thiazolidin-2-ylidene)hydrazino]-2,3-dioxopropyl}cyclohexanecarboxamide hydrochloride;

N-{3-[(2Z)-2-(3-allyl-4-oxo-1,3-thiazolidin-2-ylidene)hydrazino]-2,3-dioxo-1-tetrahydro-2H-pyran-4-ylpropyl}cyclohexanecarboxamide;

N-{1-cyclohexyl-3-[(2Z)-2-(3-{4-[(dimethylamino)methyl]benzyl}-1,3-thiazolidin-2-ylidene)hydrazino]-2,3-dioxopropyl}cyclohexanecarboxamide dihydrochloride;

N-(3-{(2Z)-2-[3-(4-methoxybenzyl)-1,3-thiazolidin-2-ylidene]hydrazino}-2,3-dioxo-1-tetrahydro-2H-pyran-4-ylpropyl)cyclohexanecarboxamide;

N-((1R)-3-{(2Z)-2-[(4R)-3-(4-fluorobenzyl)-4-methyl-1,3-thiazolidin-2-ylidene]hydrazino}-2,3-dioxo-1-tetrahydro-2H-pyran-4-ylpropyl)cycloheptanecarboxamide;

N-((1R)-3-{(2Z)-2-[(4R)-3-(4-fluorobenzyl)-4-methyl-1,3-thiazolidin-2-ylidene]hydrazino}-2,3-dioxo-1-tetrahydro-2H-pyran-4-ylpropyl)cyclohexanecarboxamide;

N-((1S)-3-{(2Z)-2-[(4S)-3-(4-fluorobenzyl)-4-methyl-1,3-thiazolidin-2-ylidene]hydrazino}-2,3-dioxo-1-tetrahydro-2H-pyran-4-ylpropyl)cycloheptanecarboxamide;

N-((1S)-3-{(2Z)-2-[(4S)-3-(4-fluorobenzyl)-4-methyl-1,3-thiazolidin-2-ylidene]hydrazino}-2,3-dioxo-1-tetrahydro-2H-pyran-4-ylpropyl)cyclohexanecarboxamide; and N-((1R)-3-{(2Z)-2-[(4R)-4-ethyl-3-(4-fluorobenzyl)-1,3-thiazolidin-2-ylidene]hydrazino}-2,3-dioxo-1-tetrahydro-2H-pyran-4-ylpropyl)cycloheptanecarboxamide.

\* \* \* \* \*